US012667584B2

(12) United States Patent
Zhang et al.

(10) Patent No.: US 12,667,584 B2
(45) Date of Patent: Jun. 30, 2026

(54) ADENOSINE ANALOG AND ITS USE IN REGULATING THE CIRCADIAN CLOCK

(71) Applicant: NATIONAL INSTITUTE OF BIOLOGICAL SCIENCES, BEIJING, Beijing (CN)

(72) Inventors: Erquan Zhang, Beijing (CN); Xiangbing Qi, Beijing (CN); Dapeng Ju, Beijing (CN); Zhiqiang Wang, Beijing (CN); Qingcui Wu, Beijing (CN); Haijiao Zhao, Beijing (CN); Long Mei, Beijing (CN)

(73) Assignee: NATIONAL INSTITUTE OF BIOLOGICAL SCIENCES, BEIJING, Beijing (CN)

( * ) Notice: Subject to any disclaimer, the term of this patent is extended or adjusted under 35 U.S.C. 154(b) by 466 days.

(21) Appl. No.: 16/479,844

(22) PCT Filed: Jan. 20, 2018

(86) PCT No.: PCT/CN2018/073526
§ 371 (c)(1),
(2) Date: Jul. 22, 2019

(87) PCT Pub. No.: WO2018/133854
PCT Pub. Date: Jul. 26, 2018

(65) Prior Publication Data

US 2021/0338706 A1 Nov. 4, 2021

(30) Foreign Application Priority Data

Jan. 20, 2017 (WO) ................ PCT/CN2017/071903

(51) Int. Cl.

| | |
|---|---|
| ***A61K 31/7076*** | (2006.01) |
| ***A61K 31/519*** | (2006.01) |
| ***A61K 31/52*** | (2006.01) |
| ***A61K 31/7056*** | (2006.01) |
| ***A61K 31/706*** | (2006.01) |
| ***A61K 31/708*** | (2006.01) |
| ***A61P 25/20*** | (2006.01) |
| ***C07D 473/34*** | (2006.01) |
| ***C07H 19/052*** | (2006.01) |
| ***C07H 19/16*** | (2006.01) |
| ***C07H 19/20*** | (2006.01) |
| ***C07H 19/207*** | (2006.01) |
| ***C07H 19/23*** | (2006.01) |

(52) U.S. Cl.

CPC ........ *A61K 31/7076* (2013.01); *A61K 31/519* (2013.01); *A61K 31/52* (2013.01); *A61K 31/7056* (2013.01); *A61K 31/706* (2013.01); *A61K 31/708* (2013.01); *A61P 25/20* (2018.01); *C07D 473/34* (2013.01); *C07H 19/052* (2013.01); *C07H 19/16* (2013.01); *C07H 19/20* (2013.01); *C07H 19/207* (2013.01); *C07H 19/23* (2013.01)

(58) Field of Classification Search

USPC ........................................................ 514/43, 45

See application file for complete search history.

(56) References Cited

U.S. PATENT DOCUMENTS

| | | | | |
|---|---|---|---|---|
| 5,155,216 | A * | 10/1992 | Mock | C07H 21/00 435/6.11 |
| 5,366,960 | A * | 11/1994 | Gallagher | A61K 31/70 514/45 |
| 2004/0044064 | A1 | 3/2004 | Lewy et al. | |
| 2007/0238694 | A1 | 10/2007 | Salzman et al. | |
| 2009/0264383 | A1 * | 10/2009 | Hastings | A61P 43/00 514/263.1 |
| 2013/0005677 | A1 | 1/2013 | Chu et al. | |

FOREIGN PATENT DOCUMENTS

| | | | |
|---|---|---|---|
| WO | 1998048796 | 11/1998 | |
| WO | 2007111954 | 10/2007 | |
| WO | 2011060408 | 5/2011 | |
| WO | WO-2016107776 A1 * | 7/2016 | A61K 36/068 |

OTHER PUBLICATIONS

Zyk et al., Biochemistry, 1970, 9(3), 677-83. (Year: 1970).*

O'Neill et al., Nature, vol/ 469, No. 7331, Jan. 27, 2011, pp. 554-558. (Year: 2011).*

O'Neill, Nature, vol. 469 No. 731, Jan. 27, 2011, pp. 554-558. (Year: 2011).*

Wennefors et al., "Stereospecificity, substrate, and inhibitory properties of nucleoside diphosphates analogs for creatine and pyruvate kinases", *Bioorganic Chemistry*, vol. 36, 2008, 10 sheets.

Wei et al., "Synthesis and pharmacokinetic evaluation of novel N-acyl-cordycepin derivatives with a normal alkyl chain", *European Journal of Medicinal Chemistry*, vol. 44, 2009, 6 sheets.

De Zwart et al., "A Functional Screening of Adenosine Analogues at the Adenosine $A_{2B}$ Receptor: a Search for Potent Agonists", *Nucleosides & Nucleotides*, vol. 17, No. 6, 1998, 18 sheets.

Wnuk et al., "Nucleic Acid Related Compounds. 84. Synthesis of 6'-(E and Z)-Halohomovinyl Derivatives of Adenosine, Inactivation of *S*-Adenosyl-L-homocysteine Hydrolase, and Correlation of Anticancer and Antiviral Potencies with Enzyme Inhibition", *J.Med. Chem.*, vol. 37, 1994, 10 sheets.

J. Reist et al., "Potential Anticancer Agents.[1] XV. Synthesis of 9-β-D-Glucofuranosyladenine", The Journal of Organic Chemistry, vol. 23, No. 12, 1958, 6 sheets.

(Continued)

*Primary Examiner* — Traviss C McIntosh, III

(74) *Attorney, Agent, or Firm* — NKL Law; Bin Lu; Allen Xue

(57) ABSTRACT

The present invention provides a kind of nucleoside analogue compounds, and a composition comprising the compound and pentostatin, their use for modulating circadian rhythm, preferably, for shifting circadian phase, and methods for modulating circadian rhythm, preferably, for shifting circadian phase via the compound or the composition.

14 Claims, 13 Drawing Sheets

(56) References Cited

OTHER PUBLICATIONS

Ikehara et al., "Studies of Nucleosides and Nucleotides. L. [1]) Purine Cyclonucleosides. (14). Synthesis and Properties of Cyclonucleosides derived from 9-D-Xylofuranosyladenine[2])", *Chem. Pharm. Bull.*, vol. 19, No. 3, 1971, 8 sheets.
Elzein et al., "2-Pyrazolyl-$N^6$-*Substituted Adenosine Derivatives as High Affinity and Selective Adenosine $A_3$* Receptor Agonists", J. Med. Chem., vol. 47, 2004, 8 sheets.
Golub et al., "Evaluation of 3-Carboxy-4(1*H*)-quinolones as Inhibitors of Human Protein Kinase CK2", *J. Med. Chem.*, vol. 49, 2006, 8 sheets.
Froy, "The relationship between nutrition and circadian rhythms in mammals", *Frontiers in Neuroendocrinology*, vol. 28, 2007, 11 sheets.
Van Diepen et al., "Caffeine increases light responsiveness of the mouse circadian pacemaker", *European Journal of Neuroscience*, vol. 40, 2014, 8 sheets.

* cited by examiner

Figure 1
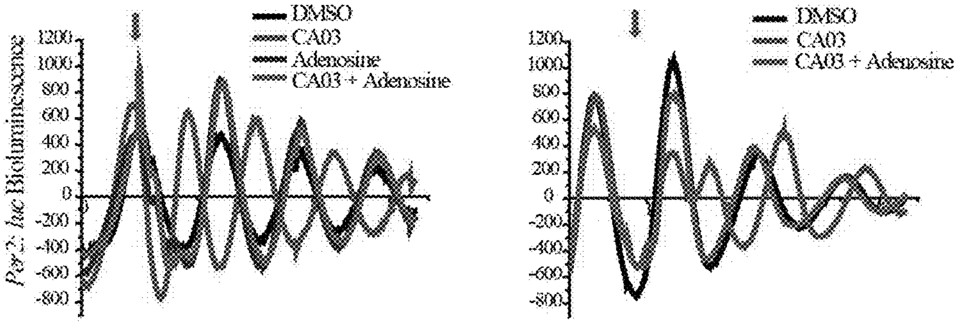
Figure 1A
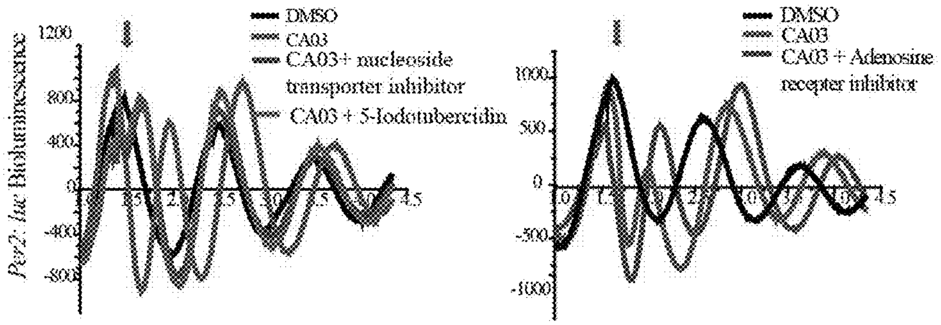
Figure 1B
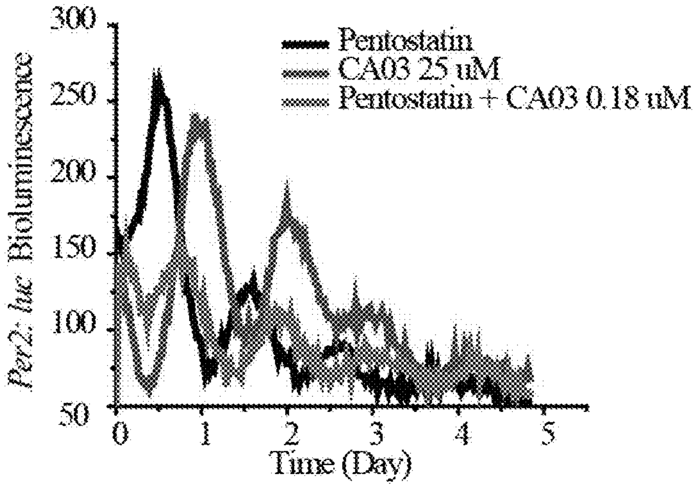
Figure 1C

Figure 2
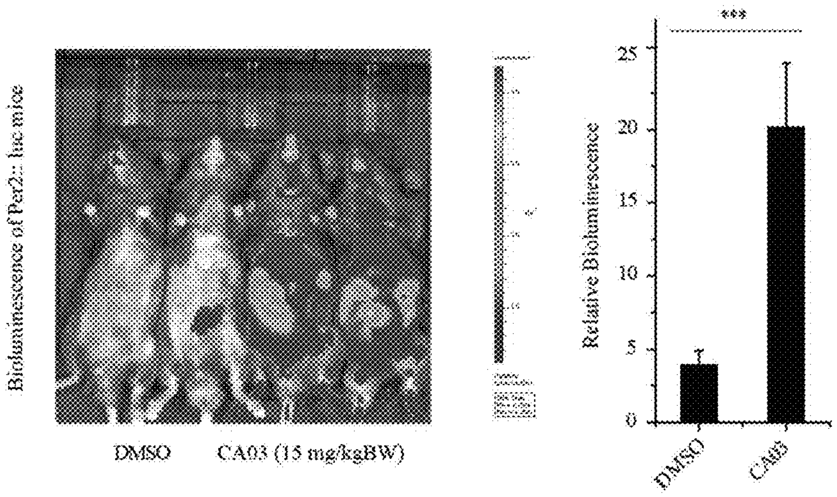
Figure 2A
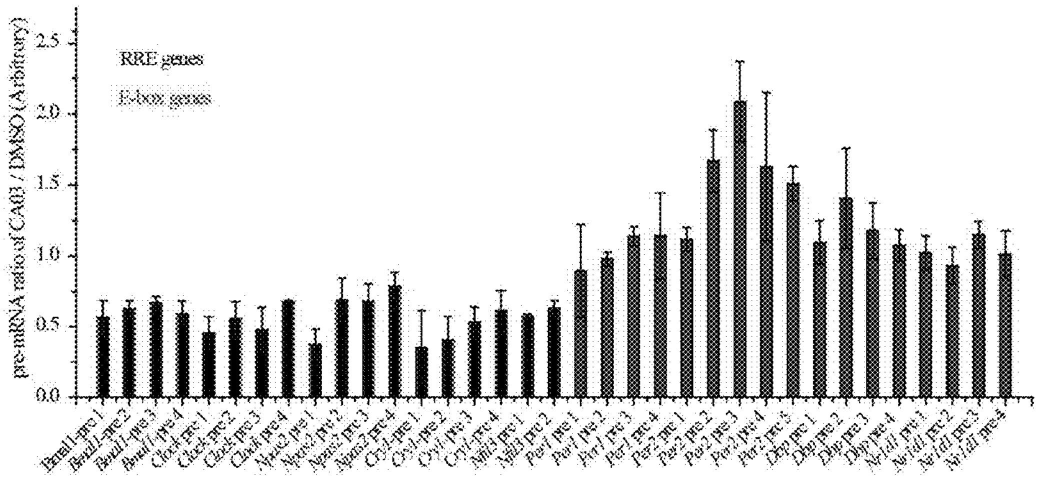
Figure 2B
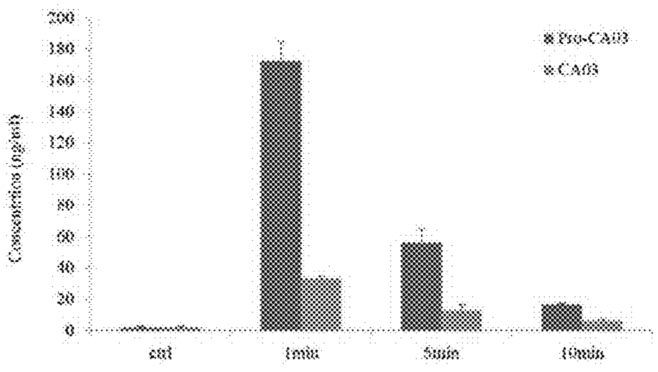
Figure 2C

Figure 3
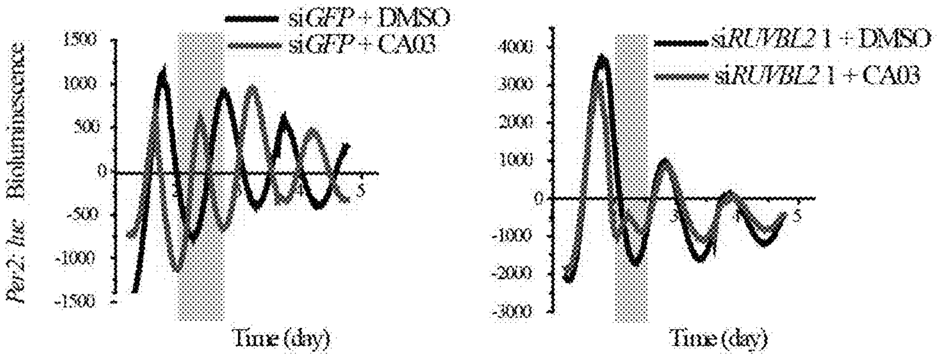
Figure 3A
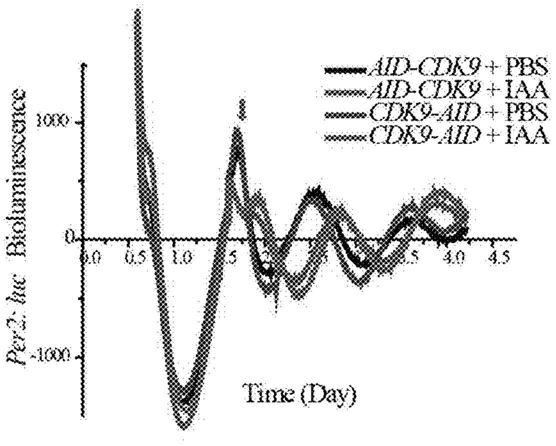
Figure 3B
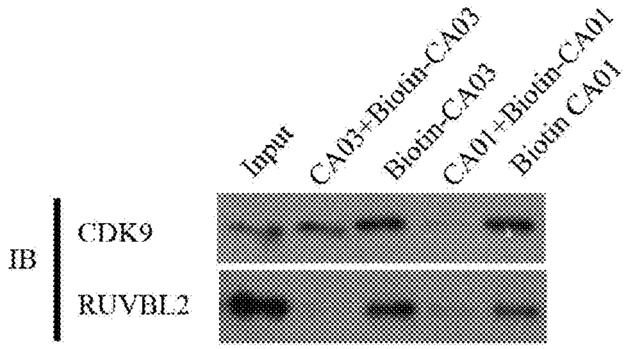
Figure 3C

Figure 7
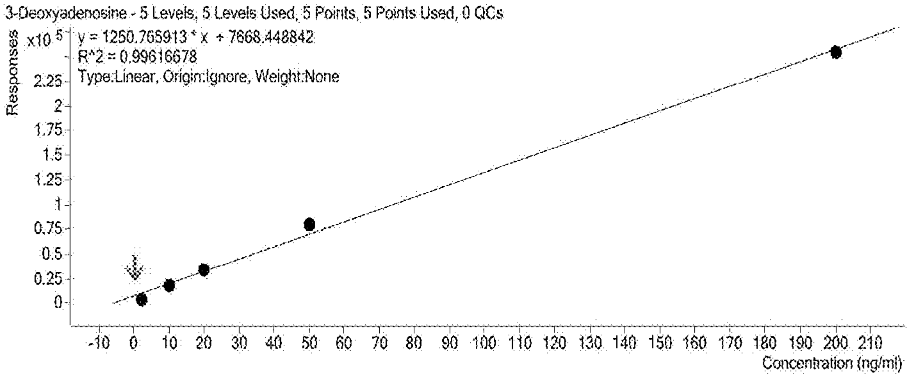
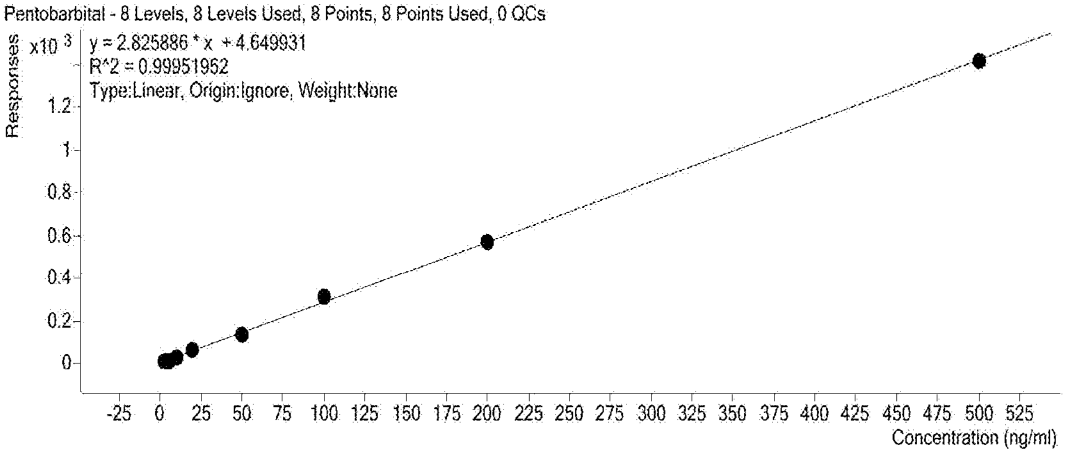
Figure 7A

HPLC signal of standard 3-Deoxyadenosine (CA03,Cordycepin)

HPLC signal of Pentobarbital:

Cordycepin concentration in cerebrospinal fluid (CSF)

HPLC signal of 3-Deoxyadenosine(CA03,Cordycepin) in cerebrospinal fluid:

ADENOSINE ANALOG AND ITS USE IN REGULATING THE CIRCADIAN CLOCK

PRIORITY CLAIM

This application is a National Stage Application, filed under 35 U.S.C. § 371, of PCT Patent Application Serial No. PCT/CN2018/073526 filed on Jan. 20, 2018, entitled "Adenosine Analog and its use in Regulating the Circadian Clock", which claims priority to PCT Patent Application Serial No. PCT/CN2017/071903, entitled "Regulating Mammalian Circadian Rhythm," filed on Jan. 20, 2017, both of which are hereby incorporated by reference in their entirety.

BACKGROUND

In modern society, people frequently travel across multiple time-zones in a single trip, thereby suffering a notorious "jet-lag". World Tourism Organization (UNWTO) estimates that there are annually more than 200 million transcontinental travelers world-wide. For them, the most-hurting discomfort is the completely antiphasic changes of daily rhythmic physiology in humans (thus, a roughly 12 h day-night difference). For instance, people flying from Beijing to New York City, or from London to Hawaii islands, find their bodies requiring more than a week to adjust to the destination time. In addition, shift-workers (such as nurses and truck-drivers), who reportedly contribute to one-out-of-six work force in USA, commonly experience drastic "sleep-wake" phase changes in accommodation to their work schedules. These dismal changes in behavior could result in fatigue and uneasiness in short-terms, and mental/physical disorders in long-runs.

Our endogenous clockworks are believed to govern daily "sleep-wake" cycles. Three parameters are used to describe the general process of oscillation: period, amplitude, and phase (Dunlap, 1999). Most previous investigations of circadian oscillation have focused on the clock period, since it is generally thought to be the most robust (i.e., resilient to perturbation by environmental factors) of the three parameters and is thought to be directly related to the core regulation of the clock (Takahashi et al., 2008b). Only a few studies have focused on the amplitude of circadian oscillations, but it is notable that at least two studies have implicated the activity of the Clock/dClk protein in the regulation of amplitude (Allada et al., 2003; He et al., 2015). Even fewer studies have examined the phase of the clock, which is very sensitive to environmental perturbations; indeed, current opinion holds that phase-related phenomena are difficult to reliably reproduce experimentally (Chen et al., 2018). Nevertheless, it has been recognized that the phase may actually be equally, if not more important for the clock than either the period or amplitude, as the phase defines the "go/no-go" moments for circadian transcription and determines the point at which clock oscillation starts.

SUMMARY OF THE INVENTION

In this application, we used a new chemical screening strategy with stringent criteria to monitor clock phase phenotypes, and successfully identified a group of small molecules that shift the clock phase. In particular, we investigated adenosine analogs, and their related compounds, in regulating the circadian clock in human cells. Surprisingly, we found that these compounds, if administrated in right time, could completely reverse the course of the clock-phase, resulting in a 12 h time difference of circadian oscillation. Structure-Activity Relationship (SAR) studies coupled with a pretreatment of Pentostatin, an adenosine deaminases-specific inhibitor, have improved the working concentration of these compounds to nanomolar ranges, making them possible to be used clinically. Furthermore, these compounds are able to penetrate through brain-blood-barrier (BBB), demonstrating the first effective clock-modifier compound that admission in peripheral would sufficiently lead to behavioral effects. Previously discovered clock drugs, including Longdaysin (CK1 inhibitor, *PLoS Biol* 2010), KL001 series (CRY1/2 stabilizer, *Science* 2012), and OPC-21268/SSR-149415 (V1a/b antagonists, *Science* 2013), are either no effects on behaviors, or requiring an intracerebroventricular (ICV) injection into the brain to facilitate the BBB penetration, precluding them from practical usage in clinics for behavioral rearrangement. To our knowledge, ours are the first clock-drugs that do not need to be injected into the brain to be functional.

In one aspect, the invention discloses a compound of the following formula I, II and III:

Formula I

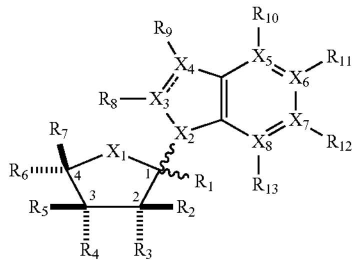

Formula II

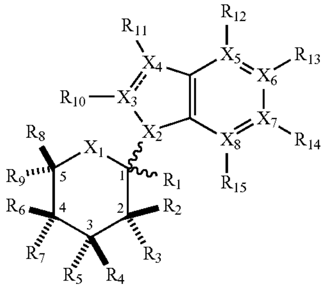

Formula III

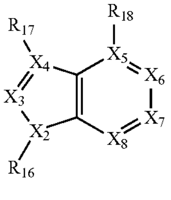

wherein $R_1$-$R_{18}$ are independently of each other preferably an unsubstituted or substituted straight or branched chain hydrocarbon residue containing 1 to 8 carbon atoms, hydrogen, hydroxyl, alkyl, alkenyl, alkynyl, alkylene, haloalkyl, cycloalkyl, alkoxy, alkylthio, aryl, aryloxy, arylthio, heterocyclyl, heterocyclylamino, halogen, alkylamino, dialkylamino, aminoxide, alkylhydroxylamino, azide, nitro, cyano and isocyano, alkyl carbonyl, cycloalkyl carbonyl, aryl carbonyl, heterocyclyl carbonyl, alkylvinyl, allyl, carboxy, alkylthio, amide, ester, phosphonate, cycloalkylphosphonate, cycloalkylphosphonamide, sulfonate, cycloalkylsulfonate or heterocyclylsulfonate, wherein alkyl, alkenyl, alkynyl, alkylene, haloalkyl, cycloalkyl, alkoxy and alkylthio are C1-C8 alkyl, C2-C8 alkenyl, C2-C8 alkynyl, C2-C8 alkylene, haloalkyl (C1-C8), cycloalkyl(C1-C8), alkoxy(C1-C8) and alkylthio(C1-C8) respectively. For example, $R_1$-$R_{13}$ may be arylmethyl, arylethyl, arylpropyl, arylbutyl, heteroarylmethyl, heteroarylethyl, heteroarylpropyl, heteroarylbutyl, in particular, $R_1$-$R_{13}$ may be phenyl, phenylmethyl, 1-methyl-2-phenylethyl, 1-phenylpropyl, 2-phenylpropyl, 3-phenylpropyl, henylbutyl, phenylpentyl, phenylhexyl or 1-benzyl-1-methylethyl. $R_1$-$R_{13}$ may be fluorine, chlorine, bromine, iodine, fluoromethoxy, chloromethoxy, bromometoxy, fluoroethoxy, chloroethoxy, bromoethoxy, aminomethoxy, aminoethoxy, aminopropyloxy, or other heteroatoms such as O, S, P, Si and Se. $R_1$-$R_{13}$ may be —OR', —OC(O)R', —NR'R", —SR', —R', —CN, $—NO_2$, $—CO_2R'$, —CONR'R", —C(O)R', —OC(O)NR'R", —NR"C(O)R', $—NR"CO_2R'$, —NR'—C(O)NR"R'", $—NR'—SO_2NR"R'"$, $—NH—C(NH_2)═NH$, $—NR'C(NH_2)═NH$, $—NH—C(NH_2)═NR'$, $—OP(O)(OH)_2$, $—OP(O)(OR')_2$, —OP(O)(OR')(OR"), —OP(O)R'(OR"), —OP(O)R'R", $—OP(OH)_2$, $—OP(OR')_2$, —OP(OR')(OR"), —OPR'R", —OPR'(OR"), —OS(O)R', —OS(O)(OR'), $—OSO_2R'$, $—OSO_2(OR')$, $—OSO_2NR'R"$, —S(O)R', —S(O)(OR'), $—SO_2R'$, $—SO_2(OR')$, $—SO_2NR'R"$, $—NR"SO_2R$, $—OSi(R')_3$, $—OSi(OR')_3$, $—Si(OR')_3$, —Si(OR')(OR")(OR'"), —OSi(OR')(OR")(OR'), $—N_3$, $—CH(Ph)_2$, perfluoro(C1-C4)alkoxy- or perfluoro(C1-C4)alkyl-, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl.

$R_1$-$R_{18}$ may also be cyclic version by connection with each other through unsubstituted or substituted poly-carbons, poly-ethers, poly-alkylamino, amide, ester, phosphonate, polyphosphonate, phosphonamide, polyphosphonate, polyphosphonamide, sulfonate, sulfinate, sulforic, polysulfonate, polysulfinate, polysulforic linkers. Preferably linkers are polyether, epoxides, amide, ester, phosphonate, polyphosphonate, phosphonamide, polyphosphonate, polyphosphonamide.

In particular embodiments:

—$R_1$ is either α- or β-hydrogen, hydroxyl, alkyl, alkenyl, alkynyl, alkylene, haloalkyl, cycloalkyl, alkoxy, alkylthio, aryl, aryloxy, arylthio, heterocyclyl, heterocyclylamino, epoxide, alkylepoxide, alkylamino, dialkylamino, wherein alkyl, alkenyl, alkynyl, alkylene, haloalkyl, cycloalkyl, alkoxy and alkylthio are C1-C8 alkyl, C2-C8 alkenyl, C2-C8 alkynyl, C2-C8 alkylene, haloalkyl (C1-C8), cycloalkyl(C1-C8), alkoxy(C1-C8) and alkylthio(C1-C8) respectively.

$R_2$-$R_{18}$ are independently hydrogen, oxygen (═O), hydroxyl, alkyl, alkenyl, alkynyl, alkylene, haloalkyl, cycloalkyl, alkoxy, alkylthio, aryl, aryloxy, arylthio, heterocyclyl, heterocyclylamino, epoxide, alkylepoxide, alkylamino, dialkylamino, wherein alkyl, alkenyl, alkynyl, alkylene, haloalkyl, cycloalkyl, alkoxy and alkylthio are C1-C8 alkyl, C2-C8 alkenyl, C2-C8 alkynyl, C2-C8 alkylene, haloalkyl (C1-C8), cycloalkyl (C1-C8), alkoxy (C1-C8) and alkylthio (C1-C8) respectively.

$X_1$-$X_8$ are independently of each other heteroatoms selected from oxygen (O), sulfur (S), selenium (—Se—), saturated or unsaturated, substituted or unsubstituted nitrogen (═N—, —NH—, $—NR_{14}—$), and hydrocarbon residue with valence in a number ranging from zero to the total number of open valences of the indicated atom on the carbocyclyl- or heterocyclyl-ring system. For example, $X_1$-$X_8$ may be independently —O—, —S—, ═N—, —NH—, $—CH_2—$, ═CH—, —CHR—, ═CR—, —CRR'— or —CR—. Herein, the definition to R is equal to the above definition to $R_2$-$R_{18}$.

The ring system of $X_2$-$X_8$ is substituted or unsubstituted, saturated or unsaturated 5-fused 6-membered carbocyclic or heterocyclic ring system, preferably, substituted or unsubstituted purines, indene, cyclopentapyridine, cyclopentapyridazine, cyclopentatriazine, cyclopentatetrazine, indole, pyrrolopyridine, pyrrolopyridazine, pyrrolotriazine, pyrrolotetrazine, indazole, pyrazolopyridine, pyrazolopyridazine, pyrazolotriazine, pyrazolotetrazine, benzoimidazole, imidazolepyridine, imidazopyridazine, imidazotriazine, imidazotetrazine, benzotriazole, triazolopyridine, triazolopyridazine, triazolotriazine, triazolotetrazine, benzoimidazol-2-one.

In addition to salt forms, the invention provides compounds which are in a prodrug form. Prodrugs of the compounds described herein are those compounds that undergo chemical changes under physiological or medical conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, such as Deuterium ($^2H$), Carbon-13 ($^{13}C$) whether radioactive or not, are intended to be encompassed within the scope of the invention.

In another aspect, the invention discloses a compound of the following formula I:

Formula I

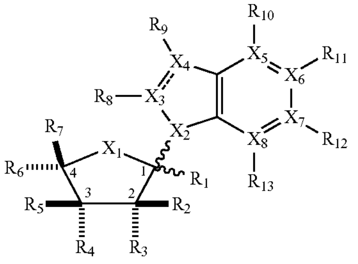

wherein: $R_1$ is H; $R_2$ and $R_3$ are independently H, OH, OBiotin, OAc, OTBS, F, Cl, Br, I, or ═O, or $R_2$ and $R_3$ are independently absent; $R_4$ and $R_5$ are independently H, OH, F, Cl, Br, I, ═O, OBiotin or $N_3$; or $R_2$/$R_3$ and $R_4$/$R_5$ form expoxy ethane together with the carbons they are connected to; $R_6$ and $R_7$ are independently H, $CH_2$—OH, $CH_2$—$N_3$, $CH_2$—OBiotin, $CH_2$—AcO, $CH_2$—OTBS, $CO_2Me$, triphosphorylated methylene, 1,2-bishydroxyethane, tetrabutylammonium monophosphate, 1-hydroxyprop-2-yn-1-yl, or diazacymene; $R_8$ is H, ═S, ═O, NH—$CH_3$, F, Cl, Br, I, —O—$CH_3$, or deuterium; $R_9$ is absent, or $R_9$ is H, $CH_3$, F, Cl, Br, or I; $R_{10}$ is H, —$CH_3$, F, Cl, Br, I, $NH_2$, NH—$CH_3$, NH—$NH_2$, ═O, NHBn, Biotinamide, m-hydroxyaniline, amino-cyclopropane, amino-cyclobutane, amino-cyclopentane, amino-cyclohexane, OMe or octamide; $R_{11}$ is absent, or $R_{11}$ is H, F, Cl, Br, or I; $R_{12}$ is absent, or $R_{12}$ is H, $NH_2$, F, Cl, Br, I, OMe, 4-formamide-substituted pyrazole; $R_{13}$ is absent or $R_{13}$ is H, O—$CH_3$ or Ome; and $X_1$ is O, N or C; $X_2$ is N or C; $X_3$ is C; $X_4$ is C or N; $X_5$ is C or N; $X_6$ is C or N; $X_7$ is C or N; and $X_8$ is C or N.

In another aspect, the invention discloses a compound of the following formula II:

Formula II

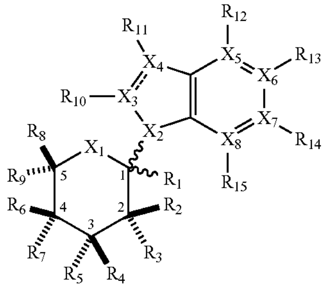

wherein $R_1$ is H; $R_2$ is H or OH; $R_3$ is H or OH; $R_4$ is H or OH; $R_5$ is H or OH; $R_6$ is H or OH; $R_7$ is H or OH; $R_8$ is H; $R_9$ is H; $R_{10}$ is H, F, Cl, Br, or I; $R_{11}$ is absent or $R_1$ is H; $R_{12}$ is $CH_3$, $NH_2$, NH—$CH_3$ or OMe; $R_{13}$ is absent or $R_{13}$ is H; $R_4$ is H; $R_{15}$ is absent or $R_{15}$ is H; and $X_1$ is O; $X_2$ is N; $X_3$ is C; $X_4$ is C or N; $X_5$ is C; $X_6$ is N; $X_7$ is C; and $X_8$ is C or N.

In another aspect, the invention discloses a compound of the following formula III:

Formula III

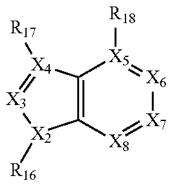

wherein $R_{16}$ is tetrahydrofuran or t-butyl; $R_{17}$ is $CH_2$-methylbenzyl; and $R_{18}$ is $NH_2$ or amino-benzyl; and $X_2$ is N; $X_3$ is C or N; $X_4$ is C or N; $X_5$ is C; $X_6$ is N; $X_7$ is C; and $X_8$ is N.

Preferably, the invention discloses a compound of the following formula I:

Formula I

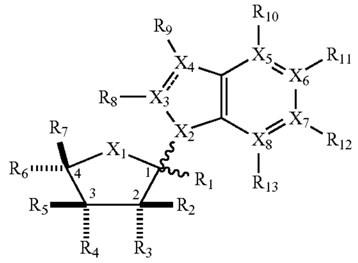

wherein: $R_1$ is H; $R_2$ and $R_3$ are independently H, OH, OBiotin, OAc, OTBS, F, Cl, Br, I, or ═O, or $R_2$ and $R_3$ are independently absent; $R_4$ and $R_5$ are independently H, OH, F, Cl, Br, I, ═O, or OBiotin; or $R_2$/$R_3$ and $R_4$/$R_5$ form expoxy ethane together with the carbons they are connected to; $R_6$ and $R_7$ are independently H, $CH_2$—OH, $CH_2$—$N_3$, $CH_2$—OBiotin, $CO_2Me$, triphosphorylated methylene, 1,2-bishydroxyethane, tetrabutylammonium monophosphate, 1-hydroxyprop-2-yn-1-yl, or diazacymene; or hydroxyl of $R_4$/$R_5$ and methyl hydroxyl of $R_6$/$R_7$ form cyclic phosphate lactone together with the carbons they are connected to; $R_8$ is H, ═S, ═O, NH—$CH_3$, F, Cl, Br, I, —O—$CH_3$, or deuterium; $R_9$ is absent, or $R_9$ is H, $CH_3$, F, Cl, Br, or I; $R_{10}$ is H, —$CH_3$, F, Cl, Br, I, $NH_2$, NH—$NH_2$, ═O, NHBn, Biotinamide, m-hydroxyaniline, amino-cyclopropane, or octamide; $R_{11}$ is absent, or $R_{11}$ is H, F, Cl, Br, or I; $R_{12}$ is absent, or $R_{12}$ is H, $NH_2$, F, Cl, Br, I, OMe, 4-formamide-substituted pyrazole; $R_{13}$ is absent or $R_{13}$ is H, O—$CH_3$ or Ome; and $X_1$ is O, N or C; $X_2$ is N or C; $X_3$ is C; $X_4$ is C or N; $X_5$ is C or N; $X_6$ is C or N; $X_7$ is C or N; and $X_8$ is C or N.

Preferably, the invention discloses a compound selected from:

TABLE 1

| Name | Structure |
|---|---|
| 1 | 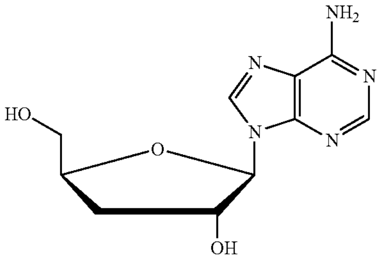 [SMILES: Nc1ncnc2c1ncn2[C@@H]1O[C@H](CO)C[C@@H]1O] Cordycepin NQZ-001 (CA03) |

TABLE 1-continued
| Name | Structure |
| --- | --- |
| 2 | 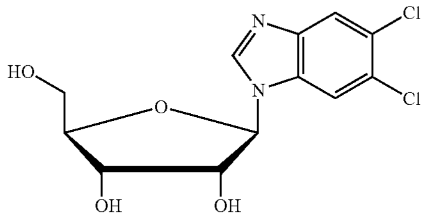<br>NQZ-002 |
| 3 | 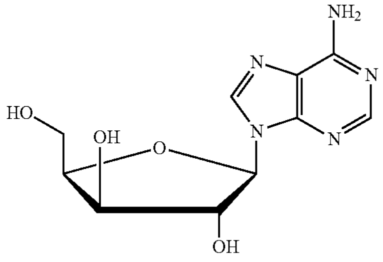<br>NQZ-007 |
| 4 | 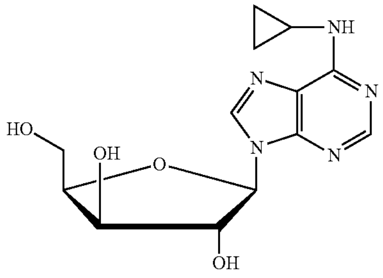<br>NQZ-090 |
| 5 | 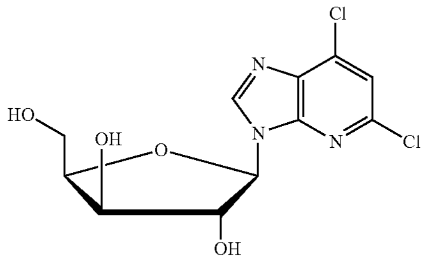<br>NQZ-097 |
| 6 | 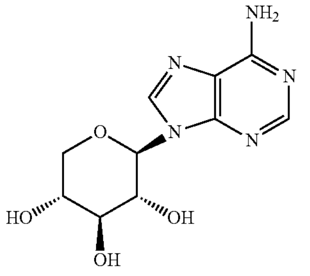 [SMILES: Nc1ncnc2c1ncn2[C@@H]1OC[C@@H](O)[C@H](O)[C@H]1O]<br>NQZ-086 |

TABLE 1-continued
| Name | Structure |
| --- | --- |
| 7 | 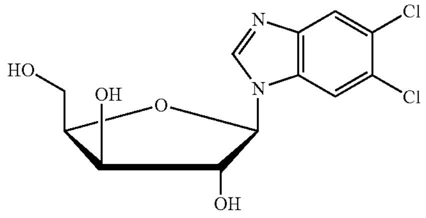 NQZ-118 |
| 8 | 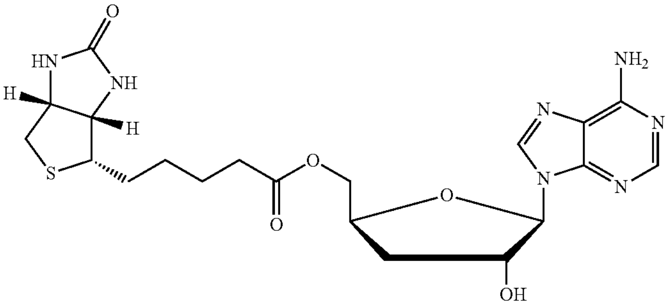 [SMILES: Nc1ncnc2c1ncn2[C@@H]1O[C@H](COC(=O)CCCC[C@@H]2SC[C@@H]3NC(=O)N[C@@H]32)C[C@@H]1O] NQZ-069 |
| 9 | 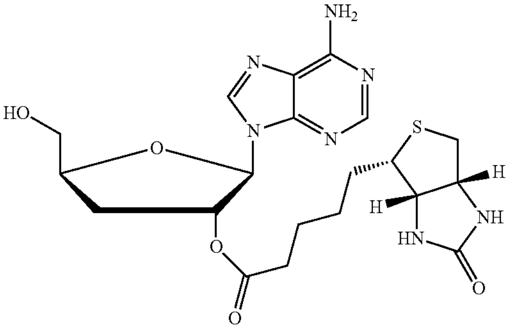 [SMILES: Nc1ncnc2c1ncn2[C@@H]1O[C@H](CO)C[C@@H]1OC(=O)CCCC[C@@H]1SC[C@@H]2NC(=O)N[C@@H]21] NQZ-119 |
| 10 | 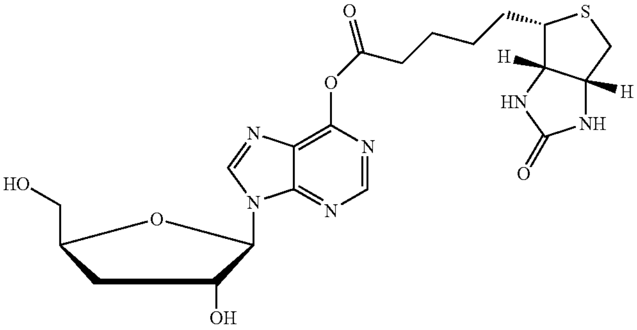 [SMILES: O=C1N[C@H]2[C@H](CS[C@H]2CCCCC(=O)Oc2ncnc3c2ncn3[C@@H]2O[C@H](CO)C[C@@H]2O)N1] NQZ-068 |

TABLE 1-continued
| Name | Structure |
| --- | --- |
| 11 | 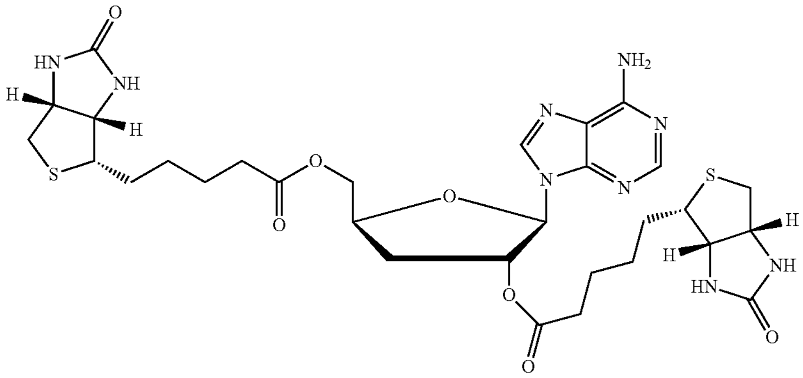 [SMILES: Nc1ncnc2c1ncn2[C@@H]1O[C@H](COC(=O)CCCC[C@@H]2SC[C@@H]3NC(=O)N[C@@H]32)C[C@@H]1OC(=O)CCCC[C@@H]1SC[C@@H]2NC(=O)N[C@@H]21] NQZ-121 |
| 12 | 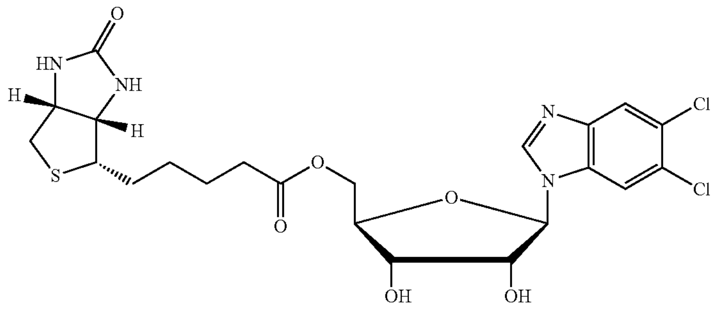 NQZ-112 |
| 13 | 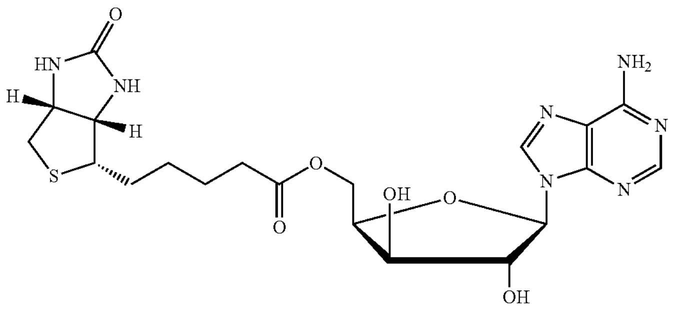 NQZ-122 |
| 14 | 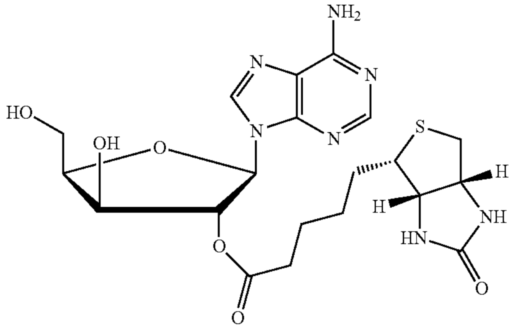 NQZ-123 |

TABLE 1-continued
| Name | Structure |
| --- | --- |
| 15 | 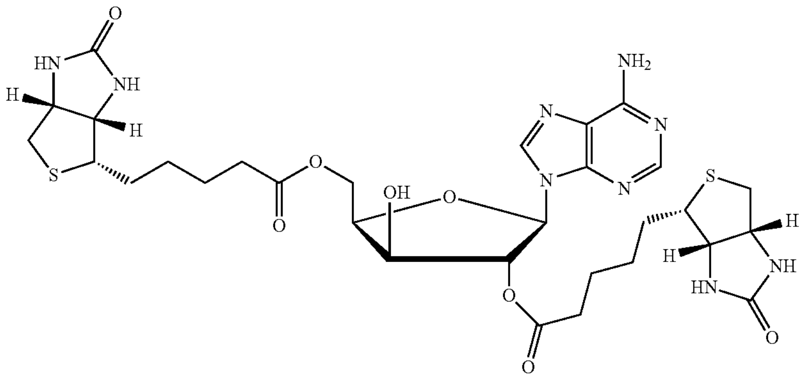 NQZ-124 |
| 16 | 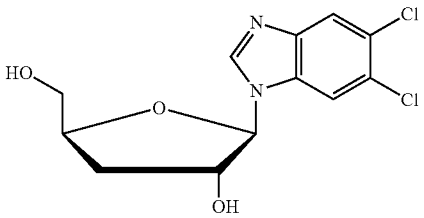 NQZ-006 |
| 17 | 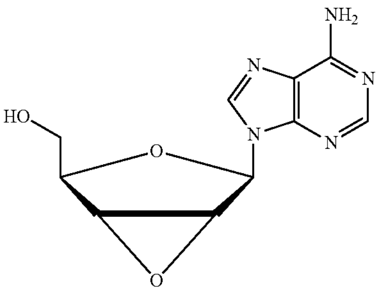 NQZ-062 |
| 18 | 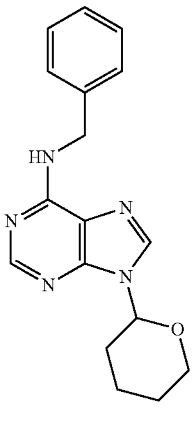 [SMILES: c1ccc(CNc2ncnc3c2ncn3C2CCCCO2)cc1] |

TABLE 1-continued
| Name | Structure |
| --- | --- |
| 19 | 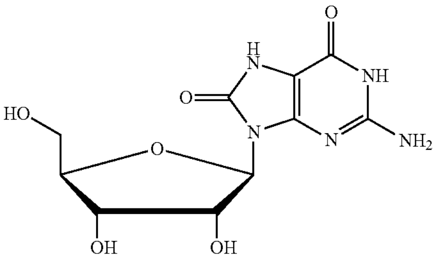 NQZ-013 |
| 20 | 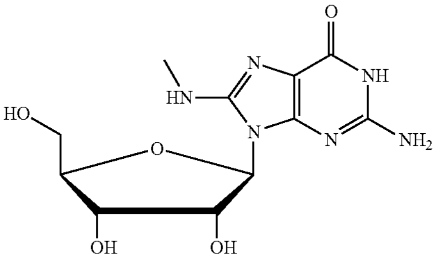 |
| 21 | 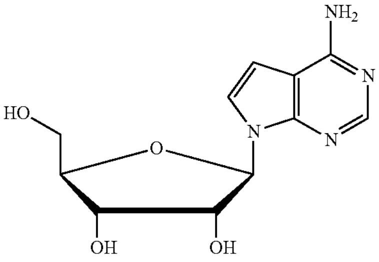 NQZ-003 |
| 22 | 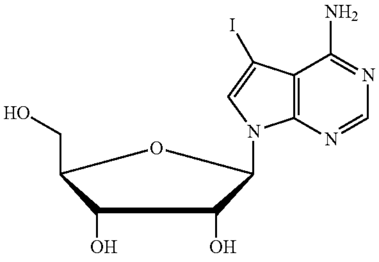 todo-Tubercidine (NQZ-020) |
| 23 | 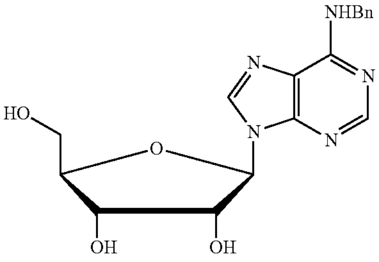 NQZ-004 |

TABLE 1-continued
| Name | Structure |
| --- | --- |
| 24 | 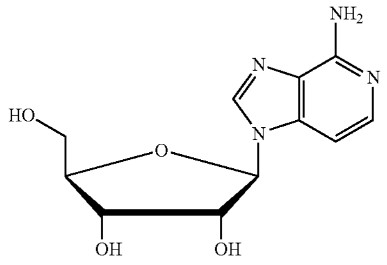<br>3-Deazaadenosine<br>NQZ-010 |
| 25 | 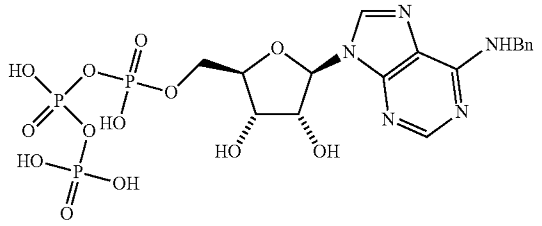<br>NQZ-005 |
| 26 | 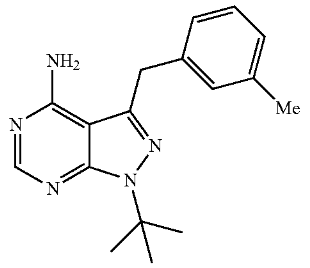 [SMILES: Cc1cccc(Cc2nn(C(C)(C)C)c3ncnc(N)c23)c1]<br>NQZ-008 |
| 27 | 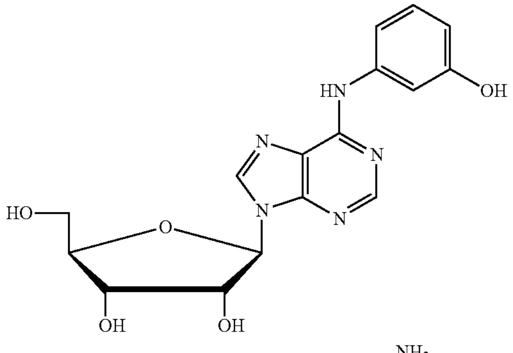<br>NQZ-011 |
| 28 | 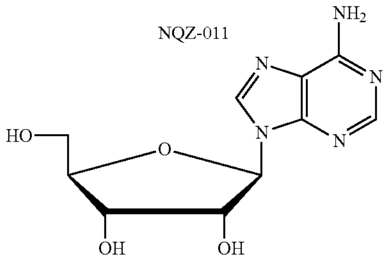<br>Adenosine<br>NQZ-012 |

TABLE 1-continued
| Name | Structure |
| --- | --- |
| 29 | 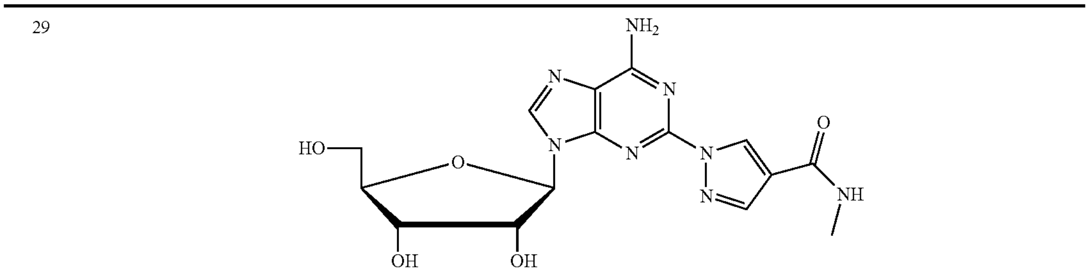<br>Regadenoson<br>NQZ-021 |
| 30 | 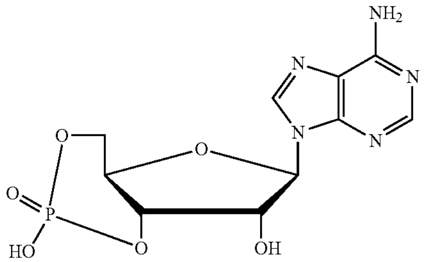<br>NQZ-026 |
| 31 | 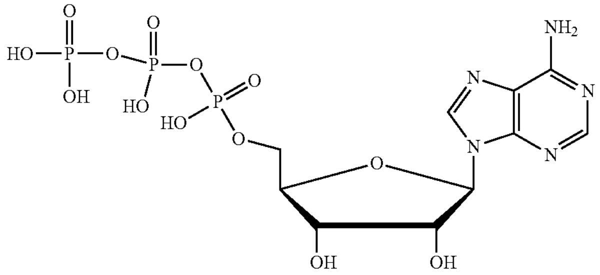<br>NQZ-034 |
| 32 | 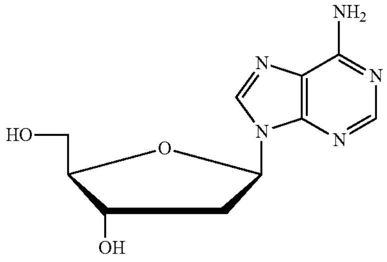<br>NQZ-035 |
| 33 | 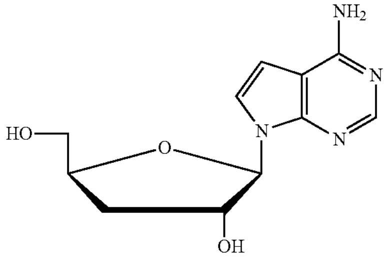 [SMILES: Nc1ncnc2c1ccn2[C@@H]1O[C@H](CO)C[C@@H]1O]<br>NQZ-036 |

TABLE 1-continued
| Name | Structure |
|---|---|
| 34 | 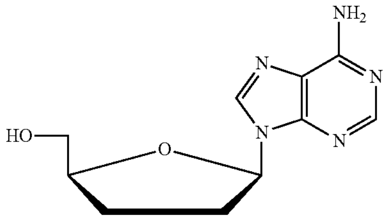<br>NQZ-047 |
| 35 | 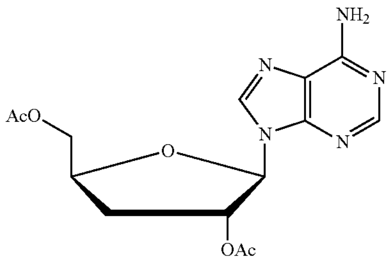 [SMILES: CC(=O)OC[C@@H]1C[C@H](OC(C)=O)[C@H](n2cnc3c(N)ncnc32)O1]<br>NQZ-061 |
| 36 | 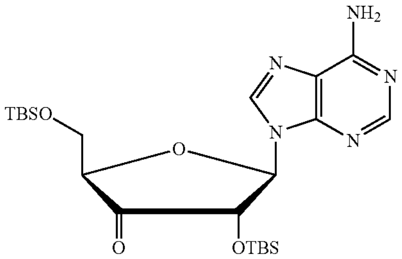 [SMILES: CC(C)(C)[Si](C)(C)OC[C@H]1O[C@@H](n2cnc3c(N)ncnc32)[C@@H](O[Si](C)(C)C(C)(C)C)C1=O]<br>NQZ-064 |
| 37 | 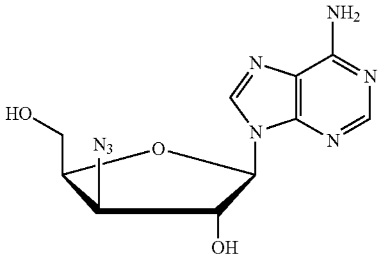<br>NQZ-065 |
| 38 | 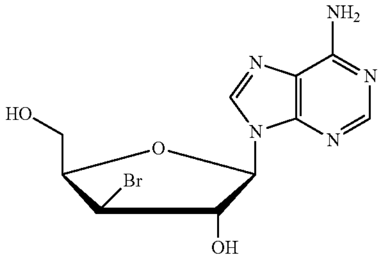<br>NQZ-066 |

TABLE 1-continued
| Name | Structure |
| --- | --- |
| 39 | 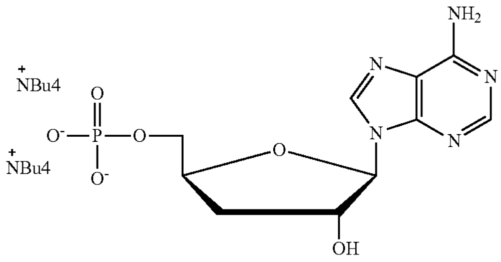 [SMILES: Nc1ncnc2c1ncn2[C@@H]1O[C@H](COP(=O)([O-])[O-])C[C@@H]1O] NQZ-067 |
| 40 | 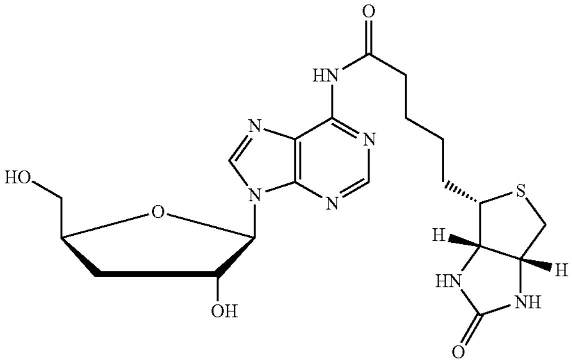 [SMILES: O=C(CCCC[C@@H]1SC[C@@H]2NC(=O)N[C@@H]21)Nc1ncnc2c1ncn2[C@@H]1O[C@H](CO)C[C@@H]1O] NQZ-068 |
| 41 | 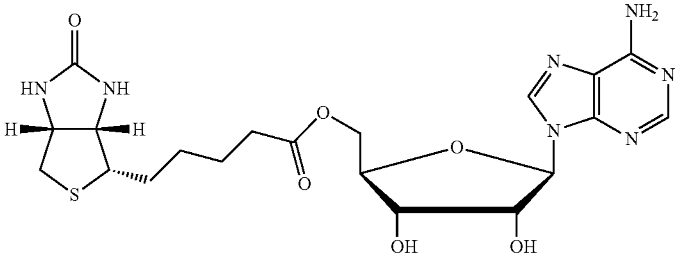 NQZ-069 |
| 42 | 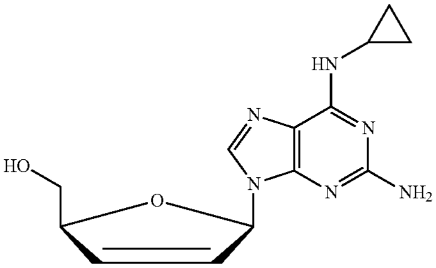 [SMILES: Nc1nc(NC2CC2)c2ncn([C@H]3C=C[C@@H](CO)O3)c2n1] Abacavir NQZ-078 |

TABLE 1-continued
| Name | Structure |
| --- | --- |
| 43 | 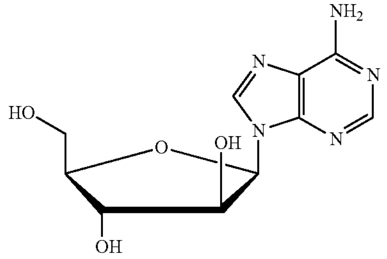<br>Vidarabine<br>NQZ-071 |
| 44 | 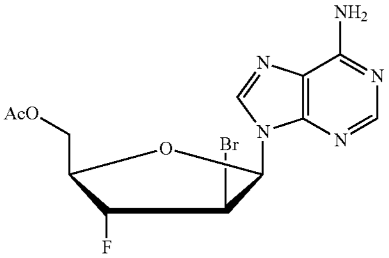<br>NQZ-082 |
| 45 | 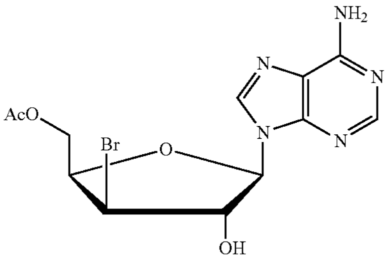<br>NQZ-081 |
| 46 | 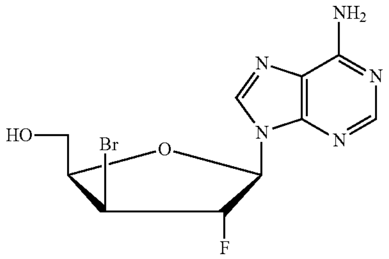<br>NQZ-083 |
| 47 | 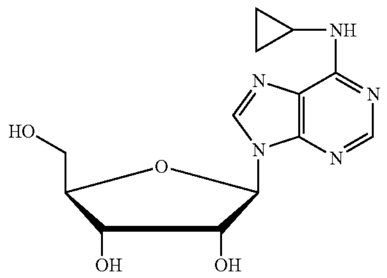<br>NOZ-084 |

TABLE 1-continued
| Name | Structure |
| --- | --- |
| 48 | 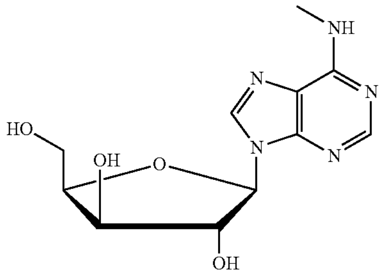 NQZ-089 |
| 49 | 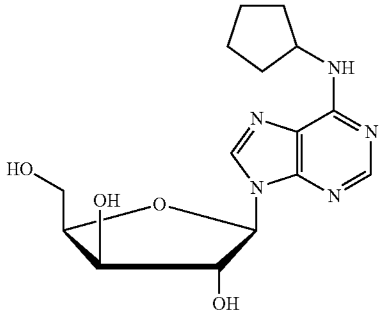 NQZ-091 |
| 50 | 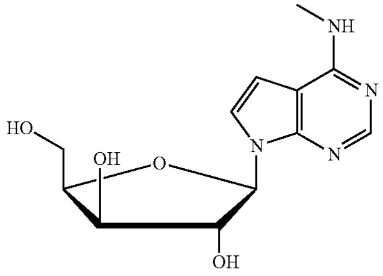 NQZ-092 |
| 51 | 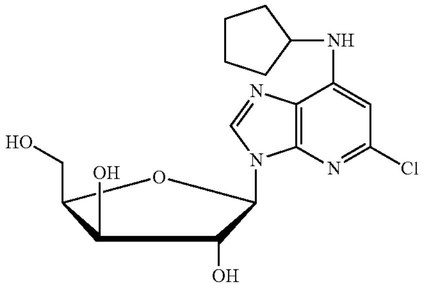 NQZ-093 |
| 52 | 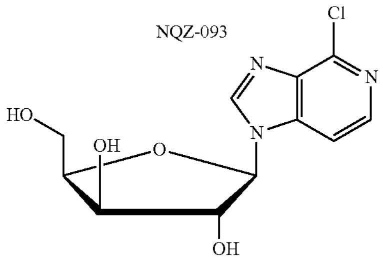 NQZ-096 |

TABLE 1-continued
| Name | Structure |
| --- | --- |
| 53 | 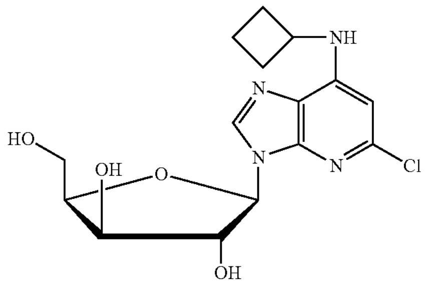<br>NQZ-095 |
| 54 | 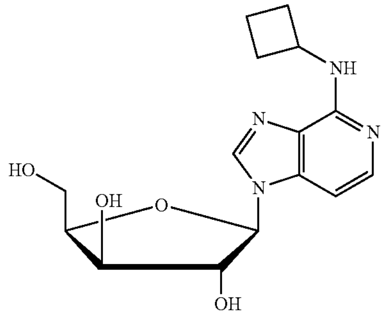<br>NQZ-094 |
| 55 | 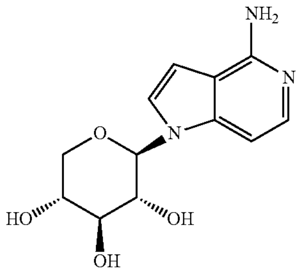 [SMILES: Nc1nccc2c1ccn2[C@@H]1OC[C@@H](O)[C@H](O)[C@H]1O]<br>NQZ-098 |
| 56 | 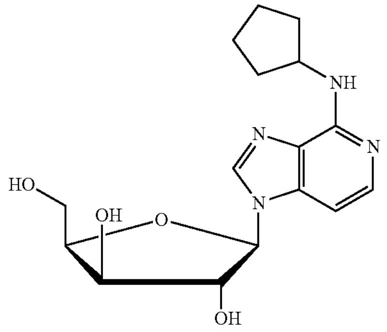<br>NQZ-099 |

TABLE 1-continued
| Name | Structure |
|---|---|
| 57 | 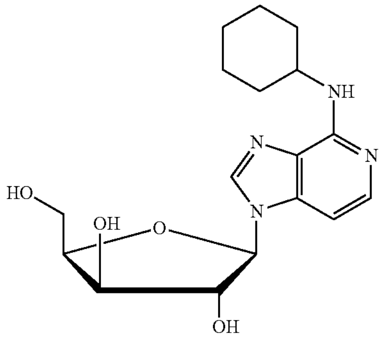 NQZ-100 |
| 58 | 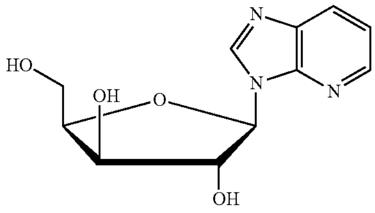 NQZ-105 |
| 59 | 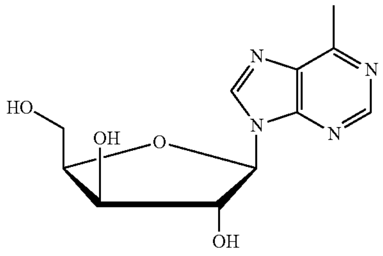 NQZ-106 |
| 60 | 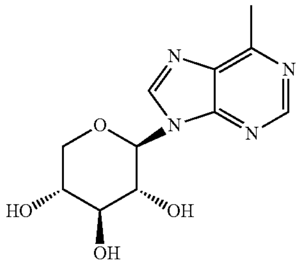 [SMILES: Cc1ncnc2c1ncn2[C@@H]1OC[C@@H](O)[C@H](O)[C@H]1O] NQZ-107 |
| 61 | 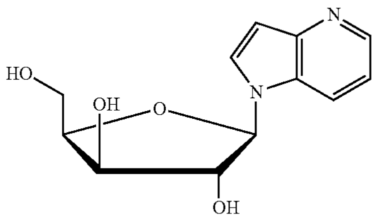 NQZ-108 |

TABLE 1-continued
| Name | Structure |
| --- | --- |
| 62 | 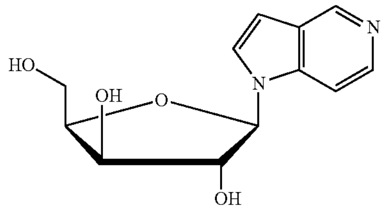 NQZ-109 |
| 63 | 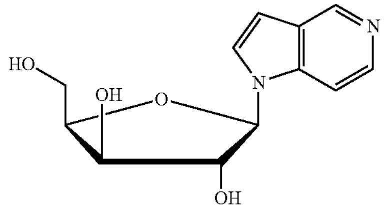 NQZ-110 |
| 64 | 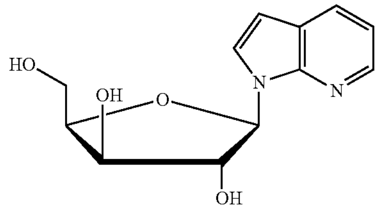 NQZ-111 |
| 65 | 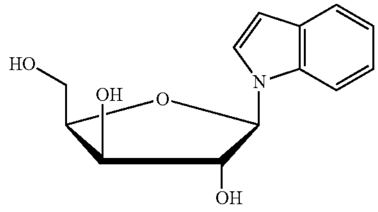 NQZ-113 |
| 66 | 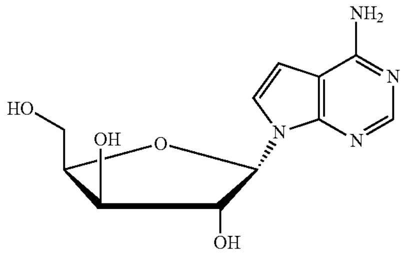 NQZ-114 |
| 67 | 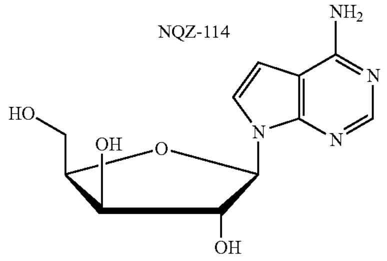 NQZ-115 |

TABLE 1-continued
| Name | Structure |
| --- | --- |
| 68 | 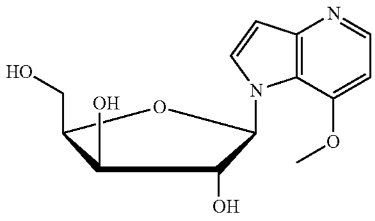<br>NQZ-116 |
| 69 | 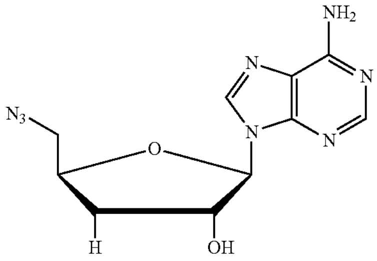 [SMILES: [N-]=[N+]=NC[C@@H]1C[C@H](O)[C@H](n2cnc3c(N)ncnc32)O1]<br>NQZ-117 |
| 70 | 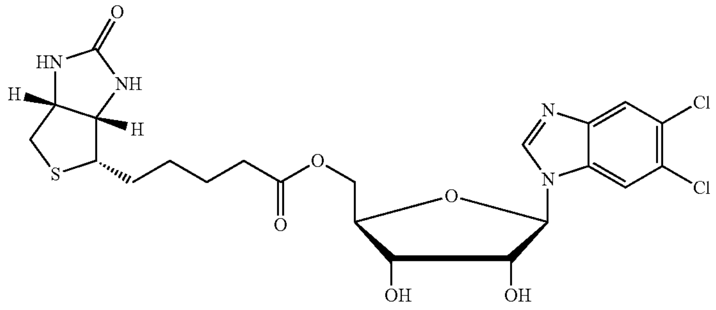<br>NQZ-120 |
| 71 | 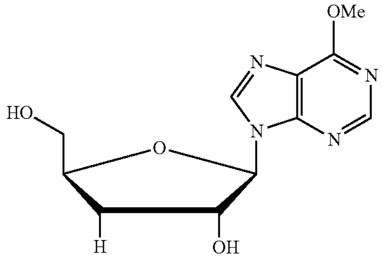<br>NQZ-125 |
| 72 | 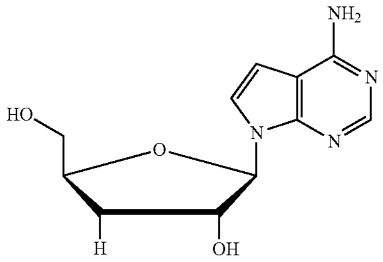 [SMILES: Nc1ncnc2c1ccn2[C@@H]1O[C@H](CO)C[C@@H]1O]<br>NQZ-126 |

TABLE 1-continued
| Name | Structure |
| --- | --- |
| 73 | 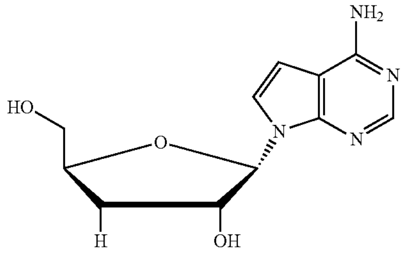 NQZ-127 |
| 74 | 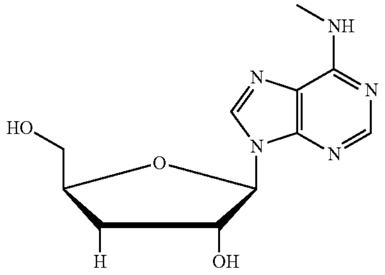 [SMILES: CNc1ncnc2c1ncn2[C@@H]1O[C@H](CO)C[C@@H]1O] NQZ-128 |
| 75 | 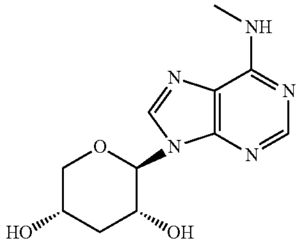 [SMILES: CNc1ncnc2c1ncn2[C@@H]1OC[C@@H](O)C[C@H]1O] NQZ-129 |
| 76 | 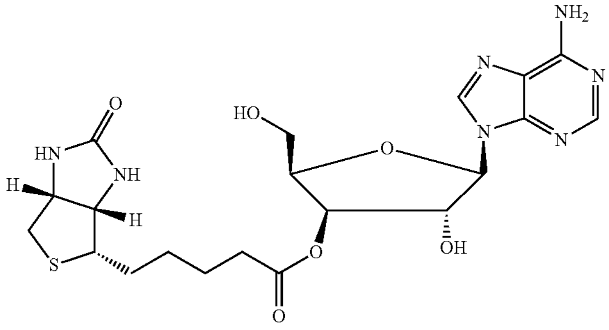 NQZ-132 |
| 77 | 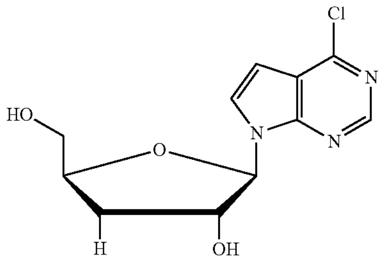 NQZ-133 |

TABLE 1-continued
| Name | Structure |
| --- | --- |
| 78 | 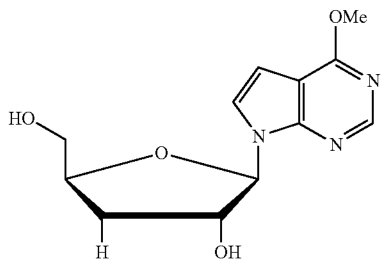 [SMILES: COc1ncnc2c1ccn2[C@@H]1O[C@H](CO)C[C@@H]1O]<br>NQZ-134 |
| 79 | 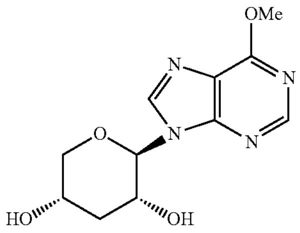 [SMILES: COc1ncnc2c1ncn2[C@@H]1OC[C@@H](O)C[C@H]1O]<br>NQZ-135 |
| 80 | 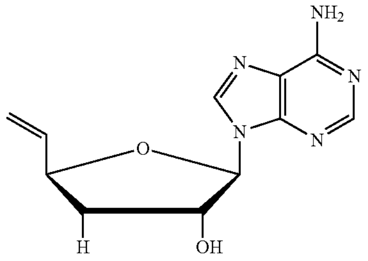<br>NQZ-136 |
| 81 | 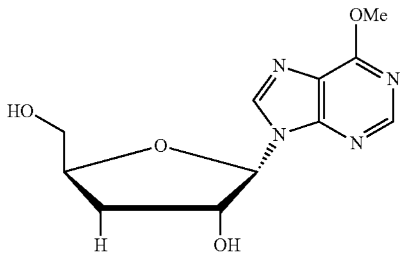<br>NQZ-137 |
| 82 | 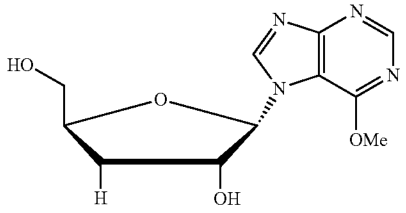<br>NQZ-138 |

TABLE 1-continued
| Name | Structure |
| --- | --- |
| 83 | 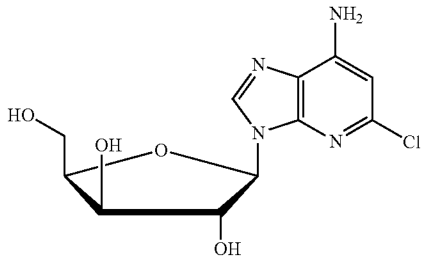<br>NQZ-140 |
| 84 | 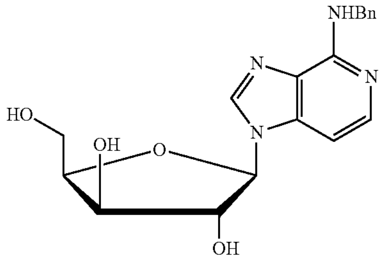<br>NQZ-141 |
| 85 | 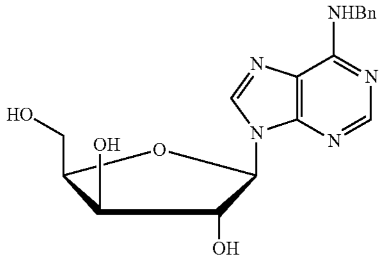<br>NQZ-142 |
| 86 | 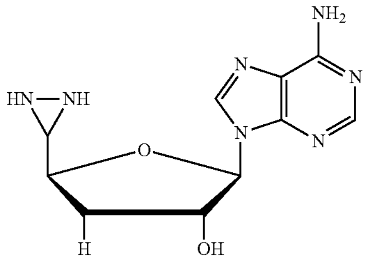 [SMILES: Nc1ncnc2c1ncn2[C@@H]1O[C@H](C2NN2)C[C@@H]1O]<br>NQZ-143 |
| 87 | 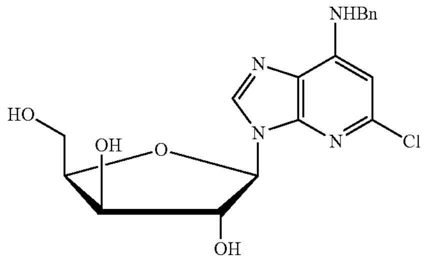<br>NQZ-144 |

TABLE 1-continued
| Name | Structure |
|---|---|
| 88 | 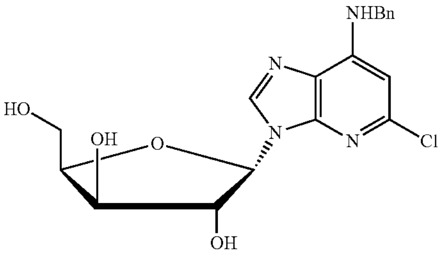 NQZ-145 |
| 89 | 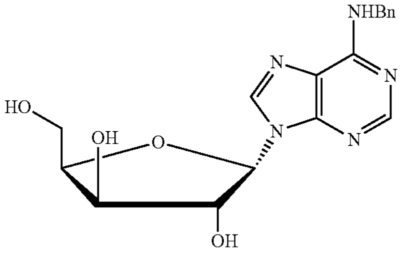 NQZ-146 |
| 90 | 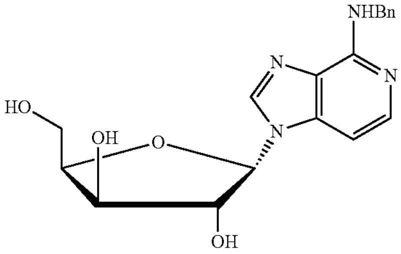 NQZ-147 |
| 91 | 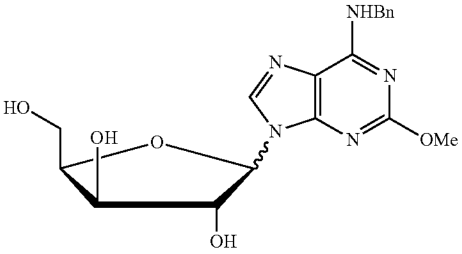 NQZ-148 |
| 92 | 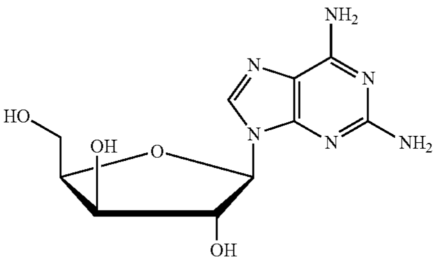 NQZ-149 |

TABLE 1-continued
| Name | Structure |
|---|---|
| 93 | 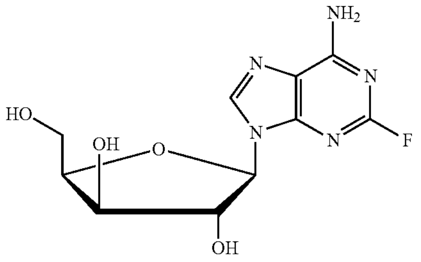<br>NQZ-150 |
| 94 | 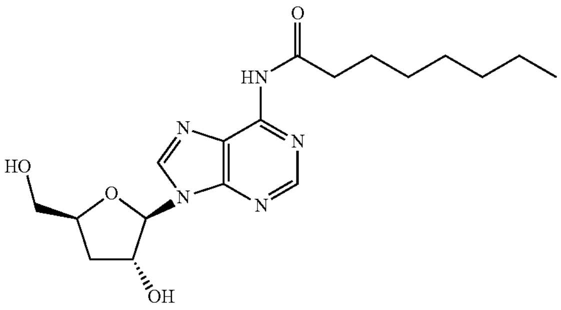 [SMILES: CCCCCCCC(=O)Nc1ncnc2c1ncn2[C@@H]1O[C@H](CO)C[C@H]1O]<br>NQZ-162 |
| 95 | 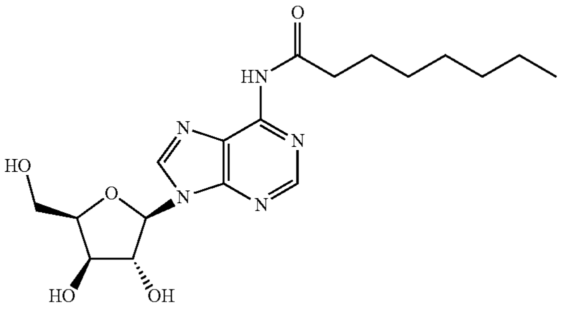 [SMILES: CCCCCCCC(=O)Nc1ncnc2c1ncn2[C@@H]1O[C@H](CO)[C@H](O)[C@H]1O]<br>NQZ-163 |
| 96 | 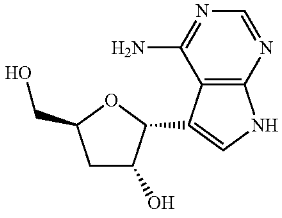 [SMILES: Nc1ncnc2[nH]cc([C@H]3O[C@H](CO)C[C@H]3O)c12]<br>NQZ-164 |
| 97 | 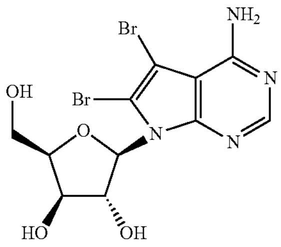 [SMILES: Nc1ncnc2c1c(Br)c(Br)n2[C@@H]1O[C@H](CO)[C@H](O)[C@H]1O]<br>NQZ-165 |

TABLE 1-continued
| Name | Structure |
| --- | --- |
| 98 | 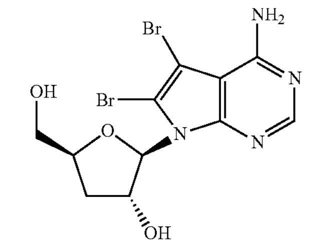 [SMILES: Nc1ncnc2c1c(Br)c(Br)n2[C@@H]1O[C@H](CO)C[C@H]1O] NQZ-166 |
| 99 | 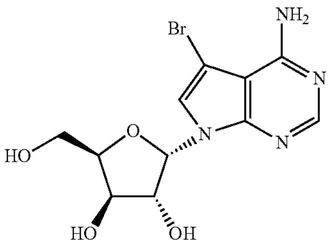 [SMILES: Nc1ncnc2c1c(Br)cn2[C@H]1O[C@H](CO)[C@H](O)[C@H]1O] NQZ-167 |
| 100 | 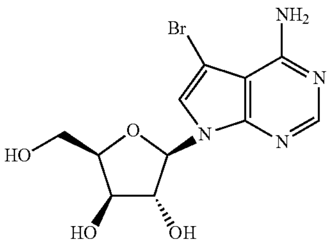 [SMILES: Nc1ncnc2c1c(Br)cn2[C@@H]1O[C@H](CO)[C@H](O)[C@H]1O] NQZ-168 |
| 101 | 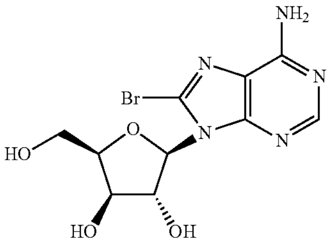 [SMILES: Nc1ncnc2c1nc(Br)n2[C@@H]1O[C@H](CO)[C@H](O)[C@H]1O] NQZ-169 |
| 102 | 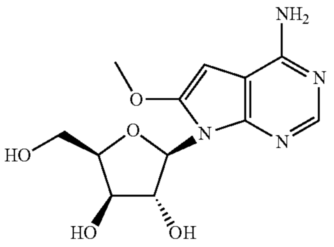 [SMILES: COc1cc2c(N)ncnc2n1[C@@H]1O[C@H](CO)[C@H](O)[C@H]1O] NQZ-170 |

TABLE 1-continued
| Name | Structure |
| --- | --- |
| 103 | 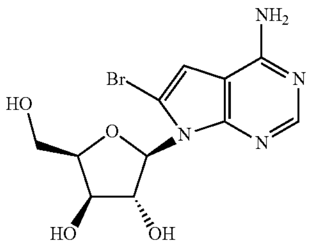 [SMILES: Nc1ncnc2c1cc(Br)n2[C@@H]1O[C@H](CO)[C@H](O)[C@H]1O] NQZ-171 |
| 104 | 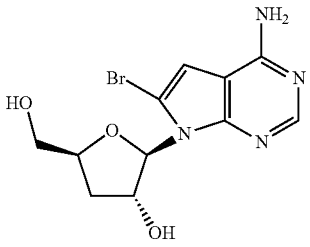 [SMILES: Nc1ncnc2c1cc(Br)n2[C@@H]1O[C@H](CO)C[C@H]1O] NQZ-173 |
| 105 | 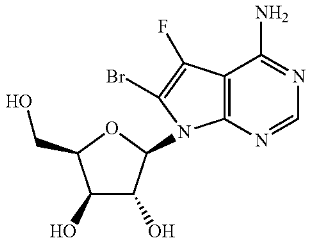 [SMILES: Nc1ncnc2c1c(F)c(Br)n2[C@@H]1O[C@H](CO)[C@H](O)[C@H]1O] NQZ-174 |
| 106 | 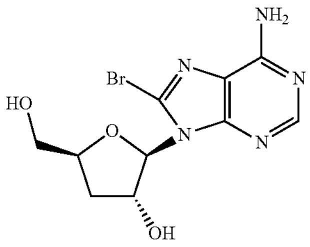 [SMILES: Nc1ncnc2c1nc(Br)n2[C@@H]1O[C@H](CO)C[C@H]1O] NQZ-175 |
| 107 | 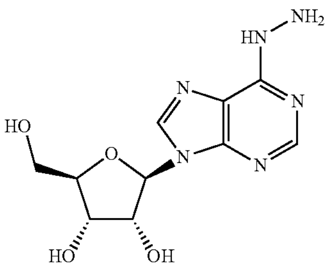 [SMILES: NNc1ncnc2c1ncn2[C@@H]1O[C@H](CO)[C@@H](O)[C@H]1O] NQZ-176 |

TABLE 1-continued
| Name | Structure |
| --- | --- |
| 108 | 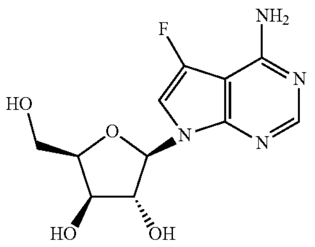 [SMILES: Nc1ncnc2c1c(F)cn2[C@@H]1O[C@H](CO)[C@H](O)[C@H]1O] NQZ-177 |
| 109 | 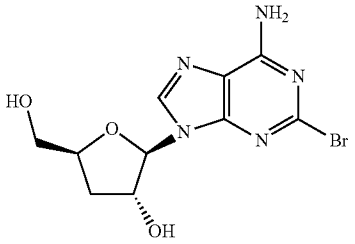 [SMILES: Nc1nc(Br)nc2c1ncn2[C@@H]1O[C@H](CO)C[C@H]1O] NQZ-178 |
| 110 | 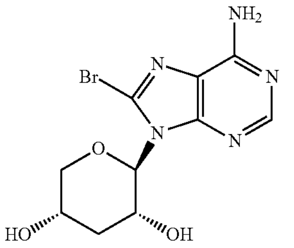 [SMILES: Nc1ncnc2c1nc(Br)n2[C@@H]1OC[C@@H](O)C[C@H]1O] NQZ-179 |
| 111 | 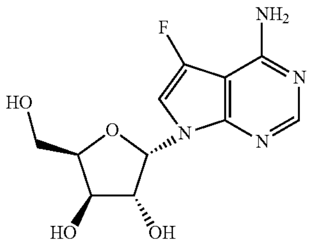 [SMILES: Nc1ncnc2c1c(F)cn2[C@H]1O[C@H](CO)[C@H](O)[C@H]1O] NQZ-180 |
| 112 | 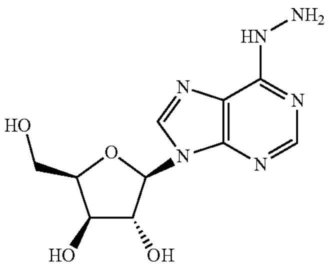 [SMILES: NNc1ncnc2c1ncn2[C@@H]1O[C@H](CO)[C@H](O)[C@H]1O] NQZ-182 |

TABLE 1-continued
| Name | Structure |
| --- | --- |
| 113 | 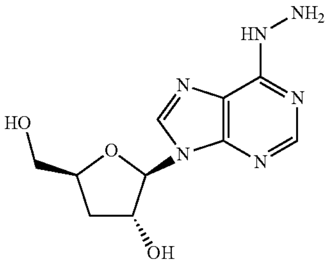 [SMILES: NNc1ncnc2c1ncn2[C@@H]1O[C@H](CO)C[C@H]1O] NQZ-183 |
| 114 | 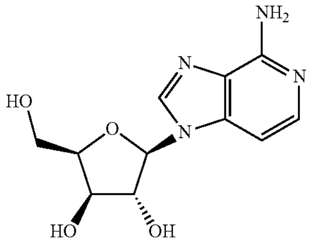 [SMILES: Nc1nccc2c1ncn2[C@@H]1O[C@H](CO)[C@H](O)[C@H]1O] NQZ-186 |
| 115 | 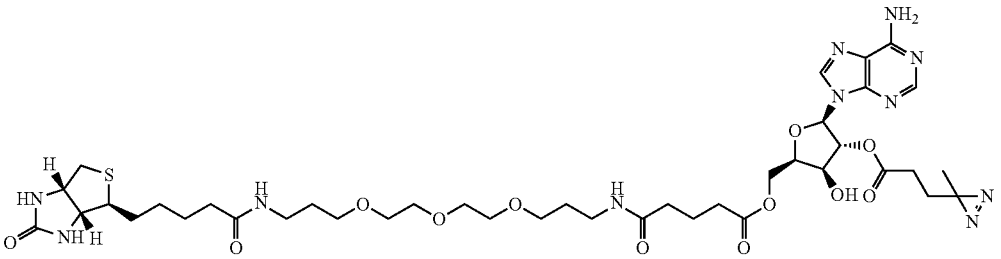 [SMILES: CC1(CCC(=O)O[C@@H]2[C@@H](O)[C@@H](COC(=O)CCCC(=O)NCCCOCCOCCOCCCNC(=O)CCCC[C@@H]3SC[C@H]4NC(=O)N[C@@H]34)O[C@H]2n2cnc3c(N)ncnc32)N=N1] NQZ-187-1 |
| 116 | 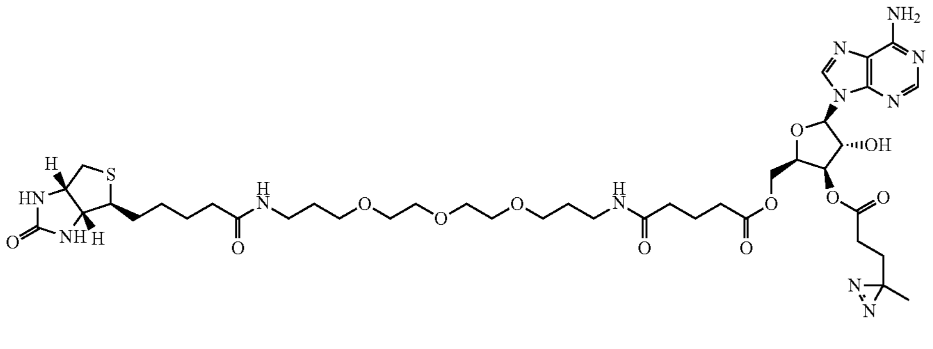 [SMILES: CC1(CCC(=O)O[C@@H]2[C@@H](O)[C@H](n3cnc4c(N)ncnc43)O[C@@H]2COC(=O)CCCC(=O)NCCCOCCOCCOCCCNC(=O)CCCC[C@@H]2SC[C@H]3NC(=O)N[C@@H]23)N=N1] NQZ-187-2 |
| 117 | 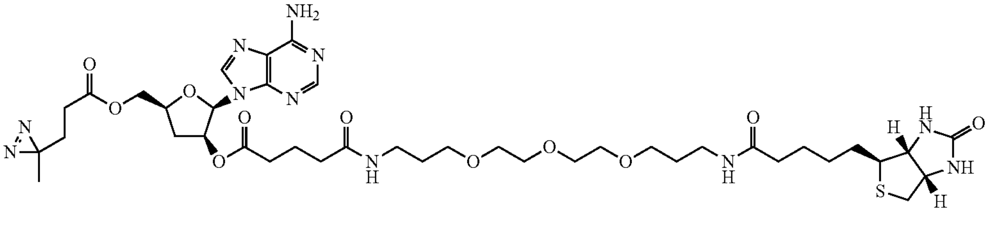 [SMILES: CC1(CCC(=O)OC[C@@H]2C[C@H](OC(=O)CCCC(=O)NCCCOCCOCCOCCCNC(=O)CCCC[C@@H]3SC[C@H]4NC(=O)N[C@@H]34)[C@H](n3cnc4c(N)ncnc43)O2)N=N1] NQZ-189 |

TABLE 1-continued
| Name | Structure |
|---|---|
| 118 | 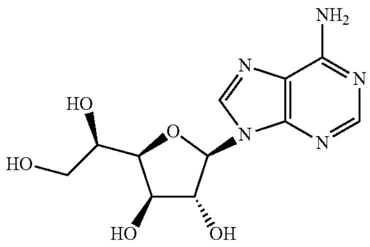 [SMILES: Nc1ncnc2c1ncn2[C@@H]1O[C@H]([C@H](O)CO)[C@H](O)[C@H]1O] NQZ-190 |
| 119 | 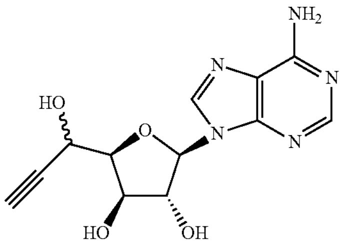 [SMILES: C#CC(O)[C@H]1O[C@@H](n2cnc3c(N)ncnc32)[C@H](O)[C@H]1O] NQZ-192 |
| 120 | 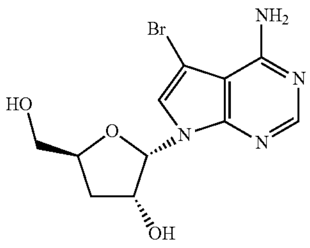 [SMILES: Nc1ncnc2c1c(Br)cn2[C@H]1O[C@H](CO)C[C@H]1O] NQZ-193 |
| 121 | 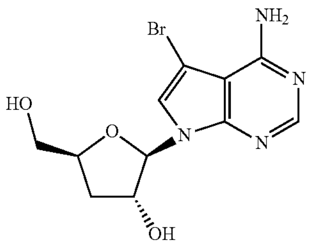 [SMILES: Nc1ncnc2c1c(Br)cn2[C@@H]1O[C@H](CO)C[C@H]1O] NQZ-194 |
| 122 | 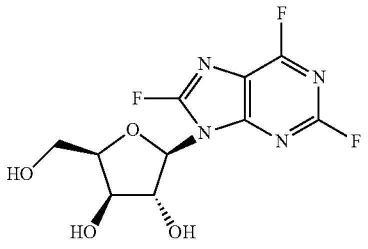 [SMILES: OC[C@H]1O[C@@H](n2c(F)nc3c(F)nc(F)nc32)[C@H](O)[C@H]1O] NQZ-195 |

TABLE 1-continued
| Name | Structure |
|---|---|
| 123 | 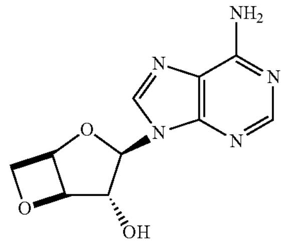 NQZ-196 |
| 124 | 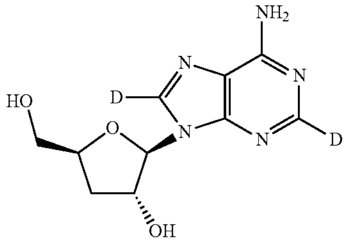 NQZ-197 |
| 125 | 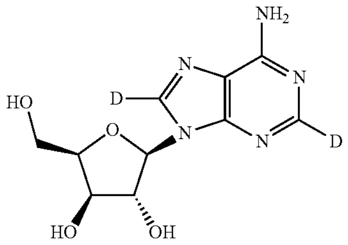 [SMILES: [2H]c1nc(N)c2nc([2H])n([C@@H]3O[C@H](CO)[C@H](O)[C@H]3O)c2n1] NQZ-198 |
Preferably, the invention discloses a compound selected from:
TABLE 2
| | |
|---|---|
| 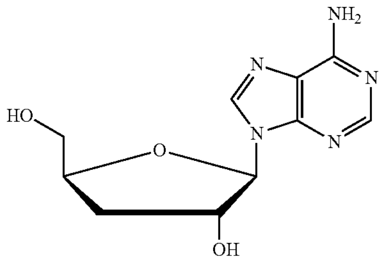 [SMILES: Nc1ncnc2c1ncn2[C@@H]1O[C@H](CO)C[C@@H]1O] Cordycepin | NQZ-001 (CA03) |
| 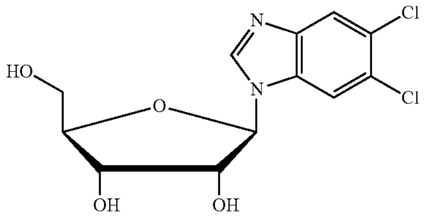 | NQZ-002 |

TABLE 2-continued
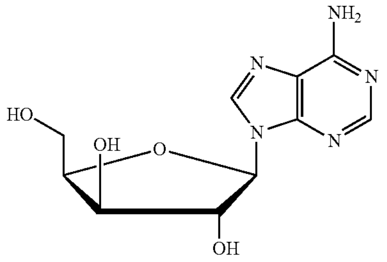
NQZ-007
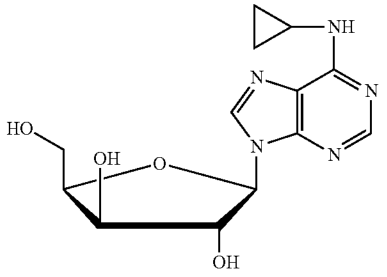
NQZ-090
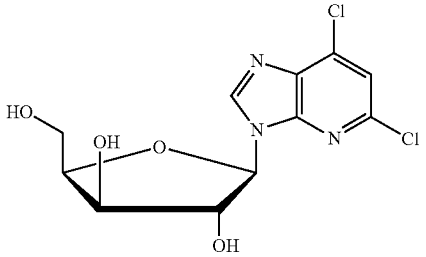
NQZ-097
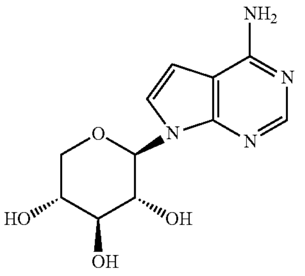 [SMILES: Nc1ncnc2c1ccn2[C@@H]1OC[C@@H](O)[C@H](O)[C@H]1O]
NQZ-086
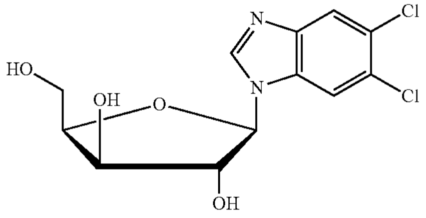
NQZ-118
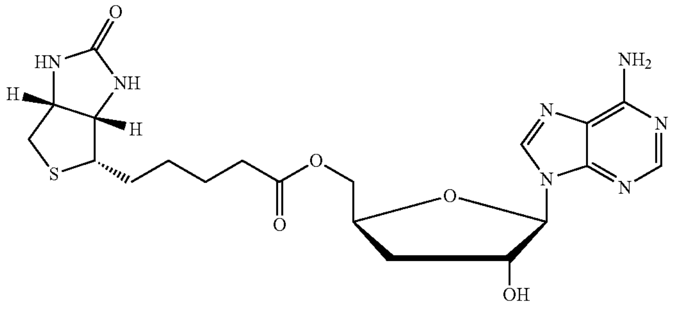 [SMILES: Nc1ncnc2c1ncn2[C@@H]1O[C@H](COC(=O)CCCC[C@@H]2SC[C@@H]3NC(=O)N[C@@H]32)C[C@@H]1O]
NQZ-069

TABLE 2-continued
NQZ-119
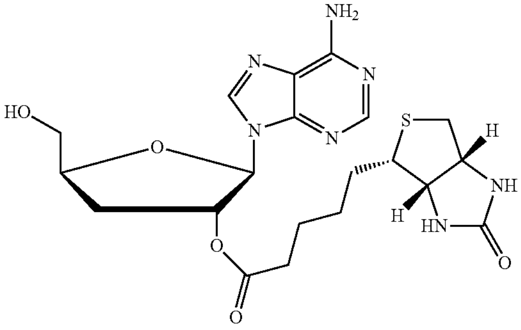 [SMILES: Nc1ncnc2c1ncn2[C@@H]1O[C@H](CO)C[C@@H]1OC(=O)CCCC[C@@H]1SC[C@@H]2NC(=O)N[C@@H]21]
NQZ-068
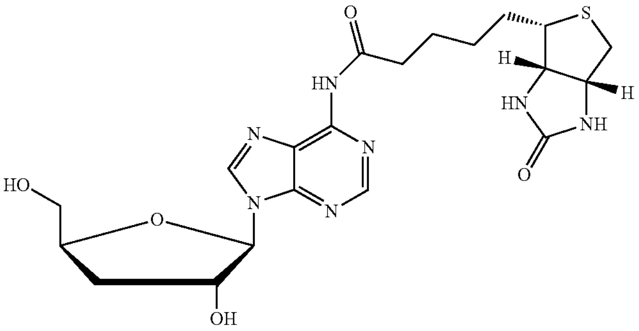 [SMILES: O=C(CCCC[C@@H]1SC[C@@H]2NC(=O)N[C@@H]21)Nc1ncnc2c1ncn2[C@@H]1O[C@H](CO)C[C@@H]1O]
NQZ-121
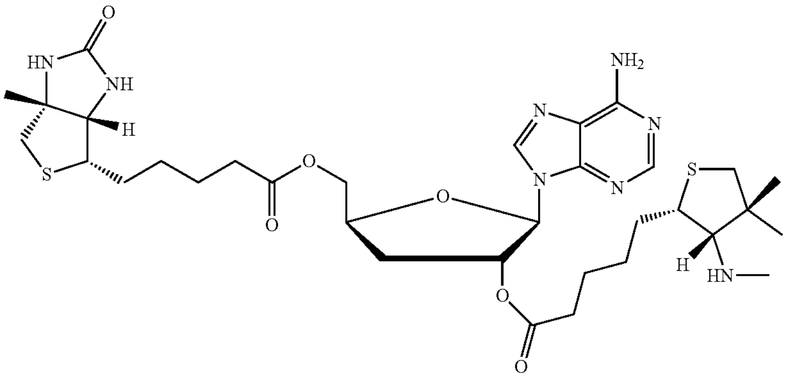
NQZ-123
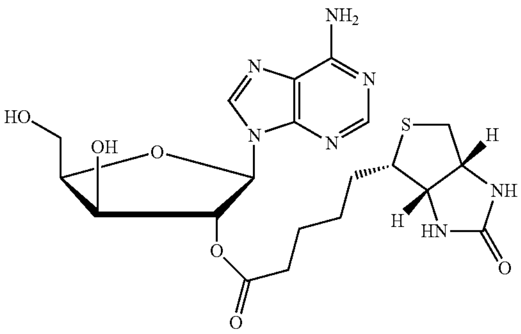

TABLE 2-continued
NQZ-112
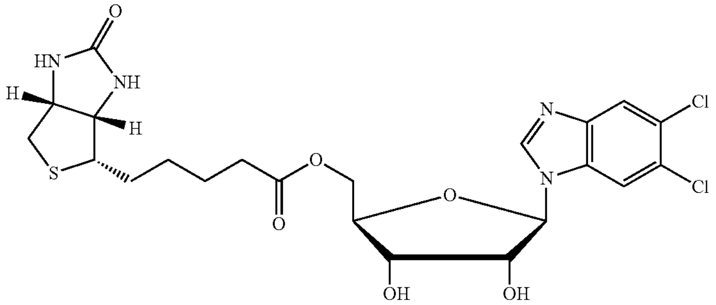
NQZ-122
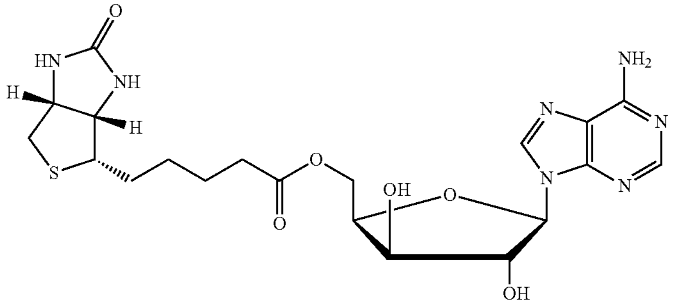
NQZ-006
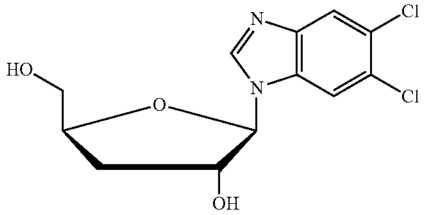 [SMILES: OC[C@@H]1C[C@H](O)[C@H](n2cnc3cc(Cl)c(Cl)cc32)O1]
NQZ-124
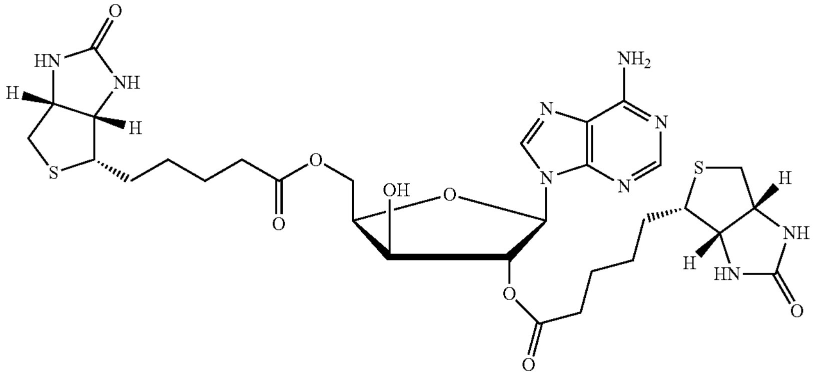
NQZ-062
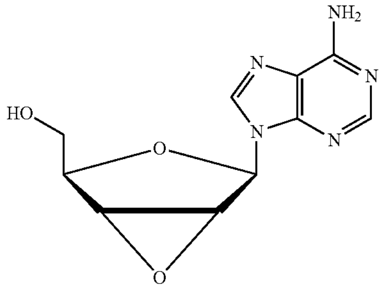

TABLE 2-continued
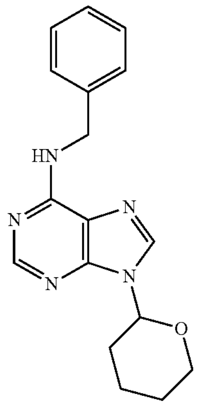 [SMILES: c1ccc(CNc2ncnc3c2ncn3C2CCCCO2)cc1]
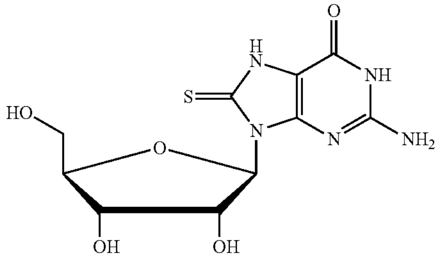
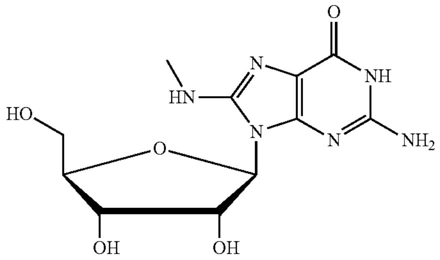
NQZ-003
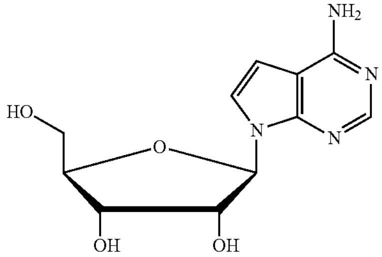
NQZ-020
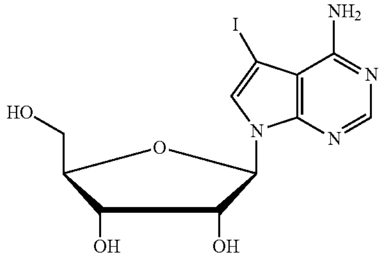
Iodo-Tubercidine TABLE 2-continued
NQZ-004
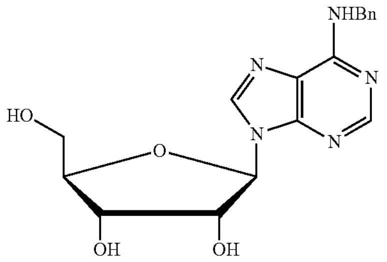
NQZ-010
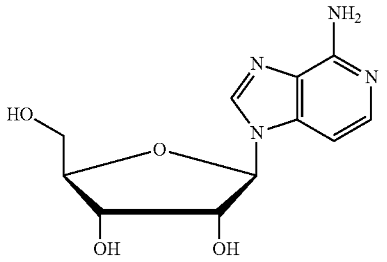
3-Deazaadenosine
NQZ-005
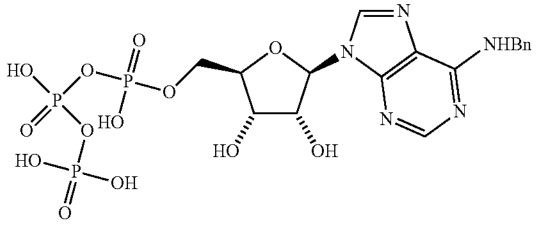
NQZ-008
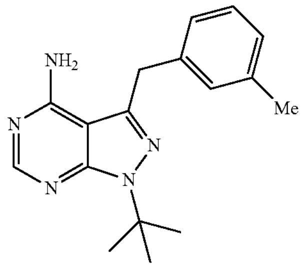 [SMILES: Cc1cccc(Cc2nn(C(C)(C)C)c3ncnc(N)c23)c1]
NQZ-011
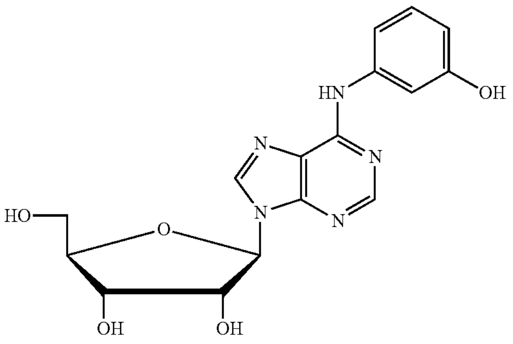

TABLE 2-continued
NQZ-021
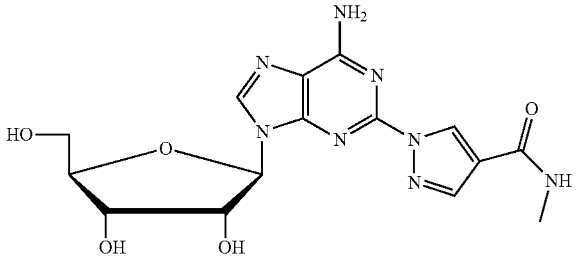
NQZ-026
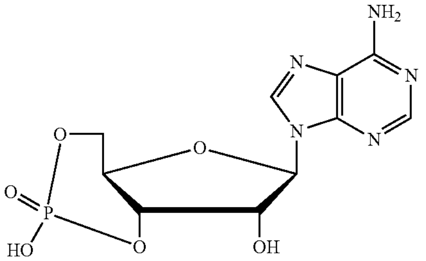
NQZ-034
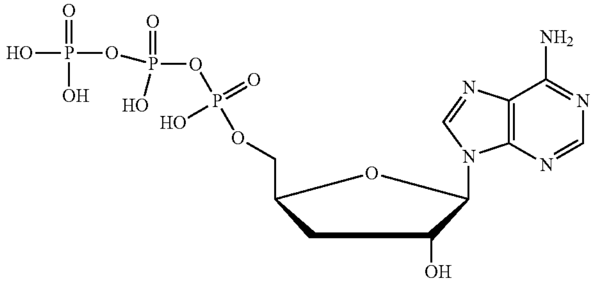 [SMILES: Nc1ncnc2c1ncn2[C@@H]1O[C@H](COP(=O)(O)OP(=O)(O)OP(=O)(O)O)C[C@@H]1O]
NQZ-047
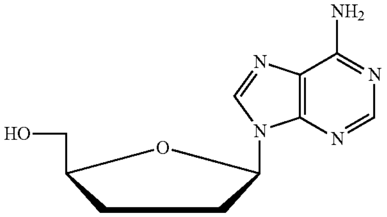
NQZ-067
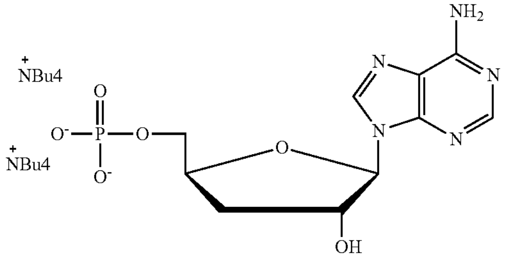 [SMILES: Nc1ncnc2c1ncn2[C@@H]1O[C@H](COP(=O)([O-])[O-])C[C@@H]1O ; "NBu4" ; "NBu4"]

TABLE 2-continued
NQZ-068
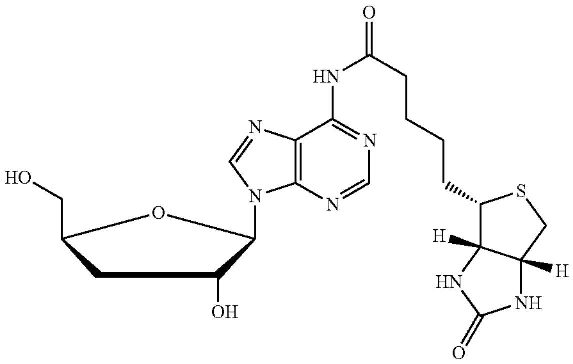 [SMILES: O=C(CCCC[C@@H]1SC[C@@H]2NC(=O)N[C@@H]21)Nc1ncnc2c1ncn2[C@@H]1O[C@H](CO)C[C@@H]1O]
NQZ-069
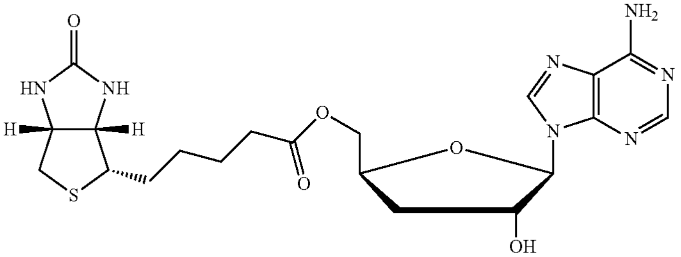 [SMILES: Nc1ncnc2c1ncn2[C@@H]1O[C@H](COC(=O)CCCC[C@@H]2SC[C@@H]3NC(=O)N[C@@H]32)C[C@@H]1O]
NQZ-078
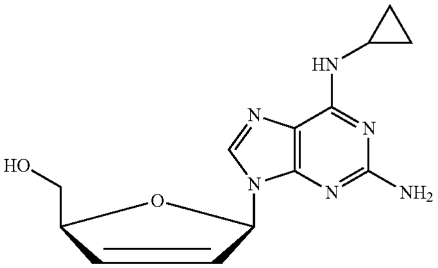 [SMILES: Nc1nc(NC2CC2)c2ncn([C@H]3C=C[C@@H](CO)O3)c2n1]
Abacavir
NQZ-071
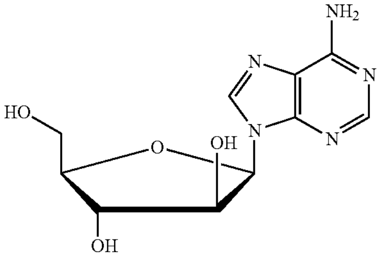
Vidarabine
NQZ-115
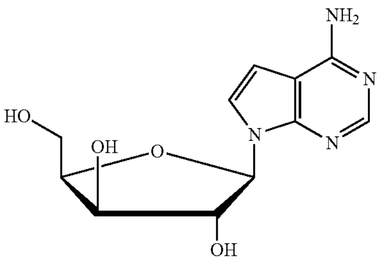

TABLE 2-continued
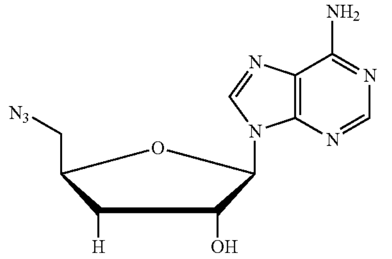 [SMILES: [N-]=[N+]=NC[C@@H]1C[C@H](O)[C@H](n2cnc3c(N)ncnc32)O1]
NQZ-117
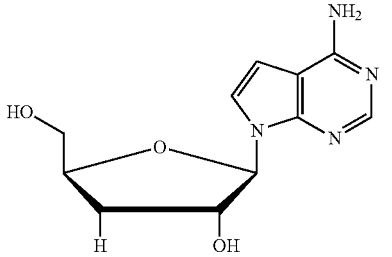 [SMILES: Nc1ncnc2c1ccn2[C@@H]1O[C@H](CO)C[C@@H]1O]
NQZ-126
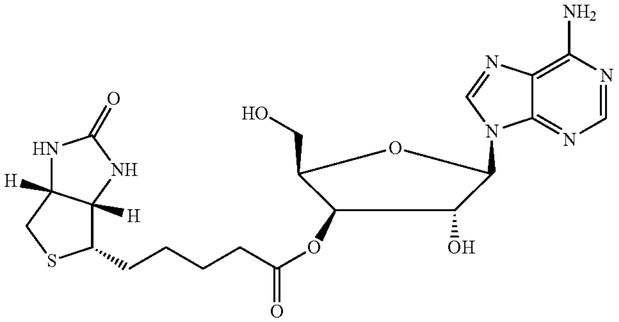
NQZ-132
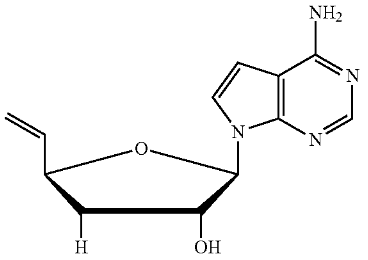 [SMILES: C=C[C@@H]1C[C@H](O)[C@H](n2ccc3c(N)ncnc32)O1]
NQZ-136
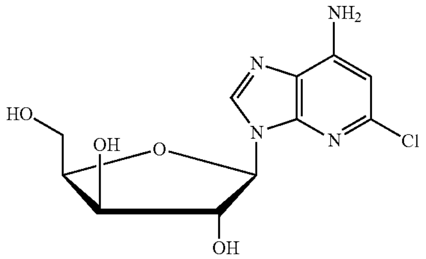
NQZ-140
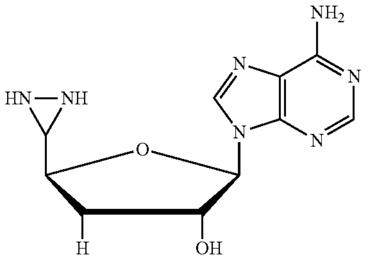 [SMILES: Nc1ncnc2c1ncn2[C@@H]1O[C@H](C2NN2)C[C@@H]1O]
NQZ-143

TABLE 2-continued
NQZ-148
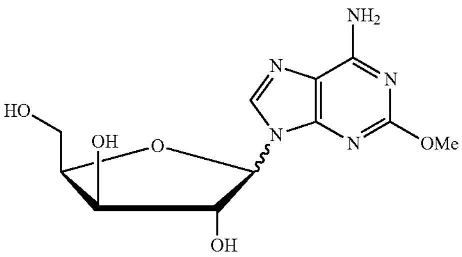
NQZ-149
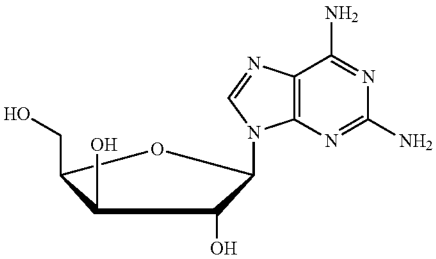
NQZ-150
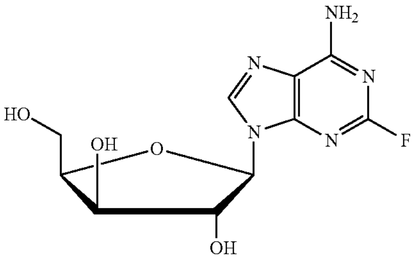
NQZ-162
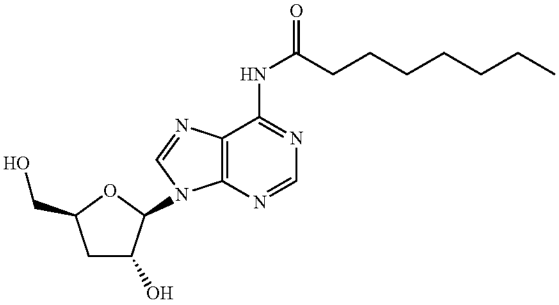 [SMILES: CCCCCCCC(=O)Nc1ncnc2c1ncn2[C@@H]1O[C@H](CO)C[C@H]1O]
NQZ-163
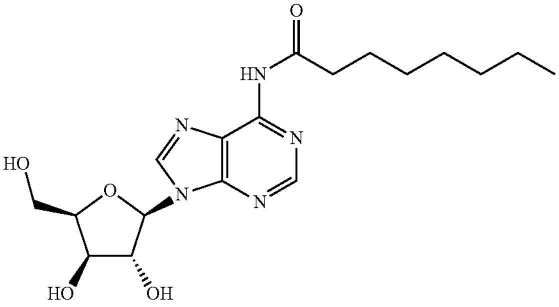 [SMILES: CCCCCCCC(=O)Nc1ncnc2c1ncn2[C@@H]1O[C@H](CO)[C@H](O)[C@H]1O]

TABLE 2-continued
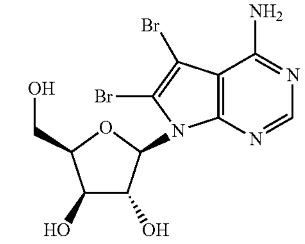 [SMILES: Nc1ncnc2c1c(Br)c(Br)n2[C@@H]1O[C@H](CO)[C@H](O)[C@H]1O]
NQZ-165
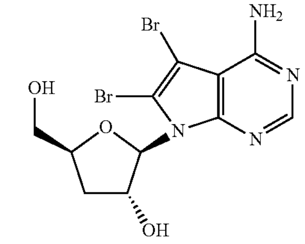 [SMILES: Nc1ncnc2c1c(Br)c(Br)n2[C@@H]1O[C@H](CO)C[C@H]1O]
NOZ-166
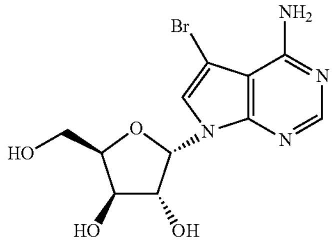 [SMILES: Nc1ncnc2c1c(Br)cn2[C@H]1O[C@H](CO)[C@H](O)[C@H]1O]
NQZ-167
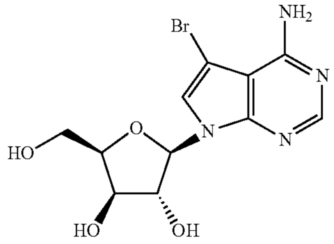 [SMILES: Nc1ncnc2c1c(Br)cn2[C@@H]1O[C@H](CO)[C@H](O)[C@H]1O]
NQZ-168
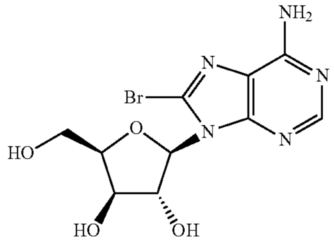 [SMILES: Nc1ncnc2c1nc(Br)n2[C@@H]1O[C@H](CO)[C@H](O)[C@H]1O]
NQZ-169
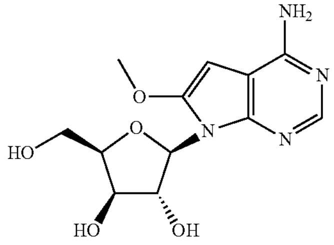 [SMILES: COc1cc2c(N)ncnc2n1[C@@H]1O[C@H](CO)[C@H](O)[C@H]1O]
NQZ-170

TABLE 2-continued
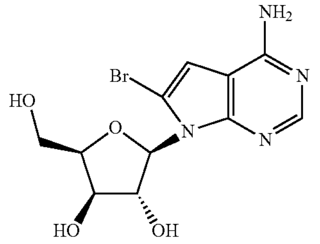 [SMILES: Nc1ncnc2c1cc(Br)n2[C@@H]1O[C@H](CO)[C@H](O)[C@H]1O]
NQZ-171
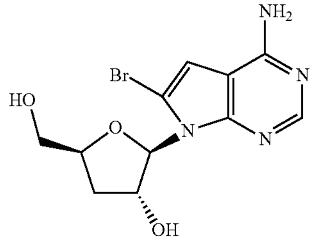 [SMILES: Nc1ncnc2c1cc(Br)n2[C@@H]1O[C@H](CO)C[C@H]1O]
NQZ-173
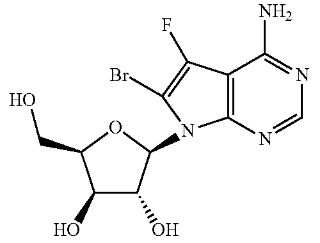 [SMILES: Nc1ncnc2c1c(F)c(Br)n2[C@@H]1O[C@H](CO)[C@H](O)[C@H]1O]
NQZ-174
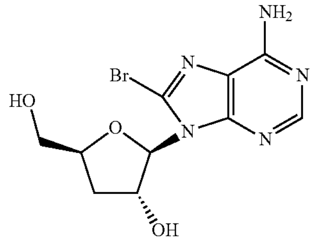 [SMILES: Nc1ncnc2c1nc(Br)n2[C@@H]1O[C@H](CO)C[C@H]1O]
NQZ-175
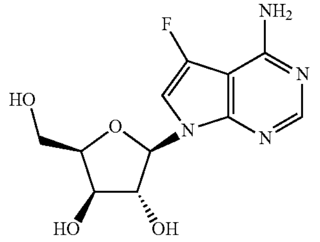 [SMILES: Nc1ncnc2c1c(F)cn2[C@@H]1O[C@H](CO)[C@H](O)[C@H]1O]
NQZ-177
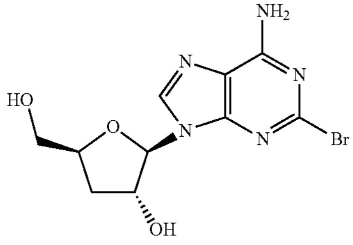 [SMILES: Nc1nc(Br)nc2c1ncn2[C@@H]1O[C@H](CO)C[C@H]1O]
NQZ-178

TABLE 2-continued
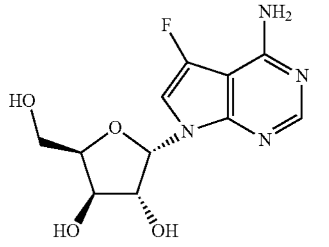 [SMILES: Nc1ncnc2c1c(F)cn2[C@H]1O[C@H](CO)[C@H](O)[C@H]1O]
NQZ-180
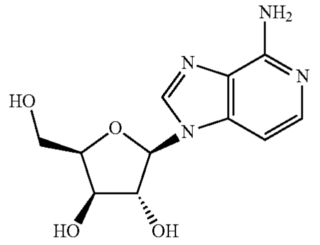 [SMILES: Nc1nccc2c1ncn2[C@@H]1O[C@H](CO)[C@H](O)[C@H]1O]
NQZ-186
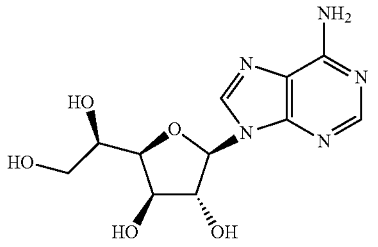 [SMILES: Nc1ncnc2c1ncn2[C@@H]1O[C@H]([C@H](O)CO)[C@H](O)[C@H]1O]
NQZ-190
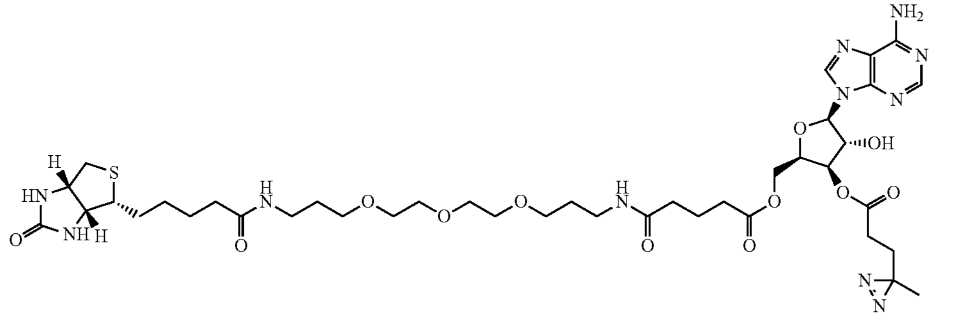 [SMILES: CC1(CCC(=O)O[C@@H]2[C@@H](O)[C@H](n3cnc4c(N)ncnc43)O[C@@H]2COC(=O)CCCC(=O)NCCCOCCOCCOCCCNC(=O)CCCC[C@H]2SC[C@H]3NC(=O)N[C@H]32)N=N1]
NQZ-187-2
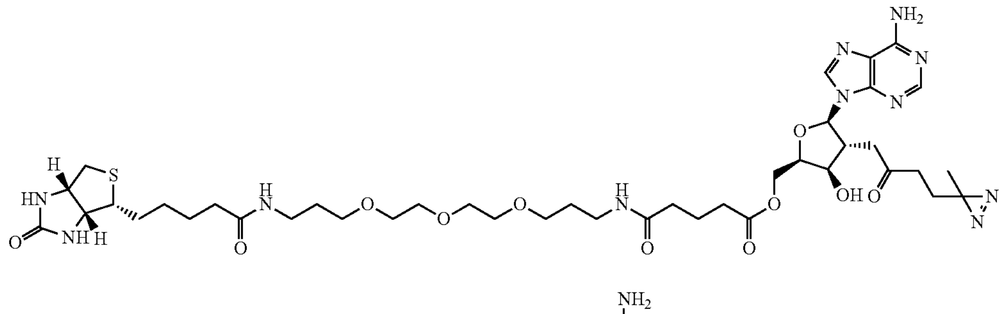
NQZ-187-1
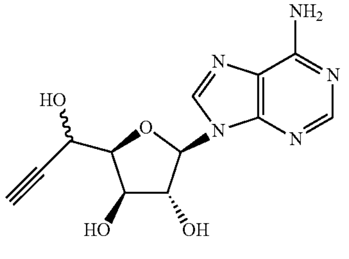 [SMILES: C#CC(O)[C@H]1O[C@@H](n2cnc3c(N)ncnc32)[C@H](O)[C@H]1O]
NQZ-192

TABLE 2-continued
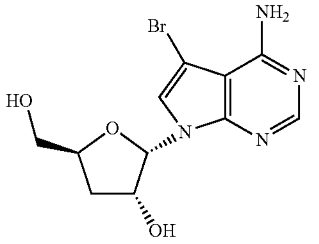 [SMILES: Nc1ncnc2c1c(Br)cn2[C@H]1O[C@H](CO)C[C@H]1O]
NQZ-193
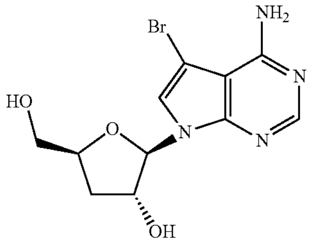 [SMILES: Nc1ncnc2c1c(Br)cn2[C@@H]1O[C@H](CO)C[C@H]1O]
NQZ-194
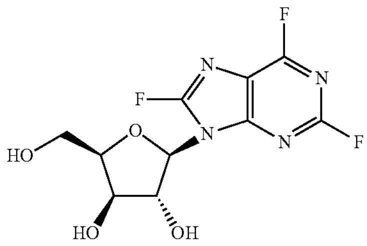 [SMILES: OC[C@H]1O[C@@H](n2c(F)nc3c(F)nc(F)nc32)[C@H](O)[C@H]1O]
NQZ-195
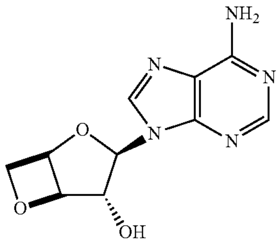
NQZ-196
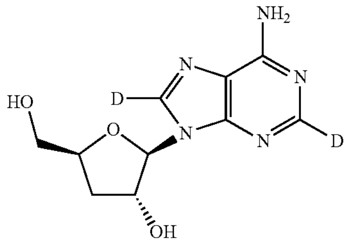 [SMILES: [2H]c1nc(N)c2nc([2H])n([C@@H]3O[C@H](CO)C[C@H]3O)c2n1]
NQZ-197
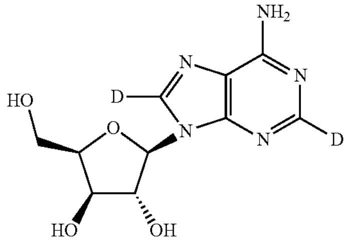
NQZ-198

Preferably, the invention discloses a compound selected from:
TABLE 3
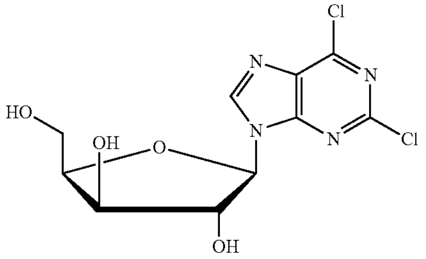
NQZ-097
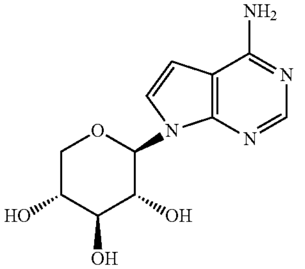 [SMILES: Nc1ncnc2c1ccn2[C@@H]1OC[C@@H](O)[C@H](O)[C@H]1O]
NQZ-086
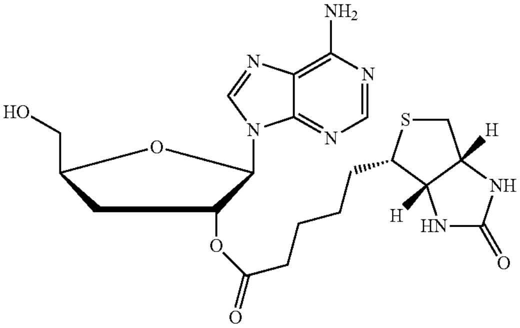 [SMILES: Nc1ncnc2c1ncn2[C@@H]1O[C@H](CO)C[C@@H]1OC(=O)CCCC[C@@H]1SC[C@@H]2NC(=O)N[C@@H]21]
NQZ-119
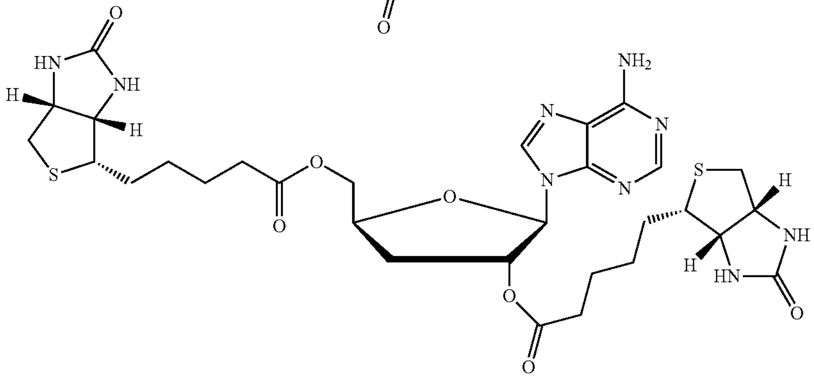
NQZ-121
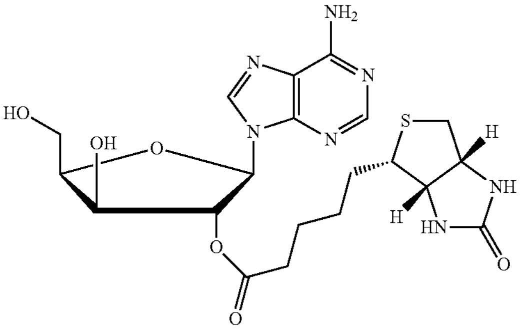
NQZ-123

TABLE 3-continued
NQZ-112
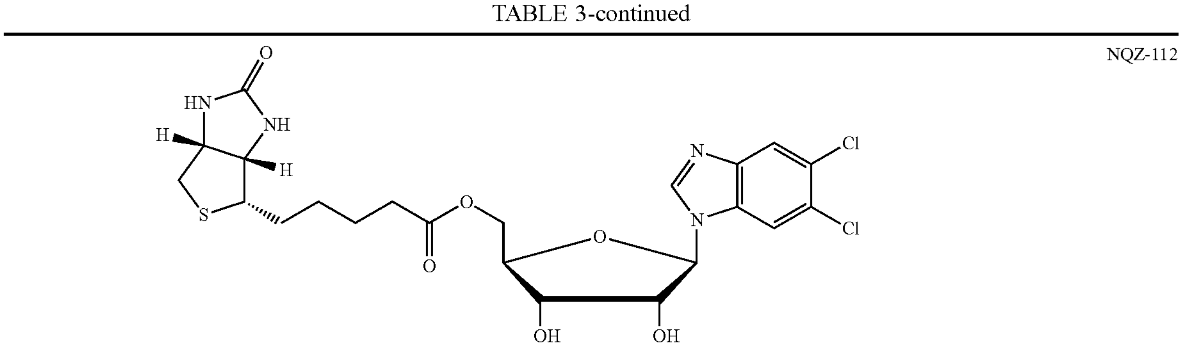
NQZ-122
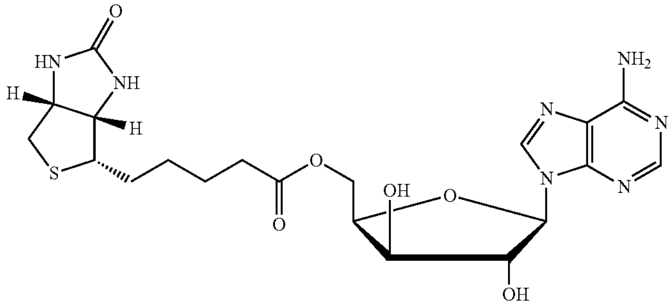
NQZ-124
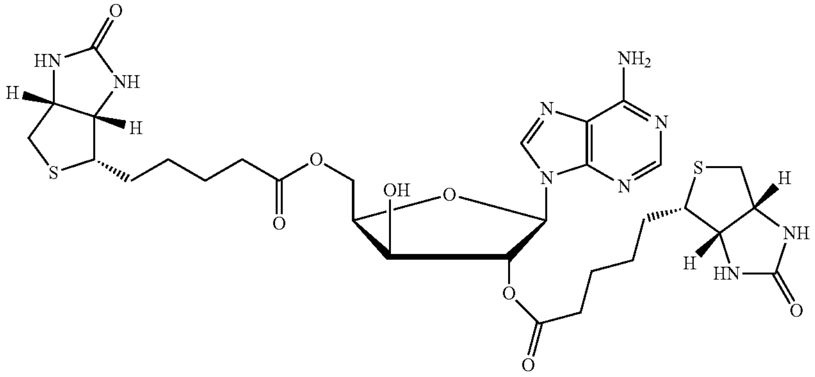
NQZ-034
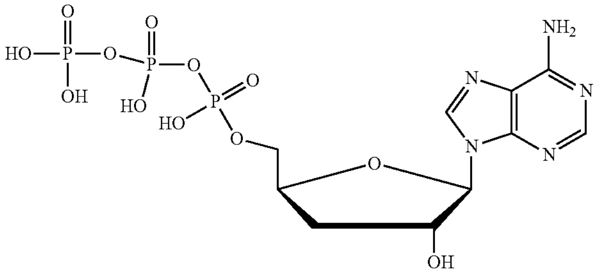 [SMILES: Nc1ncnc2c1ncn2[C@@H]1O[C@H](COP(=O)(O)OP(=O)(O)OP(=O)(O)O)C[C@@H]1O]
NQZ-068
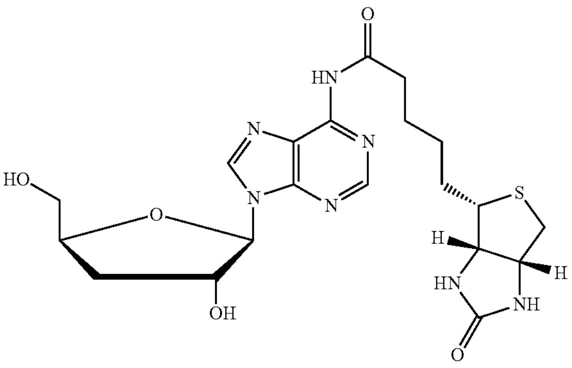 [SMILES: O=C(CCCC[C@@H]1SC[C@@H]2NC(=O)N[C@@H]21)Nc1ncnc2c1ncn2[C@@H]1O[C@H](CO)C[C@@H]1O]

TABLE 3-continued
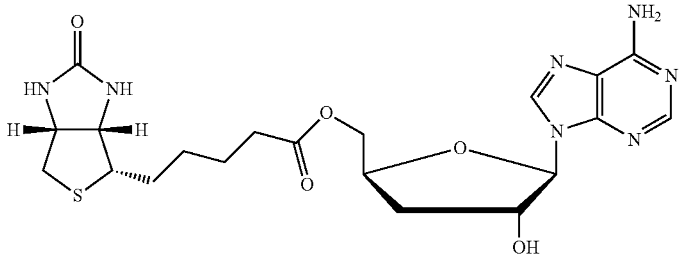 [SMILES: Nc1ncnc2c1ncn2[C@@H]1O[C@H](COC(=O)CCCC[C@@H]2SC[C@@H]3NC(=O)N[C@@H]32)C[C@@H]1O]
NQZ-069
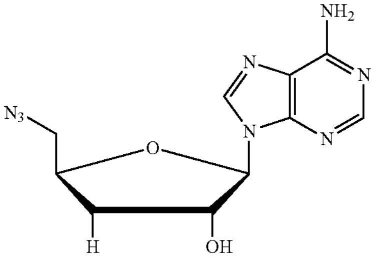 [SMILES: [N-]=[N+]=NC[C@@H]1C[C@H](O)[C@H](n2cnc3c(N)ncnc32)O1]
NQZ-117
NQZ-132
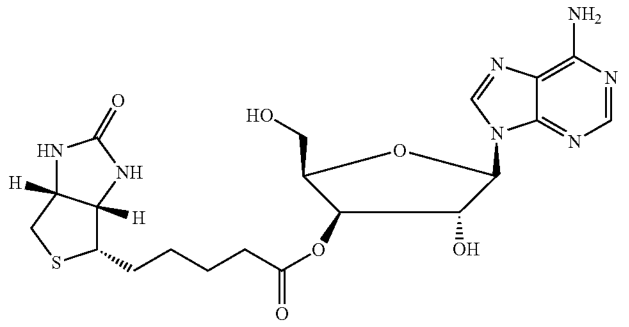
NQZ-140
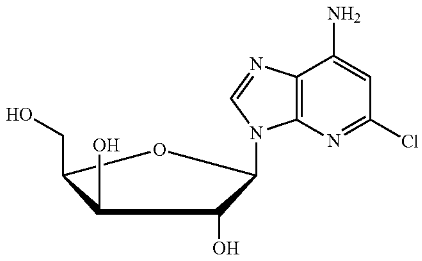
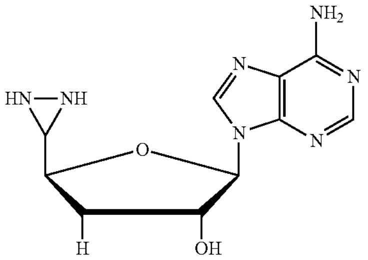 [SMILES: Nc1ncnc2c1ncn2[C@@H]1O[C@H](C2NN2)C[C@@H]1O]
NQZ-143

TABLE 3-continued
NQZ-148
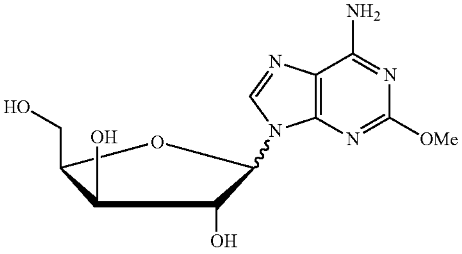
NOZ-162
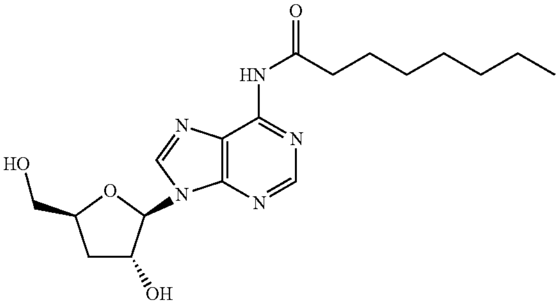 [SMILES: CCCCCCCC(=O)Nc1ncnc2c1ncn2[C@@H]1O[C@H](CO)C[C@H]1O]
NQZ-163
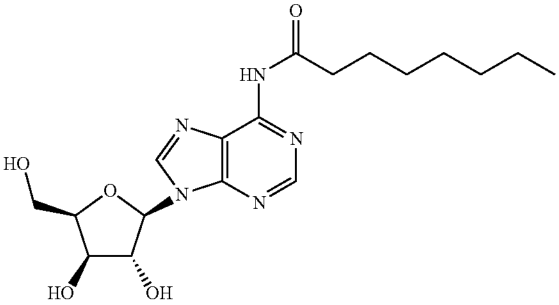 [SMILES: CCCCCCCC(=O)Nc1ncnc2c1ncn2[C@@H]1O[C@H](CO)[C@H](O)[C@H]1O]
NQZ-165
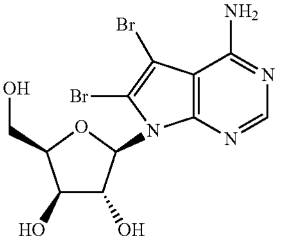 [SMILES: Nc1ncnc2c1c(Br)c(Br)n2[C@@H]1O[C@H](CO)[C@H](O)[C@H]1O]
NQZ-166
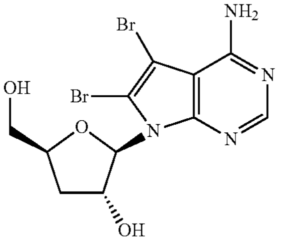 [SMILES: Nc1ncnc2c1c(Br)c(Br)n2[C@@H]1O[C@H](CO)C[C@H]1O]
NQZ-167
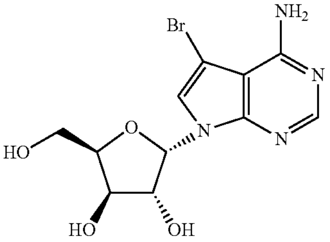 [SMILES: Nc1ncnc2c1c(Br)cn2[C@H]1O[C@H](CO)[C@H](O)[C@H]1O]

TABLE 3-continued
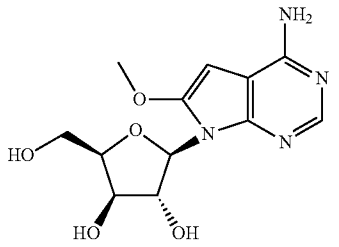 [SMILES: COc1cc2c(N)ncnc2n1[C@@H]1O[C@H](CO)[C@H](O)[C@H]1O]
NQZ-170
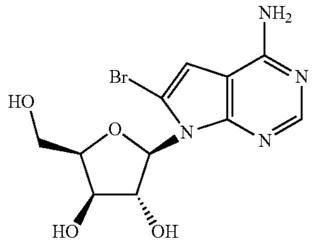 [SMILES: Nc1ncnc2c1cc(Br)n2[C@@H]1O[C@H](CO)[C@H](O)[C@H]1O]
NQZ-171
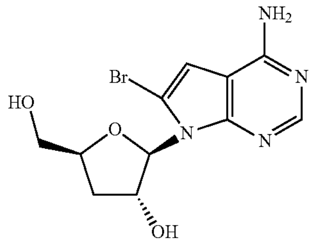 [SMILES: Nc1ncnc2c1cc(Br)n2[C@@H]1O[C@H](CO)C[C@H]1O]
NQZ-173
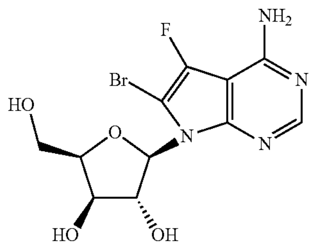 [SMILES: Nc1ncnc2c1c(F)c(Br)n2[C@@H]1O[C@H](CO)[C@H](O)[C@H]1O]
NQZ-174
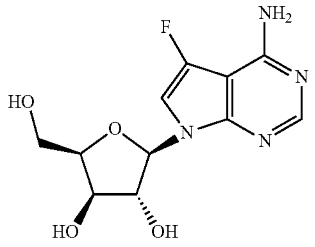 [SMILES: Nc1ncnc2c1c(F)cn2[C@@H]1O[C@H](CO)[C@H](O)[C@H]1O]
NQZ-177
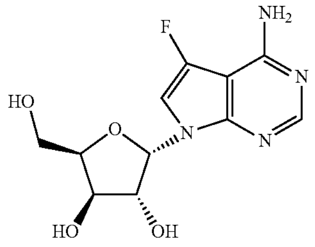 [SMILES: Nc1ncnc2c1c(F)cn2[C@H]1O[C@H](CO)[C@H](O)[C@H]1O]
NQZ-180

TABLE 3-continued
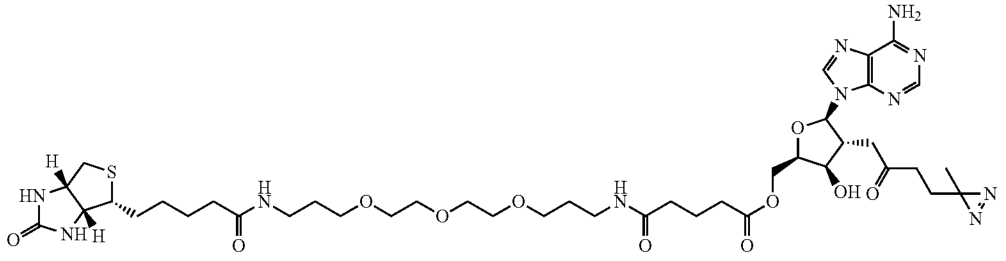 [SMILES: CC1(CCC(=O)C[C@@H]2[C@@H](O)[C@@H](COC(=O)CCCC(=O)NCCCOCCOCCOCCCNC(=O)CCCC[C@H]3SC[C@H]4NC(=O)N[C@H]43)O[C@H]2n2cnc3c(N)ncnc32)N=N1]
NQZ-187-1
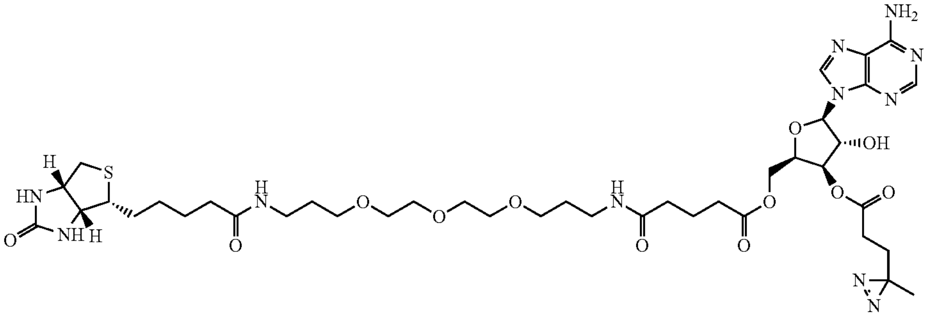 [SMILES: CC1(CCC(=O)O[C@@H]2[C@@H](O)[C@H](n3cnc4c(N)ncnc43)O[C@@H]2COC(=O)CCCC(=O)NCCCOCCOCCOCCCNC(=O)CCCC[C@H]2SC[C@H]3NC(=O)N[C@H]32)N=N1]
NQZ-187-2
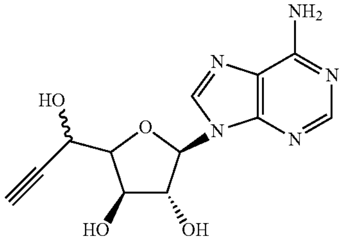 [SMILES: C#CC(O)C1O[C@@H](n2cnc3c(N)ncnc32)[C@H](O)[C@H]1O]
NQZ-192
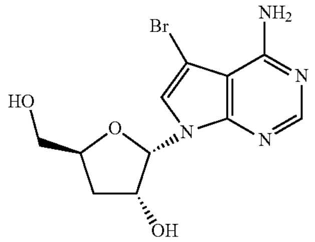 [SMILES: Nc1ncnc2c1c(Br)cn2[C@H]1O[C@H](CO)C[C@H]1O]
NQZ-193
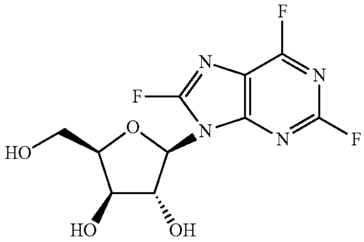 [SMILES: OC[C@H]1O[C@@H](n2c(F)nc3c(F)nc(F)nc32)[C@H](O)[C@H]1O]
NQZ-195
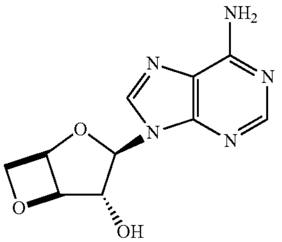
NQZ-196

TABLE 3-continued

| | |
|---|---|
| 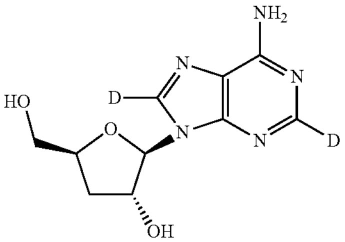 [SMILES: [2H]c1nc(N)c2nc([2H])n([C@@H]3O[C@H](CO)C[C@H]3O)c2n1] | NQZ-197 |
| 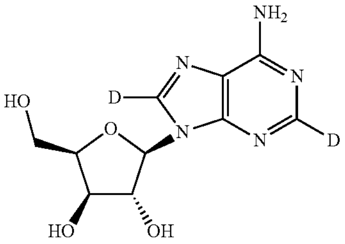 [SMILES: [2H]c1nc(N)c2nc([2H])n([C@@H]3O[C@H](CO)[C@H](O)[C@H]3O)c2n1] | NQZ-198 |

In another aspect, this invention discloses a composition comprising a nucleoside analogue compound of Formula I, II or III as defined above, or a salt (a pharmaceutically acceptable salt) thereof and pentostatin.

Preferably, the composition is consisted of cordycepin and pentostadin; the composition is consisted of one of the following compounds and pentostatin:

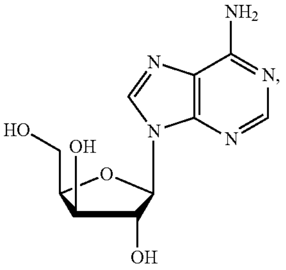

NQZ-162

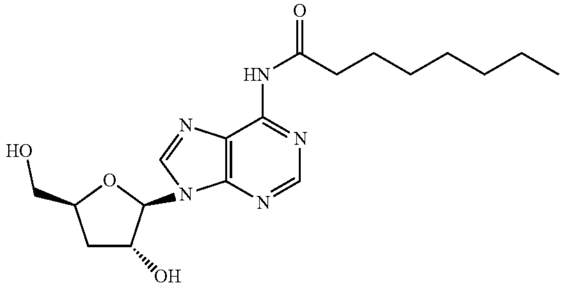

-continued

NQZ-163

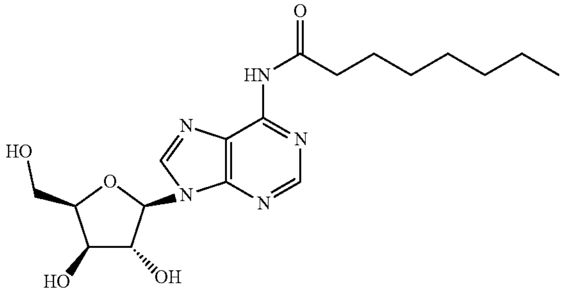

NQZ-197

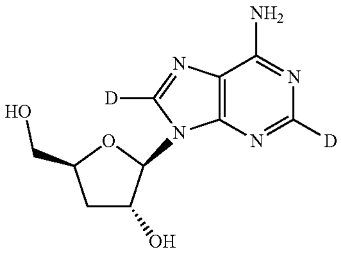

and

NQZ-198

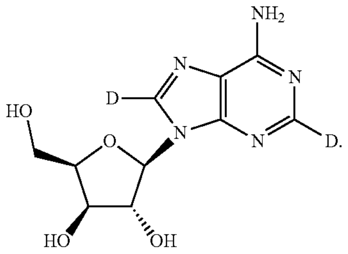

Pentostatin is a kind of deaminase inhibitor. The persons skilled in the art may choose other deaminase inhibitors as desired.

In another aspect, the invention discloses a prodrug of the following formula:

NQZ-007
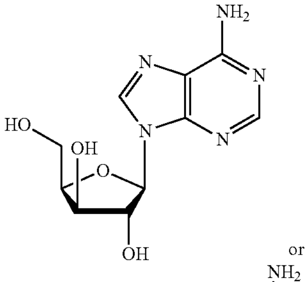
or
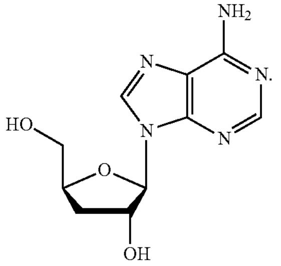
Preferably, the prodrug is selected from:
NQZ-162
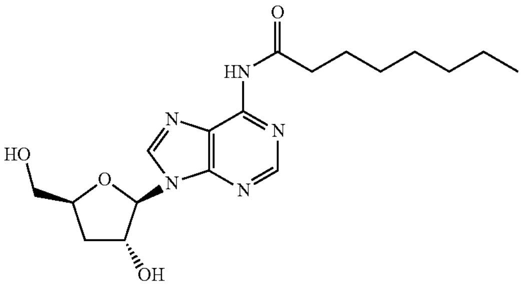
and
NQZ-122
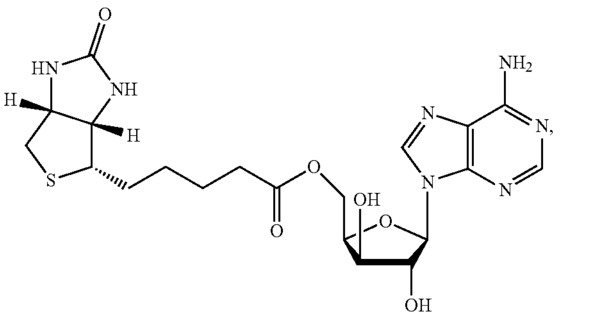
-continued
NQZ-163
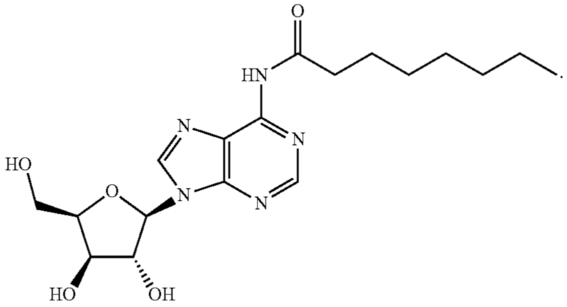
In another aspect, the invention discloses a modified compound of the following formula:
NQZ-007
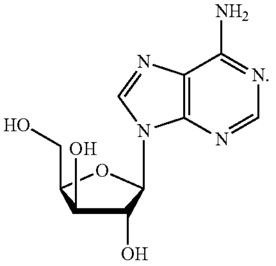
Preferably, the modified compound is selected from:
NQZ-123
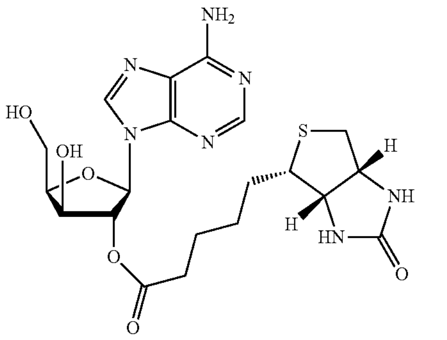

-continued

NQZ-187-1

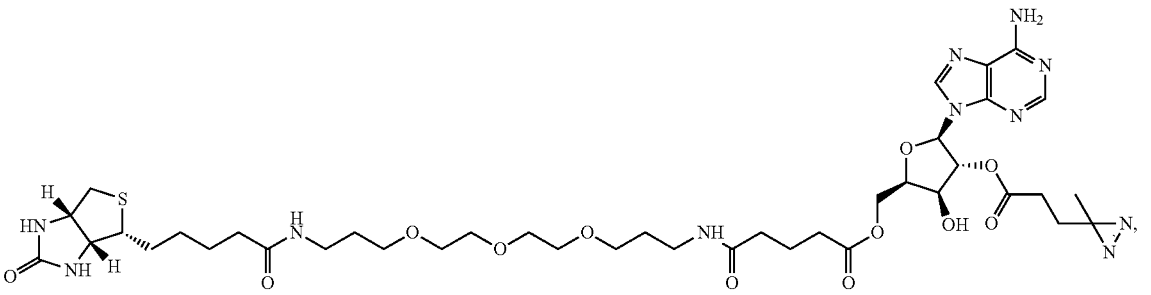

and

NQC-187-2

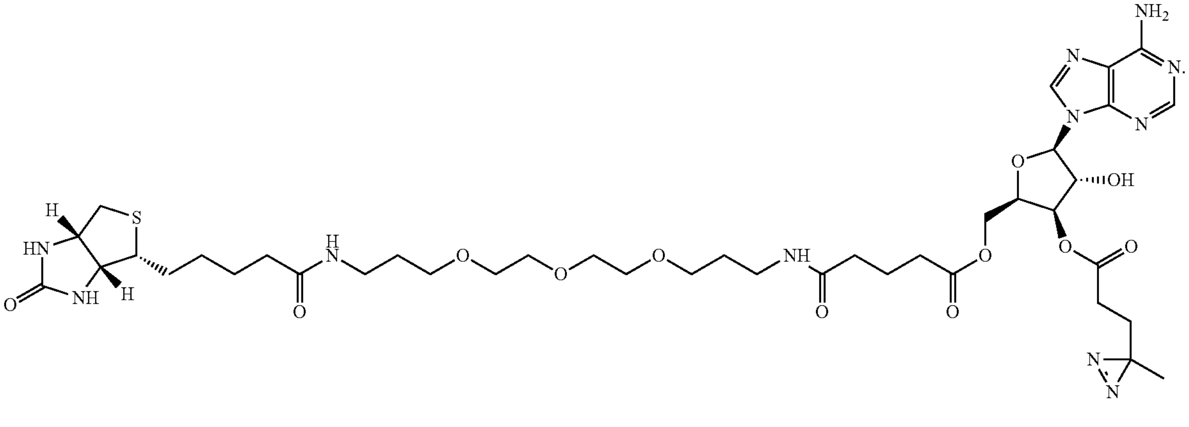

In another aspect, the invention discloses a method for modulating circadian rhythm, preferably, for shifting circadian phase, which comprises administrating to a subject a therapeutically effective amount of a nucleoside analogue compound of Formula I, Formula II or Formula III as defined above or a salt (a pharmaceutically acceptable salt) thereof.

Preferably, the compound is administrated at the time of Per2-dLuc peak, but not at the trough.

In another aspect, the invention discloses a method for modulating circadian rhythm, preferably, for shifting circadian phase, which comprises administrating to a subject a therapeutically effective amount of a composition comprising a nucleoside analogue compound of Formula I, Formula II or Formula III as defined above or a salt (a pharmaceutically acceptable salt) thereof and pentostatin.

Preferably, the composition is consisted of cordycepin and pentostadin; the composition is consisted of one of the following compounds and pentostatin:

NQZ-007

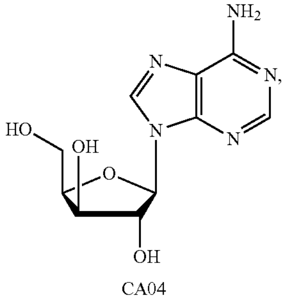

CA04

-continued

NQZ-162

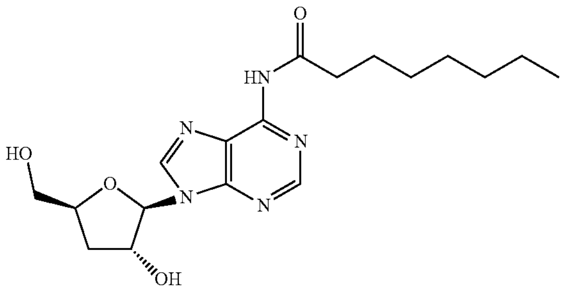

NQZ-163

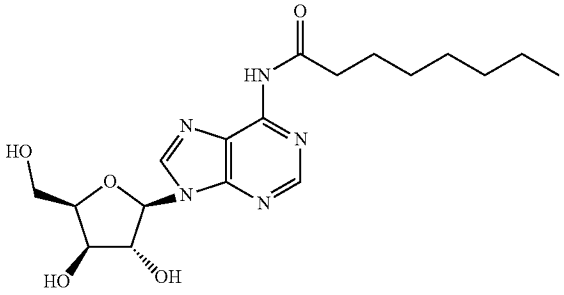

-continued

NQZ-197

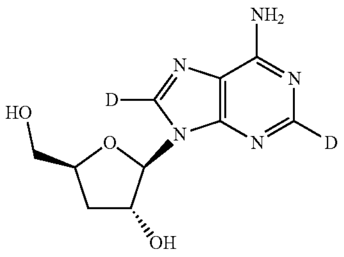

and

NQZ-198

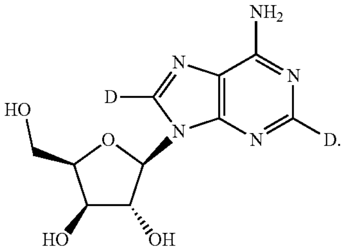

Preferably, the composition is administrated at the time of Per2-dLuc peak, but not at the trough.

Pentostatin is a kind of deaminase inhibitor. The persons skilled in the art may choose other deaminase inhibitors as desired.

In another aspect, the invention discloses a method for modulating circadian rhythm, preferably, for shifting circadian phase, which comprises administrating to a subject a therapeutically effective amount of a prodrug of the following formula:

NQZ-007

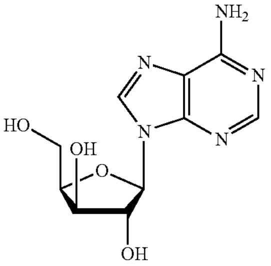

or

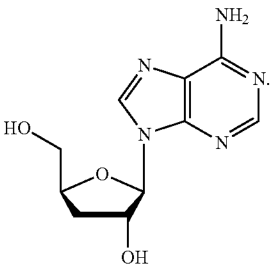

Preferably, the prodrug is selected from:

NQZ-162

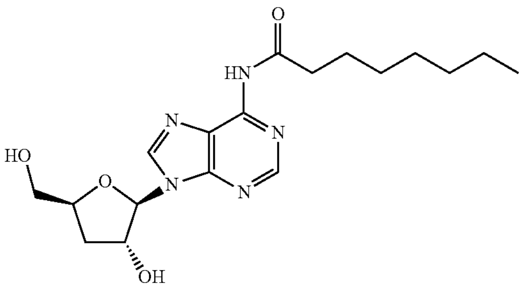

and

NQZ-163

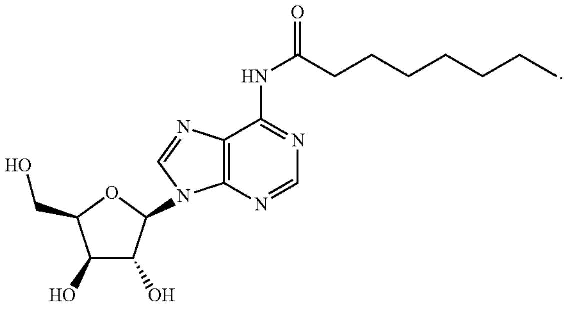

In another aspect, the invention discloses a method for modulating circadian rhythm, preferably, for shifting circadian phase, which comprises administrating to a subject a therapeutically effective amount of a modified compound of the following formula:

NQZ-007

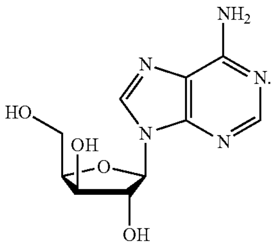

Preferably, the modified compound is selected from:

NQZ-122

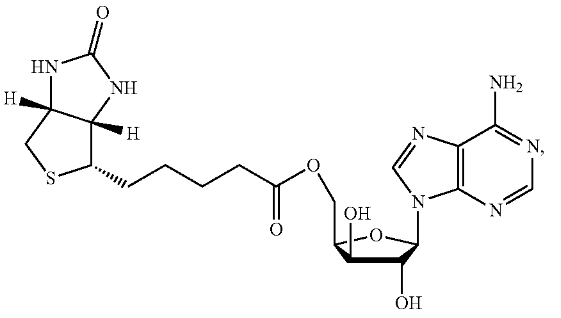

NQZ-123

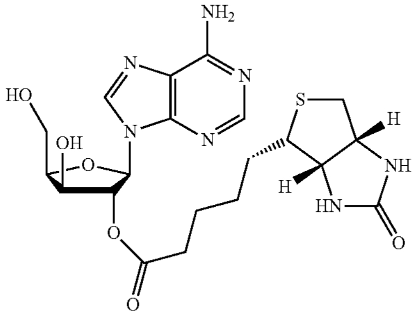

NQZ-187-1

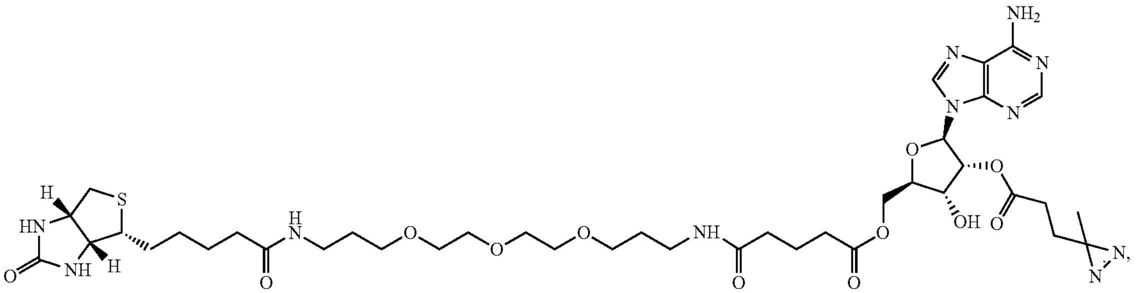

and

NQZ-187-2

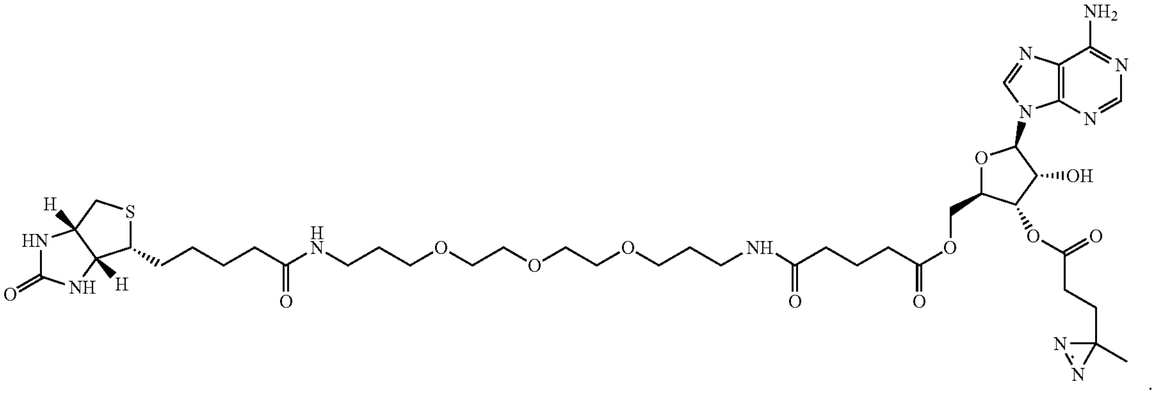

In another aspect, the invention discloses use of a nucleoside analogue compound of the following formula I, II or III as defined above, or a salt (a pharmaceutically acceptable salt) thereof in manufacturing a drug for modulating circadian rhythm, preferably, for shifting circadian phase.

In another aspect, the invention discloses use of a composition comprising a nucleoside analogue compound of the following formula I, II or III as defined above, or a salt (a pharmaceutically acceptable salt) thereof and pentostatin in manufacturing a drug for modulating circadian rhythm, preferably, for shifting circadian phase.

Preferably, the composition is consisted of cordycepin and pentostadin; the composition is consisted of one of the following compounds and pentostatin:

NQZ-007

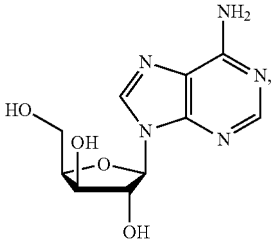

CA04

-continued

NQZ-162

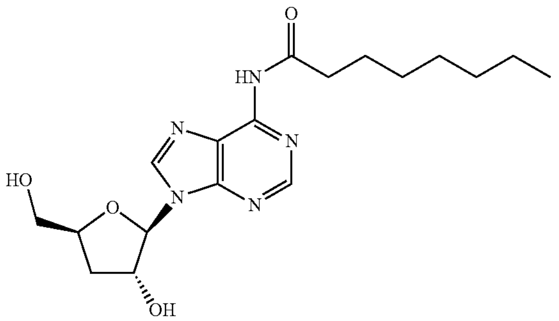

NQZ-163

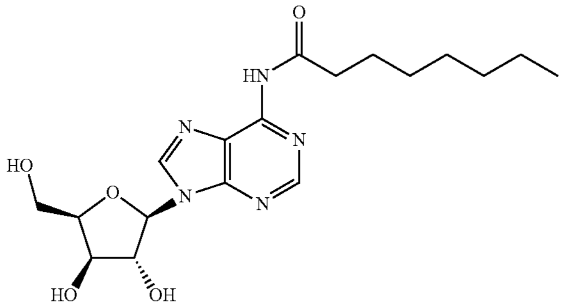

NIBS-QI-EQZ-163

NQZ-197

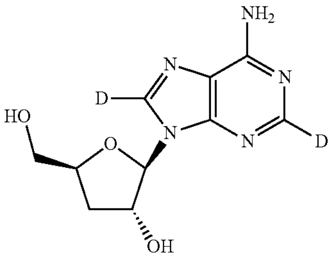

and

NQZ-198

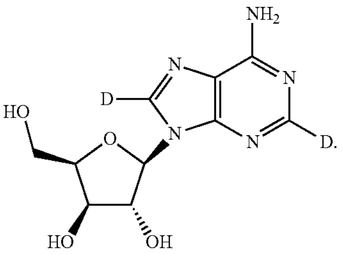

In another aspect, the invention discloses use of a prodrug of the following formula in manufacturing a drug for modulating circadian rhythm, preferably, for shifting circadian phase:

NQZ-007

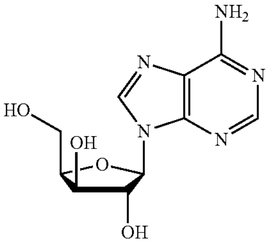

or

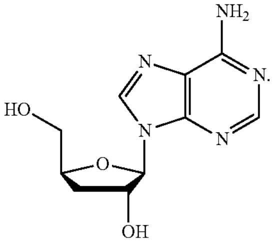

Preferably, the prodrug is selected from:

NQZ-162

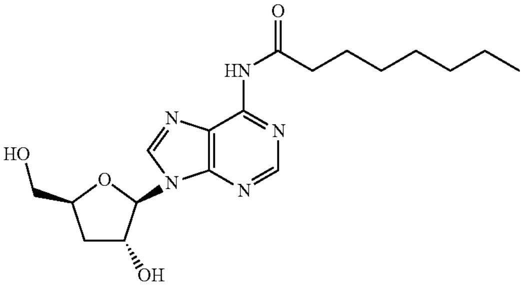

and

NQZ-163

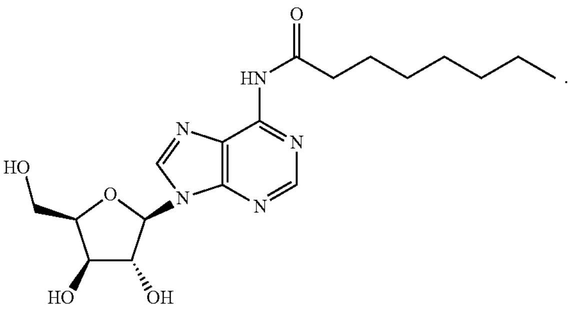

In another aspect, the invention discloses use of a modified compound of the following formula in manufacturing a drug for modulating circadian rhythm, preferably, for shifting circadian phase:

NQZ-007

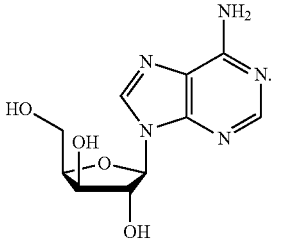

Preferably, the modified compound is selected from:

pounds of the present invention or the composition of the present invention may be formulated into formulations suitable for enteral administration, intravenous administration, oral administration or sublingual administration.

The drug may also be combined with other medicament, for example caffeine, melatonin, zolpidem, eszopiclone, zaleplon or triazolam.

The subject is a person suffering from or having a risk of suffering from jet lag, shift-work, age-related sleep disturbances, or circadian clock-related sleep disturbances.

In another aspect, the present invention discloses use of the present nucleoside analogue for regulating CDK9, thereby for shifting the phase of clock.

NQZ-122

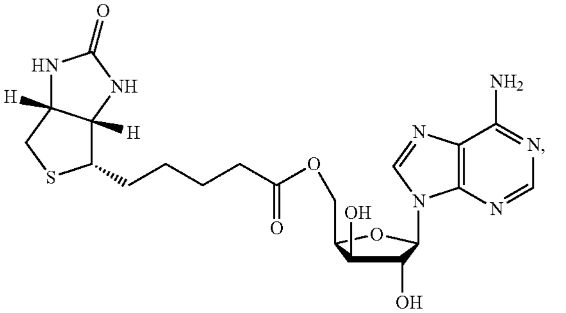

NQZ-123

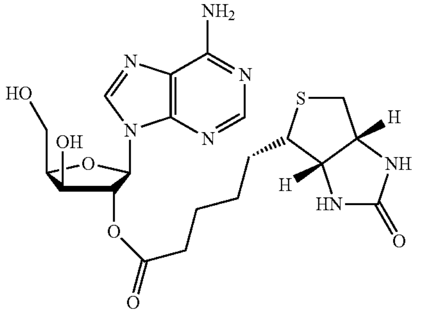

NQZ-187-1

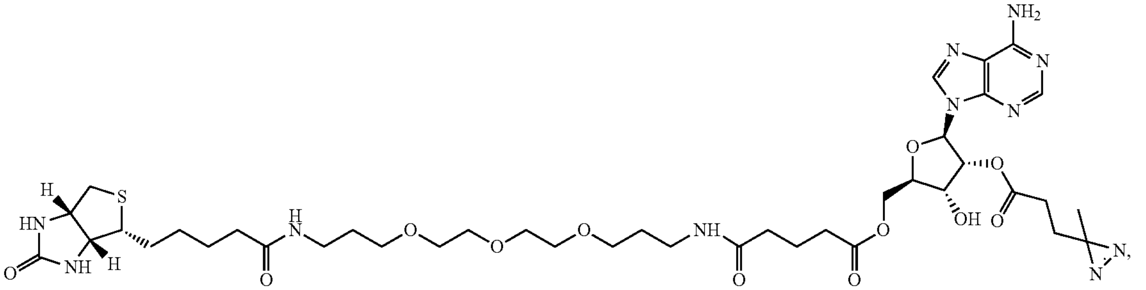

and

NQZ-187-2

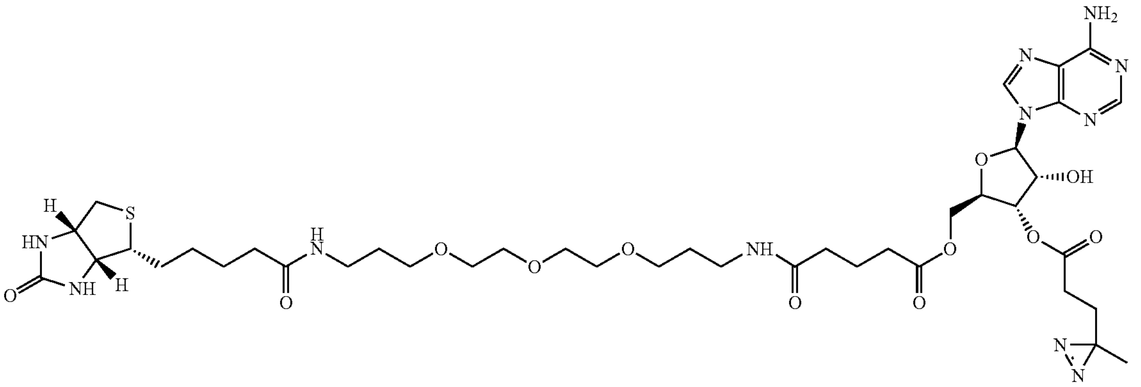

Preferably, the drug may be used to treat jet lag, shift-work, age-related sleep disturbances, or circadian clock-related sleep disturbances.

The compounds of the present invention or the composition of the present invention may be formulated with conventional carriers and excipients which will be selected in accordance with ordinary practice. Therefore, the com- In another aspect, the present invention discloses use of RUVBL helicase in mediating the cordycepin-mediated induction of Per2-dLuc and the clock phase shift, and use of RUVBL helicase as the direct target of cordycepin, wherein RUVBL helicase is the target of the nucleoside analogue compound disclosed in the present invention. RUVBL helicase may be RUVBL1 helicase or RUVBL2 helicase. That is to say, RUVBL may be used as the target of the nucleoside analogue compound of the present invention that shifts the clock phase.

The invention encompasses all combination of the particular embodiments recited herein, as if each had been separately, laboriously recited.

The invention encompasses all combination of the particular embodiments recited herein.

DESCRIPTION OF THE EMBODIMENTS

Figure 1D:
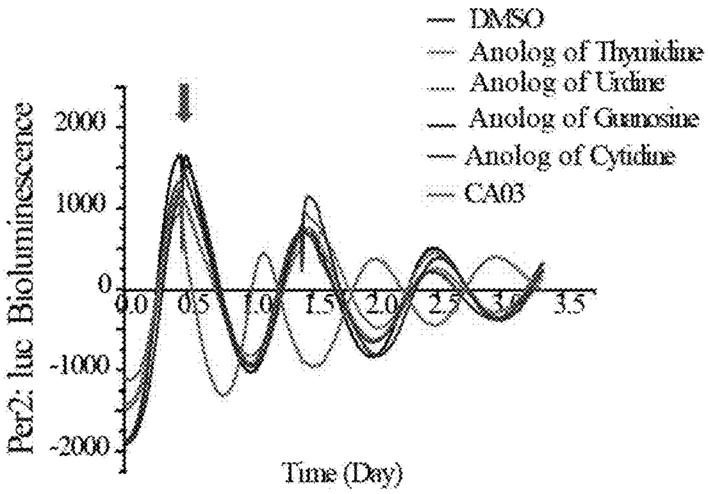
FIG. 1 shows that adenosine-like compound cordycepin resets the clock-phase.

For a better understanding of the invention and to show how the same may be carried into effect, reference will now be made, purely by way of example, to the accompanying figures. With specific reference to the figures in detail, it is stressed that the particulars shown are by way of example and for purpose of illustrative discussion of preferred embodiments of the present invention only, and are presented for the purpose of providing what is believed to be the most useful and readily understood description of principles and conceptual aspects of the invention.

The phrase "pharmaceutically acceptable salt" as used herein includes, but is not limited to sulfate, citrate, acetate, oxalate, chloride, bromide, iodide, nitrate, bisulfate, phosphate, acid phosphate, lactate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, besylate, and mesylate.

The term "therapeutically effective amount" means an amount that is effective to regulate circadian phase, so as to treat jet lag, shift-work or age-related sleep disturbances alone or in combination with other medicaments, such as caffeine, melatonin, zolpidem, eszopiclone, zaleplon, or triazolam.

The composition of the present invention may also comprise a pharmaceutically acceptable excipient. Suitable excipients or carriers and methods for preparing administrable compositions are known to those skilled in the art.

The present invention provides a kind of nucleoside analogue compounds, and a composition comprising the compound and pentostatin, their use for modulating circadian rhythm, preferably, for shifting circadian phase, and methods for modulating circadian rhythm, preferably, for shifting circadian phase via the compound or the composition.

CDK9 The protein encoded by this gene is a member of the cyclin-dependent kinase (CDK) family. This kinase was found to be a component of the multiprotein complex TAK/P-TEFb, which is an elongation factor for RNA polymerase II-directed transcription and functions by phosphorylating the C-terminal domain of the largest subunit of RNA polymerase II. This protein forms a complex with and is regulated by its regulatory subunit cyclin T or cyclin K.

RUVBL2 This gene encodes the second human homologue of the bacterial RuvB gene. Bacterial RuvB protein is a DNA helicase essential for homologous recombination and DNA double-strand break repair. Functional analysis showed that this gene product has both ATPase and DNA helicase activities. Possesses single-stranded DNA-stimulated ATPase and ATP-dependent DNA helicase (5' to 3') activity; hexamerization is thought to be critical for ATP hydrolysis and adjacent subunits in the ring-like structure contribute to the ATPase activity.

EXAMPLE

Methods and Reagents.

Chemical synthesis: All reactions were carried out under an inert atmosphere of nitrogen or argon unless otherwise noted. DMF, DMSO (99.9%, extra dry) was used as received. All other reagents were purchased commercially and used as received, unless otherwise noted. NMR spectra were recorded with Bruker spectrometers. 1H (400 MHz) and NMR chemical shifts are reported relative to internal TMS (δ=0.00 ppm) or to residual protiated solvent. Data are presented as follows: chemical shift (ppm), multiplicity (s=singlet, d=doublet, t=triplet, q=quartet, sept=septet, m=multiplet, br=broad), coupling constant J (Hz) and integration.

Cell culture, drug treatment and Real-Time Monitoring of Circadian Oscillations: Per2-Luc reporter U2OS cells (D15) and Bmal1-Luc reporter U2OS cells (C26) cells were kept in DMEM medium (Gibco), supplemented with 10% FBS (Gibco) and 1% penicillin streptomycin mixture (Gibco). For Circadian Oscillation monitored with lumicycle (Actimetrics), cells were seeded at the density of $10^6$ per 3.5 cm dish (Z688851-30EA). The medium was changed into XM medium (PH7.2, 10 mM HEPES, 350 mg/l bicarbonate, 1×B27, 100 IU/ml penicillin, 100 μg/ml streptomycin, 10 μg/ml gentamycin, and 100 μM d-Luciferin) 2 days after cell seeding. 3.5 cm dish was then sealed with high-vacuum grease (Dow Corning) and microscope cover glass, and transferred into lumicycle which was placed in an incubator (37° C.). For Drug treatment, 3.5 cm dish was taken out from lumicycle quickly at indicated time. After chemical was added into the medium, the dish was sealed again and put back into lumicycle. For Circadian Oscillation monitored with Tecan (Perkinelmer), cells were seeded at the density of $0.25\times^4$ per well for 384-well plate (CLS3610-48EA). 2 days later, the medium was changed into premixed XM medium with different chemicals with or without pentostatin (5 μg/ml). The plate was then sealing with sealing film (Sangon Biotech) and put into Tecan. Data from cells were collected in the Tecan luminometer at 37° C. for 5~7 days.

Biotinylated Compounds Pull-down, SPR analysis and Immunoprecipitation: The interaction between biotinylated compounds and their target proteins were proceeded as follow. Every $10^8$ unsynchronized U2OS cells were collected, homogenized into 2 ml lysis buffer (25 mM MOPS pH7.2, 15 mM EGTA, 15 mM MgCl2, 1 mM DTT, 60 mM β-glycerophosphate, 1 mM Na3VO4, 1 mM NaF, 1 mM phenyl phosphate, Complete Protease Inhibitor Cocktail), and sonicated 6 times for 30 s at 4° C. with a Diagenode bioruptor. After sonication, NP-40 (final 0.5%) was added, incubated 15 min on ice, centrifuged at full speed for 20 min at 4° C. The resultant supernatant was firstly incubated with Pentostatin (final concentration at 5 μg/ml) for 2 h at 4° C. with rotation, and then split into 4 groups. 200 pmol cordycepin, 200 pmol DRB, and DMSO (2 groups, final 0.1%) was added respectively and further incubated for 1 h. Finally, 200 pmol Biotin-cordycepin or 200 pmol Biotin-DRB was added and incubated for at least 4 h. Biotinylated compounds interacted proteins were isolated with 50 μl strepavidin agarose. After 5 wash with wash buffer (50 mM Tris pH7.4, 250 mM NaCl, 5 mM EDTA, 5 mM EGTA, 0.1% NP-40, 5 mM NaF, Complete Protease Inhibitor Cocktail), strepavidin agarose was boiled with 50 μl loading buffer. The eluted protein was analyzed with western blot. The binding affinity of cordycepin against the RUVBL2 protein was measured via SPR technology using a Biacore T200 instrument (GE Healthcare) at room temperature. The RUVBL2 protein was enriched on a CM5 chip in 10 mM sodium acetate (pH 4.5) and immobilized via an amine-coupling method. The system was equilibrated with HBSP+ buffer (pH 7.4). In the association phase, serially diluted compound was injected for 120 s at a flow rate of 10 μL/min. In the dissociation phase, the buffer flowed for 180 s or 600 s. The binding kinetics and binding affinity of cordycepin against the RUVBL2 protein were determined with BIA evaluation software (GE healthcare). For co-immunoprecipitation, HEK293T cells were transfected with lipofectamine 3000 (#L3000015, Thermo Fisher) strictly following the manufacture's instruction. 2 μg or 1 μg plasmid DNA was transfected into each well of 6 well-plate (0.4 μg pCDNA3.1-FLAG-BMAL1, 0.7 μg pCDNA3.1-FLAG-CLOCK, 0.2 μg pCDNA3.1-HA-CRY1, 0.1 μg pGL3-P (Dbp): dluc and 0.6 μg pCDNA3.1-EGFP) or 12 well-plate (0.5 μg pCDNA3.1-HA-RUVBL2 and 0.5 μg pCDNA3.1-FLAG-BMAL1/CRY1/CDK9 respectively). 48 h after transfection, DMSO or cordycepin (100 μM) was added and incubated for 1 h. Cells were then harvested with IP lysis buffer (#87787, Pierce, 500 μl/300 μl for each well of 6/12 well-plate), sonicated 8 times for 30 s at 4° C. with a Diagenode bioruptor, incubated 15 min on ice, centrifuged at full speed for 10 min at 4° C. and finally supernatant was collected as cell lysate. All lysate were subjected to immunoprecipitation with FLAG (#M20018, Abmart) or HA (#M20013, Abmart) conjugated agarose at 4° C. overnight with rotation. Immunoprecipitated protein complex was then washed 3 times with IP lysis buffer, boiled and analyzed with western blot.

Tissue culture, drug treatment and Real-Time Monitoring of Circadian Oscillations: 8 week-old male mPer2 Luciferase knockin mice were Sacrificed cervical dislocation. Then wipe the skin and neck with cotton containing 70% ethanol in a sterile hood. For SCN slice culture, firstly remove the eye balls from the head with scissors, decapitate and cut the skin. Then open the skull, remove all bone until the olfactory bulbs can be seen, cut the optic nerve between the olfactory bulbs and the hemispheres, and finally harvest the whole brain into ice cold HBSS. Trim the brain in HBSS by removing the cerebellum and olfactory bulbs. Attach the brain to a sample tray by glue with the rostral tip upwards and ventral surface closest to the cutting blade, then immediately fill the tray with ice cold HBSS and set the tray to the vibratome. Set the vibratome frequency at the maximum and the speed to the medium. To reach the SCN area quickly, the start cutting off thicker sections should be 500-800 μm. Reduce the sections thicker to 100 μm when the optic chiasm becomes wider. When the two SCN nuclei start to appear, collect the slice with transfer pipettes and check slices under dissecting microscope. Finally transfer the trimmed nucleus onto the culture membrane (MILLIPORE) in a 3.5 cm culture dish with 1.2 ml xm medium, remove HBSS on the membrane, seal with high-vacuum grease (Dow Corning) and microscope cover glass, and transferred into lumicycle which was placed in an incubator (37° C.). For liver slice culture, open the body and harvest the whole liver into ice cold HBSS. Wash twice to clear the blood, trim the liver along the edge with scissors and harvest the strips into a new dish with ice cold HBSS. Make a thin slice from the strip with 2 crossed blades. Finally transfer liver slices into lumicycle as previously describe as SCN slice culture. Drug treatment of tissue slices is the same as U2OS cells as described. Culture slice was placed into LumiCycle luminometer for a further 5-7 days recording. Data was extract and analyzed with LumiCycle Analysis software.

Drug injection and in-vivo imaging analysis: mPer2Luciferase knockin mice were housed in Germ Free Animal Facility, under 12 h light/dark photoperiod, with food and water ad libitum. 8 week-old male mPer2Luciferase knockin mice were intraperitoneal injection with 15 mg/kg bw CA03 or DMSO. CA03 was firstly dissolved in DMSO to the concentration of 200 μg/μl, then dilute with saline to the final concentration of 1000 μg/ml for intraperitoneal injection. 1 h later, d-luciferin (Gold Bio.) was intraperitoneally injected. Relative luciferase activity were imaged on IVIS Lumina III system and analysed with in-vivo imaging software (PerkinElmer). Then liver was sampled for further RNA extraction and qPCR analysis of pre-mRNA level. The animal experimental procedures were approved by the Institutional Animal Care and Usage Committee (IACUC) of the National Institute of Biological Sciences, Beijing. All animal experimental procedures were performed in accordance with the protocol approved by the Institutional Animal Care and Usage Committee (IACUC) of the National Institute of Biological Sciences, Beijing.

Total RNA Extraction and pre-mRNA Analysis: Total RNA from liver was extracted 1 h after treatment of either DMSO or 15 mg/kg bw with QIAGEN Rneasy Mini Kit (74104, Qiagen), then digested with RNase-Free DNase Set (79254, Qiagen) to remove DNA residual. 500 ng total was reverse transcripted into cDNA with PrimeScript™ RT Master Mix (Takara, RR036A). To compare pre-mRNA levels, equal amount of cDNA RNA from DMSO and CA03 treated samples were analyzed using SYBR Green Master Mix (Kapa Biosystems, KP-KK4601) on a BioRad CFX96 instrument. Each gene was analyzed with multiple primers across the whole gene, and the amplification products were either intronic or across an intron-exon junction. Only primers with good melt-curve were used. For quantification, gene expression in DMSO treated sample was used as control, the relative genes expression in CA03 treated sample calculated by the comparative Ct Method.

HPLC-MASS analysis CSF: 8 W SD rats are bought from Beijing Vital River, housed in individually cage in a temperature- and humidity-controlled SPF facility, with ad libitum access to food and water. The animals were entrained under 12 h light/dark photoperiod for two weeks to synchronize the endogenous circadian clock of the mice to the ambient light-dark cycle, light intensity is about 50~100 lux. After synchronization, CA03 (15 mg/kg/BW, firstly dissolved in DMSO to the concentration of 200 μg/μl, then dilute with saline to the final concentration of 1000 μg/ml) and Pro CA03 (15 mg/kg/BW, firstly dissolved in DMSO to the concentration of 200 μg/μl, then dilute with 2% tween80 (in sterilized water) to the final concentration of 1000 μg/ml) are administrated by tail vein at CT6 (1 pm).

These animals were then anesthetized by 30% $CO_2$ and 70% $O_2$ (1 min, 5 mins or 10 mins after drug injection), laid down to let the head forms a nearly 135 angle with the body. CSF was collected by using 0.45 mm venoclysis needle from the cisterna magna. Collected CSF was then put on ice, added 4 fold volume cold methanol and votex 2 mins, centrifuged at 14,000 g 4° C. for 15 min. Metabolite-containing supernatant was transferred into a new 1.5 ml tube and put into −80° C. for 1 h, then centrifuged at 14,000 g 4° C. for 15 min. Finally, each 450 μl supernatant was collected into a new 1.5 ml tube, dried with SpeedVac and analyzed with HPLC-MASS facility.

Method: Agilent 1290-Agilent 6495 QqQ, Agilent Eclipse XDB C18 column (2.1 mm×100 mm, 1.8 μm), Mobile phase A: 10 mM ammonium acetate in water: Mobile phase B: MeCN: Flow rate: 0.3 mL/min: Gradient: 5% B (0-0.5 min), 5-25% B (0.5-5.00 min), 25-60% B (5.00-7.00 min), 60-70% B (7.00-9.00 min), 70% B (9.00-11.00 min), 70-5% B (11.00-11.10 min), 5% B (11.10-13.00 min).

All animal experimental procedures were performed in accordance with the protocol approved by the Institutional Animal Care and Usage Committee (IACUC) of the National Institute of Biological Sciences, Beijing.

Wheel running experiment: Male C57Bj/6 mice at 7 w old were purchased from the Nanjing Biomedical Research Institute of Nanjing University introduced from Jackson Laboratory, housed in individually wheel-running cage in a temperature- and humidity-controlled SPF facility, with ad libitum access to food and water. The animals were entrained under 12 h light/dark photoperiod for two weeks to synchronize the endogenous circadian clock of the mice to the ambient light-dark cycle, light intensity is about 50~100 lux. After synchronization, light-dark cycles were 8-hr phase-advanced or phase-delayed. On the day of light-dark cycle was shifted advance, mice were firstly fasted at CT 3, then 15 mg/kg bw CA03, 15 and 30 mg/kg bw pro-CA03, 15 and 30 mg/kg bw pro-CA04 or DMSO were intraperitoneal injection at CT 12, and light on time (CT 0) was shifted from 7 am to 11 pm), finally re-feed and inject drug again at CT 23 of the old light-dark cycle. CA03 and pro-CA04 were firstly dissolved in DMSO to the concentration of 200 μg/μl, then dilute with saline to the final concentration of 1000 μg/ml for intraperitoneal injection. Pro-03 was firstly dissolved in DMSO to the concentration of 200 μg/μl, then dilute with 2% tween80 (in sterilized water) to the final concentration of 1000 μg/ml for intraperitoneal injection. On the day of light-dark cycle was shifted delayed, mice were firstly fasted at ZT 3, then 15 mg/kg bw CA03, 15 and 30 mg/kg bw pro-CA03, 15 and 30 mg/kg bw pro-CA04 or DMSO were intraperitoneal injection at CT 12, and light off time (CT12) was shifted from 7 μm to 3 am), finally re-feed and inject drug again at CT 23 of the old light-dark cycle. Locomotor activity was recorded in 10-min bins wheel running (Actimetrics), and the data obtained were analysed with Clocklab software (Actimetrics). All animal experimental procedures were performed in accordance with the protocol approved by the Institutional Animal Care and Usage Committee (IACUC) of the National Institute of Biological Sciences, Beijing.

Example 1

Nucleoside Analogues Regulate the Clock-Phase.

The inventors conducted a chemical screen using the human osteosarcoma U2OS cell line so as to discover small molecules that modify the phase of the intracellular clock in mammals. In the primary screen, the inventors used two reporter lines of U2OS harboring a luciferase gene under control of either Per2 or Bmal1 promoter (named Per2-dLuc or Bmal1-dLuc cells), and set the threshold for at least 6 h phase-changes with no apparent amplitude-reduction in both cell lines. As a result, these stringent criteria filtered out most irreproducible false positives. An institutional pilot chemical library consisting of approximately 10,000 small molecules was applied in this study. Strikingly, the inventors observed an anti-phasic phenotype that completely reverts the expression pattern of both clock genes as real-timely monitored. The hit compound, named cordycepin (i.e., 3'-deoxyadenosine), sharply and quickly changes the course of Per2-dLuc when applied along with medium change, while the Bmal1-dLuc reporter showed difference till 12 h later. The inventors set to allow a free-run of the clock before administration of the compound over the course in order to eliminate the possibility that this phase-changing phenomenon was due to a combinative phenotype of medium-change plus the compound effect. The inventors found that only when application of the drug at the time of Per2-dLuc peak, but not at the trough, did the oscillation display drastic phase changes. Also, the Bmal1-dLuc reporter showed phase-alteration when the drug was administrated at the trough time (corresponding to Per2-dLuc at the peak), but the overall course did not occur any changes until 12 h later, when a double-shoulder appeared and thus reversed the course for a half cycle. Therefore, the primary response of the phase reversal was due to its change in the Per2, followed by Bmal1 and other clock genes (FIG. 1A).

Figure 1E:
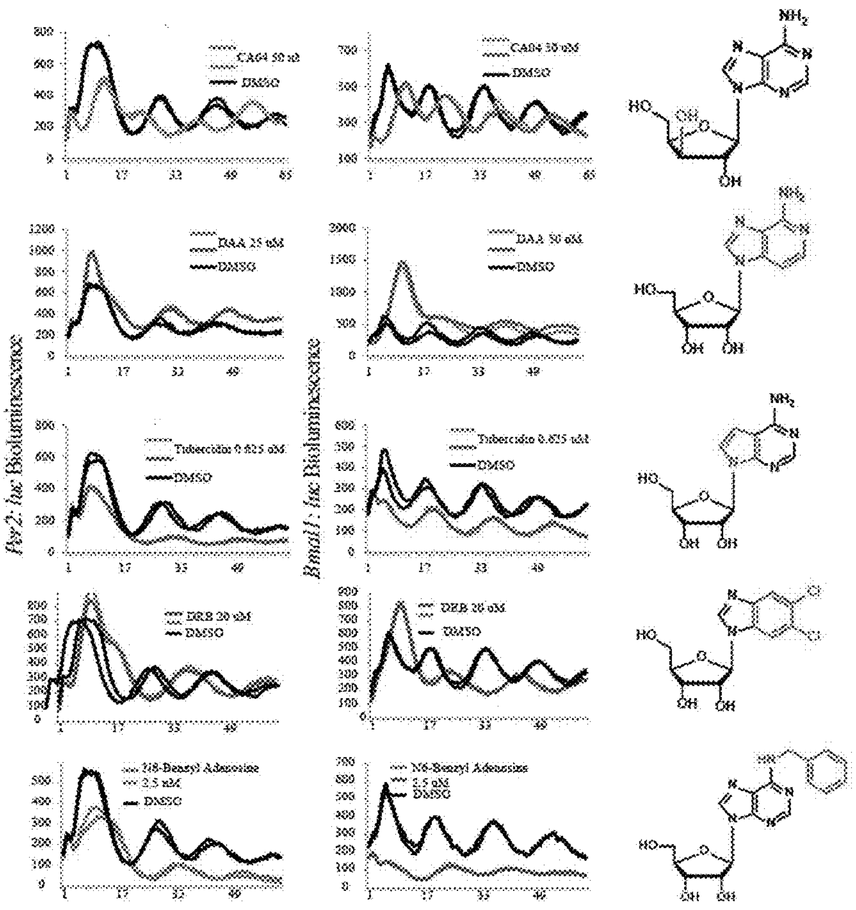
Figure 1F:
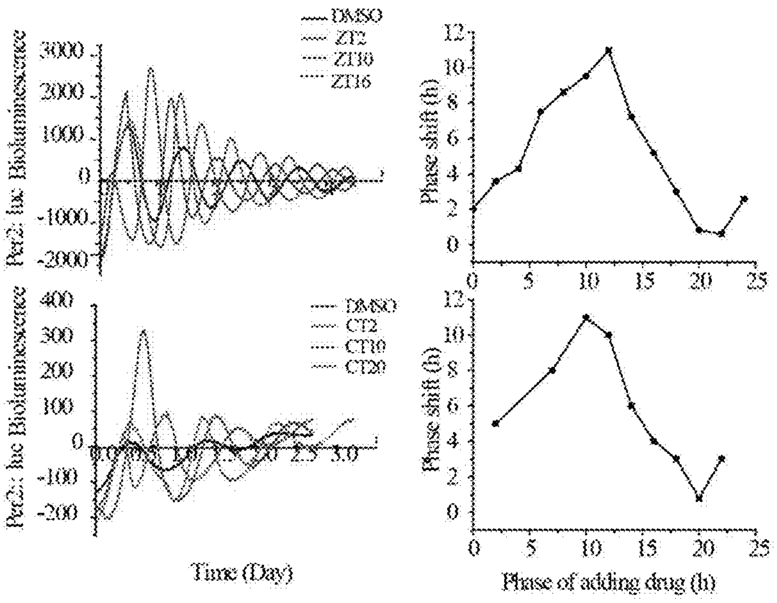
Figure 1G:
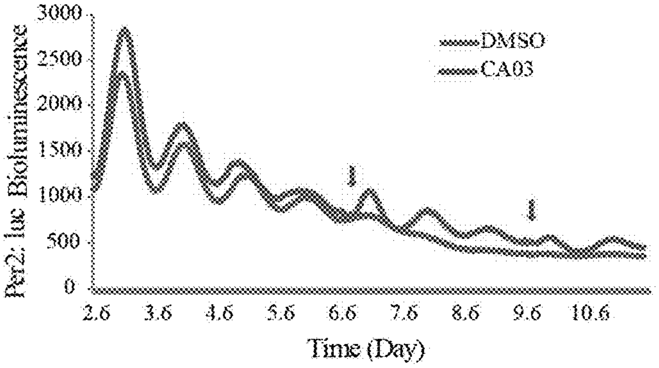

Cordycepin has obvious phase dependent effect on circadian clock, that is shifting 12 h of the Per2-dLuc phase when applied at Per2 peak while 0 h when applied at Per2 trough. Importantly, cordycepin can increase the amplitude of Per2-dLuc when applied at Per2 trough, which makes circadian clock more robust (FIG. 1F, and FIG. 1G).

3-deazaadenosine(DAA), 7-deazaadenosine(Tubercidin), N6-Benzyl Adenosine, 5,6-dichlorobenzimidazone-1-β-D-ribofuranoside(DRB), and a modified analog 3'-(R)-adenosine, are also each able to change the course of Per2-dLuc in an up to 12 h phase change manner. (FIG. 1E)

Over-dosing the system with excessive amount of regular adenosine would completely prevent the clock from these analogs-induced phase-shifting, indicating that the mechanism is unlikely due to activate the signal transduction from adenosine receptors that locate on the plasma membrane; but rather from affecting certain adenosine function(s) inside of the cell, as excessive regular adenosine in the extracellular medium could saturate adenosine-transporters, and thus prevent these analogs from entering into cells to make effects. Blocking adenosine transporter abolished cordycepin induced phase-shifting and cell entry, but not adenosine receptor inhibitor. Moreover, the inventors determined that the adenosine-deaminase inhibitor Pentostatin can substantially improve the potencies of cordycepin, 3'-(R)-adenosine, and several other cordycepin analogues, even though Pentostatin itself does not affect the clock at all (FIG. 1C). Together, these results reveal an important role of adenosine derivatives in modifying the clock-phase.

Figure 1H:
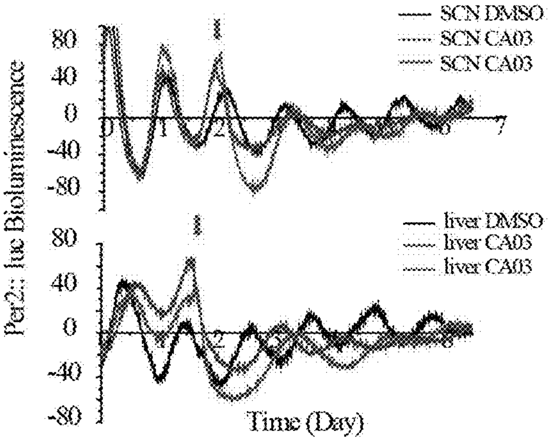

The inventors further examined cordycepin's impact on tissue clocks. Convincingly, this phase-shifting phenotype appears to be common, as tissue explants for ex vivo culture, such as the liver, from Per2::LUC knockin mice, all showed similar results. Importantly, the brain slices containing the clock master organ, suprachiasmatic nuclei (SCN), also respond to the drug treatment, generating a significant phase-shift with lower amplitude (FIG. 1H).

Figure 4:
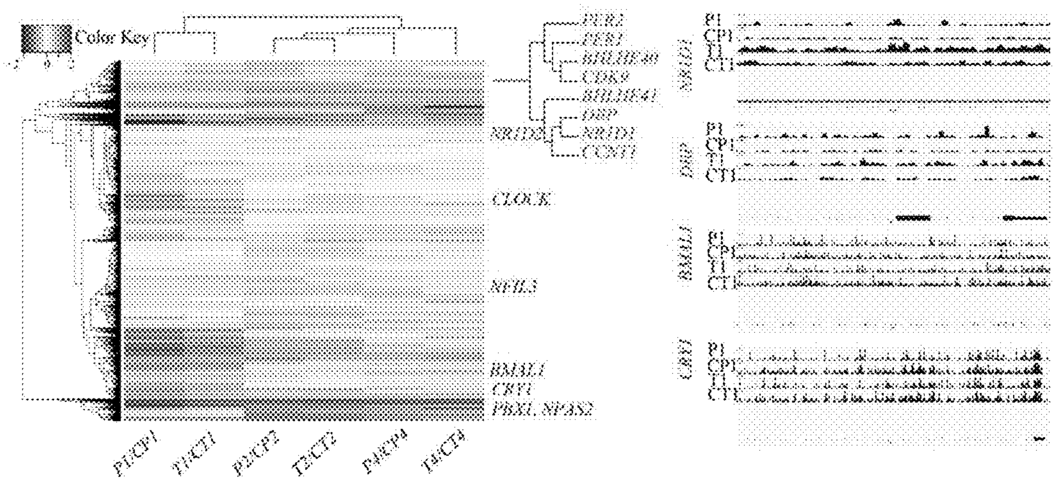
FIG. 4 shows rapid induction of E-box gene transcription by DRB.

5,6-dichlorobenzimidazone-1-β-D-ribofuranoside (DRB), another circadian phase shifter identified from chemical screen, has similar phase shift properties compared with cordycepin, and can also shift the phase of SCN and kidney clocks. Manipulating DRB's well characterized target CDK9 protein with AID degron mimics the phase shift curve of DRB in Per2-dLuc cells. This result shows CDK9 directly participating circadian phase regulation. Using nascent seq experiment, we found DRB treatment repress majority genes expression, but exclusively activates E-box containing gene both in vitro (FIG. 4).

Next, the inventors sought to determine whether the clock effects of cordycepin can be recaptured in vivo. Since above the investigation showed that DRB can activate the expression of E-box genes, we applied a live imaging system to visualize the induction of Per2::Luc in the knockin mice. Mice were intraperitoneally (i.p.) injected with the cordycepin at ZT4 (ZT, zeitgeber time; ZT0 starts light-on, and ZT12 begins light-off). Our results indicate the luciferase signal was induced as early as within 1 h after the drug administration, indicating that Per2 be induced. To confirm that the Per2 gene was indeed upregulated, we conducted a qPCR assay to measure all the core clock genes. We found that most E-box containing clock genes including Per1, Per2, Dbp, and Nr1d1, were up-regulated, while non-E-box containing clock genes such as Bmal1, as well as housekeeping genes, were either unchanged or down-regulated. This observation is especially true when nascent RNA levels were measured, highlighting the first-order, inductive response in E-box genes as previously proposed(FIG. 2B).

Figure 3D:
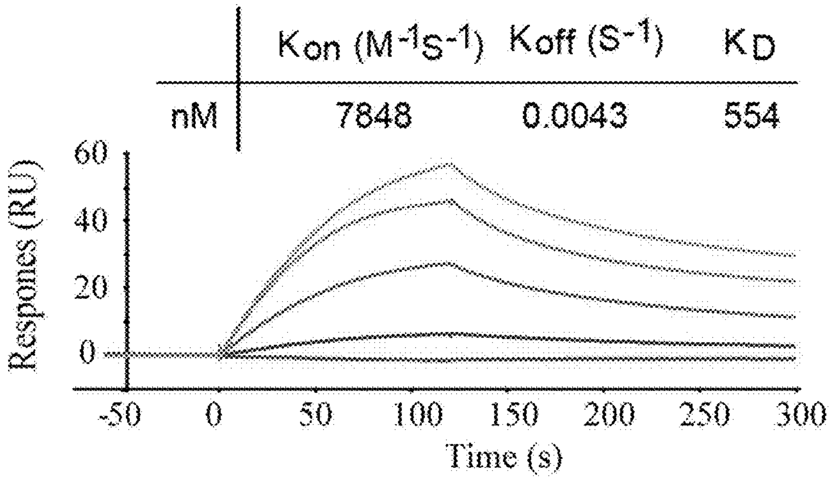
FIG. 3 shows that Ruvbl2 as the cordycepin target that shifts the clock phase.

To further understand which protein(s) may mediate the impact of cordycepin to the phase, we applied a chemical-genetic approach to investigate the gene mediating the Per2-dLuc induction by cordycepin. We reasoned that the transcriptional regulation plays a major role in this event, therefore, we applied siRNA libraries containing 1529 transcription factors and 463 epigenetic factors and to evaluate which gene(s) are responsible for the cordycepin induced Per2-dLuc activation. We found that knockdown about 17 genes could specifically abolish the induction of Per2-dLuc by applying cordycepin, including DNA helicase genes, RUVBL1 and RUVBL2. Knocking down RUVBL2 abolished cordycepin induced phase shift. To investigate the physical interaction between cordycepin and RUVBL proteins, we conducted a pull-down assay using biotinylated-cordycepin in U2OS cell lysate. In the absence of free cordycepin compound, the biotinylated drug was able to pull down RUVBL2 protein; in the presence of the free compound, however, the interaction was competed out. The direct interaction of cordycepin and RUVBL2 protein is confirmed by Biacore T200. Together, these data demonstrate that RUVBL helicases are direct targets of cordycepin, and mediating its induction of Per2-dLuc and clock effects (FIG. 3C&D).

Another helicase gene, FRH, is a possible core clock component in Neurospora, {Cheng, 2005}, and we sought to determine whether RUVBL genes may also be clock components in mammalian systems. Knockdown of either RUVBL1 or RUVBL2 gives rise to disruption of the clock, indicating that they are required for the proper clock function in U2OS cells. We subsequently performed a transient luciferase assay {Sato, 2006}, and demonstrated that both genes are sufficient to modify CLOCK:BMAL1 function, especially in the presence of CRY inhibitors. Thus, these helicases can impact the clock. Very often, clock genes can be reversely regulated by the clock itself, meaning that their expression patterns are rhythmic in vivo {Hughes, 2009}.

Figure 5:
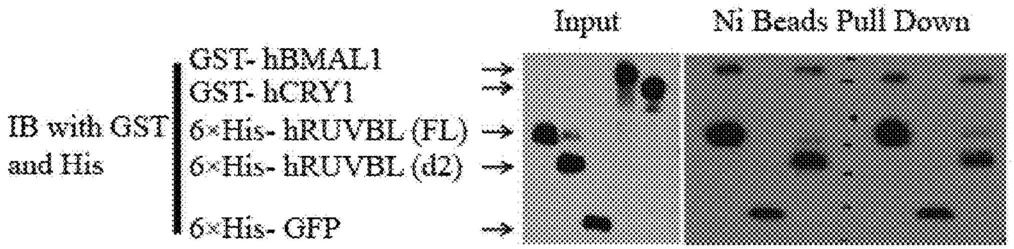
FIG. 5 shows that Ruvbl2 directly interacts with Bmal1 and Cry1.

Furthermore, we demonstrated that RUVBL2 can be co-immunoprecipitated with known clock proteins Bmal1, Clock, and Cry1, and also known transcription elongation regulator CDK9. This interaction appears to be direct for at least in between Bmal1 and RUVBL2, as they both can be mutually and specifically pull-down each other at the purified protein level (FIG. 5).

Figure 6:
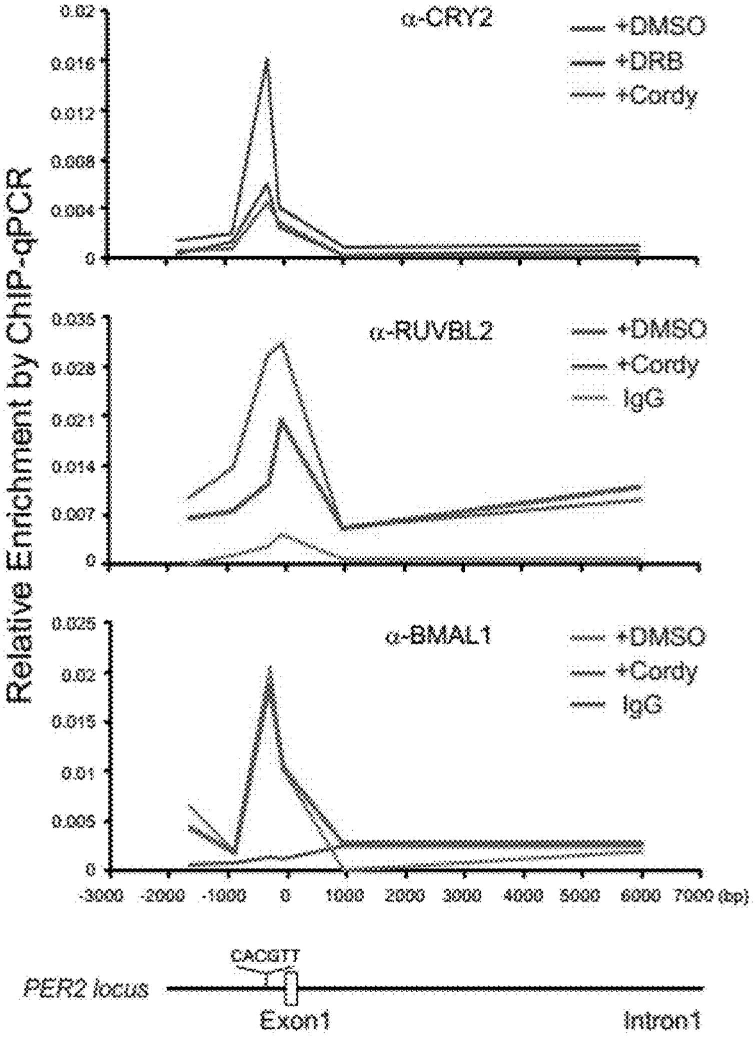
FIG. 6 shows that Cordycepin disrupt Cry2 and RUVBL2 biding with Per2 locus.
Figure 7B:
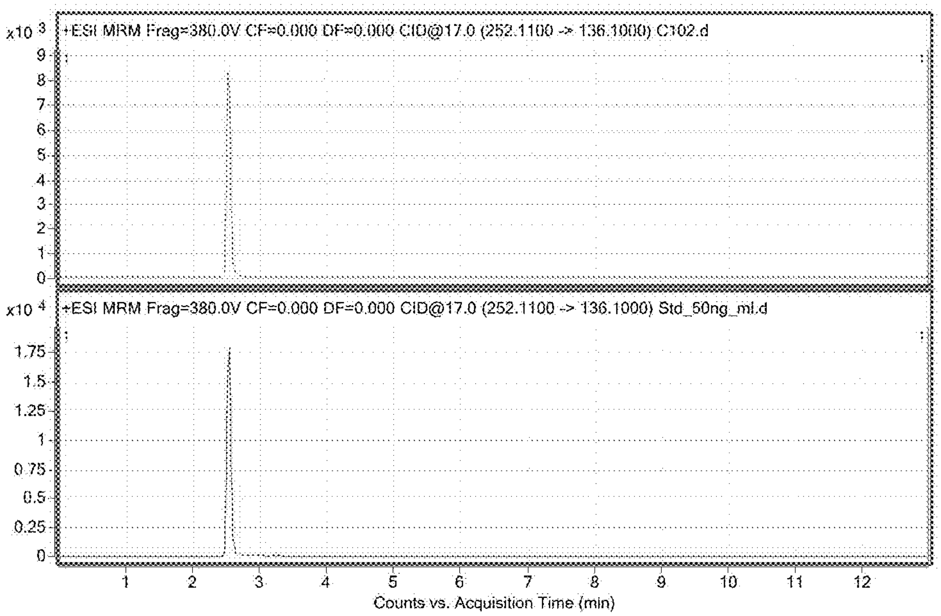
FIG. 7 shows the cordycepin concentration in cerebrospinal fluid (CSF) after the intraperitoneal (I.P.) injection with Pentobarbital as positive control.
Figure 7B:
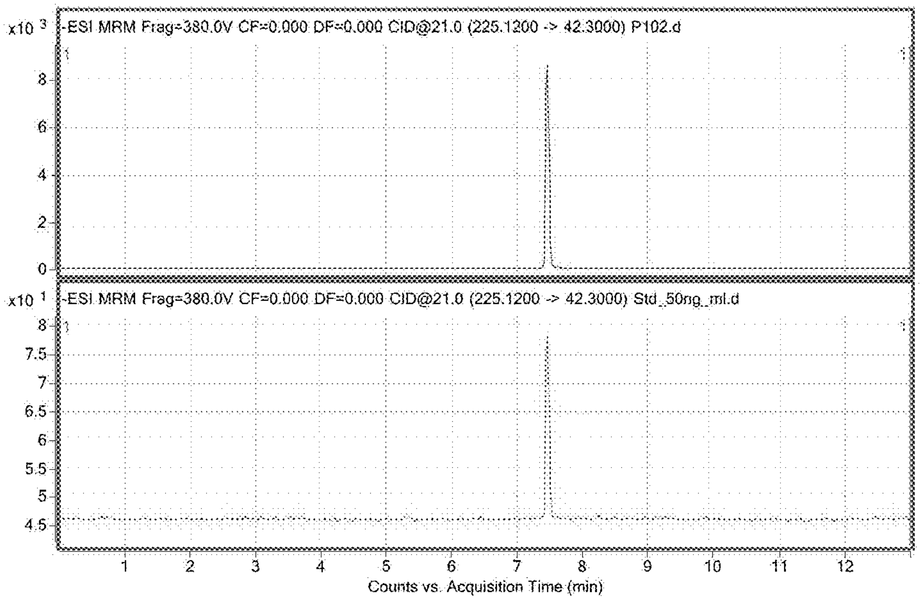
Figure 7C:
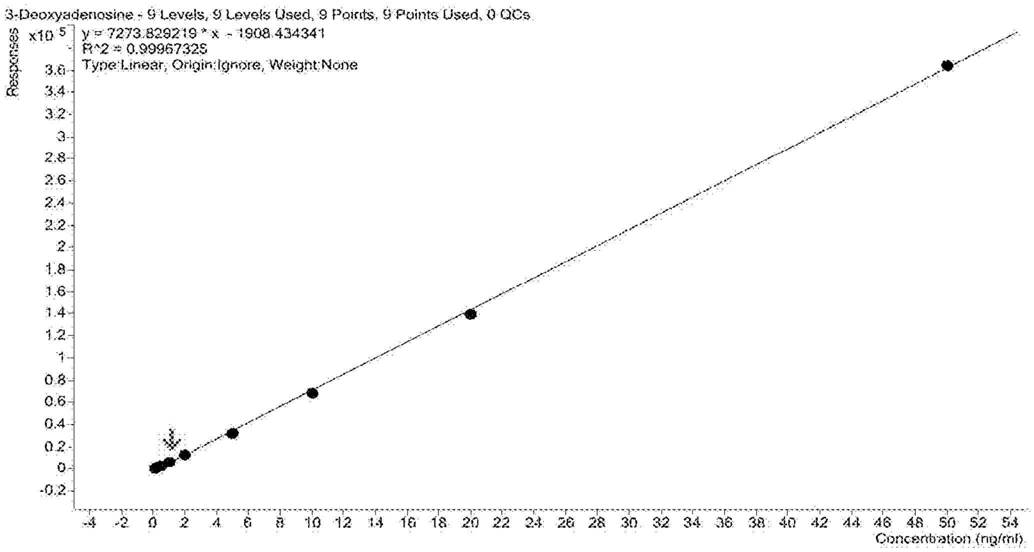
Figure 7C:
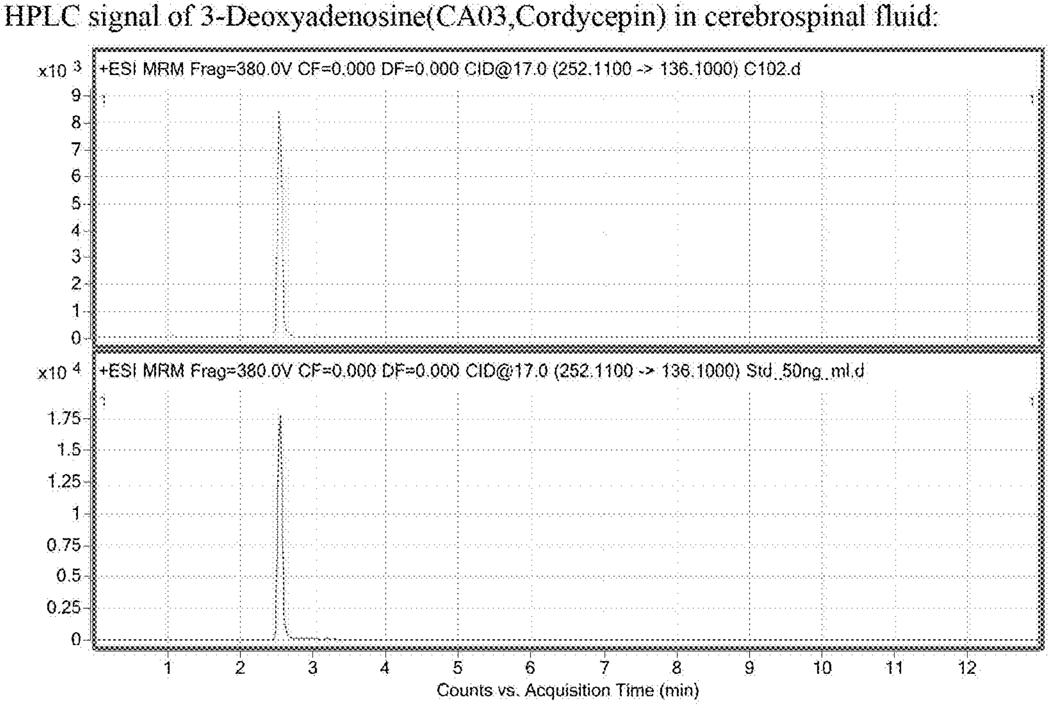

Human and mouse circadian oscillators are driven by interlocked transcriptional and translational feedback loop. Bmal1 and Clock are transcriptional factors and function as positive arm to active negative arm genes transcription, including Per and Cry. Per and Cry are transcriptional repressor and feedback repress Bmal1/Clock's transcription activity thereby inhibit its own transcription. Using co-immunoprecipitation experiment, we show that Cordycepin disassociates the interaction between Bmal1 and Ruvbl2/Cry complex, thereby de-repress Cry's inhibition and activating Bmal1/Clock transcription activity. We also confirmed this by ChIP-qPCR experiments. Cordycepin treatment 30 min immediately release Cry1/2 and Ruvbl2 binding at Per2 gene promoter. Taken together, these data demonstrate that cordycepin release Cry/Ruvbl2 repression complex from Per2 promoter, activating Per2 transcription, and then inducing circadian phase shift (FIG. 6).

We measured the cordycepin concentration in cerebrospinal fluid (CSF) after the intraperitoneal (I.P.) injection. Cordycepin can be detected in the CSF within 15 min after the injection, which indicates that cordycepin is able to penetrate into the brain.

Figure 2D:
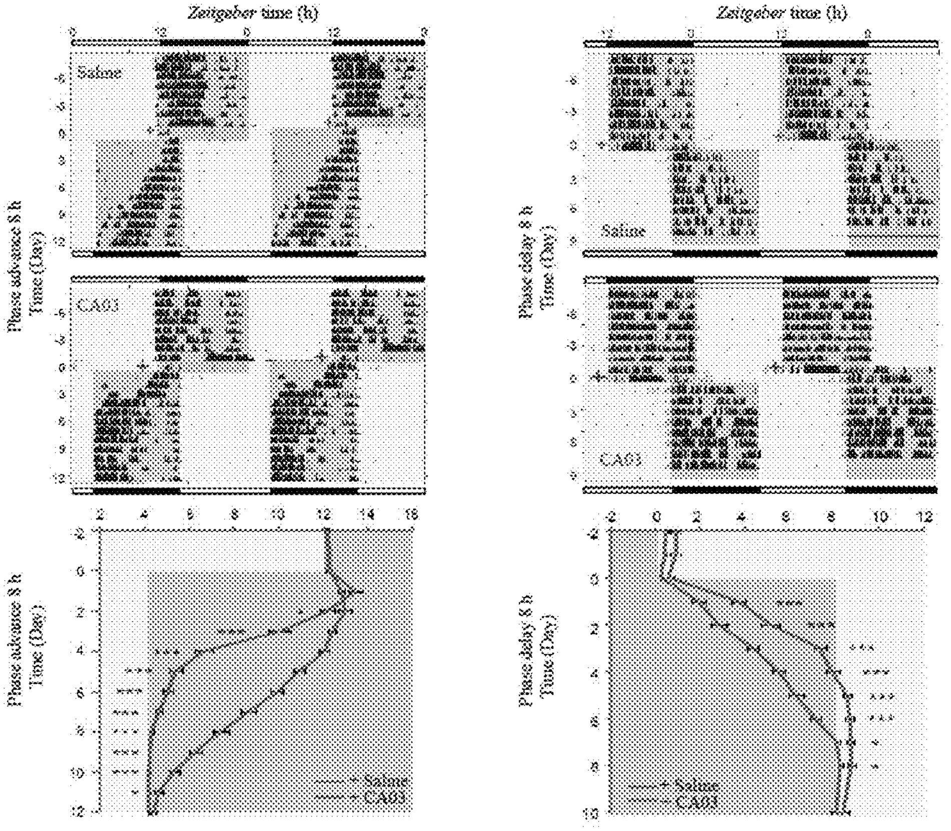
FIG. 2 shows that cordycepin induces Per2 expression in vivo and regulates the clock-phase behavior in mice.
Figure 2E:
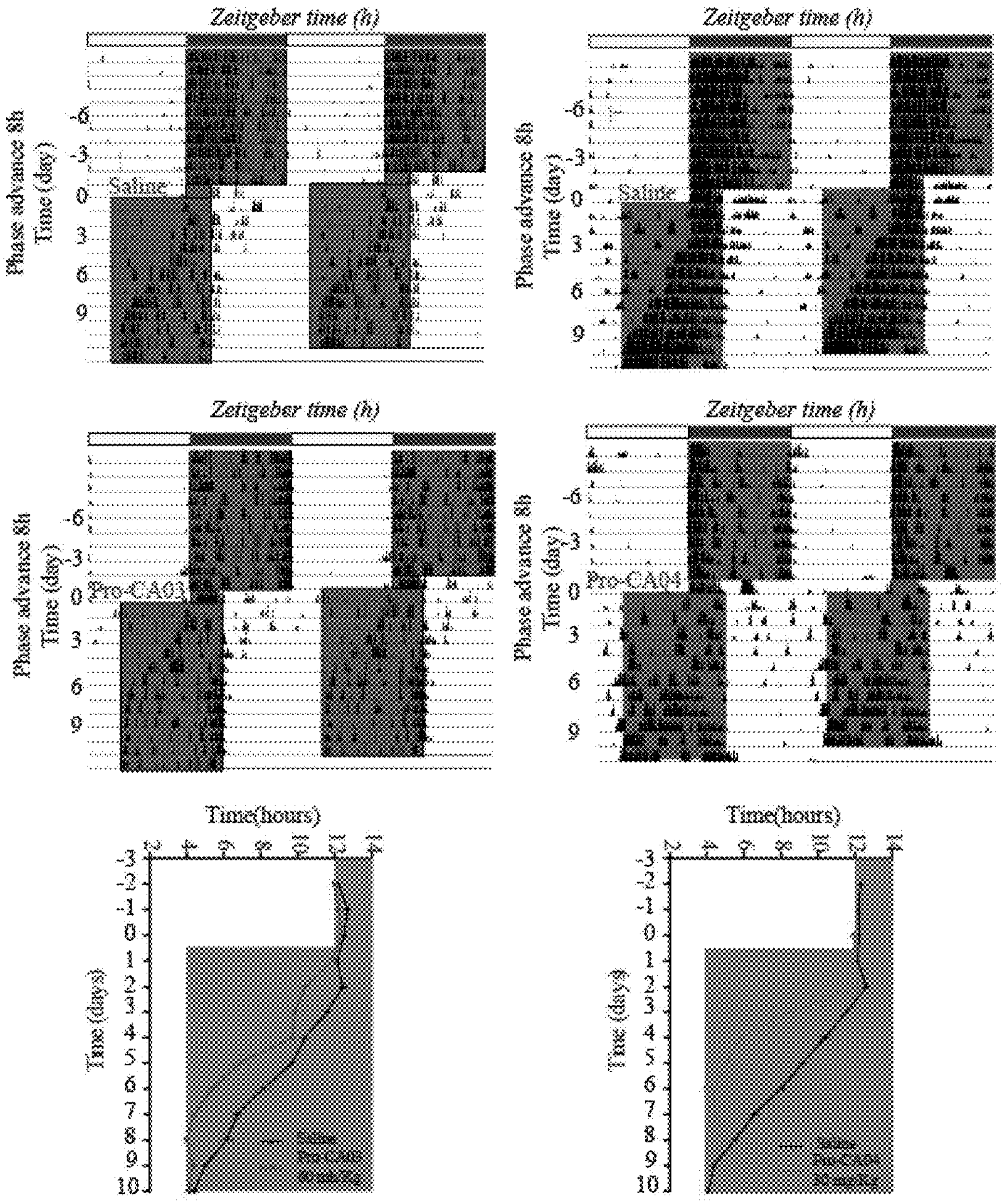

Under a standard jet-lag protocol {Yamaguchi, 2013}, wild-type C57BL/6j mice usually take ~10 d to adapt to 8 h phase advance. With twice injection of the cordycepin ($P<0.001$, n=18 per group) or prodrug ($P<0.001$, n=3 per group) in the first two consecutive days, however, the adaptation significantly shorten to only 4 d. Similarly, the drug treated mice adapt faster to the phase delay (FIG. 2D&2E).

The administration of cordycepin also leads to a sleep phenotype, as evaluated by the locomoter activity and electrophysiological recording. This is considered as a positive side-effect to adapt to jet-lag, which causes more problems on the sleep than arousal side. The adenosine receptors A1 and A2A play central roles in mediating the sleep, and a well-characterized A2A antagonist caffeine can completely abolish this induction of sleepiness {Huang, 2005}, meaning that our drugs and caffeine use the same signaling pathway to adjust the sleep-arousal balance in the brain. However, caffeine itself cannot alter the intracellular clock-phase even in extremely high dose, indicating that the phase-changing mechanism of our drugs is not through adenosine receptors. This work provide immediate and important practical applications, including use the disclosed compounds to assist humans who suffer jet-lag or shift-work can use this drug to adjust the clock-phase, and simultaneously tune the sleep-wake pattern, particularly coupled with caffeine ingestion.

FIG. 1 shows that adenosine-like compound cordycepin resets the clock-phase. Circadian clock is a transcriptional based feedback loop, however different clock genes contain different cis-element and may show different response to the same stimulation. Upon cordycepin (100 μM) treatment at Per2 peak (that is Per2:luc peak and Bmal1:luc trough), Per2:luc and Bmal1:luc show different response. Cordycepin affects the kinetics of Per2:luc more quicker than that of Bmal1:luc in human osteosarcoma U2OS cells (A). This indicated Per2 is the first response gene and introduce the effect of cordycepin into TTFL and elicit phase shift. Since the close similar structure with adenosine and potential function of inhibiting transcription by preventing mRNA elongation, we tested whether adenosine and other deoxy-nucleoside could shift circadian phase. The results showed that cordycepin is a specific derivative of adenosine to affect the clock-phase. Cordycepin, but not the regular adenosine, induces 12 h phase-shift in U2OS cells when applied at Per2:luc peak (A). Note, excessive amount of adenosine inhibits the phase effect induced by cordycepin (A), which indicate cordycepin can utilizing adenosine metabolism pathway. Therefore we further tested whether cordycepin utilize adenosine transporter to enter cell or utilize adenosine deaminase to degrade. When combining 100 μM cordycepin with adenosine transporter inhibitor (10 μM) or with adenosine receptor inhibitor (1 μM 5-lodotubercidin), only blocking adenosine transporter inhibitor abolished cordycepin induced phase shift ability (B. Adenosine deaminase pentostatin (5 μg/ml) does not affect the clock phase, substantially improve the potencies of cordycepin (from 25 μM to 0.18 μM)(C). Compared with cordycepin, other modified nucleosides are not able to induce the phase effect when applied at Per2:luc peak (D). Besides cordycepin, we also synthesized and purchased few cordycepin-like nucleosides which can shift circadian phase, including (3'R)-adenosine, 3-deazaadenosine (or DAA), 7-deazaadenosine (or Tubercidin) (E).

In above investigation, we found cordycepin (cordycepin-like nucleosides) shift the circadian phase, therefore it could be seemed as a circadian time giver (zeitgeiber). One prominent character of zeitgeiber is phase dependent function. Therefore, we further tested whether cordycepin also has the character. We use both transcriptional reporter (Per2:luc U2OS cells) translational reporter (Per2::LUC adult murine fibroblasts) model to investigate this character. The two reporter were seeded in 3.5 cm dish, transferred into lumicycle, and treated with cordycepin (100 μM in Per2:luc U2OS cells and 25 μM in Per2::LUC adult murine fibroblasts) every 2 hours from CT 0 to CT 24. 3 days after treatment and data analysis, we found in both reporter cells, cordycepin show highly "time-of-admission" dependent phase-change, 12 h phase shift when applied at CT10 and nearly 0 h phase shift when applied at CT 20 (F). Interestingly, we noted that although there is 0 h phase shift when applied cordycepin at CT20, the amplitude was increased, which indicated cordycepin could enhance the circadian oscillator and pharmaceutical potentially usage for aged people with cripple clock. To test this, we treated nearly damped Per2::LUC adult murine fibroblasts at CT 20 with DMSO or 25 μM cordycepin. We found cordycepin surely increase the amplitude and sustain the clock robust running (G).

We further tested whether cordycepin can shift the clock phase in ex vivo cultures from Per2::LUC mice. We select liver culture slice as peripheral clock reporter and SCN culture slice as central clock reporter. When applied cordycepin (100 μM) at Per2::LUC peak, both reporter curves were immediately go down for 10 h and then gradually rebound and show a nearly 30 h period oscillation, then back to 24 h period and totally antiphase with DMSO treated slices (H).

FIG. 2 shows that cordycepin induces Per2 expression in vivo and regulates the clock-phase behavior in mice. To test whether cordycepin function in vivo, we firstly tested luciferase signal level by live imaging of Per2:LUC mice after intraperitoneal injection of 15 mg/kg cordycepin or DMSO. We found cordycepin induce more than 4 folds increase of luciferase signal in liver when compared with DMSO control (A). This result shows that cordycepin could function in vivo and stimulate Per2 gene transcription. We also reconfirmed endogenous transcription rate of core clock genes by measuring the pre-mRNA with qPCR in the liver (B). We examined RRE genes (including Bmal1, Clock, Npas2, Cry1 and Nfil3), internal control genes (including Gapdh, Tbp and Actin) and E-box genes (including Per1, Per2, Dbp and Nr1d1). We designed at least 2 primers for each gene. The results showed that cordycepin treatment repress RRE gene and internal control gene transcription, but specifically activate E-box gene transcription, especially for Per2 gene. Prior evaluation the jet-leg cure ability of cordycepin, we detected whether cordycepin and it's prodrug pro-CA03 can penetrate BBB. We injected cordycepin or pro-CA03 via tail vein and time course sampled CSF and analyzed cordycepin pro-CA03 level with HPLC-MASS method. The result clearly showed that after tail vein injection, cordycepin and pro-CA03 immediately penetrated BBB and go into CSF, reached to the peak concentration 1 min after injection and gradually degraded. Note that pro-CA03 is more stable than cordycepin (C). Finally we evaluated the jet-leg cure ability of cordycepin, pro-CA03 and Pro-CA04 with mice behavioral experiment. Wild-type C57BL/6j mice typically take ~10 days to adapt to an 8 h phase advance. Encouragingly, this adaption time was shortened to only 4 d when a cordycepin injection was administered ($P<0.001$, n=18 per group) (D, left panel). Similarly, the cordycepin-treated mice were able to adapt significantly faster to a phase-delay assay, from 6 days in DMSO treated group to 3 days in cordycepin treated group ($P<0.001$, n=12 per group) (D, right panel). Pro-CA03 slightly shortened the adaption time than control group (E, left panel). Pro-CA04 has comparable jet-leg cure ability as cordycepin, which shorted the adaption time from 10 days in DMSO treated group to nearly 5 days after 8 phase advance (FIG. 2E, right panel).

Figure 3E:
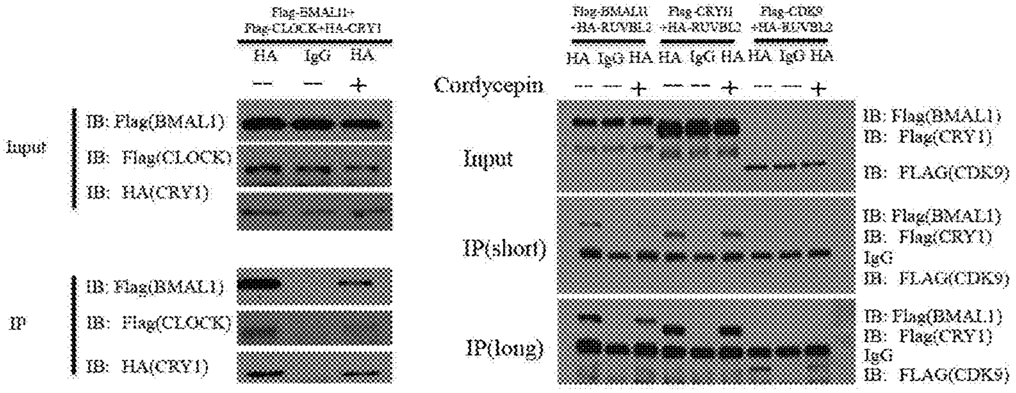

FIG. 3 shows that Ruvbl2 as the cordycepin target that shifts the clock phase: Since cordycepin activates Per2:luc signal, we used a chemical-genetics screen approach to identify possible target proteins for cordycepin. We found upon Ruvbl2 knockdown, cordycepin mediated Per2:luc induction and phase shift were abolished (A), which indicates that Ruvbl2 mediate the Per2:luc induction and phase shift function of cordycepin. Considering Ruvbl2 is a ATP dependent helicase and the structure similarity of cordycepin with ATP, Ruvbl2 maybe the direct target of cordycepin. We next use biotinylated compounds pull-down and SPR experiment to confirm this assumption. DRB, a well known inhibitor of CDK9, can also elicit nearly 12 h phase shift. To confirm DRB induces phase shift though inhibiting CDK9, we introduced AID tagged CDK9 (CDK9-AID) into Per2:luc U2OS cells to regulate it protein level. When suddenly degrading CDK9 protein with indole-3-acetic acid at Per2:luc peak, the phase was shifted for nearly 10 h (B). These results show that CDK9 directly regulates circadian phase. Using biotin-DRB as a positive control, we successfully isolated CDK9 and this binding can be competed with biotin free DRB. As we suspected, Ruvbl2 can be purified with biotin-cordycepin and this binding could also be competed with biotin free cordycepin (C).Note that biotin-DRB can pull-down Ruvbl2 and biotin-cordycepin can pull-down CDK9, which indicates Ruvbl2 and CDK9 may in a same complex. We further confirmed the direct binding of Ruvbl2 and cordycepin with SPR assay. The purified RUVBL2 protein binds to the cordycepin molecule with a $K_d$ value of about 500 nM (D). Because Ruvbl2 is essential for cordycepin induced of Per2 gene up-regulation, we next investigated the interaction between core clock protein and Ruvbl2.

Using co-immunoprecipitation we found Ruvbl2 interact with Bmal1, Cry1 and CDK9 (E). The interaction between Ruvbl2 and Bmal1, or Cry1 with Bmal1 can be disassociated by 100 μM cordycepin, while the interaction between Ruvbl2 with Cry1 or CDK9 is not disassociated by cordycepin (E). Taken together, these data show that Ruvbl2 is the direct target of cordycepin. Cordycepin induced phase shift and Per2 gene up-regulation by regulating the protein-protein between Ruvbl2, Bmal1, Cry1 and CDK9.

FIG. 4 shows rapid induction of E-box gene transcription by DRB: DRB treatment time series analysis of nascent pre-mRNA sequencing (nascent-seq) of U2OS cells to identify "first-order" DRB-responsive genes. We monitored Per2-dLuc expression in real-time in the course of our experiments and adjusted the administration times of DRB to coincide with the peaks and troughs of Per2-dLuc expression; we then sampled the cultures at 1, 2, and 4 h post-DRB administration, and analyzed with nascent-seq (left panel). we found that the amount of newly synthesized mRNA for the majority of the genes expressed in DRB-treated cells was reduced within the first hour of drug treatment (blue color). Strikingly, the seven best-studied genes with E-box signatures were all up-regulated following DRB treatment, and six of these E-box genes (NR1D1, DBP, BHLHE41, BHLHE40, PER1, and PER2, not NR1D2) were clustered in a group, reflecting the commonality of their responses to treatment at six different time. (red color). Examination of the other genes in the cluster that contained the E-box genes revealed that it also contained CDK9 itself and its binding partner CCNT1. Thus, perhaps the partial inhibition of CDK9 stimulates, rather than represses, the transcription of E-box genes. Right napel is UCSC genome browser views of E-box containing (NR1D1 and DBP) or non-E-box containing (BMAL1 and CRY1) clock genes FIG. 5 shows that Ruvbl2 directly interacts with Bmal1 and Cry1: In vitro expressed RUVBL2 proteins can be pulled down by the pure BMAL1 protein. FL: full-length; d2: Domain 2 (the regulatory domain for helicase activity) deletion of RUVBL2 protein.

FIG. 6 shows that Cordycepin disrupt Cry2 and RUVBL2 biding with Per2 locus: ChIP-qPCR analysis for the PER2 locus showed that the binding of CRY2/RUVBL2 was released by treatment with either DRB or cordycepin, while the binding of BMAL1 remained unchanged.

FIG. 7 shows the cordycepin concentration in cerebrospinal fluid (CSF) after the intraperitoneal (I.P.) injection with Pentobarbital as positive control. The standard concentration curve of both Cordycepin and Pentobarbital were shown in FIG. 7A, the retention time of cordycepin is compared with the Pentobarbital retention time in HPLC analysis were showed in FIG. 7B. Cordycepin can be quantitatively and qualitatively detected in the CSF within 15 min after the injection (FIG. 7C), which indicates that cordycepin is able to penetrate into the brain.

Example 2 the Synthesis of the Typical Compounds

Methods, Reagents and Bioactivity Data.

Chemical synthesis: All reactions were carried out under an inert atmosphere of nitrogen or argon unless otherwise noted. DMF, DMSO (99.9%, extra dry) was used as received. All other reagents were purchased commercially and used as received, unless otherwise noted. NMR spectra were recorded with Bruker spectrometers. 1H (400 MHz) and NMR chemical shifts are reported relative to internal TMS (δ=0.00 ppm) or to residual protiated solvent. Data are presented as follows: chemical shift (ppm), multiplicity (s=singlet, d=doublet, t=triplet, q=quartet, sept=septet, m=multiplet, br=broad), coupling constant J (Hz) and integration.

The number of the compounds corresponds to the number in Table 1.

Synthesis of Compound 1:

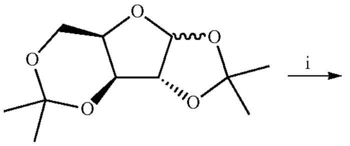

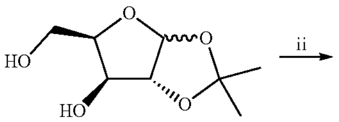

Intermediate 1

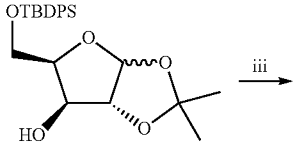

Intermediate 2

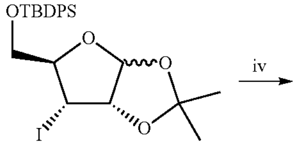

Intermediate 3

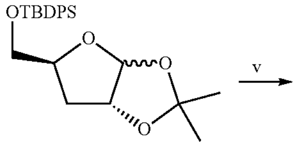

Intermediate 4

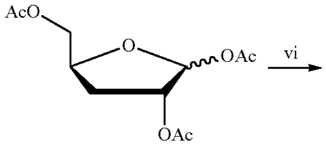

Intermediate 5

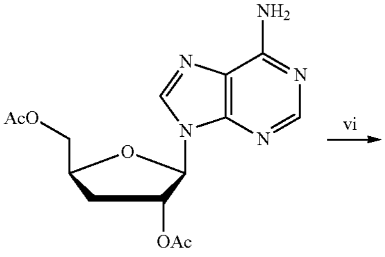

Intermediate 6

-continued

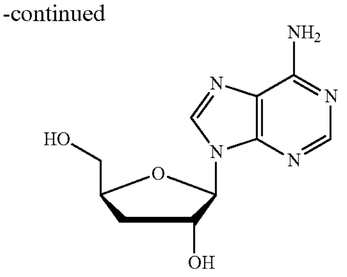

Compound 1

Conditions: i) 0.2% HCl; ii) TBDPSCl, DMAP, pyridine; iii) imidazole, iodine, triphenylphosphine, toluene; iv) $H_2$, Pd/C, triethylamine, ethyl acetate, methanol; v) acetic acid, acetic anhydride, conc. $H_2SO_4$; vi) adenine, N, O-bis(trimethylsilyl) acetamide, TMSOTf, acetontrile; vii) $K_2CO_3$, methanol, water.

Conditions: i) 0.2% HCl; ii) TBDPSCl, DMAP, pyridine; iii) imidazole, iodine, triphenylphosphine, toluene; iv) $H_2$, Pd/C, triethylamine, ethyl acetate, methanol; v) acetic acid, acetic anhydride, conc. $H_2SO_4$; vi) adenine, N,O-bis(trimethylsilyl) acetamide, TMSOTf, acetonitrile; vii) $K_2CO_3$, methanol, water.

Step 1: Synthesis of 1,2-O-isopropylidene-D-xylofuranose (Intermediate 1)[1]

A suspension of 1,2:3,5-di-O-isopropylidene-D-xylofuranose (16.00 g, 69.49 mmol) in 0.2% HCl (200 mL) was stirred at room temperature for 6 h followed by the addition of sodium bicarbonate to adjust the pH value to 8, the solvent was evaporated under reduced pressure and the residue was suspended in water (150 mL) and extracted with dichloromethane (150 mL×5), dried over $MgSO_4$ and concentrated to obtain 1,2-O-isopropylidene-D-xylofuranose as a colorless oil (12.25 g, yield 92.69%). Mass spectrum (ESI) m/z calc. for $C_8H_{14}O_5$ $[M+H]^+$ 191.08. found 191.56. $^1H$ NMR (400 MHz, $CDCl_3$) δ (ppm) 5.99 (d, 1H, J=3.6 Hz), 4.53 (d, 1H, J=3.6 Hz), 4.32-4.35 (m, 1H), 4.53 (d, 1H, J'3.6 Hz), 4.14-4.18 (m, 2H), 3.99-4.08 (m, 2H), 2.60 (br s, 1H), 1.73 (br s, 1H), 1.49 (s, 3H), 1.32 (s, 3H).

Step 2: Synthesis of 1,2-O-isopropylidene-5-[(tert-butyl)-diphenylsilyl]-D-xylofuranose (Intermediate 2)

To a solution of 1,2-O-isopropylidene-D-xylofuranose (12.25 g, 64.41 mmol) in dry pyridine (250 mL), TBDPSCl (20.04 mL, 77.29 mmol) was added dropwise at room temperature. The mixture was heated to 40° C. and stirred for 5 h before $H_2O$ (5 mL) was added to quench the reaction, the mixture was filtered and the filtrate was concentrated under reduced pressure, the residue was suspended in dichloromethane (200 mL), washed with $H_2O$ (200 mL) and 5% aqueous $CuSO_4$ (200 mL) and brine (200 mL) respectively, dried over $MgSO_4$, concentrated and the residue was subject to column chromatography (silica gel, petroleum ether/ethyl acetate=9:1 to 1:1) to obtain 1,2-O-isopropylidene-5-[(tert-butyl)-diphenylsilyl]-D-xylofuranose as a pale yellow oil (23.77 g, yield 86.11%). Mass spectrum (ESI) m/z calc. for $C_{24}H_{32}O_5Si[M-H]^-$ 427.60. found 427.75. $^1H$ NMR (400 MHz, $CDCl_3$) δ (ppm) 7.66-7.73 (m, 4H), 7.39-7.45 (m, 6H), 6.01 (d, 1H, J=3.6 Hz), 4.55 (d, 1H, J=3.6 Hz), 4.37 (m, 1H), 4.10-4.13 (m, 2H), 4.01 (d, 1H, J=3.2 Hz), 1.47 (s, 3H), 1.33 (s, 3H), 1.05 (s, 9H).

Step 3: Synthesis of 3-deoxy-3-iodo-1,2-O-isopropylidene-5-[(tert-butyl)-diphenylsilyl]-D-ribofuranose (Intermediate 3)

A solution of 1,2-O-isopropylidene-5-[(tert-butyl)-diphenylsilyl]-D-xylofuranose (23.77 g, 55.46 mmol) in absolute toluene (500 mL) was treated with imidazole (7.55 g, 110.92 mmol) and triphenylphosphine (29.09 g, 110.9 mmol) respectively, afterwards, iodine (21.11 g, 83.19 mmol) was added in five portions at 0° C., then the mixture was heated to refluxed for overnight and allowed to cool to room temperature, 30% hydrogen peroxide (100 mL) was added and stirred for 1 h, the inorganic solution was extracted with toluene (100 mL×2), and the organic solutions were gathered, washed with saturated sodium bicarbonate (200 mL) and brine (200 mL) respectively, dried over $MgSO_4$, and recrystallized in petroleum ether/ethanol to expel triphenylphosphine oxide, and then the mother solution was purified by column chromatography (silica gel, petroleum ether/ethyl acetate=5:1) to obtain 3-deoxy-3-iodo-1,2-O-isopropylidene-5-[(tert-butyl)-diphenylsilyl]-D-ribofuranose as a colorless oil (20.83 g, yield 69.75%). Mass spectrum (ESI) m/z calc. for $C_{24}H_{31}IO_4Si$ $[M+H]^+$ 539.50. found 539.74. $^1H$ NMR (400 MHz, $CDCl_3$) δ (ppm) 7.67-7.69 (m, 4H), 7.29-7.37 (m, 6H), 5.82 (d, 1H, J=3.6 Hz), 4.60 (t, 1H, J=3.2 Hz), 4.15-4.16 (m, 2H), 4.00 (d, 1H, J=12.0 Hz), 3.89 (dd, 1H, $J_1$=12.0 Hz, $J_2$=1.6 Hz), 1.50 (s, 3H), 1.33 (s, 3H), 1.03 (s, 9H).

Step 4: Synthesis of 3-deoxy-1,2-O-isopropylidene-5-[(tert-butyl)-diphenylsilyl]-D-ribofuranose (Intermediate 4)

A solution of 3-deoxy-3-iodo-1,2-O-isopropylidene-5-[(tert-butyl)-diphenylsilyl]-D-ribofuranose (20.83 g, 38.68 mmol) in methanol (180 mL) and ethyl acetate (20 mL) was added Pd/C (2.13 g) and triethylamine (10.72 mL), the mixture was stirred under $H_2$ atmosphere at 32° C. for 3 h before the mixture was allowed to cooled to room temperature, afterwards, celite (20 g) was added and the mixture was filtered, the filtrate was concentrated and subject to column chromatography (silica gel, petroleum ether/ethyl acetate=30:1) to obtain 3-deoxy-1,2-O-isopropylidene-5-[(tert-butyl)-diphenylsilyl]-D-ribofuranose (14.70 g, yield 92.10% h). Mass spectrum (ESI) m/z calc. for $C_{24}H_{32}O_4Si$ $[M+H]^+$ 413.60. found 413.70. $^1H$ NMR (400 MHz, $CDCl_3$) δ (ppm) 7.67-7.72 (m, 4H), 7.36-7.44 (m, 6H), 5.83 (d, 1H, J=3.6 Hz), 4.67-4.69 (m, 1H), 4.14-4.22 (m, 1H), 3.81 (dd, 1H, $J_1$=11.2 Hz, $J_2$=4.0 Hz), 3.75 (dd, 1H, $J_1$=11.2 Hz, $J_2$=4.0 Hz), 2.08 (dd, 1H, $J_1$=13.2 Hz, $J_2$=4.8 Hz), 1.87 (ddd, 1H, $J_1$=13.2 Hz, $J_2$=10.4 Hz, $J_3$=4.8 Hz), 1.51 (s, 3H), 1.33 (s, 3H), 1.06 (s, 9H).

Step 5: Synthesis of 1,2,5-tri-O-acetyl-3-deoxy-D-ribofuranose (Intermediate 5)

A solution of 3-deoxy-1,2-O-isopropylidene-5-[(tert-butyl)-diphenylsilyl]-D-ribofuranose (14.70 g, 35.63 mmol) in acetic anhydride (20.21 mL, 213.77 mmol) was added conc. $H_2SO_4$ (7.64 mL, 142.51 mmol) dropwise at 0° C., and then acetic acid (350 ml), the mixture was allowed to warm to room temperature and stirred for 16 h, the mixture was poured into ice-water (500 mL) under violent stirring before extracted with dichloromethane (150 mL×2), the organic solutions were combined and washed with water (300 mL), saturated sodium bicarbonate (300 mL), brine (300 mL)

respectively, dried over $MgSO_4$, concentrated and subject to column chromatography (silica gel, petroleum ether/ethyl acetate=10:1 to 1:1) to obtain 1,2,5-tri-O-acetyl-3-deoxy-D-ribofuranose as a yellow oil (4.80 g, yield 51.77%). Mass spectrum (ESI) m/z calc. for $C_{11}H_{16}O_7$ $[M+H]^+$ 261.24. found 261.70. $^1H$ NMR (400 MHz, $d_6$-DMSO) δ (ppm) 6.17 (s, 1H), 5.20 (d, 1H, J=4.7 Hz), 4.44-4.51 (m, 1H), 4.21 (dd, 1H, $J_1$=11.6 Hz, $J_2$=3.6 Hz), 2.10-2.13 (m, 2H), 2.09 (s, 3H), 2.08 (s, 3H), 2.07 (s, 3H).

Step 6: Synthesis of 2,5-di-O-acetyl-3-deoxy-β-D-ribofuranosyl-adenine (Intermediate 6)

A suspension of adenine (66 mg, 0.49 mmol) and 1,2,5-tri-O-acetyl-3-deoxy-D-ribofuranose (128 mg, 0.49 mmol) in anhydrous acetonitrile (3 mL) was added N,O-bis(trimethylsilyl) acetamide (0.19 mL, 0.74 mmol) and stirred at room temperature for 1 h before TMSOTf (0.18 mL, 0.98 mmol) was added. The mixture was heated to 80° C. for 3 h before cooled to room temperature and saturated sodium bicarbonate (2 mL) was added to quench the reaction. Afterwards, the solvents were removed under reduced pressure and the residue was suspended in water (10 mL) and extracted with dichloromethane (10 mL×3), the organic solutions were gathered and washed with water (30 mL) and brine (30 mL) respectively, dried over $MgSO_4$, and purified by column chromatography (silica gel, petroleum ether/ethyl acetate=1:0 to 3:7) to give 2,5-di-O-acetyl-3-deoxy-β-D-ribofuranosyl-adenine as a colorless oil (103 mg, yield 62.4%). Mass spectrum (ESI) m/z calc. for $C_{14}H_{17}N_5O_5$ $[M+H]^+$ 336.12. found 336.42.

Step 7: Synthesis of 3'-deoxy-adenosine

A solution of 2,5-di-O-acetyl-3-deoxy-β-D-ribofuranosyl-adenine (103 mg, 0.31 mmol) in 50% aqueous methanol (3 mL) was treated with $K_2CO_3$ (127 mg, 0.92 mmol). The mixture was stirred at room temperature for 3 h. The solvent was removed in vacuum and the residue was purified by preparative high performance liquid chromatography to give 3'-deoxy-adenosine as a white powder (72 mg, yield 93%). Mass spectrum (ESI) m/z calc. for $C_{10}H_{13}N_5O_3$ $[M+H]^+$ 252.10. found 252.04. $^1H$ NMR (400 MHz, $CD_3OD$) δ (ppm) 8.42 (s, 1H), 8.20 (s, 1H), 5.95 (d, 1H, J=2.8 Hz), 4.69-4.71 (m, 1H), 4.50-4.55 (m, 1H), 3.93 (dd, 1H, $J_1$=12.4 Hz, $J_2$=2.8 Hz), 3.66 (dd, 1H, $J_1$=12.4 Hz, $J_2$=3.2 Hz), 2.38 (ddd, 1H, $J_1$=13.2 Hz, $J_2$=8.0 Hz, $J_3$=6.0 Hz), 2.03-2.09 (m, 1H).

Synthesis of Compound 2:

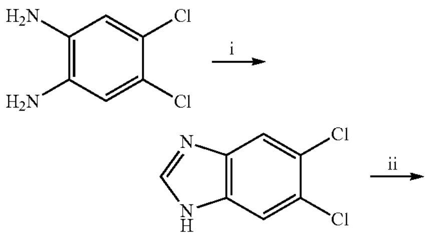

Intermediate 1

-continued

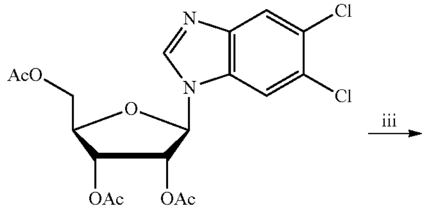

Intermediate 2

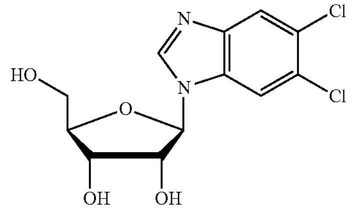

Compound 2

Conditions: i) Formic acid, 105° C.; ii) 1,2,3,5-tetra-O-acetyl-β-D-ribofuranose, N, O-bis(trimethylsilyl) acetamide, TMSOTf, acetonitrile, 75° C.; iii) $K_2CO_3$, methanol, $H_2O$.

Step 1: Synthesis of 5,6-dichloro-1H-benzo[d]imidazole (Intermediate 1)[2]

A solution of 4,5-dichlorobenzene-1,2-diamine (1.00 g, 5.65 mmol) in formic acid (5 mL) was heated to 105° C. in a sealed tube for 1 h. After the mixture was cooled to room temperature, the solvent was removed in vacuum to give a crude product, which was purified by column chromatography (silica gel, dichloromethane/methanol=10:1 to 5:1) to afford 5,6-dichloro-1H-benzo[d]imidazole as a light brown powder (1.05 g, yield 99.1%). Mass spectrum (ESI) m/z calc. for $C_7H_4Cl_2N_2$ $[M+H]^+$ 185.98 and 187.97. found 186.26, 188.34. $^1H$ NMR (400 MHz, $d_6$-DMSO) δ (ppm) 12.73 (br s, 1H), 8.34 (s, 1H), 7.87 (s, 2H).

Step 2: Synthesis of 5,6-dichloro-1-(2,3,5-tri-O-acetyl-β-D-ribofuranosyl)-benzimidazole (Intermediate 2)

A suspension of 5,6-dichloro-1H-benzo[d]imidazole (600 mg, 3.21 mmol) and 1,2,3,5-tetra-O-acetyl-β-D-ribofuranose (1.23 g, 3.85 mmol) in anhydrous acetonitrile (10 mL) was treated with N,O-bis(trimethylsilyl) acetamide (1.16 mL, 4.81 mmol), the suspension was stirred at room temperature for 2 h before TMSOTf (1.16 mL, 6.42 mmol) was added. The mixture was heated to 75° C. for 3 h before cooled to room temperature. After quenched with saturated sodium bicarbonate (5 mL), the resulting solution was extracted with dichloromethane (10 mL×3), the organic solutions were gathered and washed with water (30 mL) and brine (30 mL) respectively. The solution was dried over $MgSO_4$, concentrated and the residue was purified by column chromatography (silica gel, ethyl acetate/methanol=1:0 to 20:1) to give 5,6-dichloro-1-(2,3,5-tri-O-acetyl-β-D-ribofuranosyl)-benzimidazole as a colorless oil (670 mg, yield 46.9%). Mass spectrum (ESI) m/z calc. for $C_{18}H_{18}Cl_2N_2O_7$ $[M+H]^+$ 445.05 and 447.05. found 445.16 and 447.18. $^1H$ NMR (400 MHz, $CDCl_3$) δ (ppm) 8.10 (s, 1H), 7.79 (s, 1H), 7.69 (s, 1H), 5.95 (d, 1H, J=6.0 Hz), 5.44 (t, 1H, J=6.0 Hz), 5.34 (dd, 1H, $J_1$=5.6 Hz, $J_2$=3.6 Hz), 4.38-4.42 (m, 2H), 4.29 (dd, 1H, $J_1$=13.2 Hz, $J_2$=3.2 Hz), 2.11 (s, 3H), 2.07 (s, 3H), 1.99 (s, 3H).

Step 3: Synthesis of 5,6-dichloro-1-β-D-ribobenzimidazole

To a solution of 5,6-dichloro-1-(2,3,5-tri-O-acetyl-β-D-ribofuranosyl)-benzimidazole (280 mg, 0.629 mmol) in 50% aqueous methanol (4 mL), $K_2CO_3$ (434 mg, 3.14 mmol) was added slowly.. The mixture was stirred at room temperature for 20 min. The solvent was removed in vacuo and the residue was purified by column chromatography (silica gel, dichloromethane/methanol=10:1 to 5:1) to produce 5,6-dichloro-1-β-D-ribobenzimidazole as a white powder (125 mg, yield 62.3%). Mass spectrum (ESI) m/z calc. for $C_{12}H_{12}Cl_2N_2O_4$ $[M+H]^+$ 319.02 and 321.01. found 319.15 and 321.09. $^1H$ NMR (400 MHz, $d_6$-DMSO) δ (ppm) 8.58 (s, 1H), 8.22 (s, 1H), 7.97 (s, 1H), 5.89 (d, 1H, J=6.4 Hz), 5.50 (d, 1H, J=6.4 Hz), 5.20-5.26 (m, 2H), 4.30 (t, 1H, J=6.4 Hz), 4.11 (dd, 1H, $J_1$=5.2 Hz, $J_2$=3.2 Hz), 3.99 (dd, 1H, $J_1$=5.6 Hz, $J_2$=3.2 Hz), 3.61-3.70 (m, 2H).

Synthesis of Compound 3:

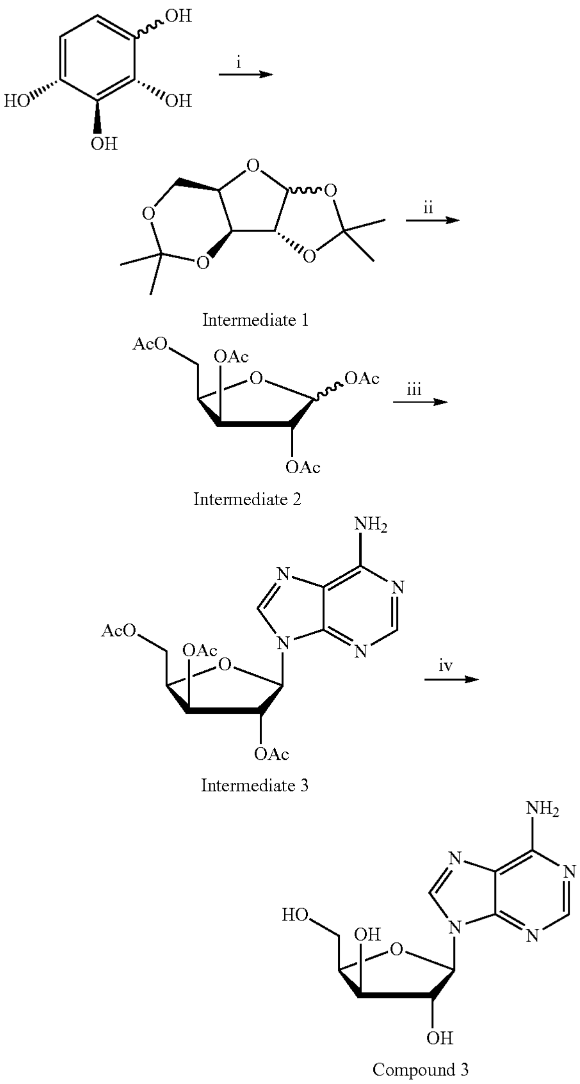

Conditions: i) $CuSO_4$, conc. $H_2SO_4$, acetone; ii) acetic anhydride, $TsOH{\cdot}H_2O$, acetic acid; iii) adenine, $SnCl_4$, acetonitrile; iv) $K_2CO_3$, methanol, $H_2O$.

Step 1: Synthesis of 1,2:3,5-di-O-isopropylidene-D-xylofuranose (Intermediate 1)[3]

To a suspension of D-xylose (10.00 g, 66.61 mmol) and $CuSO_4$ (10.00 g, 62.66 mmol) in acetone (200 ml), conc. $H_2SO_4$ (0.4 ml) was added dropwise. The mixture was stirred at room temperature for 16 h. The solid was filtered off and the residue was washed with acetone (50 mL×3). The filtrate was neutralized with sodium bicarbonate and filtered. The solvent was removed in vacuo and the residue was dissolved in dichloromethane and washed with saturated sodium bicarbonate (100 mL), water (100 mL) and brine (100 mL) respectively, the organic solution was gathered and evaporated to dryness to give 1,2:3,5-di-O-isopropylidene-D-xylofuranose as a colorless oil (13.30 g, yield 86.72%). Mass spectrum (ESI) m/z calc. for $C_{11}H_{18}O_5$ $[M+H]^+$ 231.12. found 231.20. $^1H$ NMR (400 MHz, $CDCl_3$) δ (ppm) 5.99 (d, 1H, J=4.0 Hz), 4.53 (d, 1H, J=3.6 Hz), 4.33 (d, 1H, J=2.0 Hz), 4.14-4.18 (m, 2H), 4.04-4.08 (m, 1H), 1.49 (s, 3H), 1.45 (s, 3H), 1.38 (s, 3H), 1.33 (s, 3H).

Step 2: Synthesis of 1,2,3,5-tetra-O-acetyl-D-xylofuranose (Intermediate 2)

A solution of 1,2:3,5-di-O-isopropylidene-D-xylofuranose (12.72 g, 55.24 mmol) in acetic acid (275 mL) was treated with acetic anhydride (37.0 mL, 338 mmol) and $TsOH{\cdot}H_2O$ (1.26 g, 6.62 mmol). The mixture was heated to reflux for 2 h before poured into ice water (300 mL) and extracted with dichloromethane (500 mL×3). The organic solutions were collected and washed with saturated sodium bicarbonate (500 mL), $H_2O$ (500 mL) and brine (500 mL) respectively, dried over $MgSO_4$ and purified by column chromatography (silica gel, petroleum ether/ethyl acetate=6:1 to 3:1) to afford 1,2,3,5-tetra-O-acetyl-D-xylofuranose as a yellowish oil (11.40 g, yield 64.84%). Mass spectrum (ESI) m/z calc. for $C_{13}H_{18}O_9$ $[M+H]^+$ 319.10. found 319.26. $^1H$ NMR (400 MHz, $CDCl_3$) δ (ppm) 6.10 (s, 1H), 5.36 (dd, 1H, $J_1$=5.6 Hz, $J_2$=1.6 Hz), 5.20 (d, 11H, J=1.6 Hz), 4.61-4.64 (m, 1H), 4.23-4.25 (m, 1H), 2.12 (s, 3H), 2.11 (s, 3H), 2.09 (s, 3H), 2.06 (s, 3H).

Step 3: Synthesis of 2,3,5-tri-O-acetyl-1-(6-amino-purin-9-yl)-β-D-1-deoxy-xylofuranose (Intermediate 3)

A suspension of 1,2,3,5-tetra-O-acetyl-D-xylofuranose (2.24 g, 7.03 mmol) and adenine (1.00 g, 7.40 mmol) in anhydrous acetonitrile (10 mL) was treated with $SnCl_4$ (1.73 mL, 14.8 mmol) under Ar protection. The mixture was stirred at room temperature for overnight. After the stirring, the reaction was quenched with saturated sodium bicarbonate (5 mL). The solvent was removed in vacuo and the residue was suspended in water (20 mL) and extracted with dichloromethane (20 mL×3), the organic solutions were collected and washed with water (50 mL) and brine (50 mL), respectively, dried over $MgSO_4$, and further purified by column chromatography (silica gel, dichloromethane/methanol=100:1 to 30:1) to give 2,3,5-tri-O-acetyl-1-(6-amino-purin-9-yl)-β-D-1-deoxy-xylofuranose as a colorless oil (1.93 g, yield 69.7%). Mass spectrum (ESI) m/z calc. for $C_{16}H_{19}N_5O_7$ $[M+H]^+$ 394.13. found 394.46. $^1H$ NMR (400 MHz, $d_6$-DMSO) δ (ppm) 8.49 (s, 1H), 8.35 (s, 1H), 6.20 (d, 1H, J=3.2 Hz), 5.76 (m, 1H), 5.49 (dd, 1H, $J_1$=4.8 Hz, $J_2$=2.4 Hz), 4.60 (m, 1H), 4.26-4.37 (m, 2H), 2.10 (s, 3H), 2.08 (s, 3H), 2.03 (s, 3H).

Step 4: Synthesis of 9-(β-D-xylofuranosyl)-adenine

A solution of 2,3,5-tri-O-acetyl-1-(6-amino-purin-9-yl)-β-D-1-deoxy-xylofuranose (0.95 g, 2.42 mmol) in 50% aqueous methanol (10 mL) was treated with $K_2CO_3$ (1.34 g, 9.66 mmol). The mixture was stirred at room temperature for 20 min. The solvent was removed in vacuo and the residue was purified by column chromatography (silica gel, dichloromethane/methanol=10:1 to 5:1) to yield 9-(β-D-xylofuranosyl)-adenine as a white powder (448 mg, yield 69.4%). Mass spectrum (ESI) m/z calc. for $C_{10}H_{13}N_5O_4$ $[M+H]^+$ 268.10. found 268.32. $^1$H NMR (400 MHz, $d_6$-DMSO) δ (ppm) 8.26 (s, 1H), 8.15 (s, 1H), 7.31 (br s, 2H), 5.84-5.87 (m, 3H), 4.76 (t, 1H, J=5.6 Hz), 4.31 (s, 1H), 4.13-4.17 (m, 1H), 4.03 (s, 1H), 3.73-3.78 (m, 1H), 3.63-3.68 (m, 1H).

Synthesis of Compound 4:

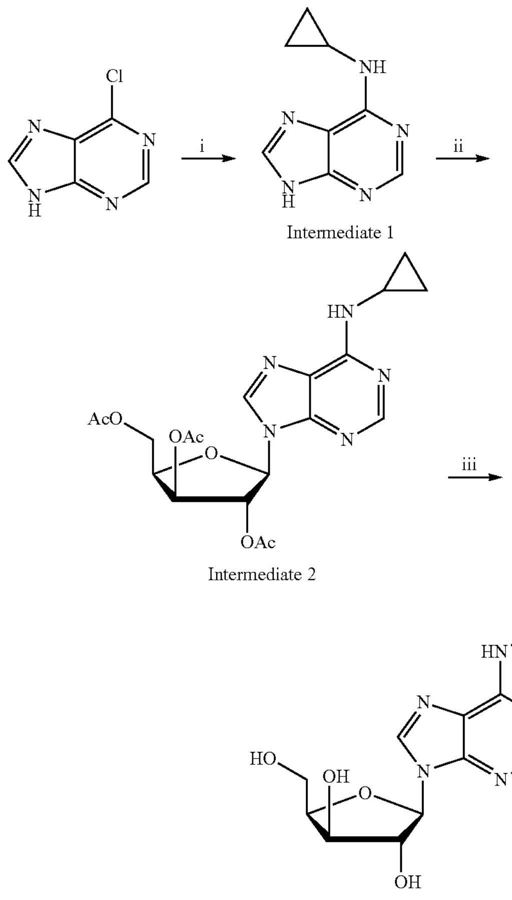

Intermediate 1
Intermediate 2
Compound 4

Conditions: i) Cyclopropylamine, isopropanol, 120° C.; ii) 1,2,3,5-tetra-O-acetyl-D-xylofuranose, $SnCl_4$, acetonitrile; iii) $K_2CO_3$, methanol, $H_2O$.

Step 1: Synthesis of 6-(cyclopropylamino)-9H-purine (Intermediate 1)[4]

A suspension of 6-chloro-9H-purine (100 mg, 0.647 mmol) and cyclopropylamine (0.18 ml, 2.6 mmol) in isopropanol (2 mL) was heated at 120° C. for 2 h, then the mixture was cooled to room temperature and recrystallized with ethanol to obtain 6-(cyclopropylamino)-9H-purine as a white powder (102 mg, yield 90.0%). Mass spectrum (ESI) m/z calc. for $C_8H_9N_5$ $[M+H]^+$ 176.09. found 176.34. $^1$H NMR (400 MHz, $d_6$-DMSO) δ (ppm) 11.51 (br s, 1H), 8.22, (s, 1H), 8.15 (br s, 1H), 8.10 (s, 1H), 3.02 (m, 1H), 0.72 (m, 2H), 0.61 (m, 2H).

Step 2 and 3 were conducted according to the last two steps of compound 3, and 9-(β-D-xylofuranosyl)-$N^6$-cyclopropyl-adenine was obtained as a white powder. Mass spectrum (ESI) m/z calc. for $C_{13}H_{17}N_5O_4$ $[M+H]^+$ 308.13. found 308.22. $^1$H NMR (400 MHz, $CD_3OD$) δ (ppm) 8.31 (s, 1H), 8.29 (s, 1H), 5.97 (d, 1H, J=1.6 Hz), 4.45 (t, 1H, J=2.0 Hz), 4.31-4.35 (m, 1H), 4.19 (dd, 1H, $J_1$=4.0 Hz, $J_2$=2.0 Hz), 3.96 (dd, 1H, $J_1$=12.0 Hz, $J_2$=4.4 Hz), 3.90 (dd, 1H, $J_1$=12.0 Hz, $J_2$=6.0 Hz), 1.94-2.10 (m, 1H), 0.87-0.92 (m, 2H), 0.63-0.67 (m, 2H).

Synthesis of Compound 5:

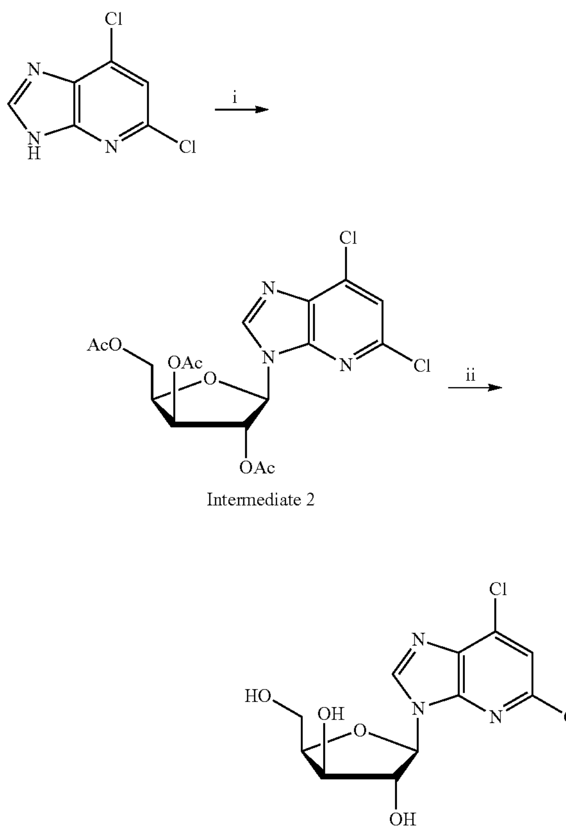

Intermediate 2
Compound 5

Conditions: i) 1,2,3,5-tetra-O-acetyl-D-xylofuranose, $SnCl_4$, acetonitrile; ii) $K_2CO_3$, methanol, $H_2O$.

Compound 5 was synthesized according to the last two steps of compound 3, and was obtained as a white powder. Mass spectrum (ESI) m/z calc. for $C_{11}H_{11}Cl_2N_3O_4$ $[M+H]^+$ 320.01 and 322.01. found 319.89 and 321.94. $^1$H NMR (400 MHz, $CD_3OD$) δ (ppm) 8.69 (s, 1H), 7.50 (s, 1H), 6.13 (d, 1H, J=1.2 Hz), 4.44 (t, 1H, J=1.6 Hz), 4.39-4.43 (m, 1H), 4.22 (dd, 1H, $J_1$=3.6 Hz, $J_2$=1.6 Hz), 4.00 (dd, 1H, $J_1$=10.0 Hz, $J_2$=3.2 Hz), 3.96 (dd, 1H, $J_1$=10.0 Hz, $J_2$=4.0 Hz).

Synthesis of Compound 6:

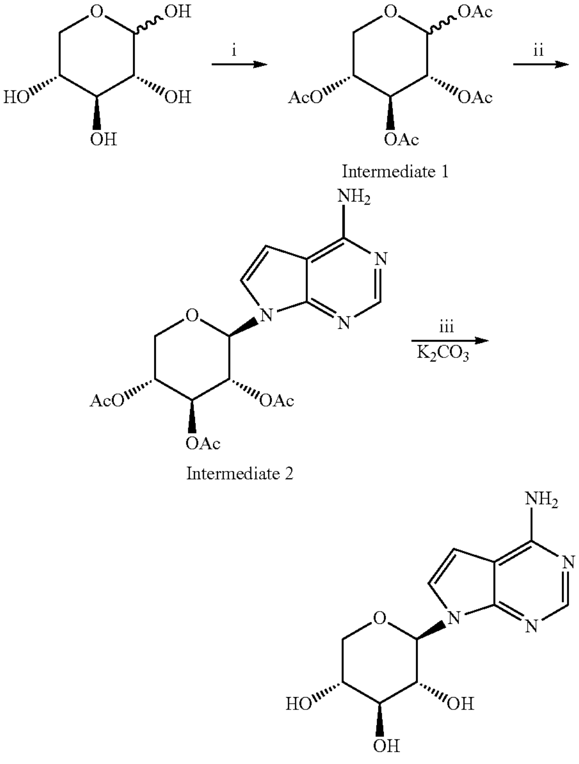

Intermediate 1
Intermediate 2
Compound 6

Conditions: i) Acetic anhydride, DMAP, pyridine; ii) 4-amino-pyrrolo[2,3-d]pyrimidine, $SnCl_4$ acetonitrile; iii) $K_2CO_3$, methanol, $H_2O$.

Step 1: Synthesis of 1,2,3,4-tetra-O-acetyl-D-xylopyranose (Intermediate 1)

To a solution of D-xylose (1.00 g, 6.66 mmol) and DMAP (163 mg, 1.33 mmol) in pyridine (15 mL),acetic anhydride (5.0 mL, 53 mmol) was added dropwise. The resulting solution was stirred at room temperature for 16 h before saturated sodium bicarbonate (20 mL) was added to quench the reaction, afterwards, the solvent was evaporated under reduced pressure and the residue was suspended in water (40 mL) and extracted with dichloromethane (40 mL×3), the organic solutions were collected and washed with saturated sodium bicarbonate (40 mL), water (40 mL) and brine (40 mL) respectively, dried over $MgSO_4$ and purified by column chromatography (silica gel, petroleum ether/ethyl acetate=5:1) to give 1,2,3,4-tetra-O-acetyl-D-xylopyranose as a colorless oil (1.33 g, yield 62.3%). Mass spectrum (ESI) m/z calc. for $C_{13}H_{18}O_9$ $[M+H]^+$ 319.10. found 319.42.

Step 2: Synthesis of 2,3,4-tri-O-acetyl-1-(4-amino-pyrrolo[2,3-d]pyrimidin-7-yl)-β-D-1-deoxy-xylopyranose (Intermediate 2)

A suspension of 1,2,3,4-tetra-O-acetyl-D-xylopyranose (107 mg, 0.336 mmol) and 4-amino-pyrrolo[2,3-d]pyrimidine (45 mg, 0.34 mmol) in anhydrous acetonitrile (3 mL) was treated with $SnCl_4$ (0.080 mL, 0.67 mmol) under argon protection, the resulting solution was stirred at room temperature for overnight before quenched with saturated sodium bicarbonate (3 mL). The solvent was removed under reduced pressure and the residue was extracted with dichloromethane (5 mL×3), the organic solutions were gathered and washed with water (5 mL) and brine (5 mL) respectively, dried over $MgSO_4$ and purified by column chromatography (silica gel, dichloromethane/methanol=50:1) to obtain 2,3,4-tri-O-acetyl-1-(4-amino-pyrrolo[2,3-d]pyrimidin-7-yl)-β-D-1-deoxy-xylopyranose as a colorless oil (87 mg, yield 66%). Mass spectrum (ESI) m/z calc. for $C_{17}H_{20}N_4O_7$ $[M+H]^+$ 392.13. found 392.01.

Step 3: Synthesis of 1-(4-amino-pyrrolo[2,3-d]pyrimidin-7-yl)-β-D-1-deoxy-xylopyranose A solution of 2,3,4-tri-O-acetyl-1-(4-amino-pyrrolo[2,3-d]pyrimidin-7-yl)-β-D-1-deoxy-xylopyranose (87 mg, 0.22 mmol) in 50% aqueous methanol (2 mL) was treated with $K_2CO_3$ (123 mg, 0.887 mmol). The mixture was stirred at room temperature for 20 min. The solvent was removed in vacuo and the residue was purified by column chromatography (silica gel, dichloromethane/methanol=10:1) to give 1-(4-amino-pyrrolo[2,3-d]pyrimidin-7-yl)-β-D-1-deoxy-xylopyranose (49 mg, yield 83%). Mass spectrum (ESI) m/z calc. for $C_{11}H_{14}N_4O_4$ $[M+H]^+$ 266.10. found 266.03. $^1H$ NMR (400 MHz, $CD_3OD$) δ (ppm) 8.32 (s, 1H), 7.22 (d, 1H, J=2.8 Hz), 6.62 (d, 1H, J=2.8 Hz), 5.73 (d, 1H, J=9.6 Hz), 4.07 (dd, 1H, $J_1$=11.2 Hz, $J_2$=5.6 Hz), 4.01 (t, 1H, J=9.2 Hz), 3.80 (m, 1H), 3.53-3.57 (m, 2H).

Synthesis of Compound 7:

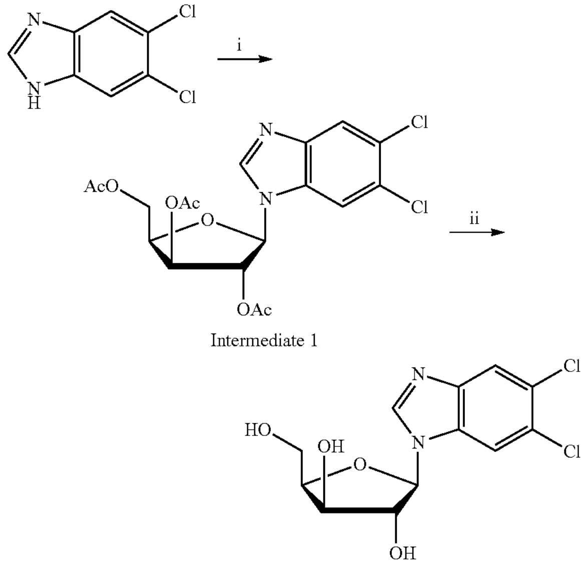

Intermediate 1
Compound 7

Conditions: i) 1,2,3,5-tetra-O-acetyl-D-xylofuranose, $SnCl_4$, acetonitrile; ii) $K_2CO_3$, methanol, $H_2O$.

Compound 7 was synthesized according to the last two steps of compound 3, and was obtained as a white powder. Mass spectrum (ESI) m/z calc. for $C_{11}H_{11}Cl_2N_3O_4$ $[M+H]^+$ 319.02 and 321.02. found 319.29 and 321.31. $^1H$ NMR (400 MHz, $CD_3OD$) δ (ppm) 8.49 (s, 1H), 8.03 (s, 1H), 7.81 (s, 1H), 5.89 (d, 1H, J=2.0 Hz), 4.36-4.40 (m, 1H), 4.33 (t, 1H, J=2.0 Hz), 4.23 (dd, 1H, $J_1$=4.0 Hz, $J_2$=2.0 Hz), 3.93-4.00 (m, 2H).

Synthesis of Compound 8:

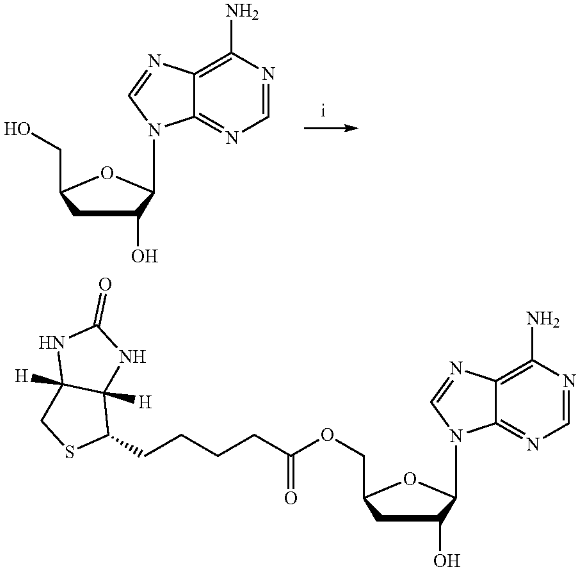

Compound 8

Conditions: i) D-(+)-biotin, EDC, DMAP, DMF.

Step 1: Synthesis of 5'-O-biotinyl-3'-deoxy-adenosine

A solution of 3'-deoxy-adenosine (25 mg, 0.10 mmol) and D-(+)-biotin (48 mg, 0.20 mmol) in dry DMF (1 mL) was treated with DMAP (25 mg, 0.20 mmol) and EDC (39 mg, 0.20 mmol), respectively, the mixture was stirred at room temperature for 2 h. The solvent was removed under reduced pressure and the residue was extracted with dichloromethane (2 mL×3), the organic solutions were gathered and washed with $H_2O$ (4 mL) and brine (4 mL), respectively, dried over $MgSO_4$, and further purified by preparative HPLC to obtain 5'-O-biotinyl-3'-deoxy-adenosine as a white powder (12 mg, yield 25%). Mass spectrum (ESI) m/z calc. for $C_{20}H_{27}N_7O_5S$ $[M+H]^+$ 478.18. found 478.41. $^1H$ NMR (400 MHz, $CD_3OD$) δ (ppm) 8.27 (s, 1H), 8.22 (s, 1H), 6.01 (s, 1H), 4.68-4.72 (m, 1H), 4.45-4.48 (m, 1H), 4.36-4.38 (m, 2H), 4.26-4.29 (m, 1H), 3.11-3.15 (m, 1H), 2.88 (dd, 1H, $J_1$=12.8 Hz, $J_2$=4.8 Hz), 2.67-2.70 (m, 2H), 2.39-2.41 (m, 1H), 2.33 (t, 2H, J=7.2 Hz), 2.28 (s, 1H), 2.08-2.12 (m, 1H), 1.58-1.71 (m, 3H), 1.38-1.42 (m, 2H).

Synthesis of Compound 9:

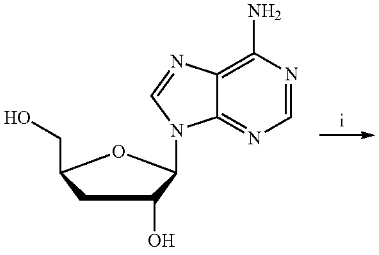

-continued

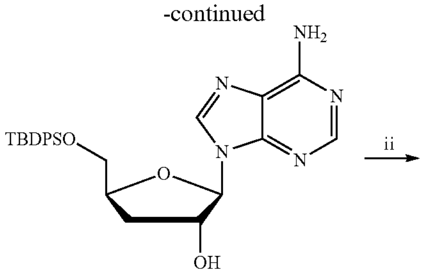

Intermediate 1

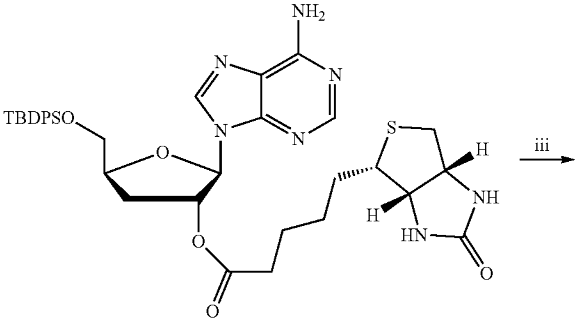

Intermediate 2

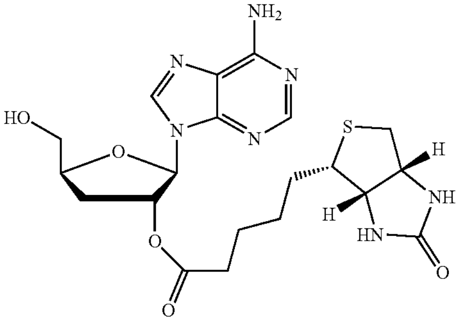

compound 9

Condition: i) TBDPSCl, pyridine; ii) D-(+)-bitotin, EDC, DMAP, DMF; iii) TBAF, THF.

Step 1: Synthesis of 3'-deoxy-5'-O-[(tert-butyl)-diphenylsilyl]-adenosine (Intermediate 1)

A solution of 3'-deoxy-adenosine (105 mg, 0.418 mmol) in dry pyridine (3 mL) was treated with TBDPSCl (0.22 mL, 0.836 mmol) and stirred at 40° C. for 6 h followed by the addition of $H_2O$ (3 mL) to quench the reaction, afterwards, the solvent was removed and the residue was extracted with dichloromethane (5 mL×3), the organic solutions were collected and washed with $H_2O$ (20 mL) and brine (20 mL), respectively, dried over $MgSO_4$, and purified by column chromatography (petroleum ether/ethyl acetate=3:1) to afford 3'-deoxy-5'-O-[(tert-butyl)-diphenylsilyl]-adenosine as a white powder (174 mg, yield 85.0%). Mass spectrum (ESI) m/z calc. for $C_{26}H_{31}N_5O_3Si$ $[M+H]^+$ 490.22. found 490.53.

Step 2: Synthesis of 2'-O-biotinyl-3'-deoxy-5'-O-[(tert-butyl)-diphenylsilyl]-adenosine (Intermediate 2)

A solution of 3'-deoxy-5'-O-[(tert-butyl)-diphenylsilyl]-adenosine (174 mg, 0.355 mmol) and D-(+)-biotin (100 mg, 0.408 mmol) in dry DMF (4 mL) was treated with DMAP (25 mg, 0.204 mmol) and EDC (157 mg, 0.817 mmol), respectively, the mixture was stirred at room temperature for 2 h. The solvent was removed under reduced pressure and the residue was extracted with dichloromethane (5 mL×3), the organic solutions were gathered and washed with $H_2O$ (15 mL) and brine (15 mL), respectively, dried over $MgSO_4$, and further purified by column chromatography (silica gel, dichloromethane/methanol=30:1 to 15:1) to obtain 2'-O-biotinyl-3'-deoxy-5'-O-[(tert-butyl)-diphenylsilyl]-adenosine as a white powder (203 mg, yield 79.8%). Mass spectrum (ESI) m/z calc. for $C_{36}H_{45}N_7O_5SSi$ [M+H]+ 716.30. found 716.02.

Step 3: Synthesis of 2'-O-biotinyl-3'-deoxy-adenosine

A solution of 2'-O-biotinyl-3'-deoxy-5'-O-[(tert-butyl)-diphenylsilyl]-adenosine (203 mg, 0.284 mmol) in dry THF (2.5 mL) was treated with TBAF (146 mg, 0.559 mmol), the resulting solution was stirred at room temperature for 1 h before the solvent was removed in vacuo, the residue was recrystallized in DMSO/methanol to give 2'-O-biotinyl-3'-deoxy-adenosine as a white powder (95.7 mg, yield 70.7%). Mass spectrum (ESI) m/z calc. for $C_{20}H_{27}N_7O_5S$ $[M+H]^+$ 478.18. found 478.05. $^1H$ NMR (400 MHz, $d_6$-DMSO) δ (ppm) 8.34 (s, 11H), 8.14 (s, 1H), 7.33 (s, 2H), 6.43 (s, 1H), 6.37 (s, 1H), 6.06 (d, 1H, J=1.6 Hz), 5.62 (d, 1H, J=6.4 Hz), 5.15 (t, 1H, J=5.6 Hz), 4.29-4.33 (m, 2H), 3.65-3.68 (m, 1H), 3.50-3.53 (m, 1H), 3.06-3.11 (m, 1H), 2.82 (dd, 1H, $J_1$=12.4 Hz, $J_2$=4.8 Hz), 2.54-2.59 (m, 2H), 2.37 (t, 1H, J=7.6 Hz), 2.11 (dd, 1H, $J_1$=12.8 Hz, $J_2$=4.8 Hz), 1.41-1.61 (m, 4H), 1.30-1.35 (m, 2H).

Synthesis of Compound 10:

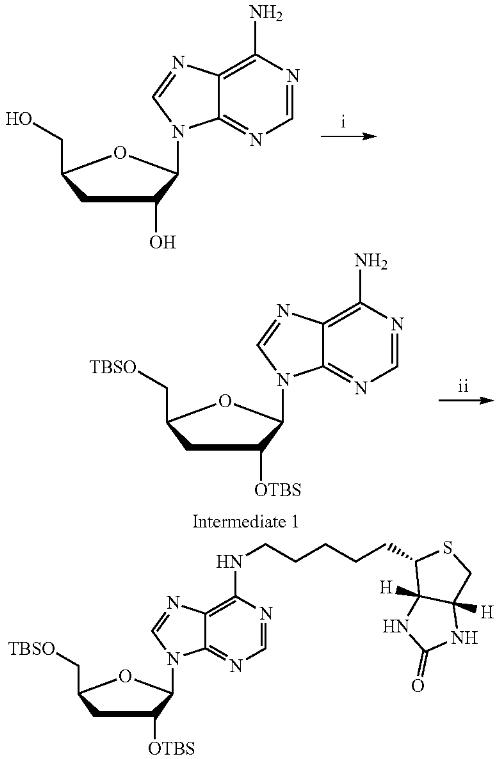

Intermediate 1

Intermediate 2

-continued

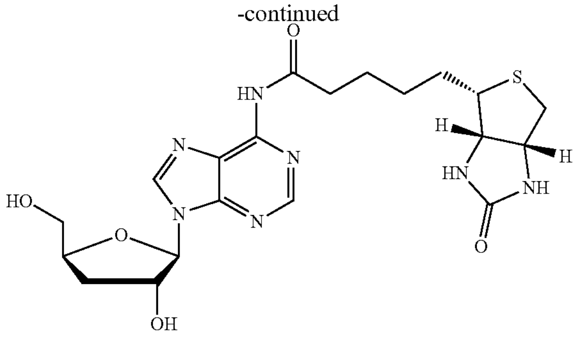

Compound 10

Condition: i) TBSCl, imidazole, DMF; ii) D-(+)-bitotin, EDC, HOBt, DMF; iii) TBAF, THF.

Step 1: Synthesis of 9-[2,5-bis-O-(tert-butyldimethylsilyl)-3-deoxy-β-D-ribofuranosyl]adenine (Intermediate 1)

A solution of 3'-deoxy-adenosine (67 mg, 0.26 mmol) in DMF (3 mL) was added imidazole (91 mg, 1.33 mmol) and TBSCl (96 mg, 0.64 mmol), the resulting mixture was stirred at room temperature for overnight, afterwards, the solvent was evaporated under reduced pressure, the residue was suspended in saturated sodium bicarbonate (3 mL) and extracted with dichloromethane (3 mL×3), the organic solutions were collected and washed with water (5 mL) and brine (5 mL), dried over $MgSO_4$, and further purified by chromatography (silica gel, petroleum ether/ethyl acetate=3:1) to give 9-[2,5-bis-O-(tert-butyldimethylsilyl)-3-deoxy-β-D-ribofuranosyl]adenine as a colorless oil (52 mg, yield 41%). Mass spectrum (ESI) m/z calc. for $C_{22}H_{41}N_5O_3Si_2$ $[M+H]^+$ 480.27. found 480.12.

Step 2: Synthesis of 9-[2,5-bis-O-(tert-butyldimethylsilyl)-3-deoxy-β-D-ribofuranosyl]-$N^6$-biotinyl-adenine (Intermediate 2)

A solution of 9-[2,5-bis-O-(tert-butyldimethylsilyl)-3-deoxy-β-D-ribofuranosyl]adenine (52 mg, 0.11 mmol) in DMF (3 mL) was added EDC (31 mg, 0.16 mmol) and HOBt (22 mg, 0.16 mmol), the mixture was stirred at room temperature for 30 min before D-(+)-biotin (26 mg, 0.11 mmol) was added, the resulting solution was stirred at room temperature for another 4 h, the solvent was evaporated under reduced pressure, the residue was suspended in water (3 mL) and extracted with dichloromethane (3 mL×3), the organic solution was collected and washed with saturated sodium bicarbonate (3 mL), water (3 mL) and brine (3 mL), dried over $MgSO_4$, purified by chromatography (silica gel, petroleum ether/ethyl acetate=3:1) to give 9-[2,5-bis-O-(tert-butyldimethylsilyl)-3-deoxy-β-D-ribofuranosyl]-$N^6$-biotinyl-adenine as a colorless oil (38 mg, yield 50%). Mass spectrum (ESI) m/z calc. for $C_{32}H_{55}N_7O_5SSi_2$ $[M+H]^+$ 706.35. found 706.14.

Step 3: Synthesis of 3-deoxy-β-D-ribofuranosyl-$N^6$-biotinyl-adenine

A solution of 9-[2,5-bis-O-(tert-butyldimethylsilyl)-3-deoxy-β-D-ribofuranosyl]-$N^6$-biotinyl-adenine (38 mg, 0.054 mmol) in dry THF (3 mL) was treated with TBAF (28 mg, 0.11 mmol), the mixture was stirred at room temperature for 4 h, the solvent was removed under reduced pressure, and the residue was subject to preparative HPLC to give 3-deoxy-β-D-ribofuranosyl-$N^6$-biotinyl-adenine as a white powder (II mg, yield 43%). Mass spectrum (ESI) m/z calc. for $C_{20}H_{27}N_7O_5S$ $[M+H]^+$ 478.18. found 478.51. $^1H$ NMR (400 MHz, $d_6$-DMSO) δ (ppm) 8.69 (s, 1H), 8.65 (s, 1H), 6.43 (s, 1H), 6.36 (s, 1H), 6.00 (s, 1H), 5.75 (s, 1H), 5.40 (m, 1H), 5.08 (m, 1H), 4.61 (m, 1H), 4.31 (m, 1H), 4.15 (m, 1H), 3.71-3.72 (m, 1H), 3.52 (m, 1H), 3.11-3.14 (m, 1H), 2.94 (m, 1H), 2.83 (dd, 1H, $J_1$=13.2 Hz, $J_2$=4.4 Hz), 2.67 (m, 1H), 2.51-2.57 (m, 2H), 2.33 (m, 1H), 1.59-1.71 (m, 2H), 1.23-1.55 (m, 4H).

Synthesis of Compound 11:

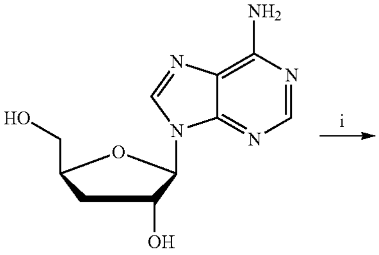

Compound 1

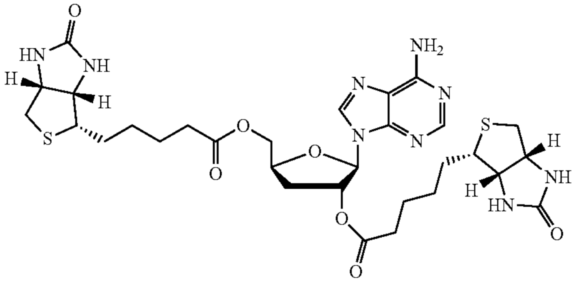

Compound 11

Conditions: i) D-(+)-bitotin, EDC, DMAP, DMF.

Compound 11 was synthesized using the method of compound 8 with 4.0 eq of D-(+)-biotin, 4.0 eq of EDC and 4.0 eq of DMAP and stirred at 40° C. for 4 h. 3',5'-bis-O-biotinyl-3'-deoxy-adenosine was obtained as a white powder. Mass spectrum (ESI) m/z calc. for $C_{30}H_{41}N_9O_7S_2$ $[M+H]^+$ 703.26. found 703.08. $^1H$ NMR (400 MHz, $d_6$-DMSO) δ (ppm).

Synthesis of Compound 12:

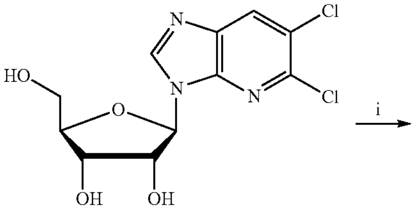

-continued

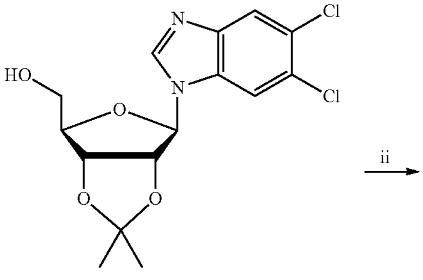

Intermediate 1

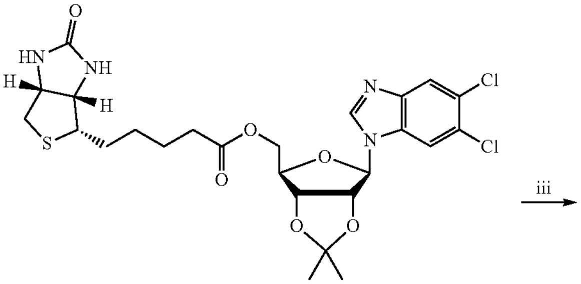

Intermediate 2

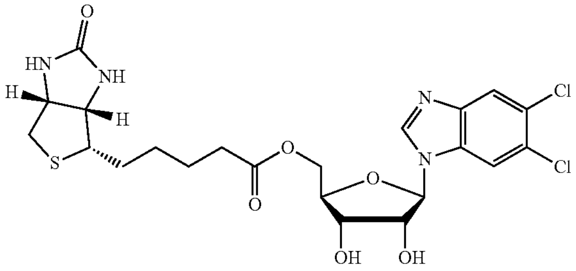

Compound 12

Conditions: i) Acetone, p-toluenesulfonic acid; ii) D-(+)-biotin, EDC, DMAP, DMF; iii) 80% aqueous acetic acid, 80° C.

Step 1: Synthesis of 5,6-dichloro-1-(2',3'-O-isopropylidene-β-D-ribofuranosyl)-benzimidazole (Intermediate 1)

A suspension of 5,6-dichloro-1-β-D-ribobenzimidazole (100 mg, 0.313 mmol) in acetone (15 mL) was treated with p-toluenesulfonic acid (178 mg, 0.940 mmol), the mixture was stirred at room temperature for 2 h and poured into 10% $Na_2CO_3$ solution (15 mL) at 0° C., the solvent was evaporated in vacuo and the residue was extracted with ethyl acetate (20 mL×3), the organic solutions were gathered and washed with $H_2O$ (20 mL) and brine (20 mL), respectively, dried over $MgSO_4$, and further purified by column chromatography (silica gel, dichloromethane/methanol=20:1) to afford 5,6-dichloro-1-(2',3'-O-isopropylidene-β-D-ribofuranosyl)-benzimidazole as a white powder (62 mg, yield 55%). Mass spectrum (ESI) m/z calc. for $C_{15}H_{16}Cl_2N_2O_4$ $[M+H]^+$ 359.05 and 361.05. found 359.26 and 361.18. $^1H$ NMR (400 MHz, $CDCl_3$) δ (ppm) 8.26 (s, 1H), 7.68 (s, 1H), 7.62 (s, 1H), 5.95 (d, 1H, J=3.2 Hz), 5.21, (br s, 1H), 5.04 (dd, 1H, $J_1$=6.4 Hz, $J_2$=2.0 Hz), 4.97 (dd, 1H, $J_1$=6.0 Hz, $J_2$=3.2 Hz), 4.54 (q, 1H, J=2.4 Hz), 3.99 (dd, 1H, $J_1$=12.0 Hz, $J_2$=2.0 Hz), 3.86 (dd, 1H, $J_1$=12.0 Hz, $J_2$=2.4 Hz), 1.66 (s, 3H), 1.40 (s, 3H).

Step 2: Synthesis of 5,6-dichloro-1-(5'-O-biotinyl-2',3'-O-isopropylidene-β-D-ribofuranosyl)-benzimidazole (Intermediate 2)

A solution of 5,6-dichloro-1-(2',3'-O-isopropylidene-β-D-ribofuranosyl)-benzimidazole (62 mg, 0.17 mmol) in dry DMF (5 mL) was added DMAP (11 mg, 0.086 mmol) and EDC (67 mg, 0.35 mmol), respectively, the resulting solution was stirred at room temperature for 2 h. The solvent was removed under reduced pressure and the residue was extracted with ethyl acetate (5 mL×3), the organic solutions were gathered and washed with $H_2O$ (5 mL) and brine (5 mL), respectively, dried over $MgSO_4$, and further purified by column chromatography (silica gel, dichloromethane/methanol=20:1) to afford 5,6-dichloro-1-(5'-O-biotinyl-2',3'-O-isopropylidene-β-D-ribofuranosyl)-benzimidazole as a white powder (71 mg, yield 70%). Mass spectrum (ESI) m/z calc. for $C_{25}H_{30}Cl_2N_4O_6S$ $[M+H]^+$ 585.13 and 587.12. found 585.32 and 587.47. $^1H$ NMR (400 MHz, $CDCl_3$) δ (ppm) 8.09 (s, 1H), 7.92 (s, 1H), 7.63 (s, 1H), 6.20 (s, 1H), 5.94 (d, 1H, J=3.2 Hz), 5.52 (s, 1H), 4.94 (dd, 1H, $J_1$=6.4 Hz, $J_2$=3.2 Hz), 4.86 (dd, 1H, $J_1$=6.4 Hz, $J_2$=3.2 Hz), 4.55 (q, 1H, J=3.2 Hz), 4.45-4.47 (m, 1H), 4.34 (dd, 1H, $J_1$=12.4 Hz, $J_2$=3.2 Hz), 4.30 (dd, 1H, $J_1$=12.4 Hz, $J_2$=3.6 Hz), 4.25 (ddd, 1H, $J_1$=8.0 Hz, $J_2$=4.8 Hz, $J_3$=1.2 Hz), 3.07 (ddd, 1H, $J_1$=8.0 Hz, $J_2$=6.8 Hz, $J_3$=4.8 Hz), 2.87 (dd, 1H, $J_1$=12.4 Hz, $J_2$=4.8 Hz), 2.70 (d, 1H, J=12.4 Hz), 2.21-2.31 (m, 2H), 2.03 (s, 1H), 1.53-1.70 (m, 7H), 1.34-1.42 (m, 5H).

Step 3: Synthesis of 5,6-dichloro-1-(5'-O-biotinyl-β-D-ribofuranosyl)-benzimidazole A solution of 5,6-dichloro-1-(5'-O-biotinyl-2',3'-O-isopropylidene-β-D-ribofuranosyl)-benzimidazole (71 mg, 0.12 mmol) in 80% aqueous acetic acid (5 mL) was stirred at 80° C. for overnight before the solvent was removed under reduced pressure and the residue was subject to column chromatography (silica gel, dichloromethane/methanol=4:1) to afford 5,6-dichloro-1-(5'-O-biotinyl-β-D-ribofuranosyl)-benzimidazole as a white powder (32 mg, yield 48%). Mass spectrum (ESI) m/z calc. for $C_{22}H_{26}Cl_2N_4O_6S$ $[M+H]^+$ 545.10 and 547.09. found 545.37 and 547.29. $^1H$ NMR (400 MHz, $CD_3OD$) δ (ppm) 8.44 (s, 1H), 7.94 (s, 1H), 7.88 (s, 1H), 5.95 (d, 1H, J=5.6 Hz), 4.42-4.49 (m, 2H), 4.32-4.38 (m, 2H), 4.21-4.25 (m, 2H), 3.10 (ddd, 1H, $J_1$=9.2 Hz, $J_2$=6.0 Hz, $J_3$=4.8 Hz), 2.86 (dd, 1H, $J_1$=12.8 Hz, $J_2$=5.2 Hz), 2.67 (d, 1H, J=12.8 Hz), 2.34-2.47 (m, 2H), 1.56-1.71 (m, 4H), 1.39-1.43 (m, 2H).

Synthesis of Compound 13-15:

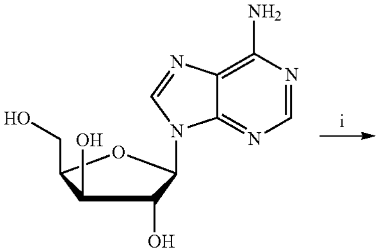

-continued

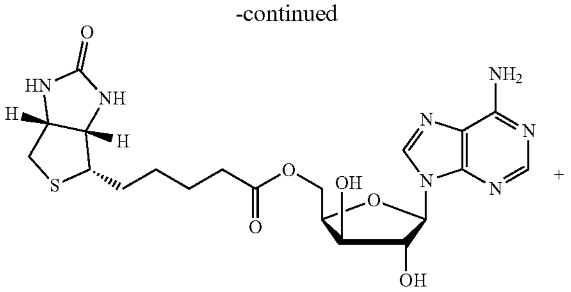

Compound 13

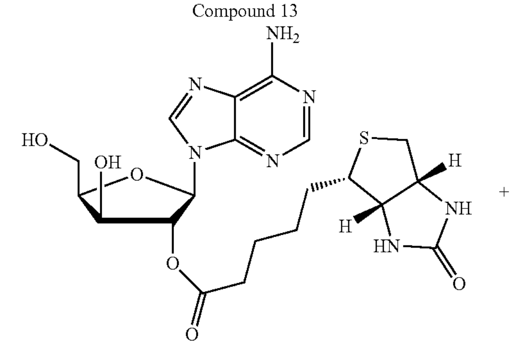

Compound 14

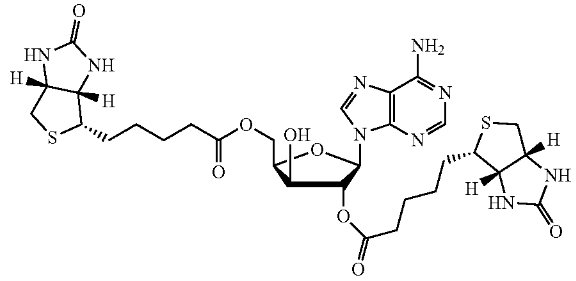

Compound 15

Conditions: i) D-(+)-bitotin, EDC, DMAP, DMF.

Compound 13-15 were synthesized according to the method of compound 8 using 4.0 eq of D-(+)-biotin, 4.0 eq of EDC and 4.0 eq of DMAP. 5'-O-biotinyl-9-(β-D-xylofuranosyl)-adenine was obtained as a white powder, mass spectrum (ESI) mi/z calc. for $C_{20}H_{27}N_7O_6S$ $[M+H]^+$ 494.17. found 494.23. $^1H$ NMR (400 MHz, $CD_3OD$) δ (ppm) 8.34 (s, 1H), 8.21 (s, 1H), 6.00 (d, 1H, J=1.6 Hz), 4.44-4.51 (in, SH), 4.26 (did, 1H, $J_1$=8.0 Hz, $J_2$=4.4 Hz), 4.20 (s, 1H), 3.14-3.16 (m, 1H), 2.90 (dd, 1H, $J_1$=12.8 Hz, $J_2$=4.8 Hz), 2.68 (d, 1H, J=12.8 Hz), 2.38 (t, 2H, J=7.2 Hz), 1.54-1.74 (m, 4H), 1.42-1.48 (m, 2H). 2'-O-biotinyl-9-(β-D-xylofuranosyl)-adenine was obtained as a white powder, mass spectrum (ESI) m/z calc. for $C_{20}H_{27}N_7O_6S$ $[M+H]^+$ 494.17. found 494.35. $^1H$ NMR (400 MHz, $CD_3OD$) δ (ppm) 8.34 (s, 1H), 8.21 (s, 1H), 6.09 (di, 1H, J=2.0 Hz), 5.39 (t, 1H, J=2.0 Hz), 4.49 (ddd, 1H, J, =8.0 Hz, $J_2$=4.8 Hz, $J_3$=0.8 Hz), 4.37 (dd, 1H, $J_1$=4.0 Hz, $J_2$=1.6 Hz), 4.26-4.31 (m, 2H), 3.96 (dd, 1H, $J_1$=12.0 Hz, $J_2$=4.4 Hz), 3.90 (dd, 1H, $J_1$=12.0 Hz, $J_2$=6.0 Hz), 3.17-3.22 (m, 1H), 2.93 (dd, 1H, $J_1$=12.8 Hz, $J_2$=4.8 Hz), 2.71 (d, 1H, J=12.8 Hz), 2.46 (t, 2H, J=7.2 Hz), 1.58-1.75 (m, 4H), 1.43-1.49 (m, 2H). 2',5'-bis-O-biotinyl-9-(β-D-xylofuranosyl)-adenine was obtained as a white powder, mass spectrum (ESI) m/z calc. for $C_{20}H_{41}N_9O_8S_2$ $[M+H]^+$ 720.25. found 720.35. $^1H$ NMR (400 MHz, $CD_3OD$) δ (ppm) 8.34 (s, 1H), 8.22 (s, 1H), 6.12 (s, 1H), 5.38 (d, 1H, J=1.6 Hz), 4.45-4.52 (m, 4H), 4.39 (s, 1H), 4.26-4.32 (m, 2H), 3.14-3.23 (m, 2H), 2.89-2.96 (m, 2H), 2.70 (dd, 2H, $J_1$=12.4 Hz, $J_2$=8.0 Hz), 2.48 (t, 2H, J=7.2 Hz), 2.37 (dt, 4H, $J_1$=15.6 Hz, $J_2$=8.0 Hz), 1.57-1.77 (m, 8H), 1.43-1.51 (m, 4H).

Synthesis of Compound 16:

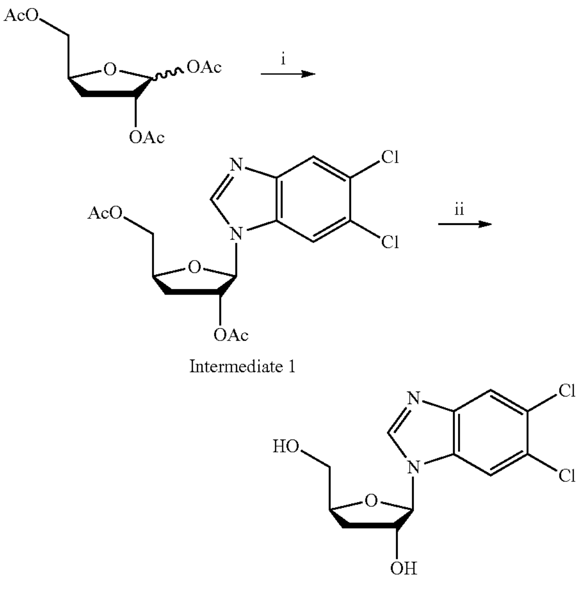

Intermediate 1
Compound 16

Conditions: i) 5,6-dichloro-1H-benzo[d]imidazole, N,O-bis(trimethylsilyl) acetamide, TMSOTf, acetonitrile, ii) $K_2CO_3$, methanol, water.

Compound 16 was synthesized using method in the last two steps of compound 1, and 5,6-dichloro-1-β-D-xylofuranosylbenzimidazole was obtained as a white powder. Mass spectrum (ESI) m/z calc. for $C_{12}H_{12}Cl_2N_2O_3$ $[M+H]^+$ 303.14 and 305.14. found 303.34 and 305.51. $^1$H NMR (400 MHz, $CD_3OD$) δ (ppm) 8.64 (s, 1H), 7.96 (s, 1H), 7.80 (s, 1H), 5.90 (d, 1H, J=1.2 Hz), 4.50-4.56 (m, 1H), 3.93 (dd, 1H, $J_1$=12.4 Hz, $J_2$=2.8 Hz), 3.69 (dd, 1H, $J_1$=12.4 Hz, $J_2$=3.6 Hz), 2.26-2.33 (m, 1H), 1.99-2.05 (m, 1H).

Synthesis of Compound 17[5]:

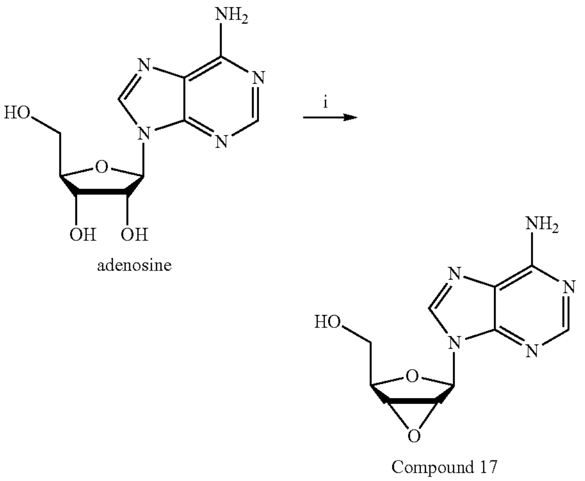

adenosine
Compound 17

Conditions: i) 2-Acetoxyisobutyryl bromide, acetonitrile, $H_2O$.

Step 1: Synthesis of 9-(2,3-anhydro-β-D-ribofuranosyl) adenine

A suspension of adenosine (3.00 g, 11.2 mmol) in absolute acetonitrile (45 mL) was added $H_2O$ (0.04 mL) and 2-acetoxyisobutyryl bromide (1.8 mL, 12.4 mmol), the resulting mixture was stirred at room temperature for 2 h, ethyl acetate (30 mL) was added and the mixture was washed with saturated $NaHCO_3$ (25 mL×2), the aqueous phase was reextracted with ethyl acetate (15 mL×5) and the organic solutions were combined and dried over $MgSO_4$, the solvent was removed under reduced pressure, the residue was dissolved in absolute methanol and $OH^-$ resin was added, the mixture was stirred at room temperature for 2 h until precipitation formed, the mixture was heated to give a clear solution and the resin was filtered and washed with hot methanol, the filtrate was further purified by chromatography (silica gel, dichloromethane/methanol=20:1) to give 9-(2,3-anhydro-β-D-ribofuranosyl)adenine as a white powder (2.02 g, yield 72.2%). Mass spectrum (ESI) m/z calc. for $C_{10}H_{11}N_5O_3$ $[M+H]^+$ 250.09. found 250.38. $^1$H NMR (400 MHz, $d_6$-DMSO) δ (ppm) 8.34 (s, 1H), 8.17 (s, 1H), 7.34 (s, 2H), 6.21 (s, 1H), 5.09 (t, 1H, J=5.2 Hz), 4.45 (d, 1H, J=2.8 Hz), 4.22 (d, 1H, J=2.8 Hz), 4.18 (t, 1H, J=5.2 Hz), 3.52-3.58 (m, 2H).

Synthesis of Compound 18:

Compound 18 was synthesized according to reference 6.

Synthesis of Compound 19:

Compound 19 was synthesized according to reference 7.

Synthesis of Compound 20:

Compound 20 was synthesized according to reference 8.

Synthesis of Compound 21[9]:

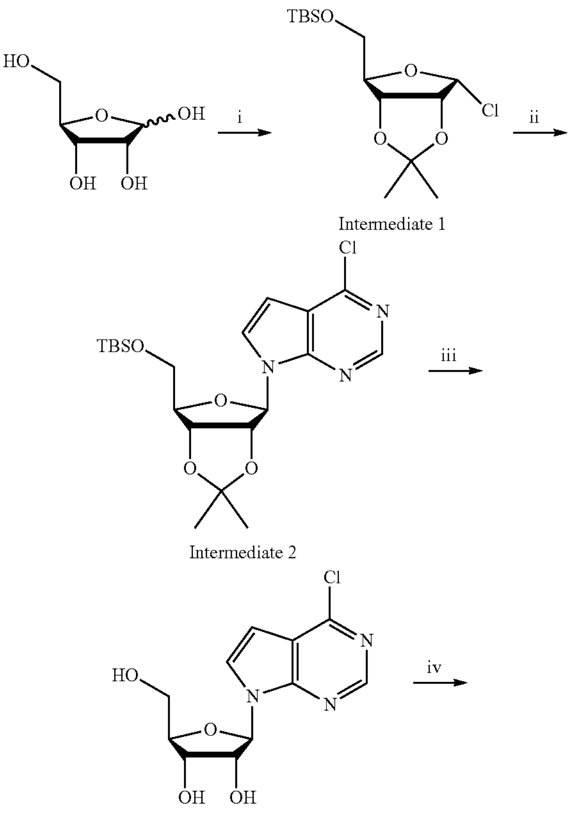

Intermediate 1
Intermediate 2
Intermediate 3

-continued

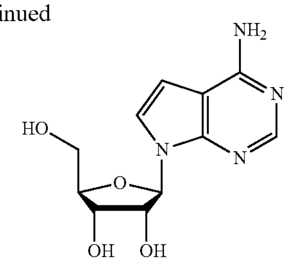

Compound 21

Conditions: i) a. acetone, conc. $H_2SO_4$, $CuSO_4$, b. TBSCl, DMAP, triethylamine, dichloromethane, c. $CCl_4$, HMPT, THF; ii) NaH, 4-chloro-1H-pyrrolo[2,3-d]pyrimidine, acetonitrile; iii) 90% aqueous TFA; iv) $NH_3$, methanol, 120° C.

Step 1: Synthesis of 2,3-O-isopropylidene-5-O-(tert-butyldimethylsilyl)-α-D-ribofuranosyl Chloride (Intermediate 1)

A solution of D-ribose (10.00 g, 66.6 mmol) in dry acetone (200 mL) was added conc. $H_2SO_4$ (0.5 mL) and $CuSO_4$ (21.26 g, 133 mmol) at room temperature, the resulting mixture was stirred at 37° C. for 40 h before filtered and washed with acetone (20 mL). The filtrate was neutralized with $Ca(OH)_2$ and stirred for 15 min, afterwards, the mixture was filtered again and the filtrate was evaporated to dryness under reduced pressure, which was dissolved in dry dichloromethane (20 mL) and treated with triethylamine (11.1 mL, 79.9 mmol), DMAP (977 mg, 7.99 mmol). The solution was cooled to 0° C. and a solution of TBSCl (12.05 g, 79.9 mmol) in dichloromethane (40 mL) was added dropwise, then the mixture was allowed to warm up to room temperature and stirred for overnight and concentrated under reduced pressure, the residue was suspended in water (50 mL) and extracted with dichloromethane (50 mL×3), dried over $MgSO_4$ and purified by chromatography (silica gel, pentane/diethyl ether=9:1) to give 5-O-tert-butyldimethylsilyl-2,3-O-isopropylidene-D-ribofuranose (6.72 g, 31.2% from D-ribose, 22.1 mmol) which was dissolved in dry THF (100 mL) and $CCl_4$ (2.6 mL, 26.5 mmol) was added, the solution was stirred and cooled to −78° C. before HMPT (3.9 mL, 22.1 mmol) was added dropwise over a period of 20 min, the resulting solution was warmed up to −40° C. after the completion of addition and held for 2 h, the solvent was removed under reduced pressure, the residue was suspended in diethyl ether/petroleum ether (1:1) and filtered, the filtrate was evaporated to give crude 2,3-O-isopropylidene-5-O-(tert-butyldimethylsilyl)-a-D-ribofuranosyl chloride as an orange oil, which was dissolved in anhydrous acetonitrile (20 mL) and directly used for the next step.

Step 2: Synthesis of 4-chloro-2,3-O-isopropylidene-5-O-(tert-butyldimethylsilyl)-7-(β-D-ribofuranosyl)-7H-pyrrolo[2,3-d]pyrimidine (Intermediate 2)

A solution of 4-chloro-1H-pyrrolo[2,3-d]pyrimidine (100 mg, 0.651 mmol) in anhydrous acetonitrile (5 mL) was added NaH (60% in mineral oil, 29 mg, 0.72 mmol) in 0° C., the resulting solution was stirred at room temperature for 30 min before the above solution (2 mL) obtained in step 1 was added under argon protection, the resulting solution was warmed to room temperature and stirred for 40 h, the mixture was poured into ice water (10 mL) and extracted with dichloromethane (15 mL×3), the organic solutions were combined and washed with saturated aqueous $NH_4Cl$ (20 mL) and brine (20 mL), dried over $MgSO_4$ and concentrated in vacuo, the residue was purified by chromatography (silica gel, petroleum ether/ethyl acetate=9:1) to give 4-chloro-2,3-O-isopropylidene-5-O-(tert-butyldimethylsilyl)-7-(β-D-ribofuranosyl)-7H-pyrrolo[2,3-d]pyrimidine as a yellowish oil (152 mg, yield 53.1%). Mass spectrum (ESI) m/z calc. for $C_{20}H_{30}ClN_3O_4Si$ $[M+H]^+$ 440.17 and 442.17. found 440.43 and 442.51.

Step 3: Synthesis of 4-chloro-7-(β-ribofuranosyl)-7H-pyrrolo[2,3-d]pyrimidine (Intermediate 3)

4-chloro-2,3-O-isopropylidene-5-O-(tert-butyldimethylsilyl)-7-(P-D-ribofuranosyl)-7H-pyrrolo[2,3-d]pyrimidine (152 mg, 0.345 mmol) was dissolved in 90% aqueous TFA (5 mL) at 0° C. and the solution was stirred at room temperature for 1 h before evaporated to dryness. The residue was dissolved in methanol (3 mL) and evaporated to dryness, and the process was repeated for 3 times to remove traces of TFA. The residue was purified by chromatography (silica gel, dichloromethane/methanol=10:1) to give 4-chloro-7-(β-D-ribofuranosyl)-7H-pyrrolo[2,3-d]pyrimidine as a yellowish powder (91 mg, yield 92.2%). Mass spectrum (ESI) m/z calc. for $C_{11}H_{12}ClN_3O_4$ $[M+H]^+$ 286.05 and 288.05. found 286.38 and 288.09.

Step 4: Synthesis of Tubercidin 4-chloro-7-(β-D-ribofuranosyl)-7H-pyrrolo[2,3-d]pyrimidine (91 mg, 0.319 mmol) was dissolved in 7 M methanolic ammonia (10 mL) in a sealed tube and heated to 120° C. for overnight, then the solution was allowed to cool and the solvent was removed under reduced pressure. The residue was subject to preparative HPLC to give tubercidin as a light yellow powder (52 mg, yield 60.6%). Mass spectrum (ESI) m/z calc. for $C_{11}H_{14}N_4O_4$ $[M+H]^+$ 267.10. found 267.02. $^1H$ NMR (400 MHz, $d_6$-DMSO) δ (ppm) 8.03 (s, 1H), 7.33 (d, 1H, J=3.6 Hz), 7.02 (br s, 2H), 6.58 (d, 1H, J=3.6 Hz), 5.96 (d, 1H, J=6.4 Hz), 5.30 (t, 1H, J=6.4 Hz), 5.25 (d, 1H, J=6.4 Hz), 5.09 (d, 1H, J=4.8 Hz), 4.42 (q, 1H, J=6.4 Hz), 4.05-4.07 (m, 1H), 3.86-3.92 (m, 1H), 3.62 (ddd, 1H, $J_1$=12.0 Hz, $J_2$=4.8 Hz, $J_3$=3.6 Hz), 3.50 (ddd, 1H, $J_1$=12.0 Hz, $J_2$=4.8 Hz, $J_3$=3.6 Hz).

Synthesis of Compound 22:

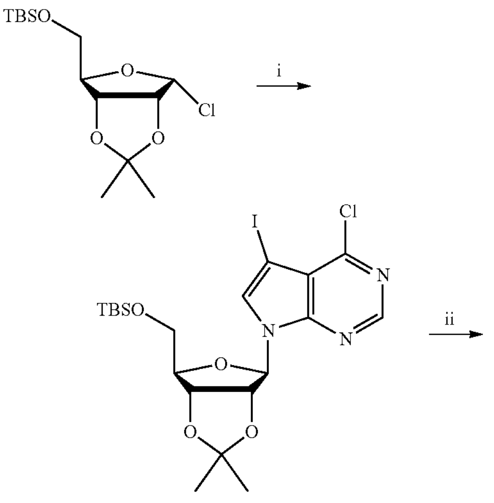

Intermediate 1

-continued

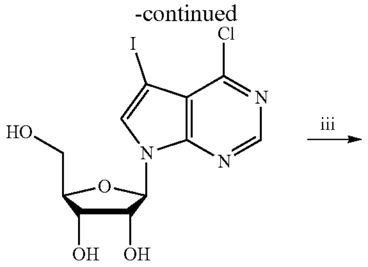

Intermediate 2

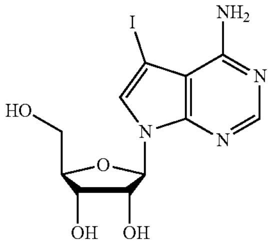

Compound 22

Compound 22 was synthesized using the same strategy of compound 21, and 5-iodotubercidin was obtained as a yellowish powder. Mass spectrum (ESI) m/z calc. for $C_{11}H_{13}IN_4O_4$ $[M+H]^+$ 393.00. found 393.28. $^1H$ NMR (400 MHz, $d_6$-DMSO) δ (ppm) 8.11 (s, 1H), 7.66 (s, 1H), 6.66 (br s, 2H), 6.00 (d, 1H, J=6.4 Hz), 5.31 (d, 1H, J=6.4 Hz), 5.14 (t, 1H, J=6.0 Hz), 5.11 (d, 1H, J=5.2 Hz), 4.34 (dt, 1H, $J_1$=6.4 Hz, $J_2$=4.8 Hz), 4.06 (dt, 1H, $J_1$=4.8 Hz, $J_2$=3.2 Hz), 3.88 (q, 1H, J=3.6 Hz), 3.62 (ddd, 1H, $J_1$=12.0 Hz, $J_2$=4.8 Hz, $J_3$=4.0 Hz), 3.53 (ddd, 1H, $J_1$=12.0 Hz, $J_2$=6.0 Hz, $J_3$=4.0 Hz).

Synthesis of Compound 23:

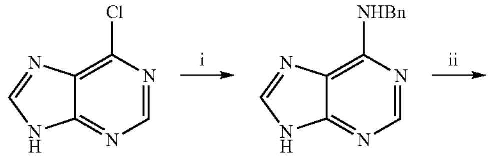

Intermediate 1

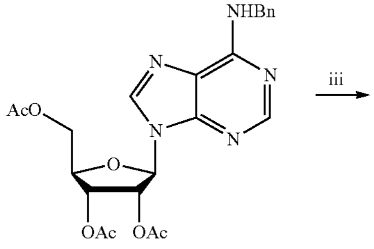

Intermediate 2

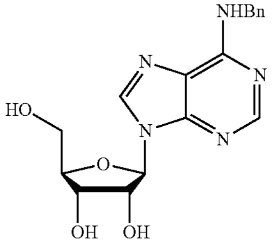

Compound 23

Compound 23 was synthesized according to the method of compound 4 while using benzylamine in the first step and 1,2,3,5-tetra-O-acetyl-D-ribofuranose in the second step. $N^6$-benzyladenosine was obtained as a white powder. Mass spectrum (ESI) m/z calc. for $C_{17}H_{19}N_5O_4$ $[M+H]^+$ 358.14. found 358.02. $^1H$ NMR (400 MHz, $d_6$-DMSO) δ (ppm) 8.45 (br s, 1H), 8.37 (s, 1H), 8.20 (s, 1H), 7.29-7.34 (m, 4H), 7.20 (t, 1H, J=7.2 Hz), 5.89 (d, 1H, J=6.0 Hz), 5.43 (d, 1H, J=6.4 Hz), 5.36 (dd, 1H, $J_1$=7.2 Hz, $J_2$=4.8 Hz), 5.17 (d, 1H, J=4.8 Hz), 4.71 (br s, 1H), 4.62 (ddd, 1H, $J_1$=6.4 Hz, $J_2$=6.0 Hz, $J_1$=4.8 Hz), 4.15 (ddd, 1H, $J_1$=4.8 Hz, $J_2$=4.4 Hz, $J_1$=3.2 Hz), 3.97 (dt, 1H, $J_1$=3.6 Hz, $J_2$=3.2 Hz), 3.67 (ddd, 1H, $J_1$=12.0 Hz, $J_2$=4.8 Hz, $J_3$=3.2 Hz), 3.55 (ddd, 1H, $J_1$=12.0 Hz, $J_2$=7.6 Hz, $J_3$=3.2 Hz).

Synthesis of Compound 24:

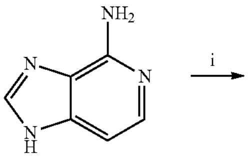

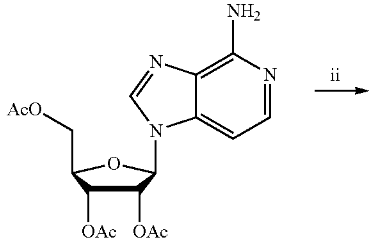

Intermediate 1

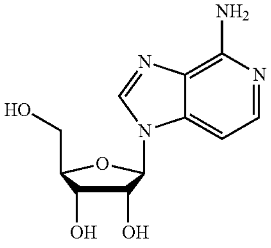

Compound 24

Compound 24 was synthesized according to the method of compound 3 while using 3-deazaadenine and 1,2,3,5-tetra-O-acetyl-D-ribofuranose. 3-Deazaadenosine was obtained as a light yellow powder. Mass spectrum (ESI) m/z calc. for $C_{11}H_{14}N_4O_4$ $[M+H]^+$ 267.10. found 267.45. $^1H$ NMR (400 MHz, $d_6$-DMSO) δ (ppm) 8.29 (s, 1H), 7.67 (d, 1H, J=5.6 Hz), 6.90 (d, 1H, J=5.6 Hz), 6.11 (br s, 2H), 5.75 (d, 1H, J=6.0 Hz), 5.41 (d, 1H, J=6.4 Hz), 5.16 (d, 1H, J=4.8 Hz), 5.05 (t, 1H, J=5.2 Hz), 4.31-4.33 (m, 1H), 4.08-4.12 (m, 1H), 3.96-3.98 (m, 1H), 3.57-3.67 (m, 2H).

Synthesis of compound 25: Compound 25 was synthesized according to reference 10

Synthesis of compound 26: Compound 26 was synthesized according to reference 11

Synthesis of compound 27: Compound 27 was synthesized using the same strategy of compound 23.

Synthesis of compound 28: Compound 28 was synthesized using the same strategy of compound 1

Synthesis of compound 29: Compound 29 was synthesized according to reference 12

Synthesis of compound 30: Compound 30 was synthesized according to reference 10

Synthesis of compound 31: Compound 31 was synthesized using the same strategy of compound 25.

Synthesis of compound 32: This is 2-deoxyl-Adenosine, Deleted~

Synthesis of compound 33: Compound 33 was synthesized using the same strategy of compound 1.

Synthesis of compound 34: Compound 34 was synthesized according to reference 13

Synthesis of compound 35: Compound 35 was synthesized using the same strategy of compound 1.

Synthesis of compound 36-38 were synthesized according to reference 14

Synthesis of compound 39: Compound 39 was synthesized according to reference 15

Synthesis of compound 40: Compound 40 was synthesized using the same strategy of compound 10.

Synthesis of compound 41: Compound 41 was synthesized using the same strategy of compound 12.

Synthesis of compound 42: Compound 42 was synthesized according to reference 16

Synthesis of compound 43: Compound 43 was synthesized according to reference 17

Synthesis of compound 44-45 were synthesized using the same strategy of compound 25.

Synthesis of compound 46: Compound 46 was synthesized according to reference 18

Synthesis of compound 47: Compound 47 was synthesized using the same strategy of compound 22.

Synthesis of compound 48-54 were synthesized using the same strategy of compound 3.

Synthesis of compound 55: Compound 55 was synthesized using the same strategy of compound 6.

Synthesis of compound 56-59 were synthesized using the same strategy of compound 3.

Synthesis of compound 60: Compound 60 was synthesized using the same strategy of compound 6.

Synthesis of compound 61-69 were synthesized using the same strategy of compound 3.

Synthesis of compound 70: Compound 70 was synthesized using the same strategy of compound 12.

Synthesis of compound 71-74 were synthesized using the same strategy of compound 1.

Synthesis of compound 75: Compound 75 was synthesized using the same strategy of compound 6.

Synthesis of compound 76: Compound 76 was synthesized using the same strategy of compound 14.

Synthesis of compound 77-78 were synthesized using the same strategy of compound 1.

Synthesis of compound 79 was synthesized using the same strategy of compound 6.

Synthesis of compound 80: Compound 80 was synthesized according to reference 19

Synthesis of compound 81-82 were synthesized using the same strategy of compound 1.

Synthesis of compound 83-93 were synthesized using the same strategy of compound 3.

Synthesis of Compound 94:

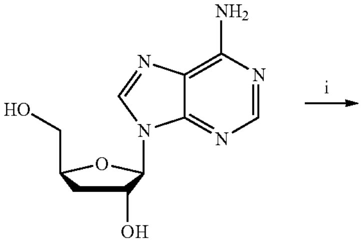

-continued

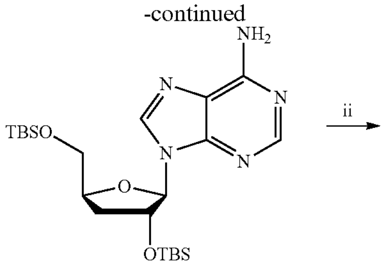

Intermediate 1

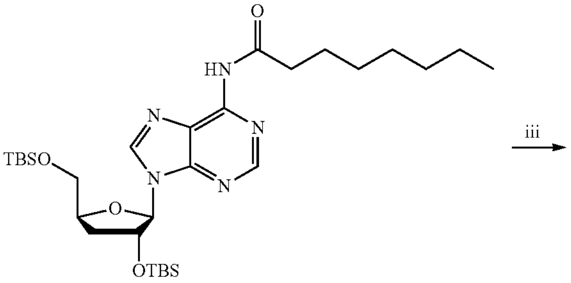

Intermediate 2

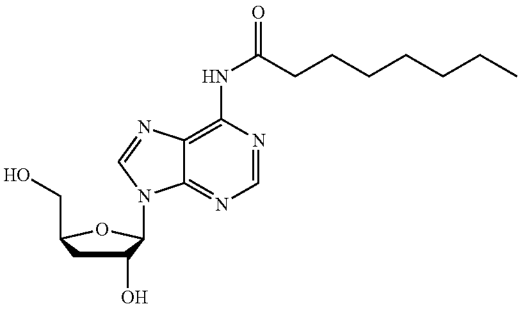

compound 94

Condition: i) TBSCl, imidazole, DMF; ii) octanoic chloride, EDC, HOBt, DMF; iii) TBAF, THF.

Step 1: Synthesis of 9-[2,5-bis-O-(tert-butyldimethylsilyl)-3-deoxy-β-D-ribofuranosyl]adenine (Intermediate 1)

A solution of 3'-deoxy-adenosine (67 mg, 0.26 mmol) in DMF (3 mL) was added imidazole (91 mg, 1.33 mmol) and TBSCl (96 mg, 0.64 mmol), the resulting mixture was stirred at room temperature for overnight, afterwards, the solvent was evaporated under reduced pressure, the residue was suspended in saturated sodium bicarbonate (3 mL) and extracted with dichloromethane (3 mL×3), the organic solutions were collected and washed with water (5 mL) and brine (5 mL), dried over $MgSO_4$, and further purified by chromatography (silica gel, petroleum ether/ethyl acetate=3:1) to give 9-[2,5-bis-O-(tert-butyldimethylsilyl)-3-deoxy-β-D-ribofuranosyl]adenine as a colorless oil (52 mg, yield 41%). Mass spectrum (ESI) m/z calc. for $C_{22}H_{41}N_5O_3Si_2$ $[M+H]^+$ 480.27. found 480.12.

Step 2: Synthesis of 9-[2,5-bis-O-(tert-butyldimethylsilyl)-3-deoxy-β-D-ribofuranosyl]-$N^6$-biotinyl-adenine (Intermediate 2)

A solution of 9-[2,5-bis-O-(tert-butyldimethylsilyl)-3-deoxy-β-D-ribofuranosyl]adenine (52 mg, 0.11 mmol) in DMF (3 mL) was added EDC (31 mg, 0.16 mmol) and HOBt (22 mg, 0.16 mmol), the mixture was stirred at room temperature for 30 min before octanoic chloride (18 mg, 0.11 mmol) was added, the resulting solution was stirred at room temperature for another 4 h, the solvent was evaporated under reduced pressure, the residue was suspended in water (3 mL) and extracted with dichloromethane (3 mL×3), the organic solution was collected and washed with saturated sodium bicarbonate (3 mL), water (3 mL) and brine (3 mL), dried over $MgSO_4$, purified by chromatography (silica gel, petroleum ether/ethyl acetate=3:1) to give 9-[2,5-bis-O-(tert-butyldimethylsilyl)-3-deoxy-β-D-ribofuranosyl]-$N^6$-biotinyl-adenine as a colorless oil (38 mg, yield 50%). Mass spectrum (ESI) m/z calc. for $C_{30}H_{55}N_5O_4Si_2$ $[M+H]^+$ 606.38. found 606.14.

Step 3: Synthesis of 3-deoxy-β-D-ribofuranosyl-$N^6$-biotinyl-adenine

A solution of 9-[2,5-bis-O-(tert-butyldimethylsilyl)-3-deoxy-β-D-ribofuranosyl]-$N^6$-biotinyl-adenine (38 mg, 0.054 mmol) in dry THF (3 mL) was treated with TBAF (28 mg, 0.11 mmol), the mixture was stirred at room temperature for 4 h, the solvent was removed under reduced pressure, and the residue was subject to preparative HPLC to give 3-deoxy-β-D-ribofuranosyl-$N^6$-biotinyl-adenine as a white powder (11 mg, yield 43%).

Mass spectrum (ESI) m/z calc. for $C_{18}H_{27}N_7O_4$ $[M+H]^+$ 378.18. found 378.51.

$^1$H NMR (400 MHz, $d_6$-DMSO) δ (ppm) 10.62 (brs, 1H), 8.70 (s, 1H), 8.64 (s, 1H), 6.00 (s, 1H), 5.77 (s, 1H), 5.10 (s, 1H), 4.62 (s, 1H), 4.39-4.42 (m, 1H), 3.74-3.71 (m, 1H), 3.56-3.53 (m, 1H), 2.57-2.53 (m, 2H), 2.27-2.24 (m, 1H), 1.95 (m, 1H), 1.59-1.61 (m, 2H), 1.24-1.29 (m, 8H), 0.83-0.86 (m, 3H).

Synthesis of Compound 95, N-Octanoyl-CA04:

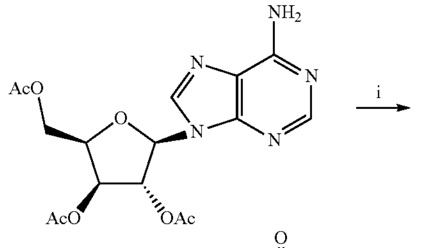

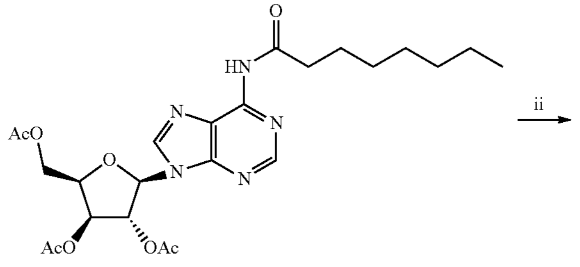

Intermediate 1

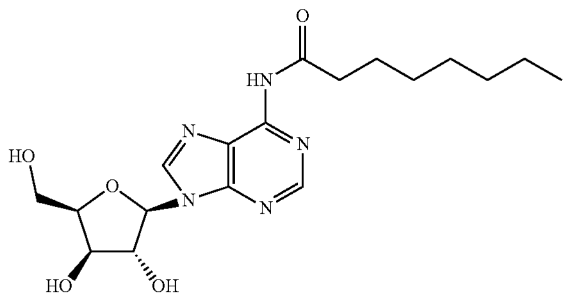

Step 1: Synthesis of 2,3,5-tri-O-acetyl-1-(6-amino-N-octanoyl-purin-9-yl)-β-D-1-deoxy-xylofuranose (Intermediate 1)

To a solution of 2,3,5-tri-O-acetyl-1-(6-amino-purin-9-yl)-β-D-1-deoxy-xylofuranose (818 mg, 2.08 mmol) in pyridine (10 ml), octanoic chloride was added dropwised at 0° C. under $Ar_2$ protect. Then the mixture was stirred 8 hours at room temperature. Quenched with saturation $NaHCO_3$ aqueous. Then which was concentrated and further purified by chromatography (silica gel, petroleum ether/ethyl acetate=1:1) to give intermediate 1 as a colorless oil (771.3 mg, yield: 71.39%).

$^1$H NMR (400 MHz, $CDCl_3$) δ 8.69 (s, 1H), 8.35 (s, 1H), 8.23 (s, 1H), 6.27 (d, J=2.4 Hz, 1H), 5.60-5.56 (m, 1H), 5.51 (dd, J=4.1, 1.8 Hz, 1H), 4.65 (dt, J=6.5, 4.5 Hz, 2H), 4.48-4.29 (m, 4H), 2.88 (t, J=7.6 Hz, 3H), 2.18 (s, 3H), 2.13 (s, 3H), 2.11 (s, 3H), 1.84-1.72 (m, 3H), 1.58 (s, 6H), 1.49-1.18 (m, 13H), 0.88 (t, J=6.9 Hz, 4H).

Step 2: Synthesis of N-octanoyl-9-(P-D-xylofuranosyl)-adenine (pro-CA04)

Intermediate 1 was treated with $K_2CO_3$, MeOH and $H_2O$. Time control was very important minimize to produce by-product (CA04). 30 minutes was suitable. Then which was concentrated and further purified by chromatography (silica gel, dichloromethane/MeOH=30:1) to give pro-CA04 as a white powder (200 mg, yield: 34.26%).

$^1$H NMR (400 MHz, $CD_3OD$) δ 8.55 (t, J=11.2 Hz, 2H), 6.08 (t, J=10.0 Hz, 1H), 4.51-4.46 (m, 1H), 4.42-4.36 (m, 1H), 4.24 (dd, J=3.8, 1.8 Hz, 1H), 4.02-3.91 (m, 2H), 2.63 (t, J=7.5 Hz, 2H), 1.72 (dt, J=15.1, 7.5 Hz, 2H), 1.46-1.22 (m, 8H), 0.93-0.81 (m, 3H).

Synthesis of Compound 96:

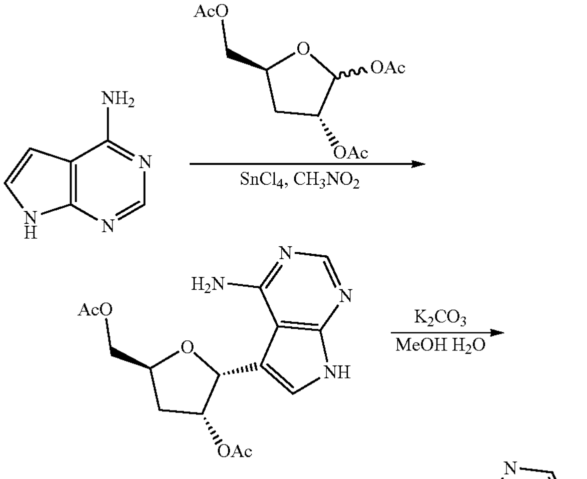

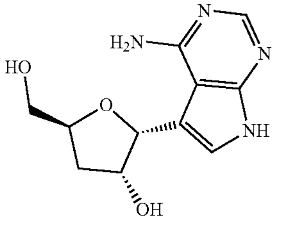

compound 96

In a similar manner to that used in step 3 and step 4 in the synthesis of compound CA04(NQZ-007). The solvent was instead of Nitromethane, other condition were same. Obtain compound 15 (4.1 mg) as white solid.

$^{1}H$ NMR (400 MHz, $CD_3OD$) δ 8.01 (s, 1H), 7.13 (d, J=0.7 Hz, 1H), 5.16-5.04 (m, 1H), 4.58-4.47 (m, 1H), 4.37 (dd, J=5.3, 2.7 Hz, 1H), 3.67 (ddd, J=17.5, 11.9, 4.7 Hz, 2H), 2.21-2.09 (m, 2H).

Synthesis of compound 97: Compound 97 was synthesized using the same strategy of compound 3.

Synthesis of compound 98: Compound 98 was synthesized using the same strategy of compound 1.

Synthesis of compound 99-103 were synthesized using the same strategy of compound 3.

Synthesis of compound 104: Compound 104 was synthesized using the same strategy of compound 1.

Synthesis of compound 105: Compound 105 was synthesized using the same strategy of compound 3.

Synthesis of compound 106: Compound 106 was synthesized using the same strategy of compound 1.

Synthesis of Compounds 107, 112 and 113: Diazinyl-Adenosine, Diazinyl-CA03, Diazinyl-CA04.

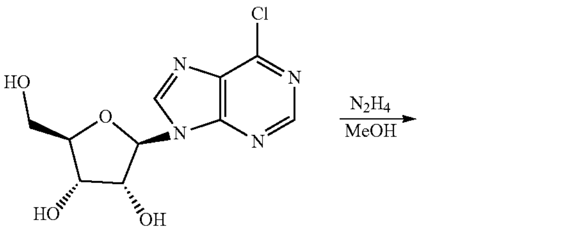

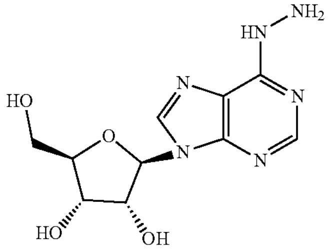

compound 107

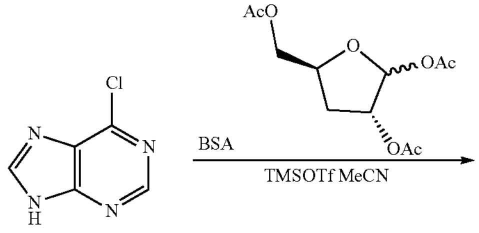

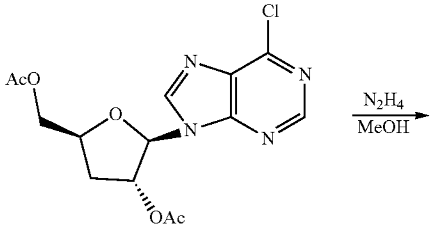

Intermediate 1

-continued

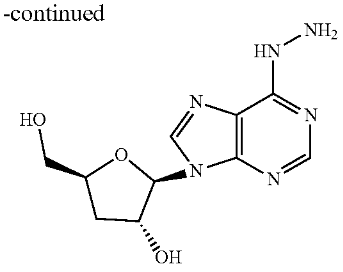

compound 113

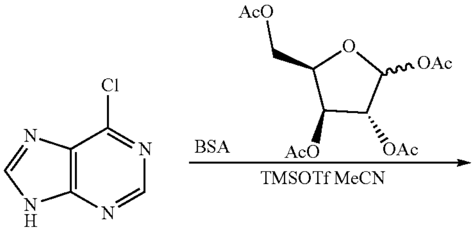

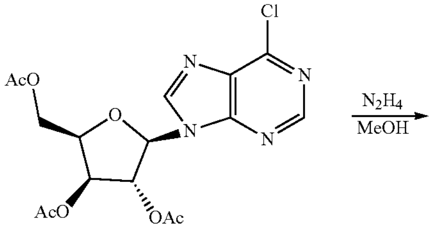

Intermediate 2

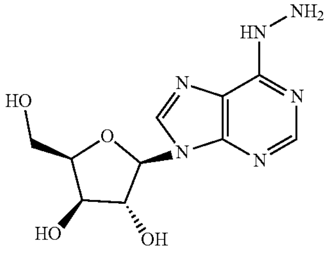

compound 112

To a turbid liquid of 6-chloroadenosine (56 mg) in MeOH, hydrazine monohydrate was added in tube sealing. The mixture was heat to 50° C. and stirred 8 hours. The mixture was allowed to cool to room temperature and then concentrated in vacuo to provide a crude residue, which was suspension in MeOH and stirred at room temperature. The solid product that separate out from the suspension was filtered, washed with MeOH and dry in vacuo to obtain compound 117 (46.5 mg). $^{1}H$ NMR (400 MHz, DMSO) δ 8.35 (s, 1H), 8.24 (s, 1H), 5.88 (t, J=6.0 Hz, 1H), 5.43 (s, 2H), 5.22 (s, 1H), 4.76-4.40 (m, 3H), 4.14 (dd, J=4.8, 3.1 Hz, 1H), 3.96 (q, J=3.5 Hz, 1H), 3.72-3.48 (m, 2H), 3.34 (s, 3H).

In a similar manner to that used in step 6 in the synthesis of compound 6. Intermediate 1 and Intermediate 2 were synthetized, after then treat them with hydrazine monohydrate to give compound 122 and compound 123.

Synthesis of compound 108: Compound 108 was synthesized using the same strategy of compound 3.

Synthesis of compound 109: Compound 109 was synthesized using the same strategy of compound 1.

Synthesis of compound 110: Compound 110 was synthesized using the same strategy of compound 6.

Synthesis of compound 111: Compound 111 was synthesized using the same strategy of compound 3.

Synthesis of compound 114: Compound 114 was synthesized using the same strategy of compound 3.

Synthesis of Compound 115 and 116:CA03-Biotinlinker-Diazirine

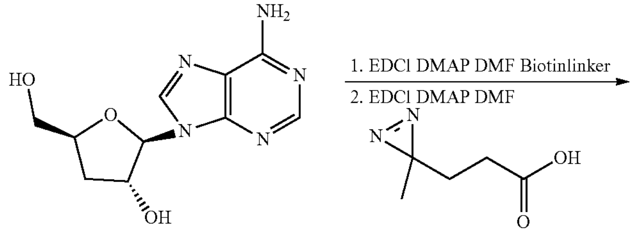

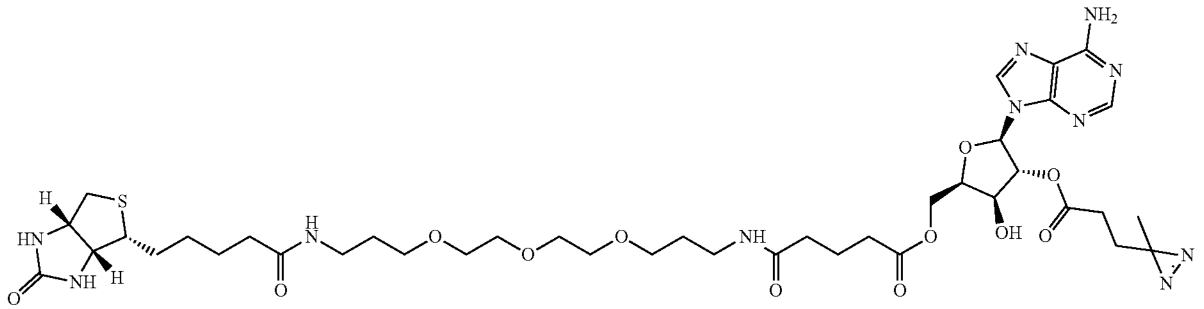

NQZ-187-1
115

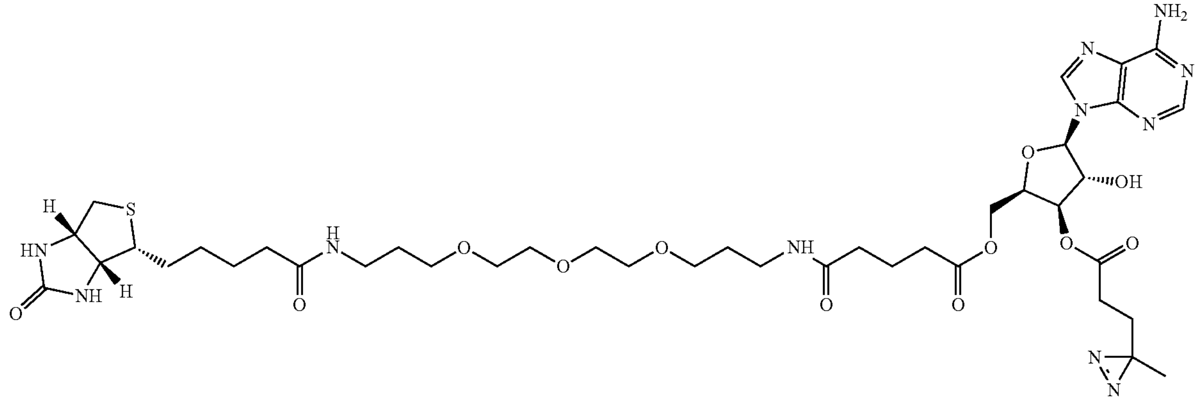

NQZ-187-2
116

The 3'-deoxy-adenosine (20 mg) was suspension in DMF (5 ml), then EDCI, DMAP and Biotinlinker was added respectively. The mixture was stirred at room temperature for 8 hours. Monitored by UPLC-MS, after starting material was disappear, other equivalent EDCI and DMAP was added, then diazirine acid was added, the mixture was stirred for other 8 hours at room temperature. The mixture was concentrated and further purified by column chromatography (silica gel, ethyl acetate/MeOH=10:1) and PTLC ethyl acetate/MeOH=4:1) to give the compound 125 & 126 mixture (1:1). Mass spectrum (ESI) m/z calc. for $C_{40}H_{61}N_{11}O_{11}S$ $[M+H]^+$ 904.43. found 904.48.

Synthesis of compound 117: Compound 117 was synthesized using the same strategy of compound 116.

Synthesis of Compound 118:

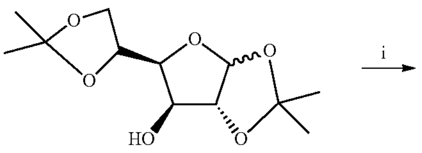

-continued

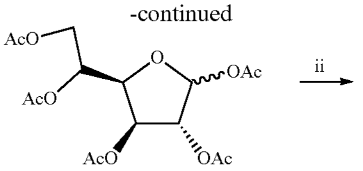

Intermediate 1

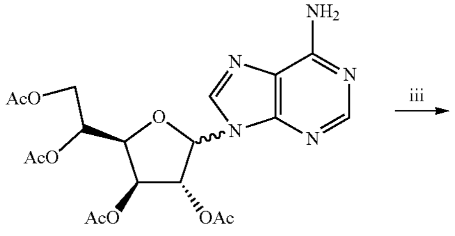

Intermediate 2

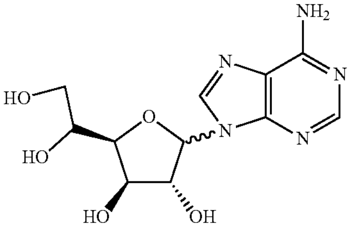
compound 118

Step 1: Synthesis of 1,2,3,4,5-pentakis-O-acetyl-D-glucofuranose (Intermediate 1)

In a similar manner to that used in step 2 in the synthesis of compound 5. the start material 1,2:5,6-di-O-isopropylidene-D-glucofuranose (6 g, 23.05 mmol) was acetylization with acetic anhydride (17.43 mL, 184.41 mmol) and TsOH·$H_2O$ (876.9 mg, 4.61 mmol). in acetic acid (115 mL) to give Intermediate 1 as a colorless oil (6.56 g, 72.9%). $^1H$ NMR (400 MHz, $CDCl_3$) δ 6.45 (d, J=4.6 Hz, 1H), 6.12 (s, 1H), 5.54 (dd, J=4.9, 2.9 Hz, 1H), 5.42 (d, J=4.8 Hz, 1H), 5.28 (ddd, J=7.5, 5.1, 2.9 Hz, 2H), 5.25-5.19 (m, 2H), 5.11 (s, 1H), 4.66-4.44 (m, 4H), 4.16-4.03 (m, 4H), 2.19-1.96 (m, 30H).

Step 2 and Step 3: Synthesis of 9-(β-D-1-deoxy-D-glucofuranosyl)-adenine (Compound 9)

In a similar manner to that used in step 6 and step 7 in the synthesis of compound 6. Intermediate 1 (217 mg, 0.55 mmol) was glycosylation and hydrolyzation respectively to give compound 9 as a white powder (1.6 mg, yield: 0.97% overall two steps) $^1H$ NMR (400 MHz, $CD_3OD$)) 8.39 (s, 1H), 8.23 (s, 1H), 6.12 (d, J=1.9 Hz, 1H), 4.72 (s, 1H), 4.44 (dd, J=7.4, 4.4 Hz, 1H), 4.31 (dd, J=4.4, 1.0 Hz, 1H), 3.72 (ddd, J=12.1, 9.4, 2.9 Hz, 2H), 3.67-3.58 (m, 1H).

Synthesis of Compound 119:

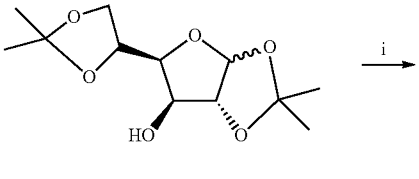

-continued

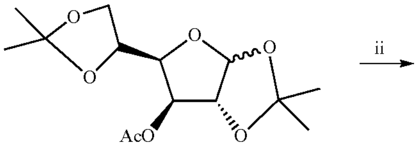

Intermediate 1

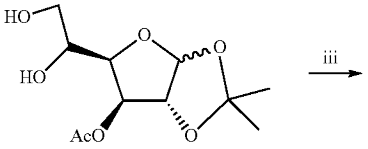

Intermediate 2

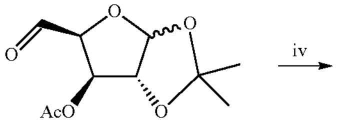

Intermediate 3

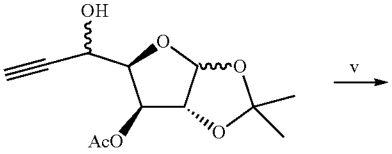

Intermediate 4

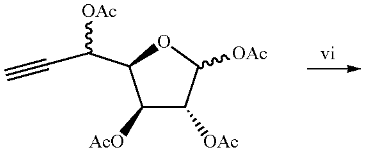

Intermediate 5

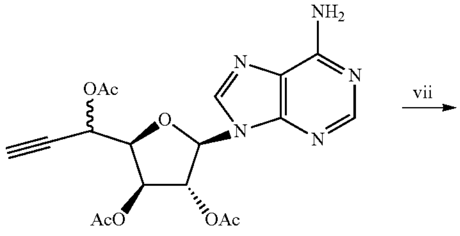

Intermediate 6

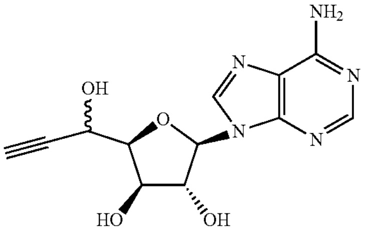
compound 119

Condtions: i) DMAP, $Ac_2O$, pyridine; ii) 0.2% HCl; iii) $NaIO_4$, $H_2O$; iv) Ethynylmagnesium Bromide, THF; v) acetic anhydride, TsOH•$H_2O$, acetic acid; vi) adenine, N,O-bis(trimethylsilyl) acetamide, TMSOTf, acetonitrile; vii) $K_2CO_3$, methanol, water.

Step 1: Synthesis of 3-acetoxyl-1,2:5,6-di-O-isopropylidene-D-glucofuranose (intermediate 1)

To a solution of 1,2:5,6-di-O-isopropylidene-D-glucofuranose (2 g, 7.68 mmol) in pyridine (20 ml) was added DMAP and $Ac_2O$ with ice-water bath. The mixture was stirred at room temperature for 2 h. the mixture was quenched with saturation $NaHCO_3$ aqueous (10 ml) and stirred 30 minutes. The solvent was evaporated under reduced pressure and the residue was suspend in DCM (30 ml). and washed with water and brine respectively. The organic layers was gathered and dried with $MgSO_4$, and concentrated to obtain pure Intermediate 1 as a yellow oil (2.31 g, yield 99%). $^1$H NMR (400 MHz, $CDCl_3$) δ 5.87 (d, J=3.7 Hz, 1H), 5.25 (d, J=2.8 Hz, 1H), 4.49 (d, J=3.7 Hz, 1H), 4.22-4.18 (m, 2H), 4.12-3.97 (m, 2H), 2.10 (d, J=1.7 Hz, 3H), 1.51 (s, 3H), 1.43-1.38 (m, 3H), 1.33-1.31 (m, 3H), 1.30 (s, 3H).

Step 2: Synthesis of 3-acetoxyl-1,2-O-isopropylidene-D-glucofuranose (Intermediate 2)

In a similar manner to that used in step 5 in the synthesis of compound 7, Intermediate 2 (310 mg, 1.03 mmol) was selectivity deprotect group with 0.2% HCl to give acid Intermediate 2 as a colorless oil (172.0 mg, yield 64.33%). $^1$H NMR (400 MHz, $CDCl_3$) δ 5.92-5.81 (m, 1H), 5.31-5.19 (m, 1H), 4.58-4.48 (m, 1H), 4.22-4.10 (m, 1H), 3.90-3.76 (m, 1H), 3.75-3.61 (m, 2H), 3.31 (s, 1H), 2.89-2.72 (m, 1H), 2.11 (s, 3H), 1.49 (s, 3H), 1.28 (s, 3H).

Step 3: Synthesis of 3-O-acetyl-1,2-O-isopropylidene-D-xylo-pentodialdo-1,4-furanose (Intermediate 3)

To a solution of Intermediate 2 (172.0 mg, 0.66 mmol) in the water (4 ml) $NaIO_4$ was added with ice-water bath, and the mixture was stirred 1.5 hour at room temperature, quenched with EtOH and stirred 30 minutes, filtered and the filtrate was concentrated, further purification was by column chromatography (silica gel, petroleum ether/ethyl acetate=3:1) to obtain Intermediate 3 as a colorless oil (121 mg, yield: 79.68%). $^1$H NMR (400 MHz, $CDCl_3$) δ 9.65 (d, J=0.9 Hz, 1H), 6.09 (d, J=3.5 Hz, 11H), 5.50 (d, J=3.5 Hz, 1H), 4.73 (dd, J=3.5, 0.8 Hz, 1H), 4.59 (d, J=3.5 Hz, 1H), 2.05-2.03 (s, 3H), 1.52 (s, 4H), 1.34 (s, 3H).

Step 4: Synthesis of 3-O-acetyl-1,2-isopropylidene-D-gluco-6,7-dideoxy-hept-6-ynofuranose (Intermediate 4)

To a solution of Intermediate 3 (117.0 mg, 0.51 mmol) in dry THF(5 ml) Ethynylmagnesium Bromide (3 mL, 0.5 m in n-hexane, 1.52 mmol, 3.0 equivs.) was added dropwise at 0° C. under Ar protect. Then the mixture was stirred 8 hours. Quenched with saturation $NaHCO_3$ aqueous (3 ml) and stirred 30 minutes. the mixture was extracted with DCM (20×3 ml), the organic layers was combined and wash with water and brine respectively. Dried with $MgSO_4$ and filtered. concentrated and further purification was by column chromatography (silica gel, petroleum ether/ethyl acetate=4:1) to obtain Intermediate 4 as a colorless oil (69 mg, 52.98%). $^1$H NMR (400 MHz, $CDCl_3$) δ 5.96 (dd, J=5.5, 3.6 Hz, 1H), 5.57 (dd, J=8.8, 2.2 Hz, 1H), 5.31 (t, J=3.3 Hz, 1H), 4.52 (dd, J=9.7, 5.2 Hz, 1H), 4.37 (dd, J=8.2, 3.0 Hz, 1H), 2.57-2.53 (m, 0.5H), 2.47 (d, J=2.2 Hz, 0.5H), 2.13 (d, J=3.0 Hz, 1.5H), 2.09 (d, J=3.0 Hz, 1.5H), 1.51 (t, J=4.6 Hz, 3H), 1.31 (s, 3H). comparison with the reference Derek Horton, Ji-Hsiung Tsai, *Carbohydrate Research* 58 1977 89-108, 5' configuration was R and S 14:11.

Step 5: Synthesis of 1,2,3,5-terad-O-acetyl-D-gluco-6,7-dideoxy-hept-6-ynofuranose (Intermediate 5)

In a similar manner to that used in step 2 in the synthesis of compound 5, Intermediate 2 (69 mg, 0.27 mmol) was acetylization with acetic anhydride (127 mmL, 1.35 mmol) and TsOH·$H_2O$ (1.24 mg, 0.053 mmol). in acetic acid (5 mL) to give Intermediate 5 as a colorless oil (64 mg, 69.4%). $^1$H NMR (400 MHz, $CDCl_3$) δ 6.43 (d, J=4.6 Hz, 1H), 6.07 (s, 1H), 5.63 (q, J=2.3 Hz, 1H), 5.61 (d, J=2.2 Hz, 1H), 5.56 (dd, J=8.4, 4.9 Hz, 1H), 5.50 (t, J=5.1 Hz, 1H), 5.46 (dd, J=5.2, 2.3 Hz, 1H), 5.32 (dd, J=6.5, 4.5 Hz, 1H), 2.49-2.47 (m, 1H), 2.44-2.43 (m, 1H), 2.13-2.03 (m, 24H).

Step 6: Synthesis of 2,3,5-tri-O-acetyl-D-gluco-6,7-dideoxy-hept-6-ynol-1-(6-amino-purin-9-yl)-β-D-1-deoxy-furanose (Intermediate 6)

In a similar manner to that used in step 6 in the synthesis of compound 6, Intermediate 5 was glycosylation with adenine (37.90 mg, 0.28 mmol), N,O-bis(trimethylsilyl) acetamide (114.11 mg, 0.59 mmol) and TMSOTf (124.66 mg, 0.98 mmol) in anhydrous acetonitrile (3 mL) to give Intermediate 6 as a colorless oil (44 mg, 56.38%). Mass spectrum (ESI) m/z calc. for $C_{18}H_{19}N_5O_7$ $[M+H]^+$ 418.13. found 418.24.

Step 7: Synthesis of 9-(6,7-dideoxy-hept-6-ynol-β-D-1-deoxy-D-glucofuranosyl)-adenine (compound 119)

In a similar manner to that used in step 7 in the synthesis of compound 6, Intermediate 6 was hydrolyzation with $K_2CO_3$ (72.85 mg, 0.11 mmol) in 50% aqueous methanol (3 mL) to give compound 8 as a white powder (3.2 mg, 10.42%). $^1$H NMR (400 MHz, $CD_3OD$) δ 8.53 (s, 1H), 8.26 (s, 1H), 6.02 (d, J=3.0 Hz, 1H), 4.70 (dd, J=6.8, 2.2 Hz, 1H), 4.55 (t, J=2.8 Hz, 1H), 4.39 (dd, J=6.8, 4.5 Hz, 1H), 4.36-4.32 (m, 1H), 2.93 (d, J=2.2 Hz, 1H).

Synthesis of Compounds 120-121, Compounds 120-121 were Synthesized Using the Same Strategy of Compound 1.

Synthesis of Compound 122: Compound 122 was Synthesized Using the Same Strategy of Compound 3.

Synthesis of Compound 123:

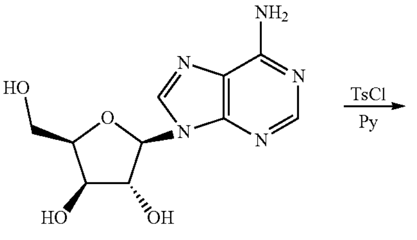

SM1

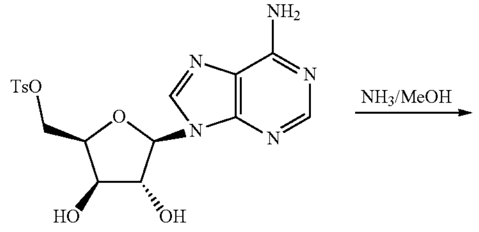

Intermediate 1

-continued

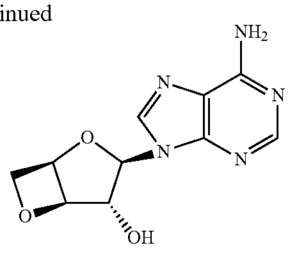

compound 123

-continued

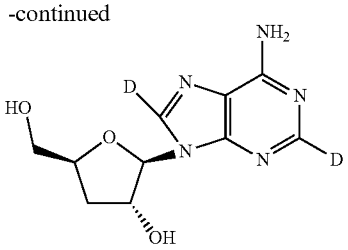

124
Deuteration CA03

Step 1: Synthesis of (Intermediate 1):

To a solution of SM1 (40 mg, 0.15 mmol) in pyridine (5 ml), TsCl (28.5 mg, 0.15 mmol) was added dropwised at 0° C. under $Ar_2$ protect. Then the mixture was stirred for 12 h at room temperature. Then the reaction mixture was concentrated and further purified by chromatography (silica gel, petroleum ether/ethyl acetate=1:1) to give intermediate 1 as a light yellow solid (16.3 mg, yield: 20.68%).

Step 2: Synthesis of Compound 123:

Intermediate 1 was treated with Ammonia solution (2.0M in MeOH). The mixture was stirred for 8 h at 50° C. Then which was concentrated and further purified by chromatography (silica gel, dichloromethane/MeOH=30:1) to give NQZ-196 as a white powder (2.4 mg, yield: 24.89%). $^1$H NMR (400 MHz, $CD_3OD$) δ 8.57 (s, 1H), 8.26 (s, 1H), 8.05 (s, 1H), 6.49 (s, 1H), 5.34-5.33 (d, J=4 Hz, 1H), 5.21-5.19 (m, 1H), 5.06 (s, 1H), 4.83-4.79 (m, 1H), 4.01-3.99 (m, 1H), 1.94 (s, 2H).

Synthesis of compound 124 & 125: Deuteration CA04 and Deuteration CA03.

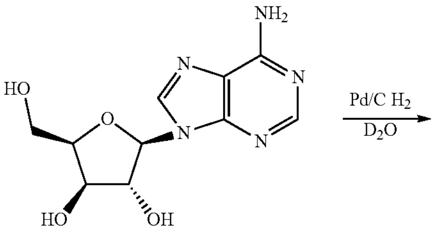

CA04

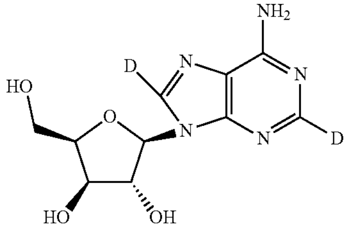

125
Deuteration CA04

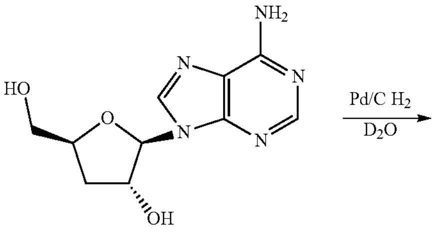

CA03

9-(β-D-xylofuranosyl)-adenine (20 mg) and 10% Pd/C (5 mg, 10 wt % of the substrate) in $D_2O$ (2 mL) was stirred at 160° C. in a sealed tube under a $H_2$ atmosphere for 24 h. After cooling, the reaction mixture was filtered. Filtrate was concentrated in vacuo to give Deuteration CA04 as a white powder (17.2 mg) $^1$H NMR (400 MHz, $CD_3OD$) δ 5.97 (d, J=2.0 Hz, 1H), 4.50-4.41 (m, 1H), 4.38-4.29 (m, 1H), 4.21 (dd, J=3.9, 1.9 Hz, 1H), 4.02-3.85 (m, 2H).

In a similar manner to that used above 3'-deoxy-adenosine was treat with $D_2O$ and Pd/C to give Deuteration CA03 as a white powder (9.7 mg) $^1$H NMR (400 MHz, $CD_3OD$) δ 5.98 (d, J=2.4 Hz, 1H), 4.88-4.94 (m, 1H), 4.61-4.45 (m, 1H), 3.93 (dd, J=12.5, 2.4 Hz, 1H), 3.69 (dd, J=12.5, 3.4 Hz, 1H), 2.42-2.29 (m, 1H), 2.12 (ddd, J=13.2, 6.4, 3.7 Hz, 1H).

Example 3 Evaluation of the Activity of the Typical Compounds of the Present Invention (Table 4)

We do a lot of work on SAR (structure activity relationship) analysis, try to increase the potency of cordycepin in phase shift ability. After get the compound, we tested the compound's phase shift activity in gradient dilution and in parallel combined with or without pentostatin (adenosine deaminase inhibitor) in D15 cells.

The detail procedure is as followed:

1. Preparation of cell suspension: Firstly we trypsinized rapidly growing cells and resuspended in DMEM containing 10% FBS with antibiotics at 5×10$^4$ cells/ml. Then seed 50 μl cells per well of 384 well plate. Finally transfer the plate back into incubator to grow for an additional 2 days to get confluent. When cells get confluent, we start to treat them with synthesized chemicals.

2. Preparation of chemicals: Synthesized compounds were firstly diluted with DMSO to a final concentration of 100 mM. Then each chemicals was diluted in 500 μl pentostatin (5 μg/ml) or DMSO containing XM medium, to the final concentration of 100 μM. 300 μl chemicals containing medium was then transferred into the first row of a 96 well plate, which with pre-allocated 150 μl of pentostatin or DMSO containing XM medium in the rest rows. Finally the chemical containing medium was diluted from the first row to the last row with 2 fold gradient.

3. Treatment of cells with gradient diluted chemicals with or without pentostatin: Cells in 384 well plate were taken out and the medium was changed into chemical containing medium. For each compound, finally, the plate was scaling with scaling film and put into Tecan. Data from cells were collected in the Tecan luminometer at 37° C. for 5 days.

4. Data analysis: we define a negative hit as which could not shift the circadian phase even at the concentration of 500 μM. We define a positive hit which has the circadian phase shift at the concentration less than 200 μM, both in pentostatin containing or non-containing medium.

For example, chemicals 1 to 7, 16 to 24 (please refers to the number in Table 1), NQZ-115, NQZ-193, NQZ-194, NQZ-197, NQZ-198 shift the circadian clock at the concentration less than 100 μM, which should be deemed as positive hits. Biotinylated compound from 8 to 15 (please refers to the number in Table 1) in Table 1 are positive hits too. Although they do not show phase shift ability, even at the concentration of 500 μM in lumicycle assay, however in 384 well plate they show circadian phase shift ability at the concentration about 5 μM. Note that Cordycepin and NQZ-007 show significant increase of potency in pentostatin containing medium, the concentration of eliciting 12 h phase shift increased from 25 μM to 0.2 μM. We also found that some cordycepin like compound has elongation period effect, including NQZ-168 and NQZ-195, under the concentration of 100 μM. Chemical NQZ-163, NQZ-187, NQZ-194, NQZ-198 have increase amplitude effect, increased the Per2:luc signal more than two fold of control, under the concentration of 100 μM.

TABLE 4

| Structure | Cell Assay (μM) | With Pentostadin Cell Assay (μM) |
|---|---|---|
| 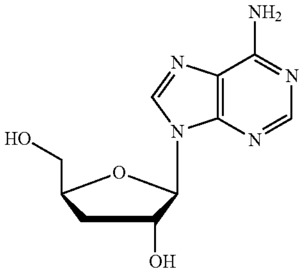 Cordycepin NQZ-001 (CA03) | 25 | 0.5 |
| 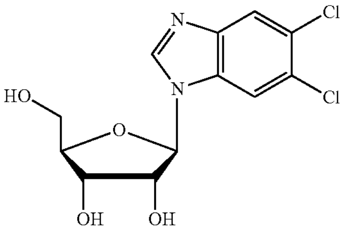 NQZ-002 | 10 | 10 |
| 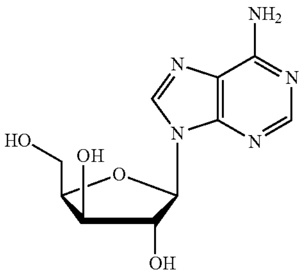 NQZ-007 | 12.5 | 0.5 |

TABLE 4-continued
| Structure | Cell Assay (μM) | With Pentostadin Cell Assay (μM) |
|---|---|---|
| 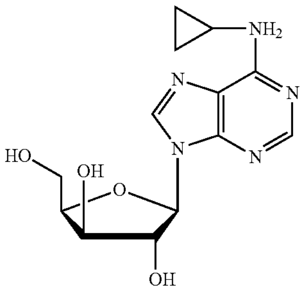 NQZ-090 | 100 | NA |
| 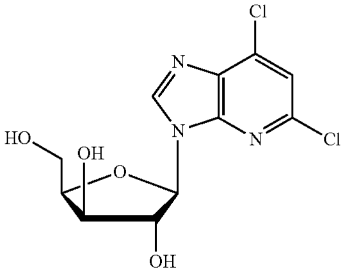 NQZ-097 | 100 | NA |
| 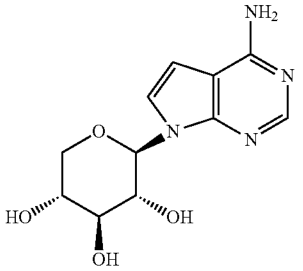 NQZ-086 | 100 | NA |
| 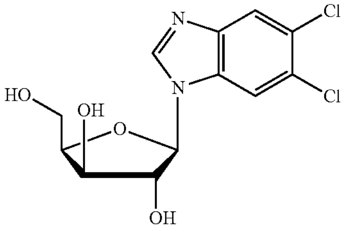 NQZ-118 | 10 | 10 |

TABLE 4-continued
| Structure | Cell Assay (μM) | With Pentostadin Cell Assay (μM) |
|---|---|---|
| 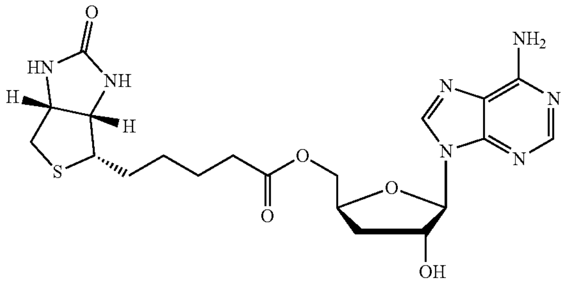 NQZ-069 | >500 | 6 |
| 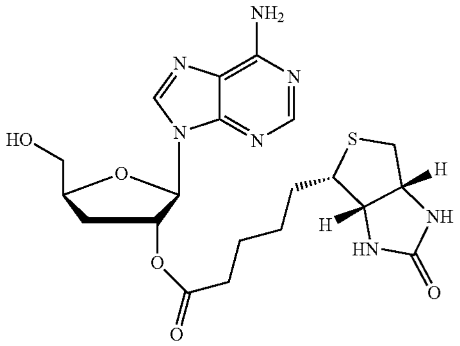 NQZ-119 | >500 | 1.5 |
| 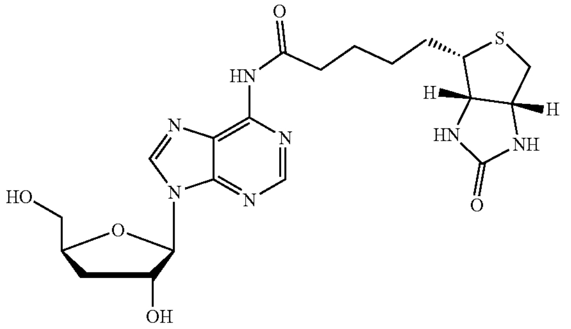 NQZ-068 | >500 | 25 |
| 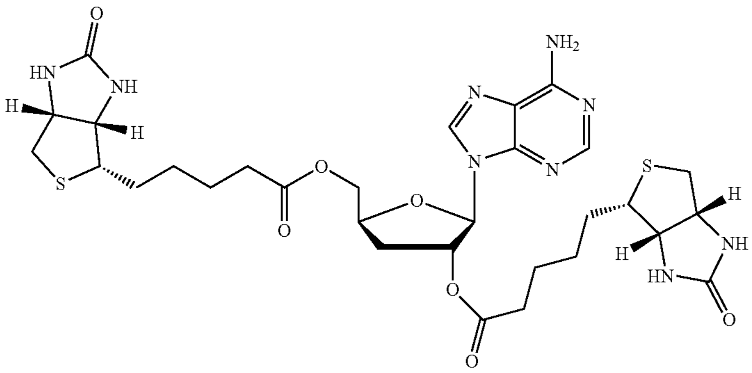 NQZ-121 | >500 | 12.5 |

TABLE 4-continued
| Structure | Cell Assay (μM) | With Pentostadin Cell Assay (μM) |
|---|---|---|
| 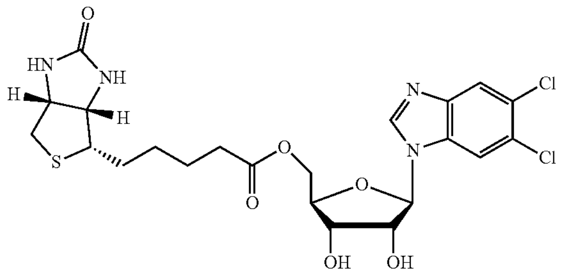 NQZ-112 | 40 | NA |
| 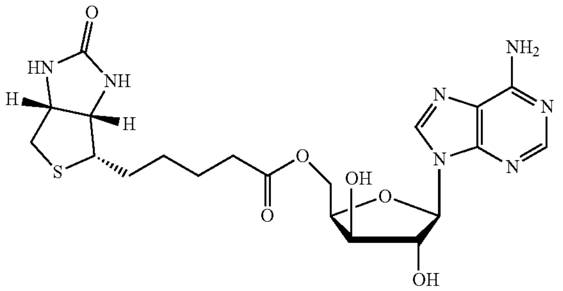 NQZ-122 | >500 | 2 |
| 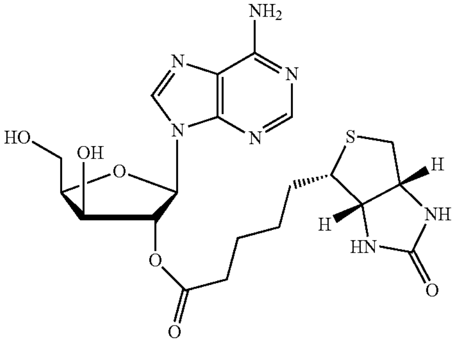 NQZ-123 | >500 | 2 |
| 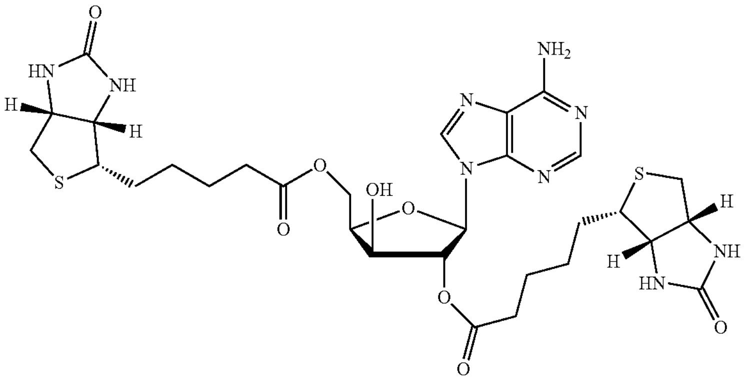 NQZ-124 | >500 | 25 |

TABLE 4-continued
| Structure | Cell Assay (μM) | With Pentostadin Cell Assay (μM) |
|---|---|---|
| 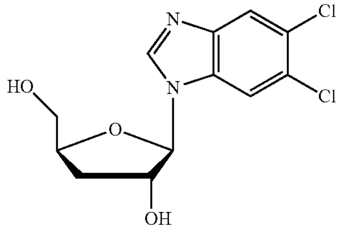 NQZ-006 | 10 | NA |
| 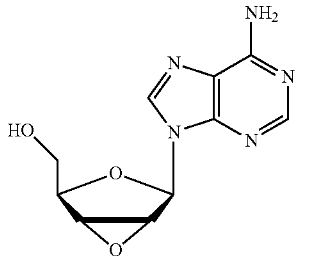 NQZ-062 | 3 | NA |
| 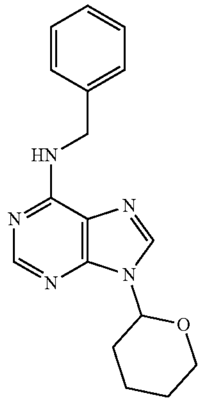 [SMILES: c1ccc(CNc2ncnc3c2ncn3C2CCCCO2)cc1] | 100 | NA |
| 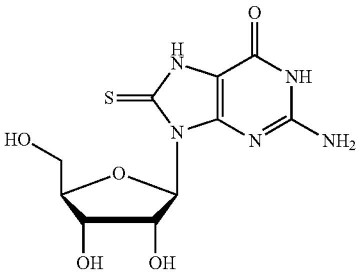 | 100 | NA |
| 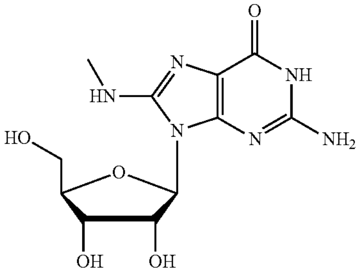 | 100 | NA |

TABLE 4-continued
| Structure | Cell Assay (μM) | With Pentostadin Cell Assay (μM) |
|---|---|---|
| 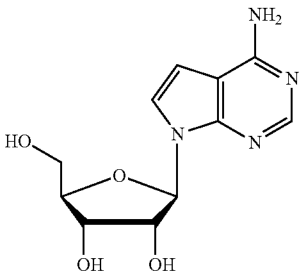 NQZ-003 | 0.3 | 0.3 |
| 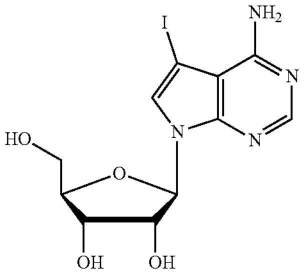 Iodo-Tubercidine (NQZ-020) | 0.3 | NA |
| 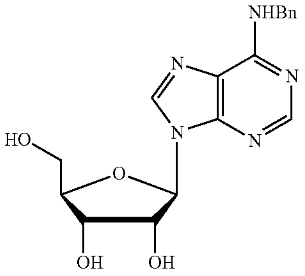 NQZ-004 | 10 | 10 |
| 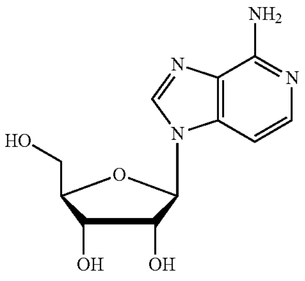 3-Deazaadenosine NQZ-010 | 50 | 50 |

TABLE 4-continued
| Structure | Cell Assay (μM) | With Pentostadin Cell Assay (μM) |
|---|---|---|
| 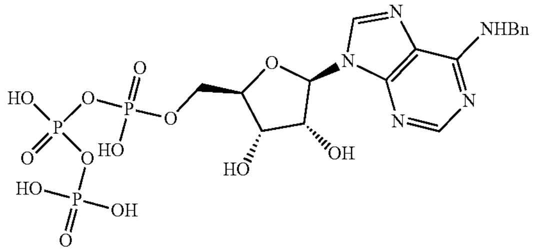 NQZ-005 | 10 | NA |
| 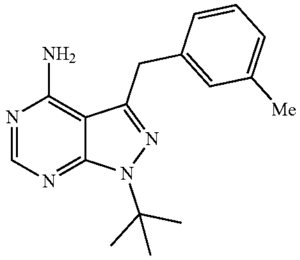 NQZ-008 | 10 | NA |
| 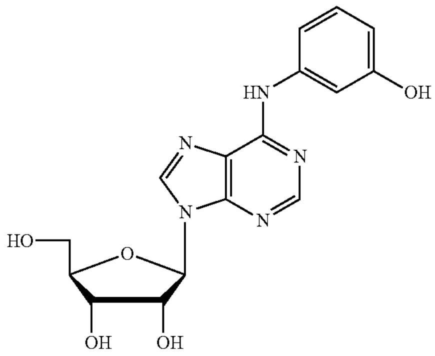 NQZ-011 | 200 | NA |
| 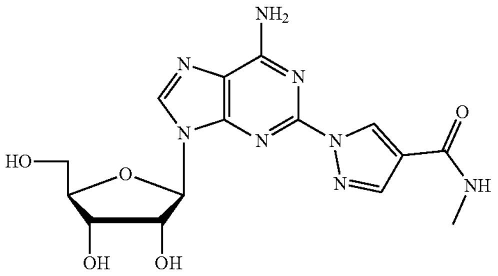 NQZ-021 | 100 | NA |

TABLE 4-continued
| Structure | Cell Assay (μM) | With Pentostadin Cell Assay (μM) |
|---|---|---|
| 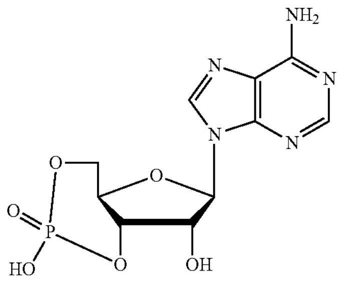 NQZ-026 | 200 | NA |
| 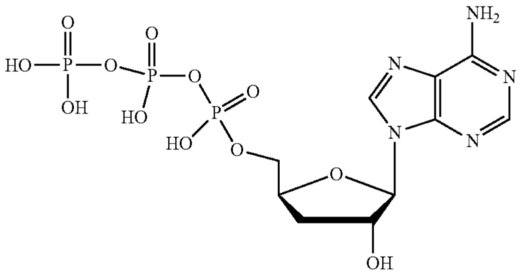 NQZ-034 | 100 | NA |
| 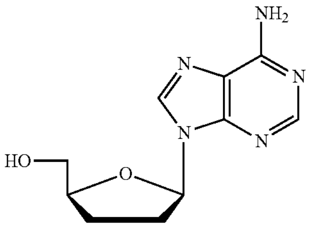 NQZ-047 | 200 | NA |
| 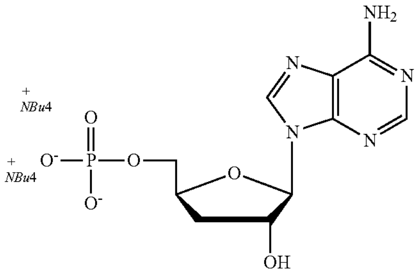 NQZ-067 | 100 | NA |

TABLE 4-continued
| Structure | Cell Assay (μM) | With Pentostadin Cell Assay (μM) |
|---|---|---|
| 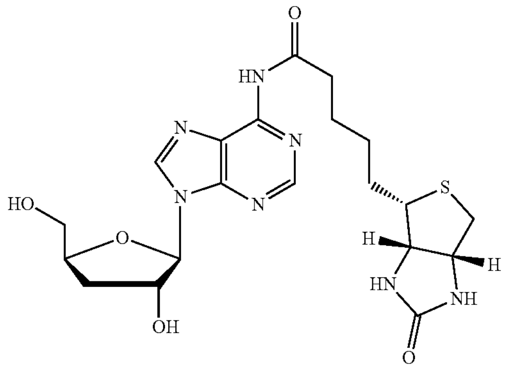 NQZ-068 | 200 | NA |
| 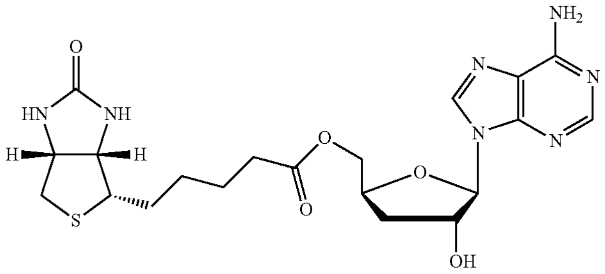 NQZ-069 | 200 | NA |
| 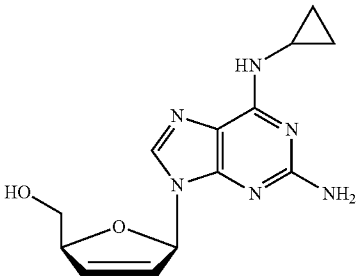 NQZ-078 | 400 | NA |
| 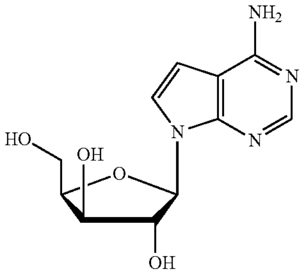 NQZ-115 | NA | 25 |

TABLE 4-continued
| Structure | Cell Assay (μM) | With Pentostadin Cell Assay (μM) |
|---|---|---|
| 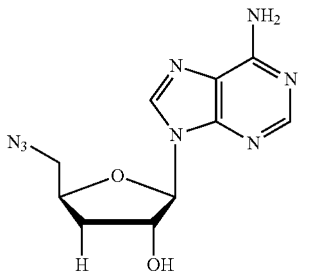 NQZ-117 | 500 | 25 |
| 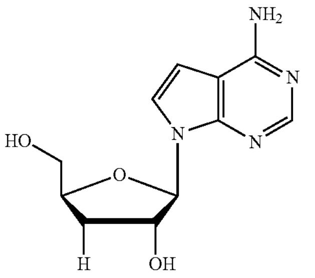 NQZ-126 | 200 | 25 |
| 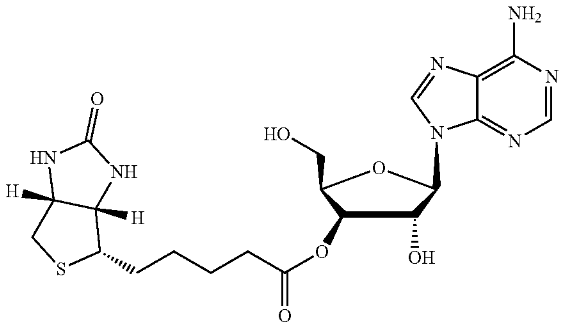 NQZ-132 | >500 | 25 |
| 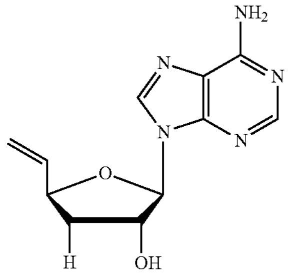 NQZ-136 | 200 | 25 |

TABLE 4-continued
| Structure | Cell Assay (μM) | With Pentostadin Cell Assay (μM) |
|---|---|---|
| 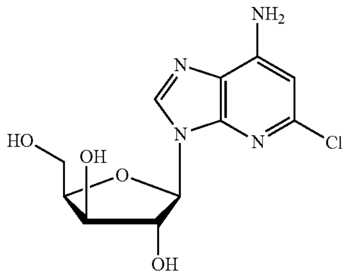 NQZ-140 | >500 | 100 |
| 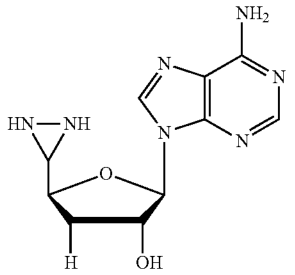 NQZ-143 | >500 | 100 |
| 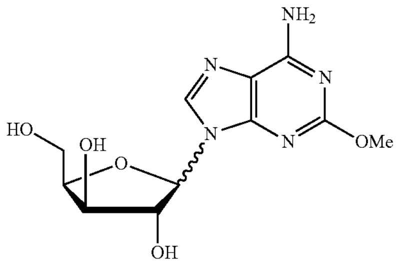 NQZ-148 | >500 | 100 |
| 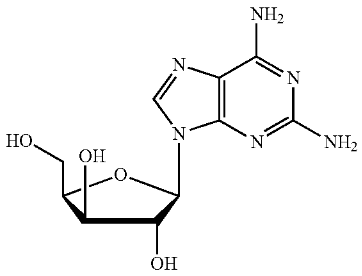 NQZ-149 | >500 | 100 |

TABLE 4-continued
| Structure | Cell Assay (μM) | With Pentostadin Cell Assay (μM) |
|---|---|---|
| 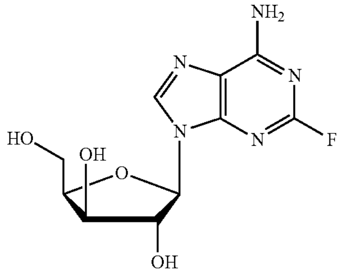 NQZ-150 | 50 | NA |
| 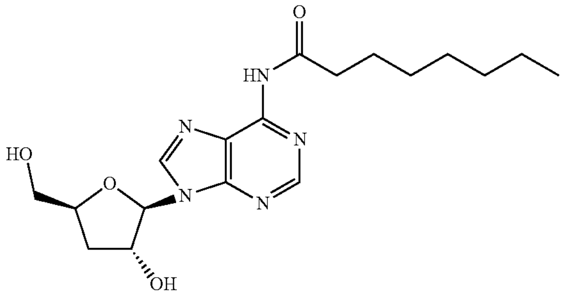 NQZ-162 | NA | Dose effect (15 mg/kg) |
| 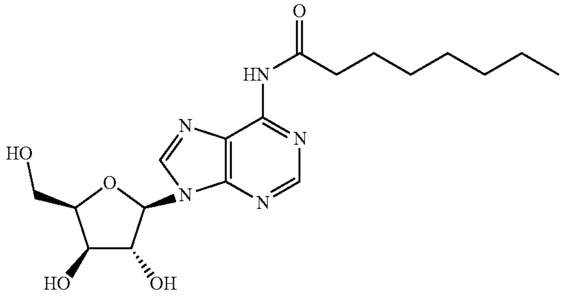 NQZ-163 | NA | Dose effect (15 mg/kg) |
| 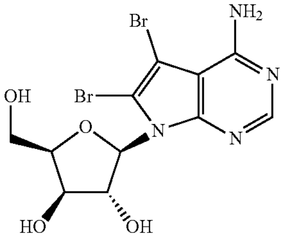 NQZ-165 | >500 | 100 |

TABLE 4-continued
| Structure | Cell Assay (μM) | With Pentostadin Cell Assay (μM) |
|---|---|---|
| 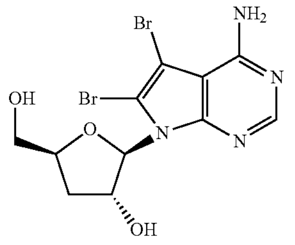 NQZ-166 | >500 | 100 |
| 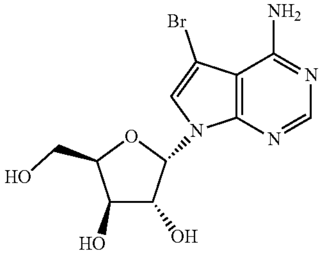 NQZ-167 | >500 | 50 |
| 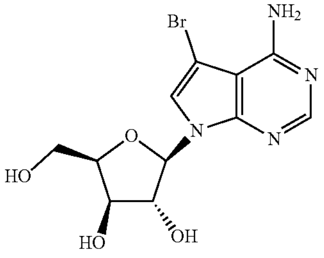 NQZ-168 | >500 | 100 |
| 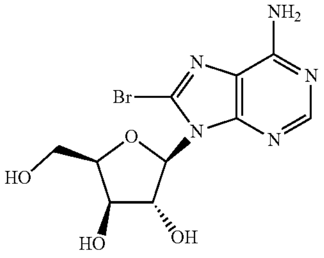 NQZ-169 | >500 | 100 |
| 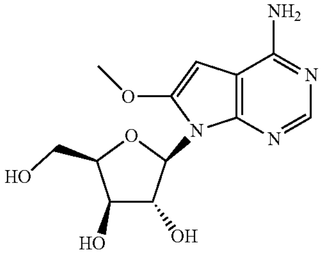 NQZ-170 | >500 | 100 |

TABLE 4-continued
| Structure | Cell Assay (μM) | With Pentostadin Cell Assay (μM) |
|---|---|---|
| 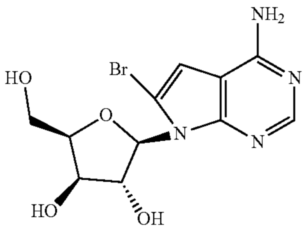 NQZ-171 | >500 | 100 |
| 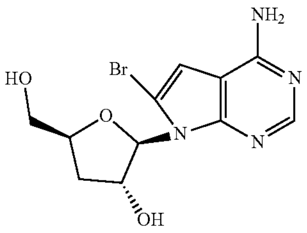 NQZ-173 | >500 | 100 |
| 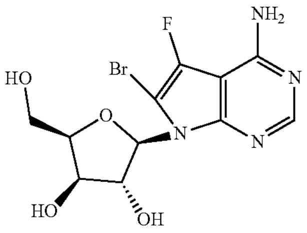 NQZ-174 | >500 | 100 |
| 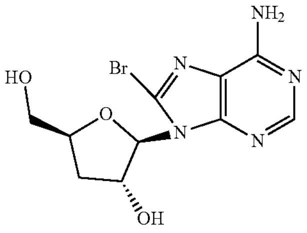 NQZ-175 | >500 | 100 |
| 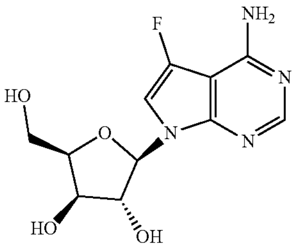 NQZ-177 | >500 | 100 |

TABLE 4-continued
| Structure | Cell Assay (μM) | With Pentostadin Cell Assay (μM) |
|---|---|---|
| 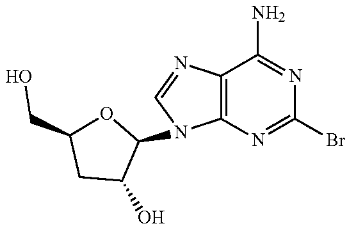 NQZ-178 | >500 | 100 |
| 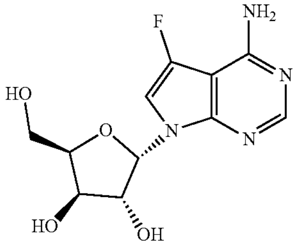 NQZ-180 | >500 | 100 |
| 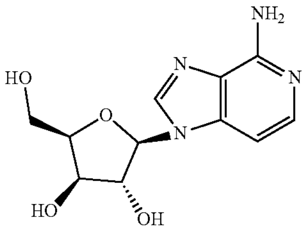 NQZ-186 | >500 | 100 |
| 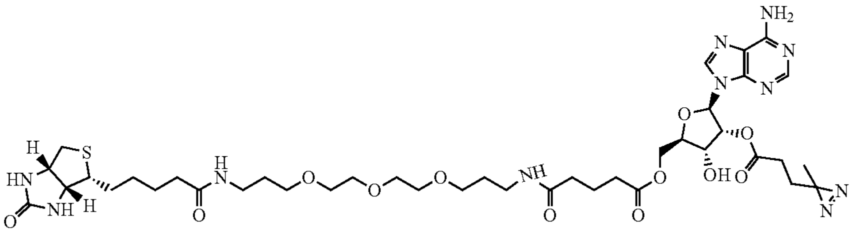 NQZ-187-1 | >500 | 100 |
| 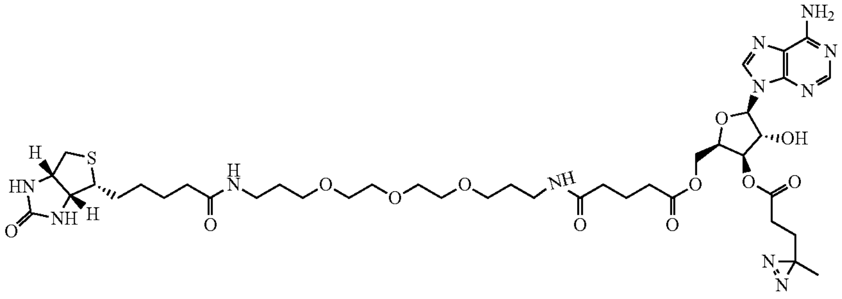 NQZ-187-2 | >500 | 100 |

TABLE 4-continued
| Structure | Cell Assay (μM) | With Pentostadin Cell Assay (μM) |
|---|---|---|
| 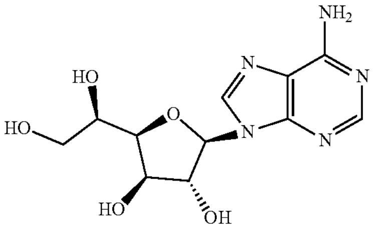 NQZ-190 | >500 | 200 |
| 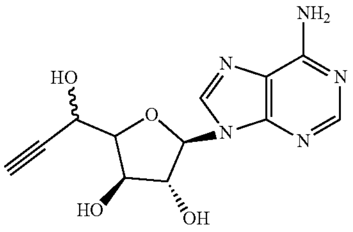 NQZ-192 | >500 | 100 |
| 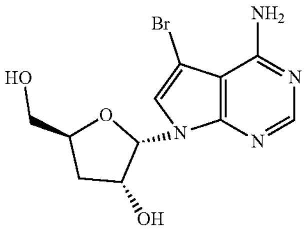 NQZ-193 | >500 | 200 |
| 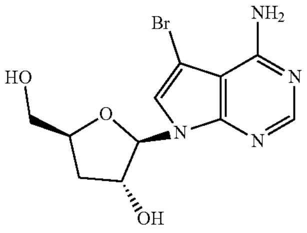 NQZ-194 | >500 | 100 |
| 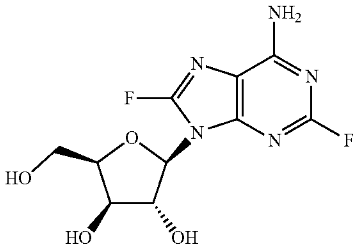 NQZ-195 | >500 | 200 |

TABLE 4-continued

| Structure | Cell Assay (μM) | With Pentostadin Cell Assay (μM) |
|---|---|---|
| 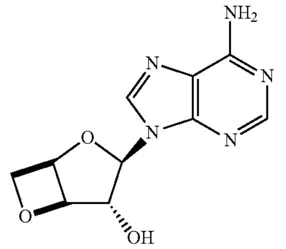 NQZ-196 | >500 | 100 |
| 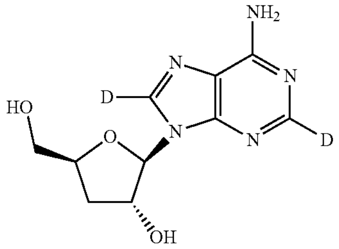 NQZ-197 | 25 | 12.5 |
| 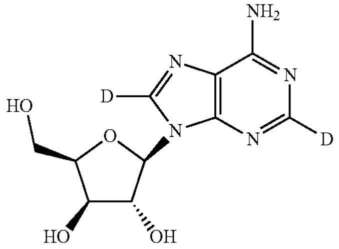 NQZ-198 | 12.5 | 25 |

*N.A.: not available

REFERENCES

1. Mohamed A.; Sarah C.; Gilles G.; et al., *Nucleos. Nucleot. Nucl.,* 2007, 26 (8-9), pp 1125-1128.
2. Valdes J.; Cedillo R.; Alicia H. C.; et al., *Bioorg. Med. Chem. Lett.,* 2002, 12 (16), pp 2221-2224.
3. Rajput V. K.; Mukhopadhyay B.; *Tetrahedron Lett.,* 2006, 47 (33), pp 5939-5941.
4. Aubin Y.; Audran G.; Monti H.; et al., *Bioorg. Med. Chem.,* 2008, 16 (1), pp 374-381.
5. Fonvielle M.; Chemama M.; Lecerf M.; et al., *Angew. Chem. Int. Edit.,* 2010, 49 (30), pp 5115-5119.
6. Szuecova L.; Spichal L.; Dolezal K.; et al., *Bioorg. Med. Chem.,* 2009, 17 (5), pp 1938-1947.
7. Bookser B. C.; Raffaele N. B., *J. Org. Chem.,* 2007, 72 (1), pp 173-179.
8. Lin T. S.; Cheng J. C.; Ishiguro K.; et al., *J. Med. Chem.,* 1985, 28 (9), pp 1194-1198.
9. Claire C.; Salim K.; Carla A. H. P.; et al., *Bioconjugate Chem.,* 2010, 21 (6), pp 1062-1069.
10. C. Hoffmann, H.-G. Genieser, M. Veron and B. Jastorff, Bioorganic & Medicinal Chemistry Letters, Vol. 6, No. 21, pp. 2571-2574, 1996.
11. Lourido, Sebastian; Zhang, Chao; Lopez, Michael S.; Tang, Keliang; Barks, Jennifer; Wang, Qiuling; Wildman, Scott A.; Shokat, Kevan M.; Sibley, L. David. *Journal of Medicinal Chemistry,* 2013, vol. 56, #7, p. 3068-3077.
12. WO2012149196A
13. Robins, Morris J.; Wilson, John, S.; Madej, Danuta; Low, Nicholas H.; Hansske, Fritz; Wnuk, Stanislaw F.—Journal of Organic Chemistry, 1995, vol. 60, #24, p. 7902-7908
14. Ikehara; Maruyama; Miki Tetrahedron, 1978, vol. 34, #8, p. 1133-1138
15. Masaharu Yoshikawa, Tetsuya Kato and Tadao Takenishi, Bulletin of The Chemical Society of Japan, VOL. 4 2 3505-3508 (1969)
16. Ray, Adrian S.; Yang, Zhenjun; Chu, Chung K.; Anderson, Karen S.—Antimicrobial Agents and Chemotherapy, 2002, vol. 46, #3, p. 887-891
17. Glaudemans, C. P. J.; Fletcher, Jr., H. G. J. Org. Chem., 1963, 28, 3004-3006
18. Mikhailopulo, Igor A; Pricota, Tamara I; Sivets, Grigorii G; Altona, Cornelis—The Journal of organic chemistry, 2003, vol. 68, #15, p. 5897-5908.
19. Robins; Neschadimenko; Ro; Yuan; Borchardt; Wnuk—Journal of Organic Chemistry, 1998, vol. 63, #4, p. 1205-1211
20. Beck, D. W., et al., J Neuropathol & Experimental Neurol 1984 43(3)219-224.

21. Cheng, P., et al. Genes & Development 2005 19(2)234-241.
22. Dentin, R., et al. Nature 2007 449(7160)366-369.
23. Gorynia, S., et al. Journal of Structural Biology 2011 176(3)279-291.
24. Hirota, T., et al. PLOS Biology 2010 8(12)e1000559.
25. Hirota, T., et al. Science 2012 337(6098)1094-1097.
26. Hu, Z., et al. Evidence-Based Complementary and Alternative Med 2013 20138.
27. Huang, Z.-L., et al. Nat Neurosci 2005 8(7)858-859.
28. Hughes, M. E., et al. PLoS Genet 2009 5(4)e1000442.
29. Hughes, M. E., et al. Journal of biological rhythms 2010 25(5)372-380.
30. Koike, N., et al. Science 2012 338(6105)349-354.
31. Liu, A. C., et al. Cell 2007 129(3)605-616.
32. 9 NIBS16-007-1WO
33. Matias, P. M., et al. Frontiers in Molecular Biosciences 2015 2(17).
34. Pardridge, W. M. NeuroRX 2005 2(1)3-14.
35. Pardridge, W. M., et al., J Pharmacol and Exper Therapeutics 1994 268(1)14-18.
36. Pizarro, A., et al. Nucleic Acids Research 2012.
37. Rosenbaum, J., et al. Science signaling 2013 6(266)mr1
38. Sato, T. K., et al. Nat Genet 2006 38(3)312-319.
39. Shi, G., et al., PNAS, USA 2013 110(12)4750-4755.
40. Takahashi, J. S., et al. Nat Rev Genet 2008 9(10)764-775.
41. Takahashi, J. S., et al. Science 2008 322(5903)909-912.
42. Woo, P. W. K., et al. Journal of Heterocyclic Chemistry 1974 11(4)641-643.
43. Yamaguchi, Y., et al. Science 2013 342(6154)85-90.
44. Yoo, S.-H., et al., PNAS, USA 2004 101(15)5339-5346.
45. Zhang, E. E. and S. A. KayNat Rev Mol Cell Biol 2010 11(11)764-776.
46. Zhang, E. E., et al. Cell 2009 139(1)199-210.
47. Zhang, R., et al. PNAS, USA 2014 111(45)16219-16224.
48. Zhao, Z., et al. Cell 2015 163(5)1064-1078.

What is claimed is:

1. A composition comprising an adenosine analogue compound of Formula I or a pharmaceutically acceptable salt thereof and pentostatin, Formula I

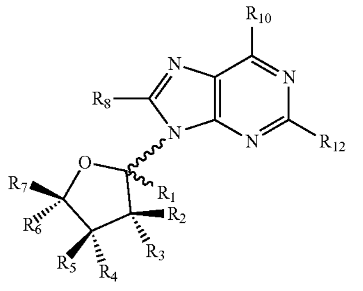

wherein:

$R_1$ is H;

$R_2$ is H, OH, O-Biotin, OAc, OTBS, F, Cl, Br, or I;

$R_3$ is OH, O-Biotin, OAc, or OTBS; or $R_2$ and $R_3$ are independently absent or =O;

$R_4$ and $R_5$ are independently H, OH, F, Cl, Br, I, =O, O-Biotin or $N_3$; or $R_2/R_3$ and $R_4/R_5$ form expoxy ethane together with the carbons they are connected to;

$R_6$ and $R_7$ are independently H, $CH_2$—OH, $CH_2$—$N_3$, $CH_2$—O-Biotin, $CH_2$—AcO, $CH_2$—OTBS, $CO_2Me$, triphosphorylated methylene, 1,2-bishydroxyethane, tetrabutylammonium monophosphate, 1-hydroxyprop-2-yn-1-yl, or diazacymene;

$R_8$ is H, NH—$CH_3$, F, Cl, Br, I, —O—$CH_3$, or deuterium;

$R_{10}$ is H, —$CH_3$, F, Cl, Br, I, $NH_2$, NH—$CH_3$, NH—$NH_2$, =O, NHBn, Biotinamide, m-hydroxyaniline, amino-cyclopropane, amino-cyclobutane, amino-cyclopentane, amino-cyclohexane, OMe or octamide; and $R_{12}$ is H, $NH_2$, F, Cl, Br, I, OMe, or 4-formamide-substituted pyrazole, wherein the adenosine analogue compound does not include adenosine itself.

2. The composition of claim 1, wherein:

$R_7$ is $CH_2$—OH, $CH_2$—$N_3$, $CH_2$—O-Biotin, $CH_2$—AcO, $CH_2$—OTBS, $CO_2Me$, triphosphorylated methylene, 1,2-bishydroxyethane, tetrabutylammonium monophosphate, 1-hydroxyprop-2-yn-1-yl, or diazacymene.

3. The composition of claim 1, wherein:

$R_4$ is H, and $R_5$ is H, OH, F, Cl, Br, I, O-Biotin or $N_3$; or $R_4$ is H, OH, F, Cl, Br, I, O-Biotin or $N_3$, and $R_5$ is H.

4. The composition of claim 1, wherein:

$R_6$ is H, and $R_7$ is $CH_2$—OH, $CH_2$—$N_3$, $CH_2$—O-Biotin, $CH_2$—AcO, $CH_2$—OTBS, $CO_2Me$, triphosphorylated methylene, 1,2-bishydroxyethane, tetrabutylammonium monophosphate, 1-hydroxyprop-2-yn-1-yl, or diazacymene; or $R_6$ is H, $CH_2$—OH, $CH_2$—$N_3$, $CH_2$—O-Biotin, $CH_2$—AcO, $CH_2$—OTBS, $CO_2Me$, triphosphorylated methylene, 1,2-bishydroxyethane, tetrabutylammonium monophosphate, 1-hydroxyprop-2-yn-1-yl, or diazacymene, and $R_7$ is H.

5. The composition of claim 1, wherein:

$R_8$ is H or deuterium;

$R_{10}$ is $NH_2$, NH—$CH_3$, NH—$NH_2$, amino-cyclopropane, amino-cyclobutane, amino-cyclopentane, or amino-cyclohexane; and $R_{12}$ is H.

6. The composition of claim 1, wherein the compound is cordycepin, or the compound is selected from:

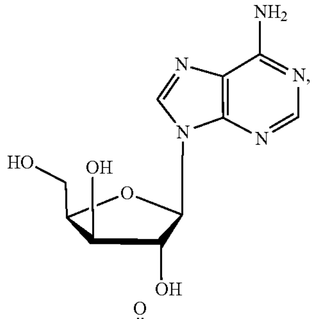

,

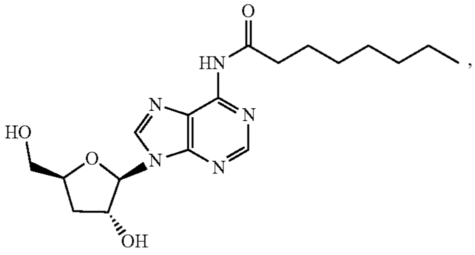

and

NQZ-162

-continued
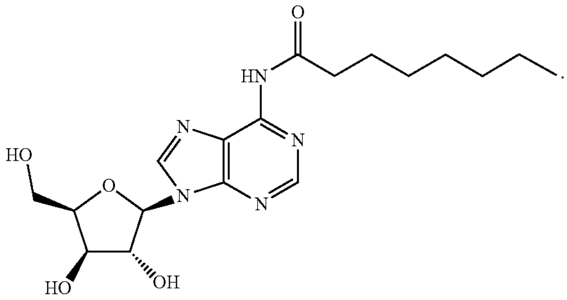
NQZ-163
7. The composition of claim 6, wherein the compound is:
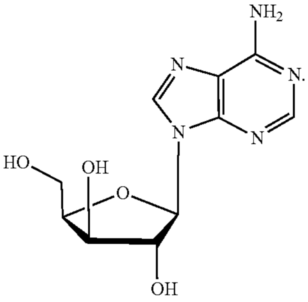
8. A composition comprising a compound, or a pharmaceutically acceptable salt thereof and pentostatin, wherein the compound is selected from:
| Name | Structure |
| --- | --- |
| 1 | 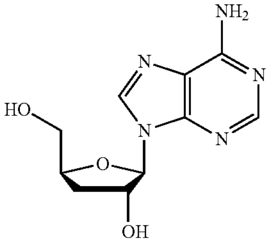 Cordycepin NQZ-001 (CA03) |
| 2 | 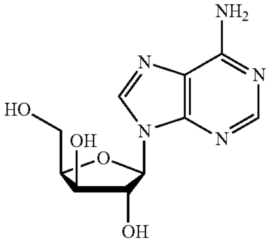 NQZ-007 |
| 3 | 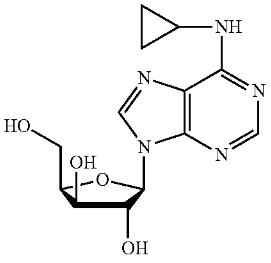 NQZ-090 |

-continued
| Name | Structure |
|---|---|
| 4 | 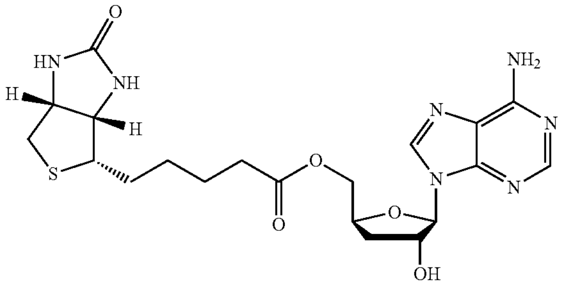 NQZ-069 |
| 5 | 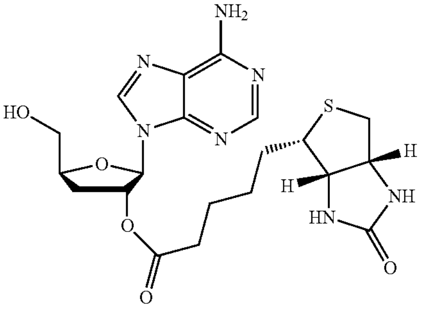 NQZ-119 |
| 6 | 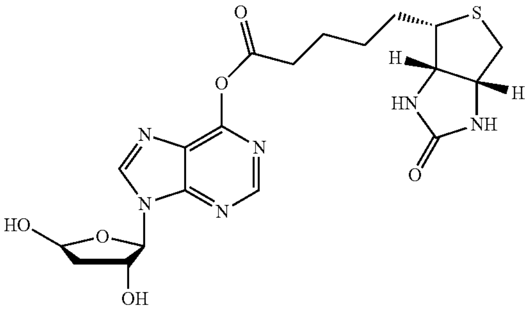 NQZ-068 |
| 7 | 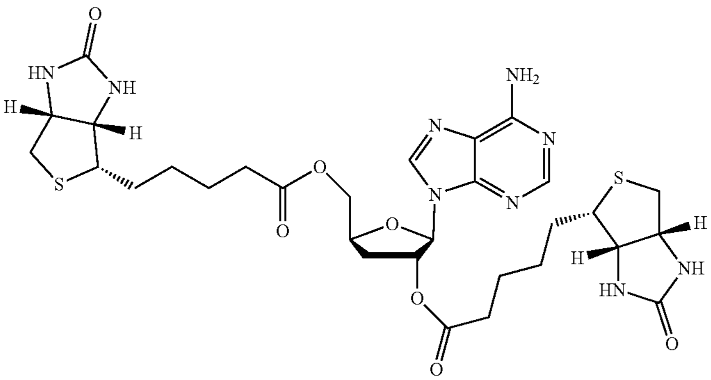 NQZ-121 |

-continued
| Name | Structure |
| --- | --- |
| 8 | 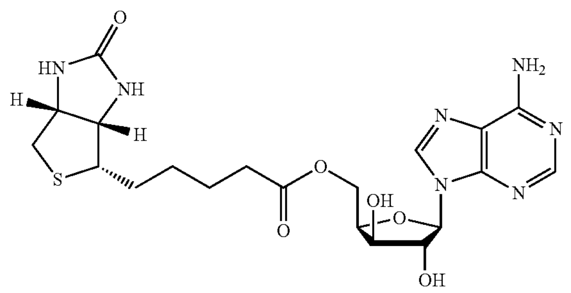 NQZ-122 |
| 9 | 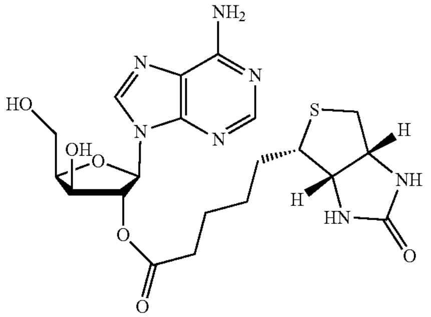 NQZ-123 |
| 10 | 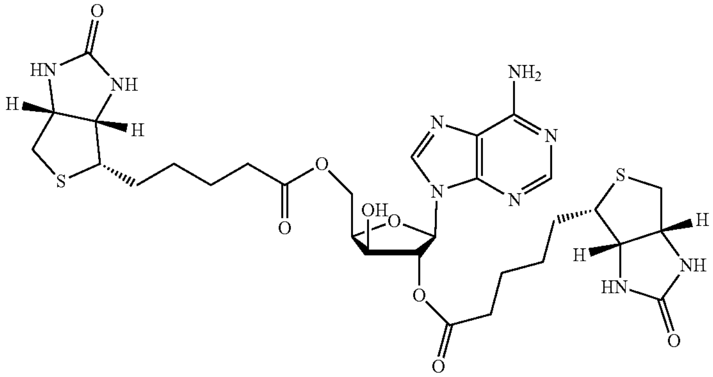 NQZ-124 |
| 11 | 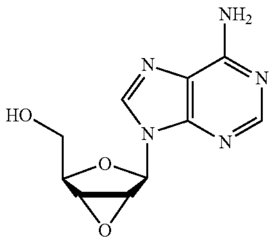 NQZ-062 |

-continued
| Name | Structure |
|---|---|
| 12 | 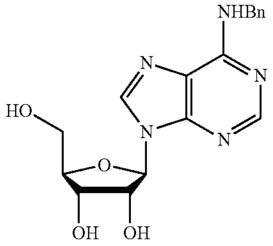<br>NQZ-004 |
| 13 | 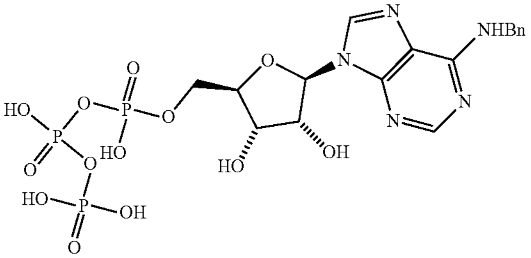<br>NQZ-005 |
| 14 | 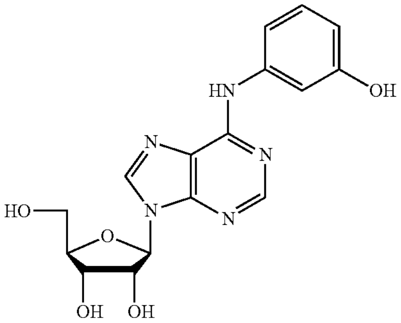<br>NQZ-011 |
| 15 | 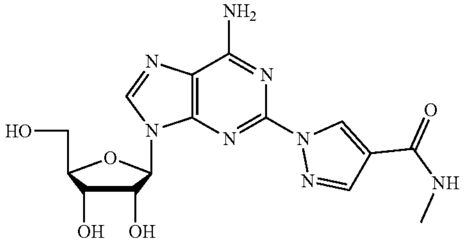<br>Regadenoson<br>NQZ-021 |
| 16 | 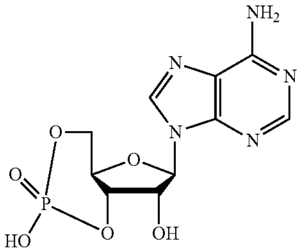<br>NQZ-026 |

-continued
| Name | Structure |
|---|---|
| 17 | 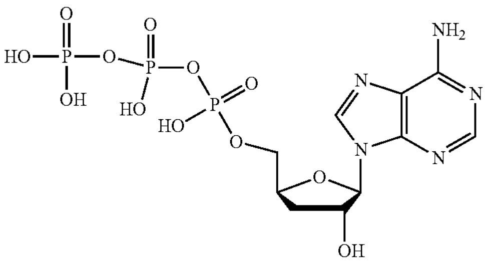 NQZ-034 |
| 18 | 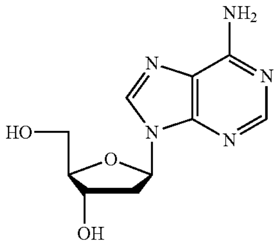 NQZ-035 |
| 19 | 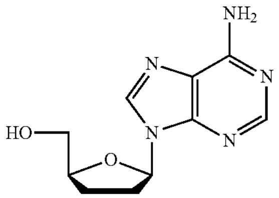 NQZ-047 |
| 20 | 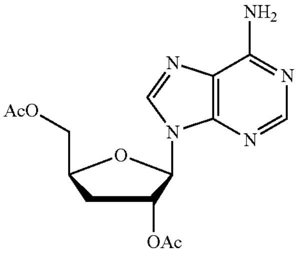 NQZ-061 |
| 21 | 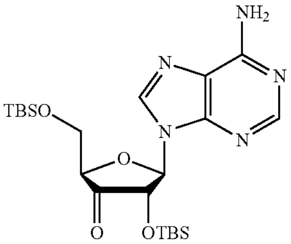 NQZ-064 |

-continued
| Name | Structure |
| --- | --- |
| 22 | 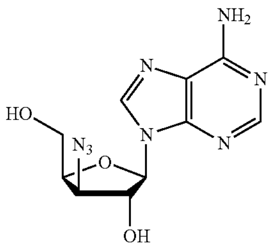 NQZ-065 |
| 23 | 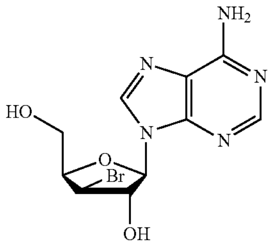 NQZ-066 |
| 24 | 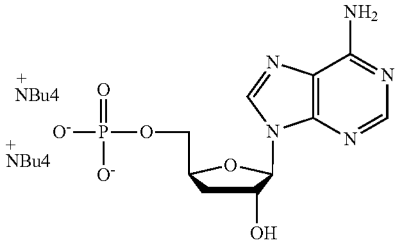 [SMILES: Nc1ncnc2c1ncn2[C@@H]1O[C@H](COP(=O)([O-])[O-])C[C@@H]1O] NQZ-067 |
| 25 | 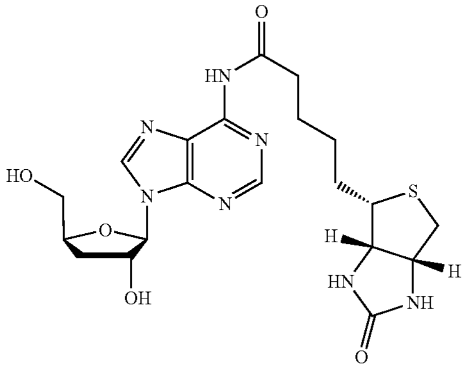 [SMILES: O=C(CCCC[C@@H]1SC[C@@H]2NC(=O)N[C@@H]21)Nc1ncnc2c1ncn2[C@@H]1O[C@H](CO)C[C@@H]1O] NQZ-068 |
| 26 | 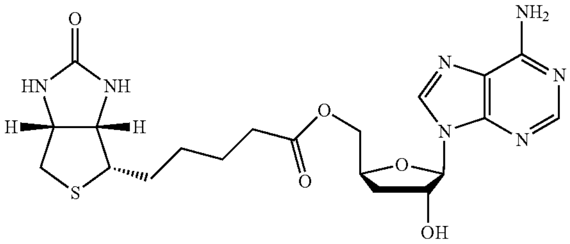 [SMILES: Nc1ncnc2c1ncn2[C@@H]1O[C@H](COC(=O)CCCC[C@@H]2SC[C@@H]3NC(=O)N[C@@H]32)C[C@@H]1O] NQZ-069 |

-continued
| Name | Structure |
| --- | --- |
| 27 | 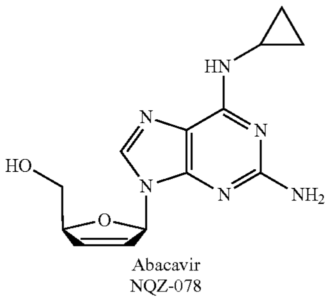<br>Abacavir<br>NQZ-078 |
| 28 | 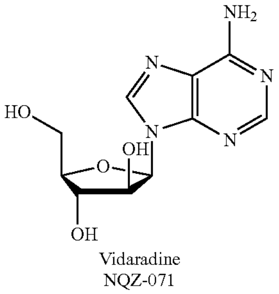<br>Vidaradine<br>NQZ-071 |
| 29 | 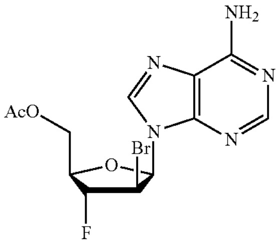<br>NQZ-082 |
| 30 | 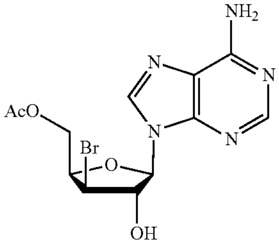<br>NQZ-081 |
| 31 | 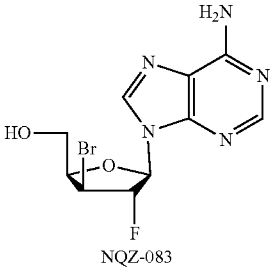<br>NQZ-083 |

-continued
| Name | Structure |
|---|---|
| 32 | 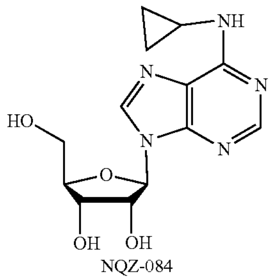 NQZ-084 |
| 33 | 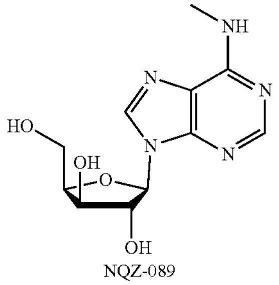 NQZ-089 |
| 34 | 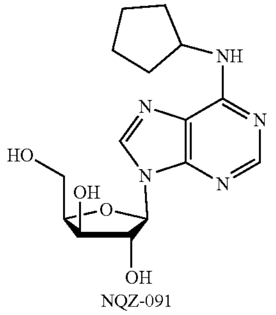 NQZ-091 |
| 35 | 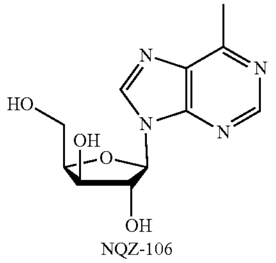 NQZ-106 |
| 36 | 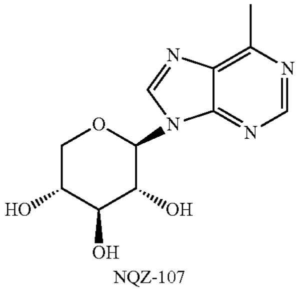 NQZ-107 |

-continued
| Name | Structure |
|---|---|
| 37 | 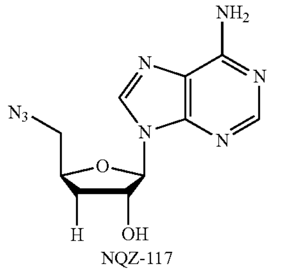<br>NQZ-117 |
| 38 | 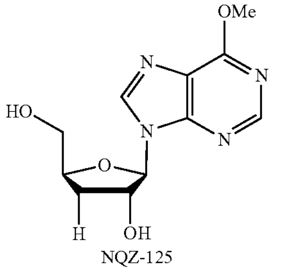<br>NQZ-125 |
| 39 | 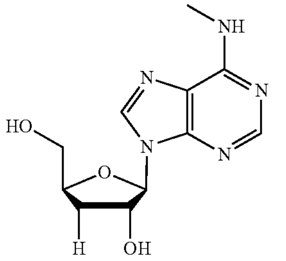<br>NQZ-128 |
| 40 | 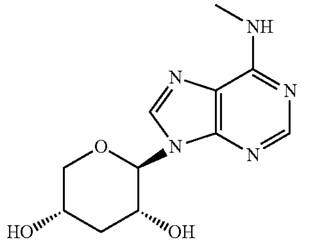<br>NQZ-129 |
| 41 | 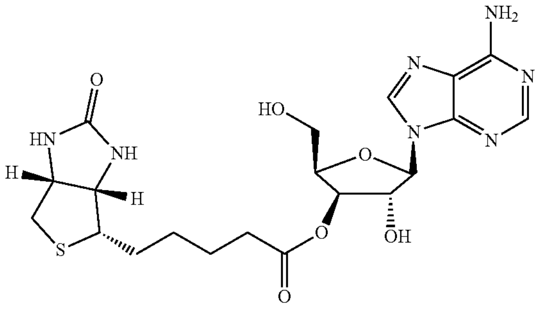<br>NQZ-132 |

-continued
| Name | Structure |
| --- | --- |
| 42 | 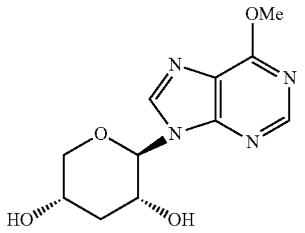 NQZ-135 |
| 43 | 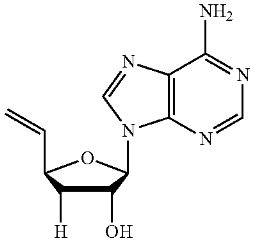 NQZ-136 |
| 44 | 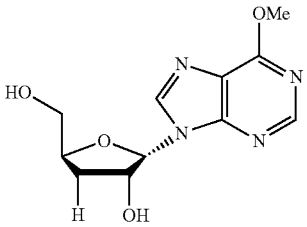 NQZ-137 |
| 45 | 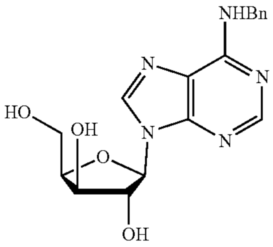 NQZ-142 |
| 46 | 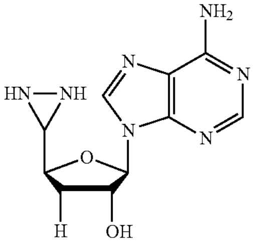 NQZ-143 |

-continued
| Name | Structure |
|---|---|
| 47 | 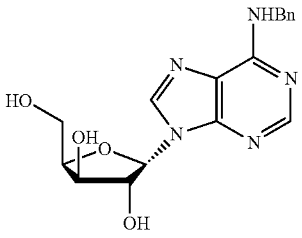 NQZ-146 |
| 48 | 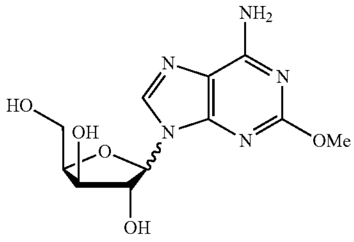 NQZ-148 |
| 49 | 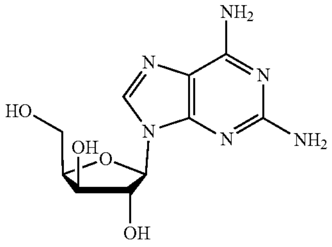 NQZ-149 |
| 50 | 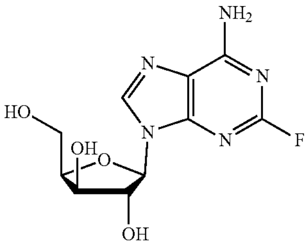 NQZ-150 |
| 51 | 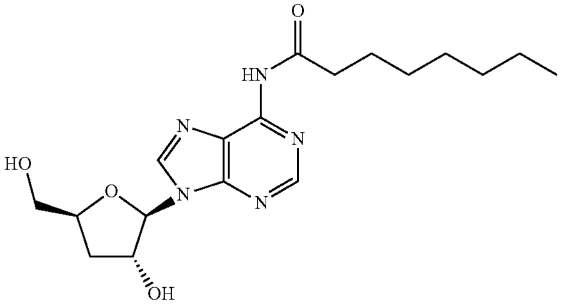 NQZ-162 |

-continued
| Name | Structure |
| --- | --- |
| 52 | 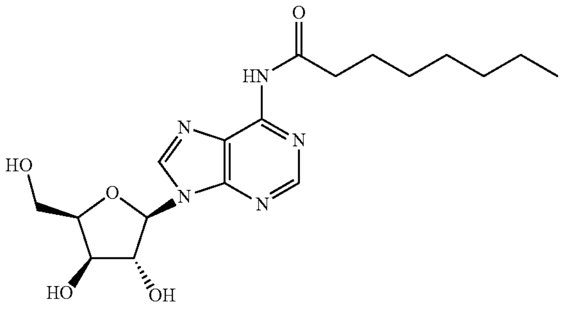 NQZ-163 |
| 53 | 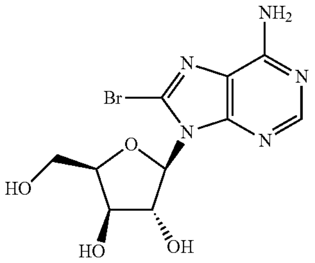 NQZ-169 |
| 54 | 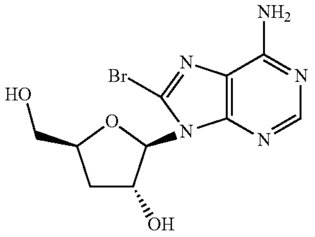 NQZ-175 |
| 55 | 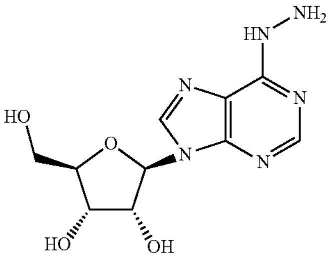 NQZ-176 |
| 56 | 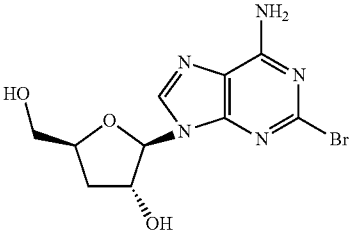 NQZ-178 |

-continued
| Name | Structure |
|---|---|
| 57 | 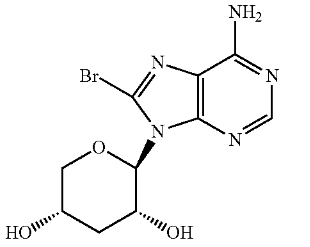<br>NQZ-179 |
| 58 | 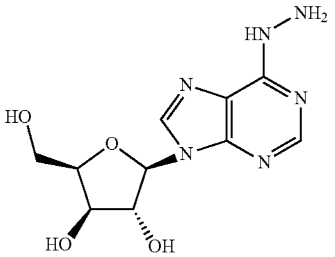<br>NQZ-182 |
| 59 | 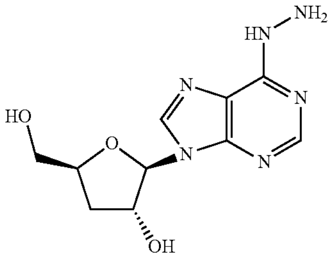<br>NQZ-183 |
| 60 | +get,574 |
| 61 | +get,575 |
| 62 | +get,576 |
| 63 | 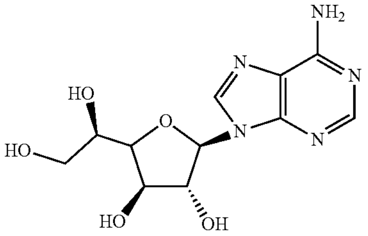<br>NQZ-190 |
| 64 | 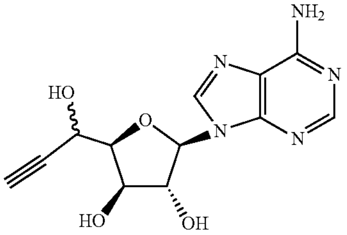<br>NQZ-192 |

-continued

| Name | Structure |
|---|---|
| 65 | 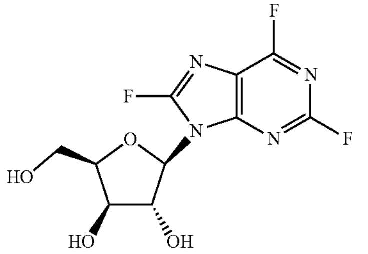 NQZ-195 |
| 66 | 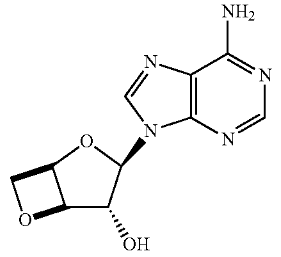 NQZ-196 |
| 67 | 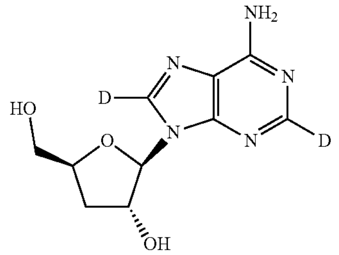 NQZ-197 |
| 68 | 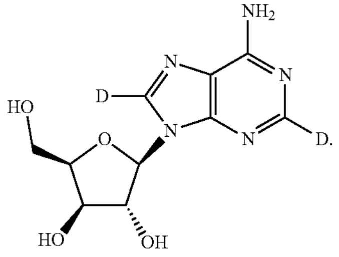 NQZ-198 |

9. A method for modulating circadian rhythm, for shifting circadian phase, for increasing circadian amplitude, for regulating RUVBL helicase, for treating jet lag, shift-work, age-related sleep disturbances, or circadian clock-related sleep disturbances, which comprises administrating to a subject a therapeutically effective amount of a substance, wherein the substance is the composition of claim 1.

10. The method of claim 9, wherein the substance is administrated at the time of Per2-dLuc peak, but not at the trough.

11. The method of claim 9, wherein the target of the substance is RUVBL helicase, which mediate cordycepin-mediated induction of Per2-dLuc and the clock phase shift, is the direct target of cordycepin, or is the target of the compound of Formula I, Formula I

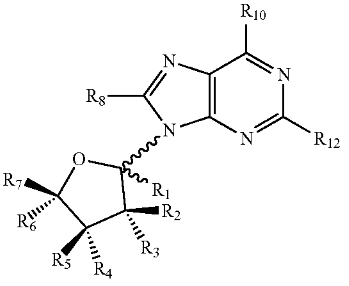

wherein:

$R_1$ is H;

$R_2$ is H, OH, O-Biotin, OAc, OTBS, F, Cl, Br, or I; $R_3$ is OH, O-Biotin, OAc, or OTBS; or $R_2$ and $R_3$ are independently absent or =O;

$R_4$ and $R_5$ are independently H, OH, F, Cl, Br, I, =O, O-Biotin or $N_3$; or $R_2/R_3$ and $R_4/R_5$ form expoxy ethane together with the carbons they are connected to;

$R_6$ and $R_7$ are independently H, $CH_2$—OH, $CH_2$—$N_3$, $CH_2$—OBiotin, $CO_2Me$, triphosphorylated methylene, 1,2-bishydroxyethane, tetrabutylammonium monophosphate, 1-hydroxyprop-2-yn-1-yl, or diazacymene;

$R_8$ is H, NH—$CH_3$, F, Cl, Br, I, —O—$CH_3$, or deuterium;

$R_{10}$ is H, —$CH_3$, F, Cl, Br, I, $NH_2$, NH—$NH_2$, =O, NHBn, Biotinamide, m-hydroxyaniline, amino-cyclopropane, or octamide; and $R_{12}$ is H, $NH_2$, F, Cl, Br, I, OMe, or 4-formamide-substituted pyrazole.

12. The method of claim 11, wherein the RUVBL helicase is RUVBL1 helicase or RUVBL2 helicase.

13. The method of claim 9, wherein the substance is formulated for enteral administration, intravenous administration, oral administration, or sublingual administration.

14. A method for increasing circadian amplitude, for regulating RUVBL helicase, for treating jet lag, shift-work, age-related sleep disturbances, or circadian clock-related sleep disturbances, which comprises administrating to a subject a therapeutically effective amount of substance, wherein the substance is a compound, or a pharmaceutically acceptable salt thereof, and the subject is a human, wherein the compound is:

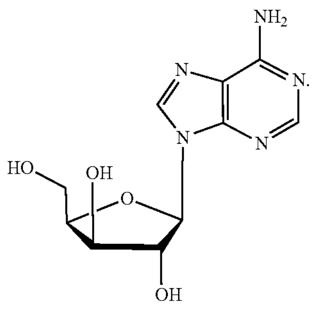

* * * * *